US011737999B2

(12) United States Patent
Wani et al.

(10) Patent No.: US 11,737,999 B2
(45) Date of Patent: Aug. 29, 2023

(54) AMINO ACID COMPOSITIONS AND METHODS FOR THE TREATMENT OF POST-ACUTE SEQUELAE OF COVID-19

(71) Applicant: AXCELLA HEALTH INC., Cambridge, MA (US)

(72) Inventors: Revati Wani, Medford, MA (US); Alison Schecter, Newton Centre, MA (US); Michael Hamill, Wellesley, MA (US); Margaret Koziel, Needham, MA (US); Matthew Russell, Wellesley, MA (US); Karim Azer, Needham, MA (US); Karen Lavery, Franklin, MA (US); Joel Pradines, Watertown, MA (US)

(73) Assignee: AXCELLA HEALTH INC., Cambridge, MA (US)

( * ) Notice: Subject to any disclaimer, the term of this patent is extended or adjusted under 35 U.S.C. 154(b) by 0 days.

(21) Appl. No.: 17/872,749

(22) Filed: Jul. 25, 2022

(65) Prior Publication Data
US 2023/0038163 A1    Feb. 9, 2023

Related U.S. Application Data

(60) Provisional application No. 63/271,665, filed on Oct. 25, 2021, provisional application No. 63/225,850, filed on Jul. 26, 2021.

(51) Int. Cl.
| | | |
|---|---|---|
| *A61K 31/198* | (2006.01) |
| *A61P 21/00* | (2006.01) |
| *A61P 25/00* | (2006.01) |
| *A61P 29/00* | (2006.01) |
| *A61K 31/4172* | (2006.01) |

(52) U.S. Cl.
CPC ........ *A61K 31/198* (2013.01); *A61K 31/4172* (2013.01); *A61P 21/00* (2018.01); *A61P 25/00* (2018.01); *A61P 29/00* (2018.01)

(58) Field of Classification Search
CPC .................................................. A61K 31/198
See application file for complete search history.

(56) References Cited

U.S. PATENT DOCUMENTS

| | | | |
|---|---|---|---|
| 9,597,367 B2 | | 3/2017 | Wolfe et al. |
| 10,471,034 B2 * | | 11/2019 | Hamill ...................... A61P 1/16 |
| 11,129,804 B2 * | | 9/2021 | Hamill ................... A61K 38/06 |
| 2019/0046486 A1 | | 2/2019 | De Rienzo et al. |
| 2019/0388374 A1 | | 12/2019 | Hanlon et al. |
| 2019/0388377 A1 | | 12/2019 | Hamill et al. |
| 2020/0163919 A1 | | 5/2020 | Carroll et al. |
| 2020/0386766 A1 | | 12/2020 | Nagourney et al. |
| 2021/0128466 A1 | | 5/2021 | Legassie et al. |
| 2021/0260010 A1 | | 8/2021 | Hamill et al. |
| 2021/0275479 A1 | | 9/2021 | Hamill et al. |
| 2021/0275480 A1 | | 9/2021 | Hamill et al. |
| 2021/0290573 A1 | | 9/2021 | Chakravarthy et al. |
| 2021/0290574 A1 | | 9/2021 | Carroll et al. |
| 2022/0354813 A1 | | 11/2022 | Hanlon et al. |

FOREIGN PATENT DOCUMENTS

| | | |
|---|---|---|
| JP | H08198748 A | 8/1996 |
| WO | 2008095093 A2 | 8/2008 |
| WO | 2019246298 A1 | 12/2019 |
| WO | 2019246310 A1 | 12/2019 |
| WO | WO 2019246310 | * 12/2019 |

OTHER PUBLICATIONS

Pedrazini et al. Br J Clin Pharmacol, 2022, 88(11): 4708-4723 (i.e., abstract).*
Yang et al., "The role of mitochondria-derived peptides in cardiovascular disease: Recent updates" Biomedicine & Pharmacotherapy (2019) vol. 17, Article 109075, pp. 1-9.
"Aminoacid Nutrient Composition Useful Muscle Fatigue Recover Comprise Arginine Isoleucine Leucine Valine Lysine Methionine Threonine Histidine Proline Phenylalanine Tryptophan Glutamine," Derwent (1995) vol. 41, No. 96, XP002092562.
Kelly M K et al: ""Effects of N-acetylcysteine on respiratorymuscle fatigue during heavy exercise"",Respiratory Physiology and Neurobiology,Elsevier, Amsterdam, NL, (2009) vol. 165, No. 1, pp. 67-72, XP025817160.
"Axcella commences trial of AXA 1125 for long Covid-19 treatment" (2021) XP055968888.
"Efficacy, Safety, Tolerability of AXA 1125 in Fatigue After COVID-19 Infection" (2022) XP055968884.
International Search Report and Written Opinion issued in PCT/US2022/038200, dated Oct. 17, 2022.
"Dr. Betty Raman leads new study on potential treatment for fatigue in long COVID patients" St. Cross College (2022).
Abdelaal et al., "Actions of L-Glutamine vs. COVID-19 Suggest Additional Benefit in Sickle Cell Disease" Blood (2020) pp. 1-4.
Ajaz et al., "Mitochondrial metabolic manipulation by SARS-CoV-2 in peripheral blood mononuclear cells of patients with COVID-19" American Journal of Physiology—Cell Physiology (2021) vol. 320, No. 1, pp. 57-65.
Al-Aly et al., "High-dimensional characterization of post-acute sequelae of COVID-19" Nature (2021) pp. 1-25.
Altay et al., "Combined Metabolic Activators accelerates recovery in mild-to-moderate COVID-19" BJM (2021) pp. 1-29.
Bartolini et al., "SARS-CoV2 infection impairs the metabolism and redox function of cellular glutathione" Redox Biology (2021) vol. 45, Article 102041, pp. 1-10.

(Continued)

*Primary Examiner* — Rei Tsang Shiao
(74) *Attorney, Agent, or Firm* — K&L Gates LLP

(57) ABSTRACT

This disclosure provides pharmaceutical compositions comprising amino acid entities and uses thereof. Methods for treating post-acute sequelae of COVID-19 comprising administering an effective amount of the compositions to a subject in need thereof are also disclosed.

25 Claims, 23 Drawing Sheets

(56) References Cited

OTHER PUBLICATIONS

Batabyal et al., "Metabolic dysfunction and immunometabolism in COVID-19pathophysiology and therapeutics" International Journal of Obesity (2021) pp. 1-7.
Belluck, "New Research Hints at 4 Factors That May Increase Chances of Long Covid" The New York Times (2022) pp. 1-4.
Bhatti et al., "Mitochondrial dysfunction and oxidative stress in metabolic disorders—A Step towards mitochondria based therapeutic strategies" Biochim Biophys Acta. (2017) vol. 1863, No. 5, pp. 1066-1077.
Bobermin et al., "COVID-19 and hyperammonemia: Potential interplay between liver andbrain dysfunctions" Brain, Behavior, & Immunity—Health (2021) vol. 14, Article 100257, pp. 1-3.
Braganza et al., "Blood-Based Bioenergetics: an Emerging Translational and Clinical Tool" Mol Aspects Med. (2020) vol. 71, No. 100835, pp. 1-31.
Cash et al., "Oxaloacetate Treatment For Mental And Physical Fatigue In Myalgic Encephalomyelitis/Chronic Fatigue Syndrome (ME/CFS) and Long-COVID fatigue patients: a non-randomized controlled clinical trial" Journal of Translational Medicine (2022) vol. 20, No. 295, pp. 1-10.
Cengiz et al., "Effect of oralL-Glutamine supplementation on Covid-19treatment" Clinical Nutrition Experimental (2020) vol. 33, pp. 24-31.
Cervia et al., "Immunoglobulin Signature Predicts Risk of Post-acute COVID-19 Syndrome" Nature Communications (2022) vol. 13, No. 446, pp. 1-12.
Charfeddine et al., "Long COVID 19 Syndrome: Is It Related to Microcirculation and Endothelial Dysfunction? Insights From TUN-EndCOV Study" frontiers in Cardiovascular Medicine (2021) vol. 8, Article 745758, pp. 1-8.
Chen et al., "Research on Influencing Factors and Classification of Patients With Mild and Severe COVID-19 Symptoms" frontiers in Cellular and Infection Microbiology (2021) vol. 11, Article 670823, pp. 1-14.
Clayton, "Is susceptibility to severe COVID-19 disease an inborn errorof metabolism?" J Inherit Metab Dis. (2020) vol. 43, pp. 906-907.
Cox et al., "Nutritional Ketosis Alters Fuel Preference andThereby Endurance Performance in Athletes" Cell Metabolism (2016) vol. 24, pp. 256-268.
Crabtree et al., "Cytosolic accumulation of L-proline disrupts GABA-ergic transmission through GAD blockade" Cell Rep. (2016) vol. 12, No. 2, pp. 570-582.
Daou et al., "A novel, multitargeted endogenous metabolic modulator composition impacts metabolism, inflammation, and fibrosis in nonalcoholic steatohepatitis-relevant primary human cell models" Nature Portfolio (2011) vol. 11, Article 11861, pp. 1-15.
Daugherty et al., "Risk of clinical sequelae after the acute phase of SARS-CoV-2 infection: retrospective cohort study" BMJ (2021) pp. 1-12.
De Boer et al., "Decreased Fatty Acid Oxidation and Altered LactateProduction during Exercise in Patients withPost-acute COVID-19 Syndrome" American Journal of Respiratory and Critical Care Medicine (2022) vol. 205, No. 1, pp. 126-129.
Debeaumont et al., "Cardiopulmonary Exercise Testing to Assess Persistent Symptoms at 6 Months in People With COVID-19 Who Survived Hospitalization—A Pilot Study" American Physical Therapy Association (2021) pp. 1-23.
Donyavi et al., "Acute and post-acute phase of COVID-19: Analyzing expression patterns of miRNA-29a-3p, 146a-3p, 155-5p, and let-7b-3p in PBMC" International Immunopharmacology (2021) vol. 97, Article 107641, pp. 1-9.
Ebrahimi et al., "A lipidomic view of SARS-CoV-2" Biosci Rep (2021) vol. 41, No. 8, pp. 1-13.
Edwards et al., "The Effect of High-Altitude on Human Skeletal Muscle Energetics:31P-MRS Results from the Caudwell Xtreme Everest Expedition" PLoS ONE (2010) vol. 5, No. 5, pp. 1-8.

Elmonem et al., "The impact of COVID-19 pandemic on the diagnosis and management ofinborn errors of metabolism: A global perspective" Molecular Genetics and Matabolism (2020) vol. 131, pp. 285-288.
Evans et al., "Physical, cognitive and mental health impacts of COVID-19 following hospitalisation—a multi-centre prospective cohort study" The Lancet Respiratory Medicine (2021) vol. 9, No. 11, pp. 1-40.
Filler et al., "Association of mitochondrial dysfunction and fatigue: A review of the literature" BBA Clinical (2014) pp. 12-23.
Ganji et al., "Impact of COVID-19 on Mitochondrial-Based Immunity in Aging and Age-Related Diseases" frontiers in Aging Neuroscience (2021) vol. 12, Article 614650, pp. 1-12.
Gassen et al., "SARS-CoV-2-mediated dysregulation ofmetabolism and autophagy uncovershost-targeting antivirals" Nature Communications (2021) vol. 12, Article 3818, pp. 1-15.
Gibellini et al., "Altered bioenergetics and mitochondrialdysfunction of monocytes in patients withCOVID-19pneumonia" EMBO Molecular Medicine (2020) vol. 12, pp. 1-13.
Hamill et al., "Endogenous Metabolic Modulators: Emerging Therapeutic Potential of Amino Acids" CellPress iScience (2020) vol. 23, Article 101628, pp. 1-13.
Harrison et al., "Safety, Tolerability, and Biologic Activity of AXA1125and AXA1957 in Subjects With Nonalcoholic FattyLiver Disease" The American Journal of Gastroenterology (2021) vol. 116, pp. 2399-2409.
Havervall et al., "Symptoms and Functional Impairment Assessed 8 Months After Mild COVID-19 Among Health Care Workers" JAMA Network (2021) vol. 325, No. 19, pp. 1-8.
Hinshaw et al., "Axcella Therapeutics R&D Day 2021 Presentation" Presented Oct. 26, 2021, Slides 1-108.
Hjollund et al., "Assessment of fatigue in chronic disease: a bibliographic study of fatigue measurement scales" Health and Quality of Life Outcomes (2007) vol. 5, No. 12, pp. 1-5.
Holecek, "The Role of Skeletal Muscle in The Pathogenesis of Altered Concentrations of Branched-Chain Amino Acids (Valine, Leucine, and Isoleucine) in Liver Cirrhosis, Diabetes, and Other Diseases" Physiol. Res. (2021) vol. 70, pp. 293-305.
Holloway et al., "A Novel Amino Acid Composition Ameliorates Short-Term Muscle Disuse Atrophy in Healthy Young Men" frontiers in Nutrition (2019) vol. 6, Article 105, pp. 1-10.
Holmes et al., "Incomplete Systemic Recovery and Metabolic Phenoreversion in Post-Acute-Phase Nonhospitalized COVID-19 Patients: Implications for Assessment of Post-Acute COVID-19 Syndrome" Journal of Protrome (2021) vol. 20, pp. 3315-3329.
Jin et al., "Endothelial activation and dysfunction in COVID-19: from basic mechanisms to potential therapeutic approaches" Signal Transduction and Targeted Therapy (2020) vol. 5, No. 293, pp. 1-13.
Kaklamanos et al., "COVID-19 Immunobiology: Lessons Learned, New Questions Arise" fronteirs in Immunology (2021) vol. 12, Article 719023, pp. 1-25.
Kalyanaraman, "Reactive oxygen species, proinflammatory and immunosuppressive mediators induced inCOVID-19: overlapping biology with cancer" Royal Society of Chemistry (2021) vol. 2, pp. 1402-1414.
Khunti et al., "Long COVID—metabolic risk factors and novel therapeutic management" Nature Reviews—Edndocrinology (2021) pp. 1-2.
Kim et al., "The Mitochondrial-Encoded Peptide MOTS-c Translocates to the Nucleus to Regulate NuclearGene Expression in Response to Metabolic Stress" Cell Metabolism (2018) vol. 28, pp. 516-524.
Koroshetz, "Post-acute COVID-19 Syndrome (PACS)" National Institute of Neurological Disorders and Stroke Event (Presented Dec. 2020) Slides 1-28.
Lerner et al., "Toward Understanding COVID-19 Recovery: National Institutes of Health Workshop on Post acute COVID-19" Annals of Internal Medicine (2021) pp. 1-6.
Lopez-Leon et al., "More than 50 Long-term effects of COVID-19: a systematic review and meta-analysis" medRXiv (2021) pp. 1-22.
Lou et al., "Elevation of Serum Cytokine Profiles and Liver Metabolomic Normalizationin Early Convalescence of COVID-19 Patients" frontiers in Medicine (2021) vol. 8, Article 626633, pp. 1-11.
Mahmudpour et al., "The COVID-19-diabetes mellitus molecular tetrahedron" Molecular Biology Reports (2021) pp. 1-12.

(56) References Cited

OTHER PUBLICATIONS

Maksoud et al., "A systematic review of nutraceutical interventions for mitochondrial dysfunctions in myalgic encephalomyelitis/chronic fatigue syndrome" Journal of Translational Medicine (2021) vol. 19, No. 81, pp. 1-11.
Merry et al., "Mitochondrial-derived peptides in energy metabolism" Am J Physiol Endocrinol Metab (2020) vol. 319, pp. 659-666.
Montefusco et al., "Acute and long-term disruption of glycometabolic control after SARS-CoV-2 infection" Nature Metabolism (2021) vol. 3, pp. 774-785.
Nashine et al., "Effects of Mitochondrial-Derived Peptides (MDPs) on Mitochondrial and Cellular Health in AMD" Cells (2020) vol. 9, No. 1102, pp. 1-12.
Newsholme et al., "Branched-Chain Amino Acids and Central Fatigue" American Society for Nutrition (2006) pp. 274S-276S.
Nunn et al., "SARS-CoV-2 and mitochondrial health:implications of lifestyle and ageing" Immunity & Ageing (2020) vol. 17, No. 33, pp. 1-21.
Ostojic, "Diagnostic and Pharmacological Potency of Creatine in Post-Viral Fatigue Syndrome" Nutrients (2021) vol. 13, No. 503, pp. 1-9.
Paul et al., "Redox imbalance links COVID-19 and myalgicencephalomyelitis/chronic fatiguesyndrome" PNAS (2021) vol. 118, No. 34, pp. 1-10.
Pezeshki et al., "Low Protein Diets and EnergyBalance: Mechanisms of Action on Energy Intake and Expenditure" frontiers in Nutrition (2021) vol. 8, Article 655833, pp. 1-8.
Philips et al., "Amino acid sensing pathway: A major check point in thepathogenesis of obesity and COVID-19" Obesity Review (2020) pp. 1-8.
Piotrowicz et al., "Post-COVID-19 acute sarcopenia: physiopathology and management" Aging Clinical and Esperimental Research (2021) vol. 33, pp. 2887-2898.
Polonikov, "Endogenous Deficiency of Glutathione as the Most Likely Cause of Serious Manifestations and Death in COVID-19 Patients" ACS Infectious Diseases (2020) vol. 6, No. 7, pp. 1558-1562.
Ramakrishnan et al., "Unraveling the Mystery Surrounding Post-Acute Sequelae of COVID-19" frontiers in Immunology (2021) vol. 12, Article 686029, pp. 1-16.
Ramos-Casals et al., "Systemic and organ-specific immune-related manifestations of COVID-19" Nature Reviews—Rheumatology (2021) vol. 17, pp. 315-332.
Rathi et al., "A Randomized Controlled Trial of the Efficacy of SystemicEnzymes and Probiotics in the Resolution of Post-COVID Fatigue" Medicines (2021) vol. 8, No. 47, pp. 1-12.
Rossato et al., "Observational study on the benefit of a nutritional supplement,supporting immune function and energy metabolism, on chronic fatigue associated with the SARS-CoV-2 post-infection progress" Clinical Nuetrition ESPEN (2021) vol. 46, pp. 510-518.
Ruocco et al., "Essential amino acid formulations to prevent mitochondrial dysfunction and oxidative stress" Current Opinion Clinical Nutrition (2021) vol. 24, No. 1, pp. 88-95.
Sadoughi et al., "Coagulopathy: Another side effect of coronavirus infection" J Cardivasc Thorac Res (2021) vol. 13, No. 1, pp. 15-22.
Saleh et al., "Mitochondria and microbiota dysfunction in COVID-19 pathogenesis" Mitochondiron (2020) vol. 54, pp. 1-7.
Sánchez-González et al., "Dysfunctional oxidative phosphorylation shuntsbranched-chain amino acid catabolism ontolipogenesis in skeletal muscle" The Embo Journal (2020) vol. 39, pp. 1-24.
Say et al., "Post-acute COVID-19 Outcomes in Children with Mild Asymptomatic Disease" The Lancet—Child & Adolescent Health (2021) vol. 5, No. 6, pp. 1-2.
Scheuermann-Freestone "Abnormal Cardiac and Skeletal Muscle Energy Metabolismin Patients With Type 2 Diabetes" Circulation (2003) pp. 3040-3046.
Schneider et al., "Editorial: Mitochondrial Biology and Its Role in Metabolic Diseases" Frontiers in Endocrinology (2022) vol. 13, Article 944728, pp. 1-4.
Sedivy et al., "Dynamic 31P MR Spectroscopy of Plantar Flexion: Influence of Ergometer Design, Magnetic Field Strength (3 and 7 T), and RF-coil Design" Med. Phys. (2015) vol. 42, No. 4, pp. 1678-1689.
Shi et al., "N-Acetylcysteine to Combat COVID-19: An Evidence Review" Therapeutics and Clincal Risk Management (2020) vol. 16, pp. 1047-1055.
Silvia Andrade et al., "Long-COVID and Post-COVID Health Complications:An Up-to-Date Review on Clinical Conditions and Their Possible Molecular Mechanisms" MDPI Viruses (2021) vol. 13, No. 700, pp. 1-24.
Singh et al., "Decoding SARS-CoV-2 Hijacking of Host Mitochondria in COVID-19 Pathogenesis" Am J Physiol Cell Physiol (2020) vol. 319, No. 2, pp. 258-267.
Soares et al., "Skeletal muscle alterations in patients with acuteCovid-19 and post-acute sequelae of Covid-19" Journal of Cachexia, Sarcopenia and Muscle (2022) vol. 13, pp. 11-22.
Spinelli., "The Multifaceted Contributions of Mitochondria to Cellular Metabolism" Nat Cell Biol. (2018) vol. 20, No. 7, pp. 745-754.
Stefano et al., "Mitochondrial DNA Heteroplasmy as an Informational Reservoir Dynamically Linked to Metabolic and Immunological Processes Associated with COVID-19 Neurological Disorders" Cellular and Molecular Nuerobiology (2021) pp. 1-9.
Stefano et al., "Selective Neuronal Mitochondrial Targeting in SARS-CoV-2 Infection Affects Cognitive Processes to Induce 'Brain Fog' and Results in Behavioral Changes that Favor Viral Survival" Medical Science Monitor (2021) vol. 27, pp. 1-4.
Stephens, "MEA Summary Review: The Role of Mitochondira in ME/CFS" the ME association (2019) pp. 1-21.
Stewart et al., "The Dynames of Mitochondiral DNA Heteroplasmy: Implications for Human Health and Disease" Nature—Genetics (2015) vol. 16, pp. 530-542.
Stussman et al., "Characterization of Post-exertional Malaise in Patients With Myalgic Encephalomyelitis/Chronic Fatigue Syndrome" frontiers in Neurology (2020) vol. 11, Article 1025, pp. 1-17.
Su et al., "Multiple Early Factors Anticipate Post-Acute COVID-19 Sequelae" Cell (2022) vol. 185, pp. 881-895.
Sullivan et al., "The COVIDome Explorer researcher portal" Cell Reports (2021) vol. 36, Article 109527, pp. 1-21.
Sun et al., "Skeletal Muscle and Bone—Emerging Targets of Fibroblast Growth Factor-21" fronteirs in Physiology (2021) vol. 12, Article 625287, pp. 1-14.
Tedesco et al., "A Special Amino-Acid Formula Tailored to Boosting Cell Respiration Prevents Mitochondrial Dysfunction and Oxidative Stress Caused by Doxorubicin in Mouse Cardiomyocytes" Nutrients (2020) vol. 12, No. 282, pp. 1-20.
Thompson et al., "Metabolic Programs Define Dysfunctional Immune Responses in Severe COVID-19 Patients" Cell Reports (2021) vol. 34, No. 11, pp. 1-30.
Tomé, "Amino acid metabolism and signaling pathways: potential targets in the control of infection and immunity" European Journal of Clinical Nurtirion (2021) pp. 4-9.
Tyrrell et al., "Blood-Cell Bioenergetics are Associated With Physical Function and Inflammation in Overweight/Obese Older Adults" Exp Gerontol (2015) vol. 70, pp. 84-91.
Valero, "Mitochondrial Biogenesis: Pharmacological Approaches" Current Pharmaceutical Design (2014) vol. 20, No. 35, pp. 5507-5509.
Varhaug et al., "Serum Biomarkers in Primary Mitochondiral Disorders" Brain Communications (2021) pp. 1-7.
Vishwanath, "Fatty Acid Beta-Oxidation Disorders: A Brief Review" Annals of Neurosciences (2016) vol. 23, pp. 51-55.
Vockley et al., "Long-Term Major Clinical Outcomes in Patients With Long Chain Fatty Acid Oxidation Disorders Before and After Transition to Triheptanoin Treatment—A Retrospective Chart Review" Mol Genet Metab (2015) vol. 116, pp. 53-60.
Wang et al., "Serum nitrite and nitrate: A potential biomarker for post-covid-19 complications?" Free Radical Biology & Medicine (2021) vol. 175, pp. 216.
Wood et al., "Role of mitochondria, oxidative stress and the response toantioxidants in myalgic encephalomyelitis/chronic fatigue

(56) References Cited

OTHER PUBLICATIONS syndrome: A possible approach to SARS-CoV-2 'long-haulers'?" KeAi Chronic Diseases and Translational Medicine (2021) vol. 7, pp. 14-26.
Wu et al., "The SARS-CoV-2 induced targeted amino acid profiling in patients at hospitalized and convalescentstage" Portland Press Bioscience Reports (2021) vol. 41, No. 3, pp. 1-11.
Xiao et al., "Integrated cytokine and metabolite analysis reveals immunometabolic reprogramming in COVID-19 patients with therapeutic implications" Nature Communications (2021) pp. 1-13.
Yan et al., "The Roles and Pharmacological Effects of FGF21 in Preventing Aging-Associated Metabolic Diseases" frontiers in Cadiovascular Medicine (2021) vol. 8, Article 655575, pp. 1-11.
Brosnan et al., "Branched-Chain Amino Acids: Metabolism, Physiological Function and Application". The Journal of Nutrition (2006) vol. 136, pp. 207S-211S.
Castro-Marrero et al., "Does oral coenzyme Q10 plus NADH supplementation improve fatigue and biochemical parameters in chronic fatigue syndrome?" Antioxidants & redox signaling (2015) vol. 22, No. 8, pp. 679-685.
Castro-Marrero et al., "Effect of coenzyme Q10 plus nicotinamide adenine dinucleotide supplementation on maximum heart rate after exercise testing in chronic fatigue syndrome—A randomized, controlled, double-blind trial" Clinical Nutrition (2006) vol. 35, No. 4, pp. 826-834.
Chakravarthy et al., "Mechanistic insights into the multimodal effects of AXA1125 in T2D subjects with NAFLD" Hepatology (2019) vol. 70, S1, pp. 1264A.
Chistiakov et al., "Mitochondrial aging and age-related dysfunction of mitochondria" BioMed research international (2014) pp. 238463.
Codo et al., "Elevated Glucose Levels Favor SARS-CoV-2 Infection and Monocyte Response through a HIF-1α/Glycolysis-Dependent Axis". Cell metabolism (2020) vol. 32, No. 3, pp. 437-446.
Cortese-Krott et al., "The Reactive Species Interactome: Evolutionary Emergence, Biological Significance, and Opportunities for Redox Metabolomics and Personalized Medicine" Antioxidants & redox signaling (2017) vol. 27, No. 10, pp. 684-712.
D'Antona et al., "Branched-chain amino acid supplementation promotes survival and supports cardiac and skeletal muscle mitochondrial biogenesis in middle-aged mice" Cell Metab (2010) vol. 12, No. 4, pp. 362-372.
Daye et al., "Metabolic reprogramming in cancer: unraveling the role of glutamine in tumorigenesis" Semin Cell Dev Biol (2012) vol. 23, No. 4, pp. 362-369.
Delgado-Roche et al., "Oxidative Stress as Key Player in Severe Acute Respiratory Syndrome Coronavirus (SARS-CoV) Infection" Archives of medical research (2020) vol. 51, No. 5, pp. 384-387.
El-Hattab et al., "Therapies for mitochondrial diseases and current clinical trials" Molecular genetics and metabolism (2017) vol. 122, No. 3, pp. 1-9.
Garone et al., "Towards a therapy for mitochondrial disease: an update". Biochemical Society transactions (2018) vol. 46, No. 5, pp. 1247-1261.
Guo et al., "Oxidative stress, mitochondrial damage and neurodegenerative diseases" Neural regeneration research (2013) vol. 8, No. 21, pp. 2003-2014.
Harrison et al., "Safety, Tolerability, and Biologic Activity of AXA1125 and AXA1957 in Subjects With Nonalcoholic Fatty Liver Disease" Am J Gastroenterol (2021) vol. 116, pp. 2399-2409.
Hirano et al., "Emerging therapies for mitochondrial diseases" Essays in biochemistry (2018) vol. 62, No. 3, pp. 467-481.
Hubens et al., "Blood biomarkers for assessment of mitochondrial dysfunction: An expert review" Mitochondrion (2022) vol. 62, pp. 187-204.
Kemp et al., "Quantification of skeletal muscle mitochondrial function by 31P magnetic resonance spectroscopy techniques: a quantitative review" Acta Physiol (2014) vol. 213, pp. 107-144.
Krishman et al., "Metabolic Perturbation Associated With COVID-19 Disease Severity and SARS-CoV-2 Replication" Molecular & cellular proteomics: MCP (2021) vol. 20, 100159.

Lee, "AXA1125, a novel designed amino acid composition (DAACTM), improves NAFLD Activity Score (NAS) and reduces fibrosis in two rodent models of nonalcoholic steatohepatitis (NASH)" Poster presented at European Association for the Study of the Liver NAFLD Summit (2017).
Lin et al., "Mitochondrial dysfunction and oxidative stress in neurodegenerative diseases" Nature (2006) vol. 443, pp. 787-795.
Marukian, "Unique composition of endogenous metabolic modulators reprograms metabolic state and impacts markers of inflammation and fibrosis in NAFLD/NASH cell model systems". Abstract #2015. Oral presentation presented at the Keystone Symposia (2019).
Missailidis et al., "An Isolated Complex V Inefficiency and Dysregulated Mitochondrial Function in Immortalized Lymphocytes from ME/CFS Patients" International journal of molecular sciences (2020) vol. 21, No. 3, 1074.
Moncada et al., "The discovery of nitric oxide and its role in vascular biology". British journal of pharmacology (2006) vol. 147, Suppl 1, S193-S201.
Montoya et al., "KPAX002 as a treatment for myalgic encephalomyelitis/chronic fatigue syndrome (ME/CFS): a prospective, randomized trial" International Journal of Clinical and Experimental Medicine (2018) vol. 11, pp. 2890-2900.
Morris et al., "Acquired Amino Acid Deficiencies: A Focus on Arginine and Glutamine" Nutrition in Clinical Practice (2017) vol. 32, pp. 30S-47S.
Morris et al., "Mitochondrial dysfunctions in Myalgic Encephalomyelitis / chronic fatigue syndrome explained by activated immuno-inflammatory, oxidative and nitrosative stress pathways" Metabolic Brain Disease (2014) vol. 29, pp. 19-36.
Morris et al., "Arginases and arginine deficiency syndromes" Current opinion in clinical nutrition and metabolic care (2012) vol. 15, No. 1, pp. 64-70.
Morris et al., "Arginine metabolism in vascular biology and disease" Vascular Medicine (2005) vol. 10, pp. S83-S87.
Myhill et al., "Targeting mitochondrial dysfunction in the treatment of Myalgic Encephalomyelitis/Chronic Fatigue Syndrome (ME/CFS)—a clinical audit" International journal of clinical and experimental medicine (2013) vol. 6, No. 1, pp. 1-15.
Naviaux et al., "Metabolic features and regulation of the healing cycle—A new model for chronic disease pathogenesis and treatment". Mitochondrion (2019) vol. 46, pp. 278-297.
Naviaux et al., "Metabolic features of chronic fatigue syndrome" Proceedings of the National Academy of Sciences of the United States of America (2016) vol. 113, No. 37, pp. E5472-E5480.
Palacios-Callender et al., "Endogenous NO regulates superoxide production at low oxygen concentrations by modifying the redox state of cytochrome c oxidase" Proceedings of the National Academy of Sciences of the United States of America (2004) vol. 101, No. 20, pp. 7630-7635.
Pedre et al., T"he mechanism of action of N-acetylcysteine (NAC): The emerging role of H2S and sulfane sulfur species" Pharmacol Ther (2021).
Poe et al., "N-Acetylcysteine: A potential therapeutic agent for SARS-CoV-2" Medical hypotheses (2020) vol. 143, 109862.
Schulz et al., "Mitochondrial redox signaling: Interaction of mitochondrial reactive oxygen species with other sources of oxidative stress" Antioxidants & redox signaling (2014) vol. 20, No. 2, pp. 308-324.
Shi et al., "N-Acetylcysteine to Combat COVID-19: An Evidence Review" Therapeutics and clinical risk management (2020) vol. 16, pp. 1047-1055.
Tomas et al., "Cellular bioenergetics is impaired in patients with chronic fatigue syndrome" PloS One (2017) vol. 12, pp. 1-16.
Tong et al., "The molecular determinants of de novo nucleotide biosynthesis in cancer cells" Current opinion in genetics & development (2009) vol. 19, No. 1, pp. 32-37.
Tzameli et al., "The evolving role of mitochondria in metabolism" Trends in Endocrinology and Metabolism (2012) vol. 23, No. 9, pp. 417-419.
Wolfe et al., "Branched-chain amino acids and muscle protein synthesis in humans: myth or reality?" J Int Soc Sports Nutr (2017) vol. 14, 30.

(56) References Cited

OTHER PUBLICATIONS

Wright et al., "N-Acetylcysteine improves mitochondrial function and ameliorates behavioral deficits in the R6/1 mouse model of Huntington's disease". Translational Psychiatry (2015).

* cited by examiner

AMINO ACID COMPOSITIONS AND METHODS FOR THE TREATMENT OF POST-ACUTE SEQUELAE OF COVID-19

This application claims priority to U.S. Ser. No. 63/225,850 filed Jul. 26, 2021, and U.S. Ser. No. 63/271,665 filed Oct. 25, 2021, the contents of all of which are incorporated herein by reference in their entireties.

BACKGROUND

Severe acute respiratory syndrome coronavirus 2 (SARS-CoV-2) is the pathogen responsible for coronavirus disease 2019 (COVID-19). Research to determine the full long-term sequelae of COVID-19 is on-going. However, studies suggest the long-term effects of COVID-19 are manifest in multiple systems, including pulmonary, cerebrovascular, musculoskeletal, neurocognitive and sensory, and cardiovascular systems; and may be driven by aberrant metabolic or inflammatory responses. As more patients recover from COVID-19, new methods of treating the diverse effects of the disease are needed.

SUMMARY

Disclosed herein, at least in part, are methods of treating chronic fatigue, e.g., chronic fatigue that results from a post-acute sequelae of a viral disease, such as post-acute sequelae of COVID-19 (PASC), also known as long COVID, or chronic fatigue that results from myalgic encephalomyelitis/chronic fatigue syndrome [or fibromyalgia]. In some embodiments, the method of treatment comprises administration of a composition including at least four different amino acid entities.

In one aspect, the disclosure provides a method of treating a subject having post-acute sequelae of COVID-19 comprising administering to a subject (e.g., administering to the subject a composition comprising):
 a) a leucine (L)-amino acid entity;
 b) an arginine (R)-amino acid entity;
 c) a glutamine (Q)-amino acid entity; and
 d) a N-acetylcysteine (NAC) entity, e.g., NAC.

In some embodiments, the subject has one or more symptoms or signs selected from the group consisting of anorexia, anxiety, arrhythmias, confusion ("brain fog"), dementia, depression, dyspnea, fatigue, hair loss, headache, heart failure, cardiomyopathy, angina, hepatic dysfunction, hyperglycemia, type 2 diabetes, increased heart rate, inflammation, loss of appetite, loss of memory, loss of smell, mood disorder, muscle weakness, myocardial ischemia, post-exertional malaise, diminished neurocognition, diminished sensory function, pulmonary infiltrates or fibrosis, postural orthostatic hypotension, renal dysfunction, and respiratory distress.

In certain embodiments, the subject has one or more symptoms or signs selected from the group consisting of myalgia, fibromyalgia, idiopathic pulmonary fibrosis, fatigue, muscle fatigue, mitochondrial dysfunction, dyspnea after exertion, postural orthostatic tachycardia syndrome, tachycardia, mood disorders, and depression.

In one aspect, the disclosure provides a method for treating one or more symptoms or signs selected from the group consisting of anorexia, anxiety, arrhythmias, confusion ("brain fog"), dementia, depression, dyspnea, fatigue, hair loss, headache, heart failure, cardiomyopathy, angina, increased heart rate, loss of appetite, loss of memory, loss of smell, mood disorder, myocardial ischemia, post-exertional malaise, diminished neurocognition, diminished sensory function, pulmonary infiltrates or fibrosis, postural orthostatic hypotension, renal dysfunction, and respiratory distress, wherein the method comprises administering to a subject (e.g., administering to the subject a composition comprising) an effective amount of:
 a) a leucine (L)-amino acid entity;
 b) an arginine (R)-amino acid entity;
 c) a glutamine (Q)-amino acid entity; and
 d) a N-acetylcysteine (NAC) entity, e.g., NAC.

In one aspect, the disclosure provides a method for treating one or more symptoms or signs selected from the group consisting of myalgia, fibromyalgia, idiopathic pulmonary fibrosis, fatigue, muscle fatigue, muscle dysfunction, mitochondrial dysfunction, dyspnea after exertion, postural orthostatic tachycardia syndrome, tachycardia, mood disorders, and depression, wherein the method comprises administering to a subject (e.g., administering to the subject a composition comprising) an effective amount of:
 a) a leucine (L)-amino acid entity;
 b) an arginine (R)-amino acid entity;
 c) a glutamine (Q)-amino acid entity; and
 d) a N-acetylcysteine (NAC) entity, e.g., NAC.

In some embodiments, the fatigue comprises one or both of persistent fatigue and exertional fatigue. In certain embodiments, the fatigue comprises one or both of mental fatigue and physical fatigue. In some embodiments, the subject had a COVID-19 infection and is experiencing fatigue. In certain embodiments, the subject experiences fatigue at at least 4, 8, 12, or 16 weeks after infection with SARS-Cov-2. In some embodiments, the subject experiences fatigue at less than 4 weeks (e.g., less than 3, less than 2, or less than 1 week) after infection with SARS-Cov-2.

In one aspect, the disclosure provides a method of treating myalgia, wherein the method comprises administering to a subject (e.g., administering to the subject a composition comprising) an effective amount of:
 a) a leucine (L)-amino acid entity;
 b) an arginine (R)-amino acid entity;
 c) a glutamine (Q)-amino acid entity; and
 d) a N-acetylcysteine (NAC) entity, e.g., NAC.

In one aspect, the disclosure provides a method of treating idiopathic pulmonary fibrosis (IPF), wherein the method comprises administering to a subject (e.g., administering to the subject a composition comprising) an effective amount of:
 a) a leucine (L)-amino acid entity;
 b) an arginine (R)-amino acid entity;
 c) a glutamine (Q)-amino acid entity; and
 d) a N-acetylcysteine (NAC) entity, e.g., NAC.

In one aspect, the disclosure provides a method of treating fatigue and/or muscle fatigue, wherein the method comprises administering to a subject (e.g., administering to the subject a composition comprising) an effective amount of:
 a) a leucine (L)-amino acid entity;
 b) an arginine (R)-amino acid entity;
 c) a glutamine (Q)-amino acid entity; and
 d) a N-acetylcysteine (NAC) entity, e.g., NAC.

In one aspect, the disclosure provides a method of treating mitochondrial dysfunction, wherein the method comprises administering to a subject (e.g., administering to the subject a composition comprising) an effective amount of:
 a) a leucine (L)-amino acid entity;
 b) an arginine (R)-amino acid entity;
 c) a glutamine (Q)-amino acid entity; and
 d) a N-acetylcysteine (NAC) entity, e.g., NAC.

In one aspect, the disclosure provides a method of treating dyspnea after exertion, wherein the method comprises administering to a subject (e.g., administering to the subject a composition comprising) an effective amount of:
 a) a leucine (L)-amino acid entity;
 b) an arginine (R)-amino acid entity;
 c) a glutamine (Q)-amino acid entity; and
 d) a N-acetylcysteine (NAC) entity, e.g., NAC.

In one aspect, the disclosure provides a method of treating confusion, wherein the method comprises administering to a subject (e.g., administering to the subject a composition comprising) an effective amount of:
 a) a leucine (L)-amino acid entity;
 b) an arginine (R)-amino acid entity;
 c) a glutamine (Q)-amino acid entity; and
 d) a N-acetylcysteine (NAC) entity, e.g., NAC.

In some aspects, the disclosure provides a method of treating a subject having post-acute sequelae of COVID-19 (PASC) comprising administering to the subject:
 a) a leucine (L)-amino acid entity chosen from L-leucine, β-hydroxy-β-methylbutyrate (HIMB), oxo-leucine, isovaleryl-CoA, and N-acetyl-leucine; or a salt thereof, a dipeptide or salt thereof, a tripeptide or salt thereof, or a combination of any of the aforesaid;
 b) an arginine (R)-amino acid entity chosen from L-arginine, ornithine, argininosuccinate, agmatine, creatine, and N-acetyl-arginine; or a salt thereof, a dipeptide or salt thereof, a tripeptide or salt thereof, or a combination of any of the aforesaid;
 c) a glutamine (Q)-amino acid entity chosen from L-glutamine, carbamoyl-P, and N-acetyl-glutamine; or a salt thereof, a dipeptide or salt thereof, a tripeptide or salt thereof, or a combination of any of the aforesaid; and
 d) a N-acetylcysteine (NAC) entity chosen from N-acetylcysteine (NAC) or a salt thereof, a dipeptide or salt thereof, a tripeptide or salt thereof, or a combination of any of the aforesaid.

In some aspects, the disclosure provides a method of treating fatigue, wherein the method comprises administering to a subject an effective amount of:
 a) a leucine (L)-amino acid entity chosen from L-leucine, β-hydroxy-β-methylbutyrate (IMB), oxo-leucine, isovaleryl-CoA, and N-acetyl-leucine; or a salt thereof, a dipeptide or salt thereof, a tripeptide or salt thereof, or a combination of any of the aforesaid;
 b) an arginine (R)-amino acid entity chosen from L-arginine, ornithine, argininosuccinate, agmatine, creatine, and N-acetyl-arginine; or a salt thereof, a dipeptide or salt thereof, a tripeptide or salt thereof, or a combination of any of the aforesaid;
 c) a glutamine (Q)-amino acid entity chosen from L-glutamine, carbamoyl-P, and N-acetyl-glutamine; or a salt thereof, a dipeptide or salt thereof, a tripeptide or salt thereof, or a combination of any of the aforesaid; and
 d) a N-acetylcysteine (NAC) entity chosen from N-acetylcysteine (NAC) or a salt thereof, a dipeptide or salt thereof, a tripeptide or salt thereof, or a combination of any of the aforesaid.

In some aspects, the disclosure provides a method of treating one or more symptoms or signs selected from the group consisting of dyspnea, arrhythmias, confusion, dementia, depression, hair loss, headache, heart failure, cardiomyopathy, angina increased heart rate, loss of appetite, loss of memory, loss of smell, mood disorder, myocardial ischemia, post-exertional malaise, diminished neurocognition, diminished sensory function, pulmonary infiltrates, postural orthostatic hypotension, renal dysfunction, and respiratory distress wherein the method comprises administering to a subject an effective amount of:
 a) a leucine (L)-amino acid entity chosen from L-leucine, β-hydroxy-β-methylbutyrate (IMB), oxo-leucine, isovaleryl-CoA, and N-acetyl-leucine; or a salt thereof, a dipeptide or salt thereof, a tripeptide or salt thereof, or a combination of any of the aforesaid;
 b) an arginine (R)-amino acid entity chosen from L-arginine, ornithine, argininosuccinate, agmatine, creatine, and N-acetyl-arginine; or a salt thereof, a dipeptide or salt thereof, a tripeptide or salt thereof, or a combination of any of the aforesaid;
 c) a glutamine (Q)-amino acid entity chosen from L-glutamine, carbamoyl-P, and N-acetyl-glutamine; or a salt thereof, a dipeptide or salt thereof, a tripeptide or salt thereof, or a combination of any of the aforesaid; and
 d) a N-acetylcysteine (NAC) entity chosen from N-acetylcysteine (NAC) or a salt thereof, a dipeptide or salt thereof, a tripeptide or salt thereof, or a combination of any of the aforesaid.

In some aspects, the disclosure provides a composition comprising:
 a) a leucine (L)-amino acid entity chosen from L-leucine, β-hydroxy-β-methylbutyrate (IEMB), oxo-leucine, isovaleryl-CoA, and N-acetyl-leucine; or a salt thereof, a dipeptide or salt thereof, a tripeptide or salt thereof, or a combination of any of the aforesaid;
 b) an arginine (R)-amino acid entity chosen from L-arginine, ornithine, argininosuccinate, agmatine, creatine, and N-acetyl-arginine; or a salt thereof, a dipeptide or salt thereof, a tripeptide or salt thereof, or a combination of any of the aforesaid;
 c) a glutamine (Q)-amino acid entity chosen from L-glutamine, carbamoyl-P, and N-acetyl-glutamine; or a salt thereof, a dipeptide or salt thereof, a tripeptide or salt thereof, or a combination of any of the aforesaid; and
 d) a N-acetylcysteine (NAC) entity chosen from N-acetylcysteine (NAC) or a salt thereof, a dipeptide or salt thereof, a tripeptide or salt thereof, or a combination of any of the aforesaid; and
 ethylenediaminetetraacetic acid (EDTA) or a salt thereof.

In certain embodiments, the subject experiences fatigue. In some embodiments, the fatigue comprises one or both of persistent fatigue and exertional fatigue. In certain embodiments, the fatigue comprises one or both of mental fatigue and physical fatigue. In certain embodiments, the subject experiences fatigue at at least 4 weeks after infection with SARS-Cov-2.

In some embodiments, the subject has one or more symptoms or signs selected from the group consisting of fatigue, myalgia, fibromyalgia, myalgic encephalomyelitis/chronic fatigue syndrome (ME/CFS), idiopathic pulmonary fibrosis, confusion, muscle dysfunction, mitochondrial dysfunction, dyspnea after exertion, postural orthostatic tachycardia syndrome, tachycardia, mood disorders, and depression.

In certain embodiments, prior to administration of (a)-(d) the subject has a score of greater than or equal to 8 on a CFQ-11 test using bimodal scoring. In some embodiments, after administration of (a)-(d) the subject has a decrease of at least 1 point on a CFQ-11 test using bimodal scoring, relative to the subject's score before administration. In some embodiments, prior to administration the subject has a score of greater than or equal to 25 on a CFQ-11 test using Likert scoring. In some embodiments, after administration (e.g., 4 weeks after start of administration) the subject has a decrease of at least 1 points on a CFQ-11 test using Likert scoring, relative to score before administration.

In certain embodiments, administration of (a)-(d) results in an increase in MOTS-c levels in the subject. In some embodiments, administration of (a)-(d) results in a decrease in bicarbonate levels or sVCAM-1 levels in the subject.

In certain embodiments, the method comprises administering a composition comprising (a)-(d) to the subject. In some embodiments, (a)-(d) are administered to the subject twice per day (BID) for at least 4 weeks. In some embodiments, at least one of (a)-(d) is a free amino acid. In certain embodiments, at least 50 wt. % of the total wt. of components administered to the subject is one or more amino acid entities in free form. In some embodiments, the total wt. % of (a)-(d) is greater than the total wt. % of other amino acid entities in the composition. In certain embodiments, at least one of (a)-(d) is in a salt form. In some embodiments, one, two, three, or more of methionine (M), tryptophan (W), or cysteine (C) is absent, or if present, is present at less than 10 weight (wt.) %. In certain embodiments, a wt. ratio of the L-amino acid entity, the R-amino acid entity, the Q-amino acid entity, and the NAC entity administered to the subject is 0.5 to 3:0.5 to 4:1 to 4:0.1 to 2.5.

In certain embodiments, the method further comprises administering one or both of:
(e) an isoleucine (I)-amino acid-entity chosen from L-isoleucine, 2-oxo-3-methyl-valerate, methylbutyryl-CoA, and N-acetyl-isoleucine; or a salt thereof, a dipeptide or salt thereof, a tripeptide or salt thereof, or a combination of any of the aforesaid; and
(f) a valine (V)-amino acid-entity chosen from L-valine, 2-oxo-valerate, isobutyryl-CoA, 3-HIB-CoA, 3-HIB, and N-acetyl-valine; or a salt thereof, a dipeptide or salt thereof, a tripeptide or salt thereof, or a combination of any of the aforesaid. In certain embodiments, the wt. ratio of the L-amino acid entity, the I-amino acid entity, the V-amino acid entity, the R-amino acid entity, the Q-amino acid entity, and the NAC entity administered is 0.5 to 2:0.1 to 1:0.1 to 1:0.5 to 3:0.5 to 4:0.1 to 0.5.

In certain embodiments, 25-40 g of the composition is administered to the subject BID, wherein weight includes amino acid entities and NAC entity but does not include excipients.

In some embodiments, the composition comprises one or more excipients selected from the group consisting of citric acid, lecithin, a sweetener, a dispersion enhancer, a flavoring, a bitterness masking agent, a chelating agent, and a natural or artificial coloring.

In some aspects, the disclosure provides a method of treating myalgic encephalomyelitis/chronic fatigue syndrome (ME/CFS), wherein the method comprises administering to a subject (e.g., administering to the subject a composition comprising) an effective amount of:
 a) a leucine (L)-amino acid entity;
 b) an arginine (R)-amino acid entity;
 c) a glutamine (Q)-amino acid entity; and
 d) a N-acetylcysteine (NAC) entity, e.g., NAC.

In some aspects, the present disclosure provides a composition comprising:
 a) a leucine (L)-amino acid entity;
 b) an arginine (R)-amino acid entity;
 c) a glutamine (Q)-amino acid entity;
 d) a N-acetylcysteine (NAC) entity, e.g., NAC; and
 e) a chelating agent, e.g., ethylenediaminetetraacetic acid (EDTA) or a salt thereof (e.g., disodium EDTA).

In certain embodiments, the chelating agent comprises EDTA or a salt thereof (e.g., disodium EDTA). In certain embodiments, the ratio of NAC entity to chelating agent is 3±20%:1±20%. In some embodiments, the chelating agent (e.g., EDTA or a salt thereof, e.g., disodium EDTA) is between about 0.1 to 1.00% (e.g., between about 0.1 to 0.3, 0.3 to 0.5, 0.5 to 0.7, 0.7 to 0.9, or 0.9 to 1.00%) of the composition.

In some embodiments, prior to administration of (a)-(d) the subject has a score of greater than or equal to 4, 5, 6, 7, 8, 9, or 10 on a CFQ-11 test using bimodal scoring.

In some embodiments, a subject is evaluated for indicia of fatigue by one or more (e.g., one, two, three, four, five, six, seven, eight, nine, ten, eleven, twelve, thirteen, or all) of the CFQ-11 test, PROMIS Fatigue Short Form 7a (PROMIS F-SF), the Multidimensional Fatigue Symptom Inventory-Short Form (MFSI-SF), the Brief Fatigue Inventory (BFI), the Functional Assessment of Chronic Illness Therapy (FACIT) measurement system, the 16-item Multidimensional Assessment of Fatigue (MAF) Scale, the Vitality Scale from the Medical Outcomes Study Short-Form 36 (SF-36), Visual Analog Scale (VAS) Fatigue Scale, Fatigue Severity Scale (FSS), the Fatigue Impact Scale, the PFRS fatigue scale, the MFTQ Energy Scale, and the MFTQ Brain Fog Scale. In some embodiments, the subject is evaluated for indicia of fatigue prior to administration of (a)-(d). In some embodiments, the subject is evaluated for indicia of fatigue after administration of (a)-(d). In some embodiments, upon administration of (a)-(d), the subject shows a reduction in fatigue using one or more of the scales listed herein, e.g., change from moderate or severe fatigue to mild fatigue, or change from mild fatigue to absence of fatigue.

In some embodiments, prior to administration of (a)-(d) the subject has indicia of fatigue. Such a diagnosis may be based on patient responses to questions or a questionnaire such as the Chronic Fatigue Questionnare (CFQ)-11 using either bimodal or Linkert scoring or the PROMIS Fatigue Short Form 7a (PROMIS F-SF), or both. Generally patients suffering from fatigue will have significantly more answers indicating fatigue than normal subjects. In particular, such a subjection will have been identified as having a score, or has received a score (e.g., a score from a test evaluating fatigue) indicative of fatigue.

In some embodiments, after administration of (a)-(d) (e.g., 4 weeks after start of administration) the subject has a decrease in indicia of fatigue, e.g., a decrease of at least 1, 2, 3, or 4 points on a CFQ-11 test using bimodal scoring, relative to score before administration.

In certain embodiments, prior to administration of (a)-(d) the subject has a score of greater than or equal to 25, 26, or 27 on a CFQ-11 test using Likert scoring.

In some embodiments, after administration of (a)-(d) (e.g., 4 weeks after start of administration) the subject has a decrease of at least 1, 2, 3, 4, 5, 6, or 7 points on a CFQ-11 test using Likert scoring, relative to score before administration, or the equivalent improvement on another indicia of fatigue.

In certain embodiments, after administration of (a)-(d) (e.g., 4 weeks after start of administration) the subject shows a reduction in one or both of physical fatigue or mental fatigue, e.g., on a CFQ-11 test using Likert scoring, relative to score before administration.

In certain embodiments, after administration of (a)-(d) (e.g., 4 weeks after start of administration) the subject shows a change from mild fatigue to absence of fatigue, e.g., on a CFQ-11 test using Likert scoring.

In some embodiments, after administration of (a)-(d) (e.g., 4 weeks after start of administration) the subject shows a change from mild physical fatigue to absence of physical fatigue on a CFQ-11 test.

In certain embodiments, after administration of (a)-(d) (e.g., 4 weeks after start of administration) the subject shows a change from mild mental fatigue to absence of mental fatigue, e.g., on a CFQ-11 test.

In some embodiments, the reduction is at least 1, 2, 3, 4, or 5 points on a CFQ-11 test using Linkert scoring.

In some embodiments, after administration of (a)-(d) (e.g., 4 weeks after start of administration) the subject shows a change from moderate or severe fatigue to mild fatigue, e.g. on a CFQ-11 test.

In some embodiments, after administration of (a)-(d) (e.g., 4 weeks after start of administration) the subject shows a change from moderate or severe fatigue to mild fatigue, e.g. on a CFQ-11 or a PROMIS Fatigue Short Form 7a (PROMIS F-SF) test, or both.

In some embodiments, after administration of (a)-(d) (e.g., 4 weeks after start of administration) the subject shows a change from moderate or severe physical fatigue to mild physical fatigue, e.g., on a CFQ-11 or a PROMIS Fatigue Short Form 7a (PROMIS F-SF) test, or both.

In certain embodiments, after administration of (a)-(d) (e.g., 4 weeks after start of administration) the subject shows a change from moderate or severe mental fatigue to mild mental fatigue, e.g., on a CFQ-11 or a PROMIS Fatigue Short Form 7a (PROMIS F-SF) test, or both.

In certain embodiments, after administration of (a)-(d) (e.g., 4 weeks after start of administration) the subject shows a change from mild fatigue to absence of fatigue on a CFQ-11 test or a PROMIS Fatigue Short Form 7a (PROMIS F-SF) test, or both.

In certain embodiments, after administration of (a)-(d) (e.g., 4 weeks after start of administration) the subject shows a change from mild physical fatigue to absence of physical fatigue on a CFQ-11 test or a PROMIS Fatigue Short Form 7a (PROMIS F-SF) test, or both.

In certain embodiments, after administration of (a)-(d) (e.g., 4 weeks after start of administration) the subject shows a change from mild mental fatigue to absence of mental fatigue on a CFQ-11 test or a PROMIS Fatigue Short Form 7a (PROMIS F-SF) test, or both.

In certain embodiments, administration of (a)-(d) results in a decrease in oxidative stress in skeletal muscle, e.g., by at least about 5%, 10%, 50%, 90%, or 99%, e.g., as measured using a CELLROX green assay.

In some embodiments, administration of (a)-(d) results in a modulation (e.g., an increase or a decrease) in the level of an adhesion factor (e.g., vWF, ICAM, PECAM, E-selectin, or P-selectin). In some embodiments, administration of (a)-(d) results in a modulation (e.g., an increase or a decrease) in the level of a clotting factor (e.g., tissue factor, thrombomodulin, P-selectin, or fibrinogen).

In some embodiments, administration of (a)-(d) results in a reduction of vWF protein level in endothelial cells, e.g., a reduction of at least about 5%, 10%, 50%, 80%, 90% or 99%. In certain embodiments, administration of (a)-(d) results in an decrease in one or both of VEGF protein level and PDGF-aa protein level in endothelial cells, e.g., a decrease of at least at least 5%, 10%, 50%, 80%, 90%, or 99%.

In some embodiments, administration of (a)-(d) results in a decrease in one, two, three, four, five, or all of VEGF protein level, PDGF-aa protein level, PDGF-AB protein level, PDGF-BB protein level, VCAM-1, or bicarbonate levels (wherein optionally bicarbonate level is used to estimate $CO_2$ levels). In some embodiments, the decrease in one, two, three, four, five, or all of VEGF protein level, PDGF-aa protein level, PDGF-AB protein level, PDGF-BB protein level, VCAM-1, or bicarbonate levels (wherein optionally bicarbonate level is used to estimate $CO_2$ levels), is a decrease compared to a sample from the subject, e.g., a sample from the subject prior to administration of (a)-(d).

In some embodiments, administration of (a)-(d) results in a decrease in one, two, three or all of VEGF protein level and PDGF-aa protein level, PDGF-AB protein level and PDGF-BB protein level, VCAM-1 and bicarbonate (itself or as a measure of $CO_2$) levels.

In some embodiments, administration of (a)-(d) results in a decrease in bicarbonate levels in the blood. In certain embodiments, administration of (a)-(d) results in a shift in metabolic fuel source from glucose to lipids in muscle. In some embodiments, administration of (a)-(d) results in improvement in endothelial health. In certain embodiments, administration of (a)-(d) results in improvement in gas exchange in the pulmonary microvasculature.

In some embodiments, administration of (a)-(d) results in an increase in MOTS-c levels.

In some embodiments, administration of (a)-(d) results in a decrease in bicarbonate levels.

In some embodiments, administration of (a)-(d) results in a reduction in endothelial inflammatory cytokine level in, or secreted from, cells. In some embodiments, administration of (a)-(d) results in a decrease in one or both of IFNγ and CCL20. In certain embodiments, administration of (a)-(d) results in a reduction in one or more pro-inflammatory cytokines (e.g., IL-8, IL-15, or TNF-α) in or secreted by cells (e.g., endothelial cells). In some embodiments, administration of (a)-(d) results in an increase in an anti-inflammatory cytokine (e.g., IL-11) in or secreted by cells (e.g., endothelial cells).

In certain embodiments, prior to administration of (a)-(d) the subject has one or more of the following characteristics:
  i. impaired or delayed immune response;
  ii. increased oxidative stress and/or proinflammatory state; or
  iii. dysregulated endothelial function (e.g., hypercoagulation or perfusion).

In certain embodiments, after administration of (a)-(d), the subject exhibits one or more of the following:
  i. increased mitochondrial biogenesis;
  ii. restored (e.g., partially or fully restored) mitochondrial oxidative capacity;
  iii. restored (e.g., partially or fully restored) cellular respiration and/or cellular energetics;
  iv. improved cellular response under higher metabolic demand conditions (e.g., exertion), e.g., in muscle;
  v. improved mitochondrial respiration (e.g., comprising increased substrate mobilization, increased nitric oxide (NO) signaling, enhanced microvascular or tissue perfusion, enhanced vascular conduction, or increased micro-vascular perfusion);
  vi. reduced inflammation (e.g., reduce liver inflammation), protein breakdown, and muscle fatigue post-exercise;
  vii. normalized (e.g., partially or fully normalized) coagulation function;
  viii. improved mitochondrial energetics and/or redox balance,
  ix. decreased oxidative stress;
  x. improved cellular respiration, antioxidant and/or anti-inflammatory effects, xi. increased nucleotide pool availability;
xii. increased preferential fatty acid oxidation relative to glycolysis;
xiii. increased level of ketone bodies;
xiv. decreased FGF-21
xv. decreased vascular permeability
xvi. decreased fatigue, e.g., from moderate or severe fatigue to mild fatigue; e.g. from mild fatigue to absence of fatigue; from moderate or severe fatigue to absence of fatigue;
xvii. improved sleep, e.g., improved sleep/wake cycle;
xviii. improved mobility;
xix. improved exercise capacity;
xx. improved epithelial cell survival;
xxi. improved T-cell response;
xxii. reduced mitochondrial ROS production;
xxiii. reduced HIF1a signaling;
xxiv. improved oxidative phosphorylation;
xxv. improved executive function; and
xxvi. increased ability to concentrate.

In certain embodiments, the fatigue comprises one or both of persistent fatigue and exertional fatigue. In some embodiments, the fatigue comprises one or both of mental fatigue and physical fatigue.

In certain embodiments, the subject had a COVID-19 infection and is experiencing fatigue.

In certain embodiments, the subject experiences fatigue at at least 4, 8, 12, or 16 weeks after infection with SARS-Cov-2.

In certain embodiments, the subject experiences fatigue at less than 4 weeks (e.g., at less than 3 weeks, 2 weeks, or 1 week) after infection with SARS-Cov-2.

In some embodiments, one or both of the R-amino acid entity and the Q-amino acid entity are present at a higher amount (wt. %) than the L-amino acid entity.

In some embodiments, the amino acid entities administered further comprises a glycine (G)-amino acid entity. In certain embodiments, the amino acid entities administered further comprise one, two, three or more (e.g., all) of a histidine (H)-amino acid entity, a lysine (K)-amino acid entity, a phenylalanine (F)-amino acid entity, and a threonine (T)-amino acid entity.

In some embodiments, the subject has post-acute sequelae of COVID-19.

In certain embodiments, (a)-(d) are administered separately. In some embodiments, (a)-(d) are administered as an admixture. In certain embodiments, (a)-(d) are administered orally. In some embodiments, (a)-(d) are administered prior to a meal. In certain embodiments, (a)-(d) are administered concurrent with a meal. In some embodiments, (a)-(d) are administered following a meal. In certain embodiments, (a)-(d) are administered one, two, or three times per day. In some embodiments, (a)-(d) are administered for at least 1, 2, 3, or 4 weeks. In certain embodiments, (a)-(d) are administered twice per day (BID) for at least 4 weeks (e.g., at least 4, at least 5, at least 6, at least 7, at least 8, at least 9, at least 10, at least 11, at least 12, or more weeks). In some embodiments, (a)-(d) are administered at a dose of about 6-8 g, about 8-12 g, about 12-16 g, about 16-18 g, about 18-20 g, about 20-30 g, about 22-28 g, or about 24-26 g. In certain embodiments, (a)-(d) are in a solution or suspension.

In certain embodiments, the method further comprises contacting (a)-(d) with a liquid (e.g., a beverage, e.g., water), thereby making a solution or suspension.

In some embodiments, (a)-(d) are present in one or more compositions (e.g., one or more stick packs), and the method comprises contacting the one or more compositions with the liquid.

In certain embodiments, not all of (a)-(d) are present in the same composition prior to contacting (a)-(d) with the liquid, e.g., wherein one, two, or three of (a)-(d) are in a first composition, and the remaining one, two, or three of (a)-(d) are in a second composition, and the method comprises contacting the liquid with the first composition and the second composition, e.g., simultaneously or sequentially.

In certain embodiments, the total wt. % of (a)-(d) is greater than the total wt. % of other amino acid entities administered to the subject.

In some embodiments, the composition is capable of one or more of:
a) decreasing or preventing myalgia;
b) decreasing or preventing fibromyalgia;
c) decreasing or preventing idiopathic pulmonary fibrosis;
d) decreasing or preventing fatigue;
e) decreasing or preventing muscle fatigue;
f) decreasing or preventing muscle dysfunction;
g) decreasing or mitochondrial dysfunction;
h) decreasing or preventing dyspnea after exertion;
i) improving exercise tolerance or the ability to conduct activities of daily living;
j) decreasing or preventing postural orthostatic tachycardia syndrome; or
k) decreasing or preventing tachycardia;
l) improving mitochondrial function;
m) improving mitochondrial capacity or energetics (e.g., improvement in oxidative ATP synthesis following exercise or exertion);
n) reducing oxidative stress and/or reducing reactive oxygen species (ROS);
o) improving mood disorders and/or depression;
p) improving cognitive function;
q) increasing skeletal muscle or other organ vascular perfusion;
r) improving endothelial function;
s) decreasing or preventing diabetes (e.g., new onset diabetes); or
t) improving inflammation;
when administered to a subject suffering from CFS or sequelae of a viral infection, e.g., Long COVID.

In some embodiments, the methods and compositions described herein comprise a combination of 4 to 20 different amino acid entities, e.g., a combination of 5 to 15 different amino acid entities. In some embodiments, the composition comprises a leucine (L)-amino acid entity, an arginine (R)-amino acid entity, a glutamine (Q)-amino acid entity; and an antioxidant or reactive oxygen species (ROS) scavenger (e.g., a N-acetylcysteine (NAC) entity, e.g., NAC). In some embodiments, the composition comprises a leucine (L)-amino acid entity, an isoleucine (I)-amino acid entity, a valine (V)-amino acid entity, an arginine (R)-amino acid entity, a glutamine (Q)-amino acid entity; and an antioxidant or reactive oxygen species (ROS) scavenger (e.g., a N-acetylcysteine (NAC) entity, e.g., NAC), or a composition comprising any five of said entities. In some embodiments, the composition comprises an isoleucine (I)-amino acid entity, a valine (V)-amino acid entity, an arginine (R)-amino acid entity, a glutamine (Q)-amino acid entity; and an antioxidant or reactive oxygen species (ROS) scavenger (e.g., a N-acetylcysteine (NAC) entity, e.g., NAC), wherein optionally a leucine (L)-amino acid entity is absent. In some embodiments, the composition comprises a leucine (L)- amino acid entity, an isoleucine (I)-amino acid entity, a valine (V)-amino acid entity, a glutamine (Q)-amino acid entity; and an antioxidant or reactive oxygen species (ROS) scavenger (e.g., a N-acetylcysteine (NAC) entity, e.g., NAC), wherein optionally an arginine (R)-amino acid entity is absent. In some embodiments, the composition comprises a leucine (L)-amino acid entity, an isoleucine (I)-amino acid entity, a valine (V)-amino acid entity, an arginine (R)-amino acid entity, and an antioxidant or reactive oxygen species (ROS) scavenger (e.g., a N-acetylcysteine (NAC) entity, e.g., NAC), wherein optionally a glutamine (Q)-amino acid entity is absent. In some embodiments, the composition comprises a leucine (L)-amino acid entity, an isoleucine (I)-amino acid entity, a valine (V)-amino acid entity, an arginine (R)-amino acid entity, and a glutamine (Q)-amino acid entity, wherein optionally an antioxidant or reactive oxygen species (ROS) scavenger (e.g., a N-acetylcysteine (NAC) entity, e.g., NAC) is absent. In some embodiments, the total wt. % of a leucine (L)-amino acid entity, an arginine (R)-amino acid entity, a glutamine (Q)-amino acid entity; and an antioxidant or reactive oxygen species (ROS) scavenger (e.g., a N-acetylcysteine (NAC) entity, e.g., NAC) in the composition is greater than the total wt. % of any other amino acid in the composition.

In some aspects, the composition comprises a leucine (L)-amino acid entity, an isoleucine (I)-amino acid entity, a valine (V)-amino acid entity, an arginine (R)-amino acid entity, a glutamine (Q)-amino acid entity; and an antioxidant or reactive oxygen species (ROS) scavenger (e.g., a N-acetylcysteine (NAC) entity, e.g., NAC), or a composition comprising any five of said entities. In some aspects, the composition comprises an isoleucine (I)-amino acid entity, a valine (V)-amino acid entity, an arginine (R)-amino acid entity, a glutamine (Q)-amino acid entity; and an antioxidant or reactive oxygen species (ROS) scavenger (e.g., a N-acetylcysteine (NAC) entity, e.g., NAC), wherein optionally a leucine (L)-amino acid entity is absent. In some aspects, the composition comprises a leucine (L)-amino acid entity, an isoleucine (I)-amino acid entity, a valine (V)-amino acid entity, a glutamine (Q)-amino acid entity; and an antioxidant or reactive oxygen species (ROS) scavenger (e.g., a N-acetylcysteine (NAC) entity, e.g., NAC), wherein optionally an arginine (R)-amino acid entity is absent. In some aspects, the composition comprises a leucine (L)-amino acid entity, an isoleucine (I)-amino acid entity, a valine (V)-amino acid entity, an arginine (R)-amino acid entity, and an antioxidant or reactive oxygen species (ROS) scavenger (e.g., a N-acetylcysteine (NAC) entity, e.g., NAC), wherein optionally a glutamine (Q)-amino acid entity is absent. In some aspects, the composition comprises a leucine (L)-amino acid entity, an isoleucine (I)-amino acid entity, a valine (V)-amino acid entity, an arginine (R)-amino acid entity, and a glutamine (Q)-amino acid entity, wherein optionally an antioxidant or reactive oxygen species (ROS) scavenger (e.g., a N-acetylcysteine (NAC) entity, e.g., NAC).

In some embodiments:
(i) an amino acid entity (e.g., at least one, two, or three of the amino acid entities) of (a) is selected from Table 2; and/or
(ii) one or both of the R-amino acid entity and the Q-amino acid entity are present at a higher amount (wt. %) than the L-amino acid entity; and/or
(iii) the composition further comprises a glycine (G)-amino acid entity.

In any of the aspects and embodiments disclosed herein, the wt. ratio of the L-amino acid entity, the R-amino acid entity, the L-glutamine or a salt thereof, and the NAC or salt thereof is about 0.5 to 3:0.5 to 4:1 to 4:0.1 to 2.5, e.g., the wt. ratio of the L-amino acid entity, the R-amino acid entity, the L-glutamine or a salt thereof, and the NAC or salt thereof is about 1:1.5:2:0.15 or about 1:1.5:2:0.3. In certain embodiments, the wt. ratio of the L-amino acid entity, the R-amino acid entity, the L-glutamine or a salt thereof, and the NAC or salt thereof is about 1+/−15%:1.5+/−15%:2+/−15%:0.15+/−15% or about 1+/−15%:1.5+/−15%:2+/−15%:0.3+/−15%. In any of the aforesaid embodiments in this paragraph, the wt. ratio of the L-amino acid entity, the R-amino acid entity, the L-glutamine or a salt thereof, and the NAC or salt thereof is about 1:0.75:2:0.15 or about 1:0.75:2:0.3. In any of the aforesaid embodiments in this paragraph, the wt. ratio of the L-amino acid entity, the R-amino acid entity, the L-glutamine or a salt thereof, and the NAC or salt thereof is about 1+/−15%:0.75+/−15%:2+/−15%:0.15+/−15% or about 1+/−15%:0.75+/−15%:2+/−15%:0.3+/−15%. In certain embodiments, the wt. ratio of the L-amino acid entity, the R-amino acid entity, the L-glutamine or a salt thereof, and the NAC or salt thereof is about 1:1.81:2:0.15. In certain embodiments, the wt. ratio of the L-amino acid entity, the R-amino acid entity, the L-glutamine or a salt thereof, and the NAC or salt thereof is about 1+/−15%:1.81+/−15%:2+/−15%:0.15+/−15%. In certain embodiments, the wt. ratio of the L-amino acid entity, the R-amino acid entity, the L-glutamine or a salt thereof, and the NAC or salt thereof is about 1+/−20%:1.81+/−20%:2+/−20%:0.15+/−20%.

In certain embodiments, the wt. ratio of the L-amino acid entity, the R-amino acid entity, the L-glutamine or a salt thereof, and the NAC or salt thereof is about 1:1.81:1.333:0.15. In certain embodiments, the wt. ratio of the L-amino acid entity, the R-amino acid entity, the L-glutamine or a salt thereof, and the NAC or salt thereof is about 1+/−15%:1.81+/−15%:1.333+/−15%:0.15+/−15%. In certain embodiments, the wt. ratio of the L-amino acid entity, the R-amino acid entity, the L-glutamine or a salt thereof, and the NAC or salt thereof is about 1+/−20%:1.81+/−20%:1.333+/−20%:0.15+/−20%.

In any of the aspects and embodiments disclosed herein, the wt. ratio of the L-amino acid entity, the I-amino acid entity, the V-amino acid entity, the R-amino acid entity, the L-glutamine or salt thereof, and the NAC or salt thereof is about 1:0.5:0.5:1.5:2:0.15 or about 1:0.5:0.5:1.5:2:0.3.

In any of the aspects and embodiments disclosed herein, the composition further comprises one or both of L-glycine and L-serine. In some embodiments, the composition comprises an L-amino acid entity, an I-amino acid entity, a V-amino acid entity, an R-amino acid entity, an L-glutamine or a salt thereof, an NAC or a salt thereof, and an L-glycine. In certain embodiments, the composition comprises an L-amino acid entity, an I-amino acid entity, a V-amino acid entity, an R-amino acid entity, an L-glutamine or a salt thereof, an NAC or a salt thereof, and an L-serine. In certain embodiments, the composition comprises an L-amino acid entity, an I-amino acid entity, an V-amino acid entity, an R-amino acid entity, an L-glutamine or a salt thereof, an NAC or a salt thereof, an L-glycine, and an L-serine. In any of the aforesaid embodiments in this paragraph, the wt. ratio of the L-amino acid entity, the I-amino acid entity, the V-amino acid entity, the R-amino acid entity, the L-glutamine or salt thereof, and the NAC or salt thereof is about 1:0.5:0.5:1.5:2:0.15 or about 1:0.5:0.5:1.5:2:0.3. In any of the aforesaid embodiments in this paragraph, the wt. ratio of the L-amino acid entity, the I-amino acid entity, the V-amino acid entity, the R-amino acid entity, the L-glutamine or salt thereof, and the NAC or salt thereof is about 1+/−15%:0.5+/−15%:0.5+/−15%:1.5+/−15%:2+/−15%:0.15+/−15% or about 1+/−15%:0.5+/−15%:0.5+/−15%:1.5+/−15%: 2+/−15%:0.3+/−15%. In any of the aforesaid embodiments in this paragraph, the wt. ratio of the L-amino acid entity, the I-amino acid entity, the V-amino acid entity, the R-amino acid entity, the L-glutamine or salt thereof, and the NAC or salt thereof is about 1:0.5:0.5:1.81:2:0.15 or about 1:0.5:0.5: 1.81:2:0.3. In any of the aforesaid embodiments in this paragraph, the wt. ratio of the L-amino acid entity, the I-amino acid entity, the V-amino acid entity, the R-amino acid entity, the L-glutamine or salt thereof, and the NAC or salt thereof is about 1+/−15%:0.5+/−15%:0.5+/−15%: 1.81+/−15%:2+/−15%:0.15+/−15% or about 1+/−15%: 0.5+/−15%:0.5+/−15%:1.81+/−15% 2+/−15%:0.3+/−15%. In any of the aforesaid embodiments in this paragraph, the wt. ratio of the L-amino acid entity, the I-amino acid entity, the V-amino acid entity, the R-amino acid entity, the L-glutamine or salt thereof, and the NAC or salt thereof is about 1+/−20%:0.5+/−20%:0.5+/−20%:1.81+/−20%:2+/−20%: 0.15+/−20% or about 1+/−20%:0.5+/−20%:0.5+/−20%: 1.81+/−20%:2+/−20%:0.3+/−20%. In any of the aforesaid embodiments in this paragraph, the wt. ratio of the L-amino acid entity, the I-amino acid entity, the V-amino acid entity, the R-amino acid entity, the L-glutamine or salt thereof, and the NAC or salt thereof is about 1+/−20%:0.5+/−20%: 0.5+/−20%:1.5+/−20%:2+/−20%:0.15+/−20% or about 1+/−20%:0.5+/−20%:0.5+/−20%:1.5+/−20%:2+/−20%: 0.3+/−20%.

In any of the aforesaid embodiments in this paragraph, the wt. ratio of the L-amino acid entity, the I-amino acid entity, the V-amino acid entity, the R-amino acid entity, the L-glutamine or salt thereof, and the NAC or salt thereof is about 1:0.5:0.5:1.81:1.333:0.15 or about 1:0.5:0.5:1.81:1.333:0.3. In any of the aforesaid embodiments in this paragraph, the wt. ratio of the L-amino acid entity, the I-amino acid entity, the V-amino acid entity, the R-amino acid entity, the L-glutamine or salt thereof, and the NAC or salt thereof is about 1+/−15%:0.5+/−15%:0.5+/−15%:1.81+/−15%: 1.333+/−15%:0.15+/−15% or about 1+/−15%:0.5+/−15%: 0.5+/−15%:1.81+/−15%:1.333+/−15%:0.3+/−15%. In any of the aforesaid embodiments in this paragraph, the wt. ratio of the L-amino acid entity, the I-amino acid entity, the V-amino acid entity, the R-amino acid entity, the L-glutamine or salt thereof, and the NAC or salt thereof is about 1+/−20%:0.5+/−20%:0.5+/−20%:1.81+/−20%: 1.333+/−20%:0.15+/−20% or about 1+/−20%:0.5+/−20%: 0.5+/−20%:1.81+/−20%:1.333+/−20%:0.3+/−20%. In any of the aforesaid embodiments in this paragraph, the wt. ratio of the L-amino acid entity, the I-amino acid entity, the V-amino acid entity, the R-amino acid entity, the L-glutamine or salt thereof, and the NAC or salt thereof is about 1+/−20%:0.5+/−20%:0.5+/−20%:1.5+/−20%:1.333+/−20%: 0.15+/−20% or about 1+/−20%:0.5+/−20%:0.5+/−20%: 1.5+/−20%:1.333+/−20%:0.3+/−20%.

In any of the aspects and embodiments disclosed herein, the composition comprises about 0.5 g to about 10 g of the L-amino acid entity, about 0.25 g to about 5 g of the I-amino acid entity, about 0.25 g to about 5 g of the V-amino acid entity, about 0.5 g to about 20 g of the R-amino acid entity, about 1 g to about 20 g of the L-glutamine or a salt thereof, and about 0.1 g to about 5 g of the NAC or a salt thereof, e.g., the composition comprises about 1 g of the L-amino acid entity, about 0.5 g of the I-amino acid entity, about 0.5 g of V-amino acid entity, about 1.5 g of R-amino acid entity, about 2 g of L-glutamine or a salt thereof, and about 0.15 g or about 0.3 g of NAC or a salt thereof. In certain embodiments, the composition comprises about 0.15 g of NAC. In certain embodiments, the composition comprises about 0.3 g of NAC. In certain embodiments, the composition comprises about 4 g of the L-amino acid entity, about 2 g of the I-amino acid entity, about 1 g of V-amino acid entity, about 3 g of R-amino acid entity, about 4 g of L-glutamine or a salt thereof, and about 0.9 g of NAC or a salt thereof. In certain embodiments, the composition comprises about 2 g of the L-amino acid entity, about 1 g of the I-amino acid entity, about 1 g of V-amino acid entity, about 3 g of R-amino acid entity, about 4 g of L-glutamine or a salt thereof, and about 0.3 g of NAC or a salt thereof. In certain embodiments, the composition comprises about 2 g of the L-amino acid entity, about 1 g of the I-amino acid entity, about 1 g of V-amino acid entity, about 3.628 g of R-amino acid entity, about 4 g of L-glutamine or a salt thereof, and about 0.3 g of NAC or a salt thereof. In certain embodiments, the composition comprises about 2 g of the L-amino acid entity, about 1 g of the I-amino acid entity, about 1 g of V-amino acid entity, about 3 g of R-amino acid entity, about 4 g of L-glutamine or a salt thereof, about 0.3 g of NAC or a salt thereof, and about 0.01 g to about 0.2 g of chelating agent (e.g., EDTA or a salt thereof, e.g., disodium EDTA). In certain embodiments, the composition comprises about 2 g of the L-amino acid entity, about 1 g of the I-amino acid entity, about 1 g of V-amino acid entity, about 3 g of R-amino acid entity, about 4 g of L-glutamine or a salt thereof, about 0.3 g of NAC or a salt thereof, and about 0.1 g of chelating agent (e.g., EDTA or a salt thereof, e.g., disodium EDTA). In certain embodiments, the composition comprises about 2 g of the L-amino acid entity, about 1 g of the I-amino acid entity, about 1 g of V-amino acid entity, about 3.628 g of R-amino acid entity, about 4 g of L-glutamine or a salt thereof, about 0.3 g of NAC or a salt thereof, and about 0.1 g of chelating agent (e.g., EDTA or a salt thereof, e.g., disodium EDTA).

In any of the aspects and embodiments disclosed herein, the composition comprises about 4 g of the L-amino acid entity, about 2 g of the I-amino acid entity, about 1 g of V-amino acid entity, about 3 g of R-amino acid entity, about 4 g of L-glutamine or a salt thereof, about 0.9 g of NAC or a salt thereof, and about 6 g of L-serine or a salt thereof. In embodiments, the composition comprises about 4 g of the L-amino acid entity, about 2 g of the I-amino acid entity, about 1 g of V-amino acid entity, about 3 g of R-amino acid entity, about 4 g of L-glutamine or a salt thereof, about 0.9 g of NAC or a salt thereof, and about 6.67 g of L-serine or a salt thereof. In embodiments, the composition comprises about 4 g of the L-amino acid entity, about 2 g of the I-amino acid entity, about 1 g of V-amino acid entity, about 3 g of R-amino acid entity, about 4 g of L-glutamine or a salt thereof, about 0.9 g of NAC or a salt thereof, about 9 g of L-serine or a salt thereof, and about 9 g of L-glycine or a salt thereof. In embodiments, the composition comprises about 4 g of the L-amino acid entity, about 2 g of the I-amino acid entity, about 1 g of V-amino acid entity, about 3 g of R-amino acid entity, about 4 g of L-glutamine or a salt thereof, about 0.9 g of NAC or a salt thereof, about 3.33 g of L-serine or a salt thereof, and about 3.33 g of L-glycine or a salt thereof.

In some embodiments, 25-40 g, e.g., 30-35 g, e.g., about 33.9 g of the composition is administered to the subject BID. In certain embodiments, 25-40 g, e.g., 30-35 g, e.g., about 33.9 g of the composition is administered to the subject daily. In some embodiments, 15-30 g, e.g., 20-25 g, e.g., about 22.6 g of the composition is administered to the subject BID. In certain embodiments, 15-30 g, e.g., 20-25 g, e.g., about 22.6 g of the composition is administered to the subject daily.

In one aspect, the invention features a composition including free amino acids, wherein the amino acids include arginine, glutamine, N-acetylcysteine, and a branched-chain amino acid chosen from one, two, or all of leucine, isoleucine, and valine.

In any of the aspects and embodiments disclosed herein, the branched-chain amino acid is leucine, isoleucine, and valine.

In certain embodiments, the L-amino acid entity is chosen from L-leucine, β-hydroxy-β-methylbutyrate (HMB), oxo-leucine, isovaleryl-CoA, and N-acetyl-leucine, or a salt thereof, a dipeptide or salt thereof, a tripeptide or salt thereof, or a combination of any of the aforesaid. In certain embodiments, the R-amino acid entity is chosen from L-arginine, ornithine, argininosuccinate, aspartate, agmatine, creatine, and N-acetyl-arginine, or a salt thereof, a dipeptide or salt thereof, a tripeptide or salt thereof, or a combination of any of the aforesaid. In certain embodiments, the Q-amino acid entity is chosen from L-glutamine, glutamate, carbamoyl-P, and N-acetylglutamine, or a salt thereof, a dipeptide or salt thereof, a tripeptide or salt thereof, or a combination of any of the aforesaid. In certain embodiments, the NAC entity is chosen from NAC, acetylserine, glutathione, homocysteine, methionine, L-cysteine, cystine, and cysteamine, or a salt thereof, a dipeptide or salt thereof, a tripeptide or salt thereof, or a combination of any of the aforesaid. In certain embodiments, the I-amino acid entity is chosen from L-isoleucine, 2-oxo-3-methyl-valerate, methylbutyryl-CoA, and N-acetyl-isoleucine, or a salt thereof, a dipeptide or salt thereof, a tripeptide or salt thereof, or a combination of any of the aforesaid. In certain embodiments, the V-amino acid entity is chosen from L-valine, 2-oxo-valerate, isobutyryl-CoA, 3-HIB-CoA, 3-HIB, and N-acetyl-valine, or a salt thereof, a dipeptide or salt thereof, a tripeptide or salt thereof, or a combination of any of the aforesaid. In certain embodiments, the G-amino acid entity is chosen from L-glycine, L-serine, glutathione, sarcosine, or a salt thereof, a dipeptide or salt thereof, a tripeptide or salt thereof, or a combination of any of the aforesaid. In certain embodiments, the H-amino acid entity is chosen from L-histidine, histidinol, histidinal, ribose-5-phosphate, carnosine, histamine, urocanate, N-acetyl histidine, or a salt thereof, a dipeptide or salt thereof, a tripeptide or salt thereof, or a combination of any of the aforesaid. In certain embodiments, the K-amino acid entity is chosen from L-lysine, diaminopimelate, trimethyllysine, carnitine, saccharopine, N-acetyl lysine, or a salt thereof, a dipeptide or salt thereof, a tripeptide or salt thereof, or a combination of any of the aforesaid. In certain embodiments, the F-amino acid entity is chosen from L-phenylalanine, phenylpyruvate, tyrosine, N-acetyl-phenylalanine, or a salt thereof, a dipeptide or salt thereof, a tripeptide or salt thereof, or a combination of any of the aforesaid. In certain embodiments, the T-amino acid entity is chosen from L-threonine, homoserine, O-phosphohomoserine, oxobutyrate, N-acetyl-threonine, or a salt thereof, a dipeptide or salt thereof, a tripeptide or salt thereof, or a combination of any of the aforesaid.

In any of the aspects and embodiments disclosed herein, the wt ratio of leucine, isoleucine, valine, arginine, glutamine, N-acetylcysteine is 1:0.5:0.5:1.5:2:0.15. In certain embodiments, the wt ratio of leucine, isoleucine, valine, arginine, glutamine, N-acetylcysteine is 1+/−15%:0.5+/−15%:0.5+/−15%:1.5+/−15%:2+/−15%:0.15+/−15%. In any of the aspects and embodiments disclosed herein, the wt ratio of leucine, isoleucine, valine, arginine, glutamine, N-acetylcysteine is 1:0.5:0.5:1.81:2:0.15. In certain embodiments, the wt ratio of leucine, isoleucine, valine, arginine, glutamine, N-acetylcysteine is 1+/−15%:0.5+/−15%:0.5+/−15%:1.81+/−15%:2+/−15%:0.15+/−15%. In any of the aspects and embodiments disclosed herein, the wt ratio of leucine, isoleucine, valine, arginine, glutamine, N-acetylcysteine is 1:0.5:0.5:1.81:2:0.15. In certain embodiments, the wt ratio of leucine, isoleucine, valine, arginine, glutamine, N-acetylcysteine is 1+/−20%:0.5+/−20%:0.5+/−20%:1.81+/−20%:2+/−20%:0.15+/−20%. In any of the aspects and embodiments disclosed herein, the wt ratio of leucine, isoleucine, valine, arginine, glutamine, N-acetylcysteine is 1:0.5:0.5:1.81:1.333:0.15. In certain embodiments, the wt ratio of leucine, isoleucine, valine, arginine, glutamine, N-acetylcysteine is 1+/−15%:0.5+/−15%:0.5+/−15%:1.81+/−15%:1.333+/−15%:0.15+/−15%. In any of the aspects and embodiments disclosed herein, the wt ratio of leucine, isoleucine, valine, arginine, glutamine, N-acetylcysteine is 1:0.5:0.5:1.81:1.333:0.15. In certain embodiments, the wt ratio of leucine, isoleucine, valine, arginine, glutamine, N-acetylcysteine is 1+/−20%:0.5+/−20%:0.5+/−20%:1.81+/−20%:1.333+/−20%:0.15+/−20%. In some embodiments, a wt. ratio of the L-amino acid entity, the R-amino acid entity, the Q-amino acid entity, and the NAC-amino acid entity is about 1 (e.g., 1±20%):about 1.81 (e.g., 1.81±20%):about 2 (e.g., 2±20%):about 0.15 (e.g., 0.15±20%). In some embodiments, a wt. ratio of the L-amino acid entity, the R-amino acid entity, the Q-amino acid entity, and the NAC-amino acid entity is about 1 (e.g., 1±15%):about 1.81 (e.g., 1.81±15%):about 2 (e.g., 2±215%):about 0.15 (e.g., 0.15±15%).

In any of the aspects and embodiments disclosed herein, a total weight (wt) of the amino acids is about 2 g to about 60 g. In some embodiments, the total wt of the amino acids is about 6 g, about 12 g, about 18 g, about 24 g, or about 48 g.

In any of the aspects and embodiments disclosed herein, the composition includes about 0.5 g to about 10 g of leucine, about 0.25 g to about 5 g of isoleucine, about 0.25 g to about 5 g of valine, about 1 g to about 20 g of arginine, about 1 g to about 20 g of glutamine, and about 0.1 g to about 5 g of N-acetylcysteine.

In any of the aspects and embodiments disclosed herein, the composition includes about 1 g of leucine, about 0.5 g of isoleucine, about 0.5 g of valine, about 1.5 g of arginine, about 2 g of glutamine, and about 0.15 g of N-acetylcysteine.

In any of the aspects and embodiments disclosed herein, the composition includes about 1 g of leucine, about 0.5 g of isoleucine, about 0.5 g of valine, about 1.5 g of arginine, about 2 g of glutamine, and about 0.3 g of N-acetylcysteine.

In any of the aspects and embodiments disclosed herein, the composition includes about 2 g of leucine, about 1 g of isoleucine, about 1 g of valine, about 3.0 g of arginine, about 4 g of glutamine, and about 0.3 g of N-acetylcysteine.

In any of the aspects and embodiments disclosed herein, the composition includes about 4 g of leucine, about 2 g of isoleucine, about 2 g of valine, about 6.0 g of arginine, about 8 g of glutamine, and about 0.6 g of N-acetylcysteine.

In some embodiments of any of the compositions or methods disclosed herein:

e) a wt. % of the Q-amino acid entity administered is greater than wt. % of the R-amino acid entity;

f) a wt. % of the Q-amino acid entity administered is greater than wt. % of the L-amino acid entity;

g) a wt. % of the R-amino acid entity administered is greater than wt. % of the L-amino acid entity; or h) a combination of two or three of (e)-(g).

In certain embodiments, wt. % of the Q-amino acid entity administered is at least 5% greater than wt. % of the R-amino acid entity, e.g., wt. % of the Q-amino acid entity is at least 10%, 15%, 20%, or 25% greater than wt. % of the R-amino acid entity. In certain embodiments, wt. % of the Q-amino acid entity administered is at least 20% greater than wt. % of the L-amino acid entity, e.g., wt. % of the Q-amino acid entity in the composition is at least 25%, 30%, 35%, 40%, 45%, or 50% greater than wt. % of the L-amino acid entity. In certain embodiments, wt. % of the R-amino acid entity administered is at least 10% greater than wt. % of the L-amino acid entity, e.g., wt. % of the R-amino acid entity administered is at least 15%, 20%, 25%, or 30% greater than wt. % of the L-amino acid entity.

In some embodiments of any of the compositions or methods disclosed herein:

i) the ratio of the L-amino acid entity to the R-amino acid entity administered is at least 1:4, or at least 2:5, and not more than 3:4, e.g., the ratio of L-amino acid entity to R-amino acid entity administered is about 2:3;

j) the ratio of the L-amino acid entity to the Q amino acid entity administered is at least 1:4, or least 1:3, and not more than 3:4, e.g., the ratio of the L-amino acid entity to the Q-amino acid entity administered is about 1:2;

k) the ratio of the R-amino acid entity to the Q amino acid entity administered is at least 1:4, or least 1:2, and not more than 6:7, e.g., the ratio of the R-amino acid entity to the Q-amino acid entity administered is about 3:4; or l) a combination of two or three of (j)-(k).

In some embodiments of any of the compositions or methods disclosed herein:

m) wt. % of the L-amino acid-entity administered is greater than or equal to wt. % of the I-amino acid-entity and the V-amino acid-entity in combination;

n) wt. % of the L-amino acid-entity, the I-amino acid-entity, and the V-amino acid-entity administered is greater than or equal to wt. % of the Q-amino acid entity;

o) wt. % of the L-amino acid-entity, the I-amino acid-entity, and the V-amino acid-entity administered is less than wt. % of the R-amino acid entity;

p) wt. % of the R-amino acid entity and the Q-amino acid entity administered is greater than wt. % of the L-amino acid-entity, the I-amino acid-entity, and the V-amino acid-entity in combination; or q) a combination of two, three, or four of (m)-(p).

In some embodiments of any of the compositions or methods disclosed herein:

r) wt. % of the R-amino acid entity, the Q-amino acid entity, and the NAC or a salt thereof is at least 50% of amino acid entities administered, or at least 70% of amino acid entities administered, but not more than 90% of amino acid entities administered;

s) wt. % of the NAC or a salt thereof is at least 1%, or at least 2%, but not more than 10% of amino acid entities administered;

t) wt. % of the L-amino acid-entity, the I-amino acid-entity, and the V-amino acid-entity in combination is at least 15%, or at least 20%, but not more than 50% of amino acid entities administered;

u) wt. % of the R-amino acid entity, the Q-amino acid entity, and the NAC or a salt thereof is at least 40%, or at least 50%, but not more than 80% of the amino acid entities administered; or v) a combination of two, three, or four of (r)-(u).

In some embodiments of any of the compositions or methods disclosed herein:

oo) a wt. % of the L-amino acid entity administered is greater than wt. % of the NAC or a salt thereof;

pp) a wt. % of the R-amino acid entity administered is greater than wt. % of the NAC or a salt thereof;

qq) a wt. % of the Q-amino acid entity administered is greater than wt. % of the NAC or a salt thereof, or rr) a combination of two or three of (oo)-(qq).

In any of the aspects and embodiments disclosed herein, the amino acid entities include about 10 wt % to about 30 wt % L-amino acid entity, about 5 wt % to about 15 wt % I-amino acid entity, about 5 wt % to about 15 wt % V-amino acid entity, about 15 wt % to about 40 wt % R-amino acid entity, about 20 wt % to about 50 wt % Q-amino acid entity, and about 1 wt % to about 8 wt % NAC entity.

In any of the aspects and embodiments disclosed herein, the amino acids include about 10 wt % to about 30 wt % leucine, about 5 wt % to about 15 wt % isoleucine, about 5 wt % to about 15 wt % valine, about 15 wt % to about 40 wt % arginine, about 20 wt % to about 50 wt % glutamine, and about 1 wt % to about 8 wt % N-acetylcysteine.

In any of the aspects and embodiments disclosed herein, the amino acids include about 16 wt % to about 18 wt % leucine, about 7 wt % to about 9 wt % isoleucine, about 7 wt % to about 9 wt % valine, about 28 wt % to about 32 wt % arginine, about 31 wt % to about 34 wt % glutamine, and about 1 wt % to about 5 wt % N-acetylcysteine.

In any of the aspects and embodiments disclosed herein, the amino acids include about 16.8 wt % leucine, about 8.4 wt % isoleucine, about 8.4 wt % valine, about 30.4 wt % arginine, about 33.6 wt % glutamine, and about 2.5 wt % N-acetylcysteine.

In an embodiment, the wt. ratio of the L-amino acid entity, the R-amino acid entity, the Q-amino acid entity, and the NAC entity administered is about 0.5 to 3:0.5 to 4:1 to 4:0.1 to 2.5. In an embodiment, the wt. ratio of the L-amino acid entity, the R-amino acid entity, the Q-amino acid entity, and the NAC entity administered is about 1:1.5:2:0.15. In an embodiment, the wt. ratio of the L-amino acid entity, the R-amino acid entity, the Q-amino acid entity, and the NAC entity administered is about 1:1.5:2:0.3. In an embodiment, the wt. ratio of the L-amino acid entity, the I-amino acid entity, the V-amino acid entity, the R-amino acid entity, the Q-amino acid entity, and the NAC entity administered is about 0.5 to 2:0.1 to 1:0.1 to 1:0.5 to 3:0.5 to 4:0.1 to 0.5. In an embodiment, the wt. ratio of the L-amino acid entity, the I-amino acid entity, the V-amino acid entity, the R-amino acid entity, the Q-amino acid entity, and the NAC entity administered is about 1:0.5:0.5:1.5:2:0.15. In an embodiment, the wt. ratio of the L-amino acid entity, the I-amino acid entity, the V-amino acid entity, the R-amino acid entity, the Q-amino acid entity, and the NAC entity administered is about 1:0.5:0.5:1.5:2:0.3.

In an embodiment, the ratio of the L-amino acid-entity, the I-amino acid-entity, and the V-amino acid-entity in combination to the R-amino acid entity, L-glutamine or a salt thereof, and NAC or a salt thereof is 12+/−15%:6+/−15%:3+/−15%:9+/−15%:12+/−15%:2.7+/−1500.

In an embodiment, the ratio of the L-amino acid-entity, the I-amino acid-entity, and the V-amino acid-entity in combination to the R-amino acid entity, L-glutamine or a salt thereof, and NAC or a salt thereof is 12+/−20%:6+/−20%:3+/−20%:9+/−20%:12+/−20%:2.7+/−20%.

In certain embodiments, at least one of the amino acids administered is a free amino acid, e.g., two, three, or four of amino acids administered are a free amino acid, e.g., at least 50 wt. % of the total wt. of components administered is one or more amino acid entities in free form. In certain embodiments, at least one of the amino acids administered is in a salt form, e.g., one, two, three, or four of amino acids administered is in a salt form, e.g., at least 10 wt. % of the total wt. of components administered is one or more amino acid entities in salt form.

In any of the aspects and embodiments disclosed herein, the composition further includes one or more pharmaceutically acceptable excipients.

In some embodiments, the excipients are selected from the group consisting of citric acid, lecithin, a sweetener, a dispersion enhancer, a flavoring, a bitterness masking agent, a natural or artificial coloring, and a chelating agent.

In some embodiments, the composition is in the form of a solid, powder, solution, or gel.

In some embodiments, the amino acids consist of leucine, isoleucine, valine, arginine, glutamine and N-acetylcysteine. In some embodiments, the amino acids consist of leucine, isoleucine, valine, arginine, glutamine, N-acetylcysteine, histidine, lysine, phenylalanine, and threonine.

Another aspect of the invention features a dietary composition including the composition of any one of the foregoing aspects or embodiments, e.g., wherein the dietary composition is chosen from a medical food, a functional food, or a supplement.

In some embodiments, the dietary composition is chosen from a medical food, a functional food, or a supplement.

In some embodiments, the subject has been infected with a virus selected from the group consisting of SARS-CoV-1, SARS-CoV-2, MERS, influenza A or B, herpesviruses (Epstein-Barr virus, human cytomegalovirus, and human herpesviruses 6A and 6B), Ebola virus, West Nile virus, dengue virus, Ross river virus, enteroviruses, and human parvovirus B19. In some embodiments, a subject has been infected with a coronavirus (e.g., human alpha coronavirus (e.g., HCoV-229E or HCoV-NL63), human betacoronavirus (HCoV-OC43 or HKU1), SARS-CoV-1, SARS-CoV-2, and/or MERS).

In some embodiments, the subject has been hospitalized for acute COVID-19.

In some embodiments, the subject has been hospitalized for one or more symptoms or signs of post-acute sequelae of COVID-19.

In some embodiments, the subject has not been vaccinated for COVID-19 prior to contracting COVID-19.

In some embodiments, the subject had been vaccinated (e.g., partially vaccinated or fully vaccinate) for COVID-19 prior to contracting COVID-19.

In some embodiments, the subject had been vaccinated for COVID-19 after contracting COVID-19. In some embodiments, the subject tested positive for SARS-CoV-2 and developed symptoms consistent with infection.

In some embodiments, the subject tested positive for SARS-CoV-2 and was asymptomatic, but later developed symptoms or signs consistent with PASC. In some embodiments, the subject tested positive for SARS-CoV-2, had symptoms of infection, became antibody negative or asymptomatic, and then was re-infected with another variant of SARS-CoV-2.

In some embodiments, the subject has tested positive for SARS-CoV-2 more than once. In certain embodiments, the subject has tested positive for SARS-CoV-2 1, 2, 3, 4, or more times. In some embodiments, the subject has been diagnosed with more than one infection of SARS-CoV-2 (e.g., 1, 2, 3, 4, or more separate SARS-CoV-2 infections).

In some embodiments, at the time of administration of (a)-(d), the subject has had one or more symptoms of PASC.

In some embodiments, at the time of administration of (a)-(d), the subject is (e.g., is determined to be) negative for SARS-CoV-2.

In some embodiments, at the time of administration of (a)-(d), the subject is (e.g., is determined to be) positive for SARS-CoV-2.

In some embodiments, at the time of administration, the subject no longer has detectable SARS-CoV-2 in a nasal sample at the time they are administered the composition.

In some embodiments, the subject was infected with an alpha strain of SARS-CoV-2 (e.g., a B.1.1.7 or Q lineage or a lineage descendent therefrom). In some embodiments, the subject was infected with a beta strain of SARS-CoV-2 (e.g., a B.1.351 lineage or a lineage descendent therefrom). In some embodiments, the subject was infected with a gamma strain of SARS-CoV-2 (e.g., a P.1 lineage or a lineage descendent therefrom). In some embodiments, the subject was infected with a delta strain of SARS-CoV-2 (e.g., a B.1.617.2 or AY lineage or a lineage descendent therefrom). In some embodiments, the subject was infected with an epsilon strain of SARS-CoV-2 (e.g., a B.1.427 or B.1.429 lineage or a lineage descendent therefrom). In some embodiments, the subject was infected with an eta strain of SARS-CoV-2 (e.g., a B.1.525 lineage or a lineage descendent therefrom). In some embodiments, the subject was infected with an iota strain of SARS-CoV-2 (e.g., a B.1.526 lineage or a lineage descendent therefrom). In some embodiments, the subject was infected with a kappa strain of SARS-CoV-2 (e.g., a B.1.617.1 lineage or a lineage descendent therefrom). In some embodiments, the subject was infected with a 1.617.3 strain of SARS-CoV-2 or a lineage descendent therefrom. In some embodiments, the subject was infected with a Mu strain of SARS-CoV-2 (e.g., a B.1.621 or B.1.621.1 lineage or a lineage descendent therefrom). In some embodiments, the subject was infected with a zeta strain of SARS-CoV-2 (e.g., a P.2 lineage or a lineage descendent therefrom). In some embodiments, the subject was infected with an Omicron strain of SARS-CoV-2 (e.g., a B.1.1.529, BA.1, BA.1.1, BA.2, BA.3, BA.4 or BA.5 lineage or a lineage descendent therefrom).

In some embodiments, the subject is an adult. In some embodiments, the subject is between 18 and 65 years of age. In some embodiments, the subject is an adolescent or a child. In some embodiments, the subject is 17 years of age or younger. In some embodiments, the subject is between 1 and 17 years of age (e.g., between 1 and 5, 5 and 10, 10 and 15, or 15 and 17). In some embodiments, the subject has fatigue-predominant PASC. In some embodiments, the subject has PCr recovery constant of >40 seconds or >50 seconds.

In some embodiments, after the administration, the subject experiences one or more of: reduction of elevated serum lactate from baseline (e.g. after 6 minute walk), improvement of fatigue PRO score or functional status (e.g. by Chalder Fatigue Questionnaire [CFQ-11]) after 6 minute walk, increase in distance walked in 6 minute walk, improvement in phosphocreatine (PCr) recovery time constant following exercise, and/or improvement in oxidative ATP synthesis. In some embodiments, the subject experiences a decrease in serum lactate level to ≤3 mmol/L (e.g. after 6 minute walk), e.g., when tested 4 weeks after administration is begun. In some embodiments, the subject exhibits an increase in distance traveled during a 6 minute walk, e.g., when tested 4 weeks after administration is begun. In some embodiments, the subject exhibits an improvement in fatigue score as assessed by CFQ-11 (by Bimodal Scoring), e.g., when tested 2 or 4 weeks after administration is begun. In some embodiments, the subject exhibits an improvement in fatigue score as assessed by CFQ-11 (by Bimodal Scoring) after a 6 minute walk, e.g., when tested 4 weeks after administration is begun.

In some embodiments, the subject exhibits an improvement in one or more of circulating mitochondrial peptides (eg, Mots-C), metabolites, proteins; a plasma biomarker of inflammation, an adhesion marker, a muscle injury marker (e.g., troponins, creatine kinase, fibroblast growth factor-21), mitochondrial function, metabolism; nitric oxide biology; immune profiles, extracellular acidification rate and oxygen consumption rate, e.g., when tested 4 weeks after administration is begun. In some embodiments, the subject exhibits an improvement in one or more energetically active metabolites, e.g., measured using proton magnetic resonance spectroscopy (IHMRS; i.e., creatine, intramyocellular lipids, acetylcarnitine, and carnosine) e.g., when tested 4 weeks after administration is begun. In some embodiments, the subject exhibits an improvement in one or more of minimal intramuscular pH after exercise, initial PCr recovery rate, adenosine diphosphate (ADP) concentration at the end of exercise, maximal mitochondrial capacity, e.g., when measured using dynamic $^{31}$P-MRS, e.g., when tested 4 weeks after administration is begun. In some embodiments, the subject exhibits an improvement in one or more markers of mitochondrial function, e.g., when tested 4 weeks after administration is begun. In some embodiments, the marker of mitochondrial function comprises one or more of growth and differentiation factor-15 (GDF-15), neurofilament light chain (NF-L), alpha lipoic acid (ALA), lipid peroxide (PerOx), total plasma antioxidant capacity (TAC), serum cytochrome c, danger-associated molecular patterns (DAMPs), mtDNA, N-formyl peptides (FPs), or novel cell free circulating-mtDNA (ccf-mtDNA). In some embodiments, the subject exhibits an improved phosphocreatine (PCr) recovery rate following moderate exercise, e.g., as assessed by $^{31}$P magnetic resonance spectroscopy (MRS), e.g., when tested 4 weeks after administration is begun. In some embodiments, after administration, the subject experiences an increase in basal respiration. In some embodiments, the increase in basal respiration comprises utilization of one or more of glucose, glutamine, and fatty acids. In some embodiments, after administration, the subject experiences an increase in mitochondrial-derived ATP. In some embodiments, after administration, the subject experiences a reduction in glycolysis-generated ATPs.

In some embodiments, after administration, the subject or cells or tissues obtained from the subject experiences an increase in basal respiration. In some embodiments, the increase in basal respiration comprises utilization of one or more of glucose, glutamine, and fatty acids. In some embodiments, after administration, the subject experiences an increase in mitochondrial-derived ATP. In some embodiments, after administration, the subject experiences a reduction in glycolysis-generated ATPs.

In some embodiments, after administration, the subject experiences increased flux through fatty acid oxidation (FAO) to acetyl-CoA. In some embodiments, after administration, the subject experiences an increase in levels or synthesis rate of the ketone body beta-hydroxybutyrate (BHB). In some embodiments, after administration, the subject experiences an increase in FAO. In some embodiments, after administration, the subject experiences an increase in ketogenesis.

In some embodiments, after administration, the subject experiences a decrease in intramyocellular lipid content, e.g., when tested 4 weeks after administration is begun. In some embodiments, after administration, the subject experiences a decrease in peak lactate, e.g., when tested 4 weeks after administration is begun. In some embodiments, after administration, the subject experiences an increase in carnosine levels, e.g., when tested 4 weeks after administration is begun.

In some embodiments, after administration, the subject experiences a decrease in blood clot formation. In some embodiments the subject experiences a decrease in vascular inflammation and endothelial dysfunction. In some embodiments the subject experiences a decrease in oxidative stress.

In some embodiments of the method or the dietary composition for use, the amino acid entities are administered separately. In some embodiments of the method or the dietary composition for use, the amino acid entities are administered as an admixture. In some embodiments of the method or the dietary composition for use, the amino acid entities are administered orally. In some embodiments of the method or the dietary composition for use, the amino acid entities are administered prior to a meal. In some embodiments of the method or the dietary composition for use, the amino acid entities are administered concurrent with a meal. In some embodiments of the method or the dietary composition for use, the amino acid entities are administered following a meal.

In some embodiments of the method or the dietary composition for use, the amino acid entities are administered in a solution or suspension. In some embodiments, the method further comprises a step of contacting the amino acids with a liquid (e.g., a beverage, e.g., water), thereby making a solution or suspension. In some embodiments, the amino acid entities are present in one or more composition (e.g., one or more stick packs). In some such embodiments, a method further comprises contacting the one or more compositions with a liquid. In some embodiments, not all of the amino acid entities administered are present in the same composition prior to contacting the amino acid entities with a liquid, e.g., one, two, or three or more of the amino acid entities administered are in a first composition, and the remaining one, two, or three, or more of the amino acid entities administered are in a second composition. In some such embodiments, the method further comprises contacting a liquid with the first and the second composition, e.g., simultaneously or sequentially.

In some embodiments of the method or the dietary composition for use, the composition is administered at a dose of about 15 g/d to about 90 g/d.

In some embodiments of the method or the dietary composition for use, the composition is administered at a dose of about 18 g/d, about 24 g/d, about 36/d, about 54 g/d, or about 72 g/d.

In some embodiments of the method or the dietary composition for use, the composition is administered one, two, to three times per day.

In some embodiments of the method or the dietary composition for use, the composition is administered at a dose of about 6 g, about 8 g, about 12 g, about 16 g, about 18 g, or about 24 g three times per day. In some embodiments of the method or the dietary composition for use, the composition is administered at a dose of about 6-8 g, about 8-12 g, about 12-16 g, about 16-18 g, about 18-20 g, about 20-30 g, about 22-28 g, or about 24-26 g.

One embodiment provides a nutritional supplement, dietary formulation, functional food, medical food, food, or beverage comprising a composition described herein. Another embodiment provides a nutritional supplement, dietary formulation, functional food, medical food, food, or beverage comprising a composition described herein for use in the management of any of the diseases or disorders described herein. The composition disclosed herein can be used to improve post-acute sequelae of COVID-19 in a subject. Thus, a method, including a dosage regimen, for treating (e.g., inhibiting, reducing, ameliorating, or preventing) various mitochondrial, musculoskeletal, neurocognition and sensory, and pulmonary disorders, diseases, or symptoms thereof using the amino acid entity compositions is disclosed herein. Thus, a method, including a dosage regimen, for treating (e.g., inhibiting, reducing, ameliorating, or preventing) myalgic encephalomyelitis/chronic fatigue syndrome (ME/CFS), postinfectious fatigue syndrome, postcritical illness syndrome, or post-intensive care unit syndrome, following illness or infection, or symptoms thereof using the amino acid entity compositions is disclosed herein. The composition can also be used as a dietary composition, e.g., a medical food, a functional food, or a supplement.

Another aspect of the invention features a method for treating a subject having post-acute sequelae of COVID-19 comprising administering to a subject in need thereof an effective amount of the composition of any one of aspects or embodiments disclosed herein. In some embodiments, a subject has one or more symptoms or signs selected from the group consisting of anorexia, anxiety, arrhythmias, confusion ("brain fog"), dementia, depression, dyspnea, fatigue, hair loss, headache, heart failure, cardiomyopathy, angina, hepatic dysfunction, hyperglycemia, type 2 diabetes, increased heart rate, inflammation, loss of appetite, loss of memory, loss of smell, mood disorder, muscle weakness, myocardial ischemia, post-exertional malaise, diminished neurocognition, diminished sensory function, pulmonary infiltrates or fibrosis, postural orthostatic hypotension, renal dysfunction, and respiratory distress. In some embodiments, a subject has one or more symptoms or signs selected from the group consisting of myalgia, fibromyalgia, idiopathic pulmonary fibrosis, fatigue, muscle fatigue, mitochondrial dysfunction (e.g., increase lactic acid production), dyspnea after exertion, postural orthostatic tachycardia syndrome, tachycardia, mood disorders, and depression.

Another aspect of the invention features a method for treating one or more symptoms or signs selected from the group consisting of anorexia, anxiety, arrhythmias, confusion ("brain fog"), dementia, depression, dyspnea, fatigue, hair loss, headache, heart failure, cardiomyopathy, angina, hepatic dysfunction, hyperglycemia, type 2 diabetes, increased heart rate, inflammation, loss of appetite, loss of memory, loss of smell, mood disorder, muscle weakness, myocardial ischemia, post-exertional malaise, diminished neurocognition, diminished sensory function, pulmonary infiltrates or fibrosis, postural orthostatic hypotension, renal dysfunction, and respiratory distress, wherein the method comprises administering to a subject in need thereof an effective amount of the composition of any one of aspects or embodiments disclosed herein. In some embodiments, the subject has post-acute sequelae of COVID-19.

Another aspect of the invention features a method for treating one or more symptoms or signs selected from the group consisting of myalgia, fibromyalgia, idiopathic pulmonary fibrosis, fatigue, muscle fatigue, muscle dysfunction, mitochondrial dysfunction, dyspnea after exertion, postural orthostatic tachycardia syndrome, tachycardia, oxidative stress or excess reactive oxygen species (ROS), myalgic encephalomyelitis/chronic fatigue syndrome (ME/CFS), mood disorders, depression, and new onset diabetes, wherein the method includes administering to a subject in need thereof an effective amount of the composition of any one of aspects or embodiments disclosed herein. In some embodiments, the subject has post-acute sequelae of COVID-19.

In some embodiments, the subject has been hospitalized for acute COVID-19.

In some embodiments, the subject has been hospitalized for one or more symptoms of post-acute sequelae of COVID-19.

In some embodiments, the subject has not been vaccinated for COVID-19 prior to contracting COVID-19.

In some embodiments, the subject had been vaccinated (e.g., partially vaccinated or fully vaccinate) for COVID-19 prior to contracting COVID-19. In some embodiments, the subject had been vaccinated (e.g., partially vaccinated or fully vaccinated) for COVID-19 (e.g., prior to contracting COVID-19). In some embodiments, the subject has received 2, 3, or 4 doses of the vaccine. In some embodiments, the subject has received at least 2 (e.g., 2, 3, 4, or more) doses of the vaccine.

In some embodiments, the subject had been vaccinated for COVID-19 after contracting COVID-19.

In some embodiments, the subject tested positive for SARS-CoV-2 and developed symptoms consistent with infection. In some embodiments, the subject tested positive for SARS-CoV-2 and was asymptomatic, but later developed symptoms consistent with PASC.

In some embodiments, the subject tested positive for SARS-CoV-2, had symptoms of infection, became antibody negative or asymptomatic, and then was re-infected with another variant of SARS-CoV-2.

In some embodiments, before administration of the composition, the subject tested positive for COVID-19 at least twice over a period of time, e.g., at least 3 or 4 weeks. In certain embodiments, before administration of the composition, the subject had COVID-19 for about 3, 4, 5, 6, 8, 10 or 12 weeks. In some embodiments, at the time of administration of the composition, the subject has had one or more symptoms of acute COVID-19 for at least 3 or 4 weeks.

In some embodiments, the subject tested positive for COVID-19 1-7, 8-14, 15-21, 22-28, or more than 28 days before administration of (a)-(d). In certain embodiments, the subject was infected with COVID-19 1-7, 8-14, 15-21, 22-28, or more than 28 days before administration of (a)-(d).

Another aspect of the invention features a method for treating post-acute sequelae of COVID-19 including administering to a subject in need thereof an effective amount of the composition of any one of the aspects or embodiments disclosed herein.

In some embodiments, the subject has been hospitalized for acute COVID-19.

In some embodiments, the subject has been hospitalized for one or more symptoms of post-acute sequelae of COVID-19.

In some embodiments, the subject has not been vaccinated for COVID-19 prior to contracting COVID-19.

In some embodiments, the subject had been vaccinated (e.g., partially vaccinated or fully vaccinate) for COVID-19 prior to contracting COVID-19.

In some embodiments, the subject had been vaccinated for COVID-19 after contracting COVID-19.

In some embodiments, the subject tested positive for SARS-CoV-2 and developed symptoms consistent with infection.

In some embodiments, the subject tested positive for SARS-CoV-2 and was asymptomatic, but later developed symptoms consistent with PASC.

In some embodiments, the subject tested positive for SARS-COV-2, had symptoms of infection, became antibody negative or asymptomatic, and then was re-infected with another variant of SARS-CoV-2.

Another aspect of the invention features a method for treating myalgia including administering to a subject in need thereof an effective amount of the composition of any one of the aspects or embodiments disclosed herein.

Another aspect of the invention features a method for treating idiopathic pulmonary fibrosis including administering to a subject in need thereof an effective amount of the composition of any one of the aspects or embodiments disclosed herein.

Another aspect of the invention features a method for treating fatigue including administering to a subject in need thereof an effective amount of the composition of any one of the aspects or embodiments disclosed herein.

Another aspect of the invention features a method for treating chronic fatigue including administering to a subject in need thereof an effective amount of the composition of any one of the aspects or embodiments disclosed herein.

Another aspect of the invention features a method for treating muscle fatigue including administering to a subject in need thereof an effective amount of the composition of any one of the aspects or embodiments disclosed herein.

Another aspect of the invention features a method for treating muscle dysfunction including administering to a subject in need thereof an effective amount of the composition of any one of the aspects or embodiments disclosed herein.

Another aspect of the invention features a method for treating mitochondrial dysfunction associated with viral infection (e.g. mitochondrial dysfunction associated with COVID-19 or PASC) including administering to a subject in need thereof an effective amount of the composition of any one of the aspects or embodiments disclosed herein.

Another aspect of the invention features a method for treating dyspnea after exertion including administering to a subject in need thereof an effective amount of the composition of any one of the aspects or embodiments disclosed herein.

Another aspect of the invention features a method for treating postural orthostatic tachycardia syndrome including administering to a subject in need thereof an effective amount of the composition of any one of the aspects or embodiments disclosed herein.

Another aspect of the invention features a method for treating tachycardia including administering to a subject in need thereof an effective amount of the composition of any one of the aspects or embodiments disclosed herein.

Another aspect of the invention features a method for improving mitochondrial capacity or energetics (e.g., improvement in oxidative adenosine triphosphate (ATP) synthesis, phosphocreatine PCr) resynthesis following exercise or exertion) including administering to a subject in need thereof an effective amount of the composition of any one of the aspects or embodiments disclosed herein.

Another aspect of the invention features a method for reducing oxidative stress and/or reducing reactive oxygen species (ROS) including administering to a subject in need thereof an effective amount of the composition of any one of the aspects or embodiments disclosed herein.

Another aspect of the invention features a method for treating mood disorders including administering to a subject in need thereof an effective amount of the composition of any one of the aspects or embodiments disclosed herein.

Another aspect of the invention features a method for treating depression including administering to a subject in need thereof an effective amount of the composition of any one of the aspects or embodiments disclosed herein.

Another aspect of the invention features a method for endothelial function including administering to a subject in need thereof an effective amount of the composition of any one of the aspects or embodiments disclosed herein.

In some embodiments, the composition is administered prior to a meal.

In some embodiments, the composition is administered concurrent with a meal.

In some embodiments, the composition is administered following a meal.

In some embodiments, the composition is administered with a second agent.

Additional features and embodiments of the present invention include one or more of the following.

In some embodiments, a method described herein comprises administering to a subject a composition comprising:

a) a L-amino acid entity chosen from L-leucine or a salt thereof, or β-hydroxy-β-methylbutyrate (HMB) or a salt thereof, or a combination of L-leucine or a salt thereof and HMB or a salt thereof;

b) an R-amino acid entity chosen from: L-arginine or a salt thereof, ornithine or a salt thereof, or creatine or a salt thereof, or a combination of two or three of L-arginine or a salt thereof, ornithine or a salt thereof, or creatine or a salt thereof;

c) L-glutamine or a salt thereof, and d) N-acetylcysteine (NAC) or a salt thereof.

In an embodiment, L-leucine is provided as part of a dipeptide comprising L-leucine, or a salt thereof, or a tripeptide comprising L-leucine, or a salt thereof.

In an embodiment, L-arginine is provided as part of a dipeptide comprising L-arginine, or a salt thereof, or a tripeptide comprising L-arginine, or a salt thereof.

In an embodiment, L-glutamine is provided as part of a dipeptide comprising L-glutamine, or a salt thereof, or a tripeptide comprising L-glutamine, or a salt thereof.

In an embodiment, NAC is provided as a part of a dipeptide comprising NAC, or a salt thereof, or a tripeptide comprising NAC, or a salt thereof.

In some embodiments of any of the compositions or methods disclosed herein, one, two, three, or four of methionine (M), tryptophan (W), valine (V), or cysteine (C) is absent, or if present, is present at a percentage of the composition by weight (wt. %) of less than 10%. In some embodiments, the total wt. % of (a)-(d) is greater than the total wt. % of other amino acid entities in the composition.

In some embodiments of any of the compositions or methods disclosed herein, one, two, three, or four of the amino acids in (a)-(d) is provided as part of a dipeptide or tripeptide, e.g., in an amount of at least 10 wt. % of the composition. In certain embodiments, the dipeptide is a homodipeptide or heterodipeptide of any of the amino acids in (a)-(d), e.g., one, two, three, or four of the amino acids in (a)-(d) is a homodipeptide or heterodipeptide. In certain embodiments, the tripeptide is a homotripeptide or heterotripeptide of any of (a)-(d), e.g., one, two, three, or four of (a)-(d) is a homotripeptide or heterotripeptide.

In some embodiments of any of the compositions or methods disclosed herein, (a) is a L-amino acid entity dipeptide or a salt thereof (e.g., a L-leucine dipeptide or a salt thereof). In some embodiments, (a) is a homodipeptide. In some embodiments, (a) is a heterodipeptide, e.g., Ala-Leu.

In some embodiments of any of the compositions or methods disclosed herein, (b) is a L-arginine dipeptide or a salt thereof. In some embodiments, (b) is a homodipeptide. In some embodiments, (b) is a heterodipeptide, e.g., Ala-Arg.

In some embodiments of any of the compositions or methods disclosed herein, (c) is a L-glutamine dipeptide or a salt thereof. In some embodiments, (c) is a homodipeptide, e.g., Gln-Gln. In some embodiments, (c) is a heterodipeptide, e.g., Ala-Gln.

In some embodiments of any of the compositions or methods disclosed herein, the composition further comprises one or both of an isoleucine (I)-amino acid-entity and a valine (V)-amino acid-entity, e.g., both the I-amino acid-entity and the V-amino acid-entity are present.

In some embodiments of any of the compositions or methods disclosed herein, the composition further comprises one, two, or three or more (e.g., all) of a histidine (H)-amino acid entity, a lysine (K)-amino acid entity, a phenylalanine (F)-amino acid entity, and a threonine (T)-amino acid entity.

In some embodiments of any of the compositions or methods disclosed herein:

m) the wt. % of the L-amino acid-entity in the composition is greater than or equal to the wt. % of the I-amino acid-entity and the V-amino acid-entity in combination;

n) the wt. % of the L-amino acid-entity, the I-amino acid-entity, and the V-amino acid-entity in combination in the composition is greater than or equal to the wt. % of the L-glutamine or a salt thereof;

o) the wt. % of the L-amino acid-entity, the I-amino acid-entity, and the V-amino acid-entity in combination in the composition is less than the wt. % of the R-amino acid entity;

p) the wt. % of the R-amino acid entity and the L-glutamine or a salt thereof in the composition is greater than the wt. % of the L-amino acid-entity, the I-amino acid-entity, and the V-amino acid-entity in combination; or q) a combination of two, three, or four of (m)-(p).

In some embodiments of any of the compositions or methods disclosed herein:

r) the wt. % of the R-amino acid entity, the L-glutamine or a salt thereof, and the NAC or a salt thereof is at least 50% of the composition, or at least 70% of the composition, but not more than 90% of the composition;

s) the wt. % of the NAC or a salt thereof is at least 1%, or at least 2%, but not more than 10% of the composition;

t) the wt. % of the L-amino acid-entity, the I-amino acid-entity, and the V-amino acid-entity in combination is at least 15%, or at least 20%, but not more than 50% of the composition;

u) the wt. % of the R-amino acid entity, the L-glutamine or a salt thereof, and the NAC or a salt thereof is at least 40%, or at least 50%, but not more than 80% of the composition; or v) a combination of two, three, or four of (r)-(u).

In some embodiments of any of the compositions or methods disclosed herein:

w) the ratio of the L-amino acid entity to the I-amino acid entity is at least 1.5:1, or at least 1.75:1, and not more than 2.5 to 1 or not more than 3:1, e.g., the ratio of the L-amino acid entity to the I-amino acid entity is about 2:1;

x) the ratio of L-amino acid entity to V-amino acid entity is at least 1.5:1, or at least 1.75:1, and not more than 2.5 to 1 or not more than 3:1, e.g., the ratio of L to V is about 2:1;

y) the ratio of the L-amino acid entity to the R-amino acid entity is greater than 1:3, greater than 1.5 to 3, and less than 3:3, e.g., the ratio of the L-amino acid entity to the R-amino acid entity is about 2:3;

z) the ratio of the L-amino acid entity to the L-glutamine or a salt thereof is greater than 1:4, greater than 1.5 to 4 and less than 4:4, or less than 3:4, e.g., the ratio of the L-amino acid entity to the L-glutamine or a salt thereof is about 1:2; or aa) a combination of two, three, or four of (w)-(z).

In an embodiment, the composition satisfies the properties of (w)-(z) defined above.

In certain embodiments, the composition satisfies the properties of at least 2, 3, 4, or 5 of any of properties (w)-(aa) defined above.

In some embodiments of any of the compositions or methods disclosed herein:

bb) the ratio of the I-amino acid entity to the V-amino acid entity is at least 0.5:1, or at least 0.75:1, and not more than 1.5 to 1 or not more than 2:1, e.g., the ratio of the L-amino acid entity to the I-amino acid entity is about 1:1;

cc) the ratio of the I-amino acid entity to the R-amino acid entity is at least 0.5:3, or at least 0.75:3, and not more than 2:3, or not more than 1.5:3, e.g., the ratio of the L-amino acid entity to the I-amino acid entity is about 1:3;

dd) the ratio of the I-amino acid entity to the L-glutamine or a salt thereof is at least 0.5:4, or at least 0.75:4, and not more than 3:4, or not more than 2:4, e.g., the ratio of the L-amino acid entity to the L-glutamine or a salt thereof is about 1:4; or ee) or a combination of two or three of (bb)-(dd).

In an embodiment, the composition satisfies the properties of (bb)-(dd) defined above.

In certain embodiments, the composition satisfies the properties of at least 2, 3, or 4 of any of properties (bb)-(ee) defined above.

In some embodiments of any of the compositions or methods disclosed herein:

ff) the ratio of the L-amino acid entity to the V-amino acid entity is at least 1.5:1, or at least 1.75:1, and not more than 2.5 to 1 or not more than 3:1, e.g., the ratio of the L-amino acid entity to the V-amino acid entity is about 2:1;

gg) the ratio of the L-amino acid entity to the R-amino acid entity is greater than 1:3 or greater than 1.5 to 3, and less than 3:3, e.g., the ratio of the L-amino acid entity to the R-amino acid entity is about 2:3;

hh) the ratio of the L-amino acid entity to the L-glutamine or a salt thereof is greater than 1:4 or greater than 1.5 to 4, and less than 4:4 or less than 3:4, e.g., the ratio of the L-amino acid entity to the L-glutamine or a salt thereof is about 1:2; or ii) a combination of two or three of (ff)-(hh).

In an embodiment, the composition satisfies the properties of (ff)-(hh) defined above.

In certain embodiments, the composition satisfies the properties of at least 2, 3, or 4 of any of properties (ff)-(ii) defined above.

In some embodiments of any of the compositions or methods disclosed herein:

jj) the ratio of the V-amino acid entity to the L-glutamine or a salt thereof is at least 0.5:4, or at least 0.75:4, and not more than 3:4, or not more than 2:4, e.g., the ratio of the L-amino acid entity to the L-glutamine or a salt thereof is about 1:4;

kk) the ratio of the V-amino acid entity to the R-amino acid entity is at least 0.5:3, or at least 0.75:3, and not more than 2:3, or not more than 1.5:3, e.g., the ratio of the V-amino acid entity to the R-amino acid entity is about 1:3;

ll) the ratio of the L-amino acid-entity, the I-amino acid-entity, and the V-amino acid-entity in combination to the R-amino acid entity, L-glutamine or a salt thereof, and NAC or a salt thereof is at least 1:4, or at least 2:3, or not more than 5:7, or not more than 6:7, e.g., the ratio is about 6:11; or mm) a combination of two or three of (jj)-(ll).

In an embodiment, the composition satisfies the properties of (jj)-(ll) defined above.

In certain embodiments, the composition satisfies the properties of at least 2, 3, or 4 of any of properties (jj)-(mm) defined above.

In some embodiments of any of the compositions or methods disclosed herein:

nn) a wt. % of the L-amino acid entity in the composition is greater than the wt. % of the NAC or a salt thereof;

oo) a wt. % of the R-amino acid entity in the composition is greater than the wt. % of the NAC or a salt thereof;

pp) a wt. % of the L-glutamine or a salt thereof in the composition is greater than the wt. % of the NAC or a salt thereof; or qq) a combination of two or three of (nn)-(pp).

In some embodiments of any of the compositions or methods disclosed herein, at least one of (a)-(d) is a free amino acid, e.g., two, three, or four of (a)-(d) are a free amino acid, e.g., at least 50 wt. % of the total wt. of the composition is one or more amino acid entities in free form.

In some embodiments of any of the compositions or methods disclosed herein, at least one of (a)-(d) is in a salt form, e.g., one, two, three, or four of (a)-(d) is in a salt form, e.g., at least 10 wt. % of the total wt. of the composition is one or more amino acid entities in salt form.

In some embodiments of any of the compositions or methods disclosed herein, the composition is capable of one or more of:

a) decreasing or preventing myalgia;
b) decreasing or preventing fibromyalgia;
c) decreasing or preventing idiopathic pulmonary fibrosis;
d) decreasing or preventing fatigue;
e) decreasing or preventing muscle fatigue;
f) decreasing or preventing muscle dysfunction;
g) decreasing or mitochondrial dysfunction;
h) decreasing or preventing dyspnea after exertion;
i) improving exercise tolerance or the ability to conduct activities of daily living;
j) decreasing or preventing postural orthostatic tachycardia syndrome; or
k) decreasing or preventing tachycardia;
l) improving mitochondrial function;
m) improving mitochondrial capacity or energetics (e.g., improvement in oxidative ATP synthesis, phosphocreatine [PCr] resynthesis following exercise or exertion);
n) reducing oxidative stress and/or reducing reactive oxygen species (ROS);
o) improving mood disorders and/or depression;
p) improving cognitive function;
q) increasing skeletal muscle or other organ vascular perfusion;
r) improving endothelial function;
s) decreasing or preventing diabetes (e.g., new onset diabetes); or
t) improving inflammation.

In some embodiments of any of the compositions or methods disclosed herein, the composition further comprises one or both of L-glycine and L-serine. In certain embodiments, the composition comprises an L-amino acid entity, an I-amino acid entity, an V-amino acid entity, an R-amino acid entity, an L-glutamine or a salt thereof, an NAC or a salt thereof, and an L-glycine. In certain embodiments, the composition comprises an L-amino acid entity, an I-amino acid entity, an V-amino acid entity, an R-amino acid entity, an L-glutamine or a salt thereof, an NAC or a salt thereof, and an L-serine. In certain embodiments, the composition comprises an L-amino acid entity, an I-amino acid entity, an V-amino acid entity, an R-amino acid entity, an L-glutamine or a salt thereof, an NAC or a salt thereof, an L-glycine, and an L-serine. In any of the aforesaid embodiments in this paragraph, the wt. ratio of the L-amino acid entity, the I-amino acid entity, the V-amino acid entity, the R-amino acid entity, the L-glutamine or salt thereof, and the NAC or salt thereof is about 1:0.5:0.5:1.5:2:0.15 or about 1:0.5:0.5:1.5:2:0.3. In any of the aforesaid embodiments in this paragraph, the wt. ratio of the L-amino acid entity, the I-amino acid entity, the V-amino acid entity, the R-amino acid entity, the L-glutamine or salt thereof, and the NAC or salt thereof is about 1:0.5:0.5:1.81:2:0.15. In any of the aforesaid embodiments in this paragraph, the wt. ratio of the L-amino acid entity, the I-amino acid entity, the V-amino acid entity, the R-amino acid entity, the L-glutamine or salt thereof, and the NAC or salt thereof is about 1+/−15%: 0.5+/−15%:0.5+/−15%:1.5+/−15%:2+/−15%:0.15+/−15% or about 1+/−15%:0.5+/−15%:0.5+/−15%:1.5+/−15%: 2+/−15%:0.3+/−15%. In any of the aforesaid embodiments in this paragraph, the wt. ratio of the L-amino acid entity, the I-amino acid entity, the V-amino acid entity, the R-amino acid entity, the L-glutamine or salt thereof, and the NAC or salt thereof is about 1+/−15%:0.5+/−15%:0.5+/−15%: 1.81+/−15%:2+/−15%:0.15+/−15%. In any of the aforesaid embodiments in this paragraph, the wt. ratio of the L-amino acid entity, the I-amino acid entity, the V-amino acid entity, the R-amino acid entity, the L-glutamine or salt thereof, and the NAC or salt thereof is about 1+/−20%:0.5+/−20%: 0.5+/−20%:1.5+/−20%:2+/−20%:0.15+/−20% or about 1+/−20%:0.5+/−20%:0.5+/−20%:1.5+/−20%:2+/−20%: 0.3+/−20%. In any of the aforesaid embodiments in this paragraph, the wt. ratio of the L-amino acid entity, the I-amino acid entity, the V-amino acid entity, the R-amino acid entity, the L-glutamine or salt thereof, and the NAC or salt thereof is about 1+/−20%:0.5+/−20%:0.5+/−20%: 1.81+/−20%:2+/−20%:0.15+/−20%. In any of the aforesaid embodiments in this paragraph, the wt. ratio of the L-amino acid entity, the I-amino acid entity, the V-amino acid entity, the R-amino acid entity, the L-glutamine or salt thereof, and the NAC or salt thereof is about 1+/−15%:0.5+/−15%: 0.5+/−15%:1.81+/−15%:1.333+/−15%:0.15+/−15%. In any of the aforesaid embodiments in this paragraph, the wt. ratio of the L-amino acid entity, the I-amino acid entity, the V-amino acid entity, the R-amino acid entity, the L-glutamine or salt thereof, and the NAC or salt thereof is about 1+/−20%:0.5+/−20%:0.5+/−20%:1.81+/−20%: 1.333+/−20%:0.15+/−20%.

In some embodiments of any of the compositions or methods disclosed herein, the wt. ratio of the L-amino acid entity, the R-amino acid entity, the L-glutamine or a salt thereof, and the NAC or salt thereof is about 0.5 to 3:0.5 to 4:1 to 4:0.1 to 2.5, e.g., the wt. ratio of the L-amino acid entity, the R-amino acid entity, the L-glutamine or a salt thereof, and the NAC or salt thereof is about 1:1.5:2:0.15, about 1:1.5:2:0.225, about 1:1.5:2:0.3, or about 1:1.5:2:0.5. In any of the aforesaid embodiments in this paragraph, the wt. ratio of the L-amino acid entity, the R-amino acid entity, the L-glutamine or a salt thereof, and the NAC or salt thereof is about 1:0.75:2:0.15, about 1:0.75:2:0.225, about 1:0.75: 2:0.3, or about 1:0.75:2:0.5. In certain embodiments, the wt. ratio of the L-amino acid entity, the R-amino acid entity, the L-glutamine or a salt thereof, and the NAC or salt thereof is about 1:1.81:2:0.15. In certain embodiments, the wt. ratio of the L-amino acid entity, the R-amino acid entity, the L-glutamine or a salt thereof, and the NAC or salt thereof is about 1+/−15%:1.81+/−15%:2+/−15%:0.15+/−15%. In certain embodiments, the wt. ratio of the L-amino acid entity, the R-amino acid entity, the L-glutamine or a salt thereof, and the NAC or salt thereof is about 1+/−20%:1.81+/−20%: 2+/−20%:0.15+/−20%. In certain embodiments, the wt. ratio of the L-amino acid entity, the R-amino acid entity, the L-glutamine or a salt thereof, and the NAC or salt thereof is about 1:1.81:1.333:0.15. In certain embodiments, the wt. ratio of the L-amino acid entity, the R-amino acid entity, the L-glutamine or a salt thereof, and the NAC or salt thereof is about 1+/−15%:1.81+/−15%:1.333+/−15%:0.15+/−15%. In certain embodiments, the wt. ratio of the L-amino acid entity, the R-amino acid entity, the L-glutamine or a salt thereof, and the NAC or salt thereof is about 1+/−20%: 1.81+/−20%:1.333+/−20%:0.15+/−20%.

In some embodiments, the wt. ratio of the L-amino acid entity, the I-amino acid entity, the V-amino acid entity, the R-amino acid entity, the L-glutamine or salt thereof, and the NAC or salt thereof is about 1:0.5:0.5:1.5:2:0.15, about 1:0.5:0.5:1.5:2:0.225, about 1:0.5:0.5:1.5:2:0.3, or about 1:0.5:0.5:1.5:2:0.5. In some embodiments, the wt. ratio of the L-amino acid entity, the I-amino acid entity, the V-amino acid entity, the R-amino acid entity, the L-glutamine or salt thereof, and the NAC or salt thereof is about 1:0.5:0.5:1.5: 2:0.15. In some embodiments, the wt. ratio of the L-amino acid entity, the I-amino acid entity, the V-amino acid entity, the R-amino acid entity, the L-glutamine or salt thereof, and the NAC or salt thereof is about 1+/−15%:0.5+/−15%: 0.5+/−15%:1.5+/−15%:2+/−15%:0.15+/−15%. In some embodiments, the wt. ratio of the L-amino acid entity, the I-amino acid entity, the V-amino acid entity, the R-amino acid entity, the L-glutamine or salt thereof, and the NAC or salt thereof is about 1+/−20%:0.5+/−20%:0.5+/−20%: 1.5+/−20%:2+/−20%:0.15+/−20%.

In some embodiments of any of the compositions or methods disclosed herein, the composition comprises about 0.5 g to about 10 g of the L-amino acid entity, about 0.25 g to about 5 g of the I-amino acid entity, about 0.25 g to about 5 g of the V-amino acid entity, about 0.5 g to about 20 g of the R-amino acid entity, about 1 g to about 20 g of the L-glutamine or a salt thereof, and about 0.1 g to about 5 g of the NAC or a salt thereof, e.g., the composition comprises about 1 g of the L-amino acid entity, about 0.5 g of the I-amino acid entity, about 0.5 g of V-amino acid entity, about 1.5 g of R-amino acid entity, about 2 g of L-glutamine or a salt thereof, and about 0.15 g, about 0.225 g, about 0.3 g, or about 0.5 g of NAC or a salt thereof. In certain embodiments, the composition comprises about 0.15 g of NAC. In certain embodiments, the composition comprises about 0.3 g of NAC. In embodiments, the composition comprises about 4 g of the L-amino acid entity, about 2 g of the I-amino acid entity, about 1 g of V-amino acid entity, about 3 g of R-amino acid entity, about 4 g of L-glutamine or a salt thereof, and about 0.9 g of NAC or a salt thereof. In embodiments, the composition comprises about 4 g of the L-amino acid entity, about 2 g of the I-amino acid entity, about 1 g of V-amino acid entity, about 3 g of R-amino acid entity, about 4 g of L-glutamine or a salt thereof, about 0.9 g of NAC or a salt thereof, and about 6 g of L-serine or a salt thereof. In embodiments, the composition comprises about 4 g of the L-amino acid entity, about 2 g of the I-amino acid entity, about 1 g of V-amino acid entity, about 3 g of R-amino acid entity, about 4 g of L-glutamine or a salt thereof, about 0.9 g of NAC or a salt thereof, and about 6.67 g of L-serine or a salt thereof. In embodiments, the composition comprises about 4 g of the L-amino acid entity, about 2 g of the I-amino acid entity, about 1 g of V-amino acid entity, about 3 g of R-amino acid entity, about 4 g of L-glutamine or a salt thereof, about 0.9 g of NAC or a salt thereof, about 3 g of L-serine or a salt thereof, and about 3 g of L-glycine or a salt thereof. In embodiments, the composition comprises about 4 g of the L-amino acid entity, about 2 g of the I-amino acid entity, about 1 g of V-amino acid entity, about 3 g of R-amino acid entity, about 4 g of L-glutamine or a salt thereof, about 0.9 g of NAC or a salt thereof, about 3.33 g of L-serine or a salt thereof, and about 3.33 g of L-glycine or a salt thereof.

In some embodiments of any of the compositions or methods disclosed herein, the composition comprises:
  a) L-Leucine or a salt thereof,
  b) L-Isoleucine or a salt thereof,
  c) L-Valine or a salt thereof;
  d) L-Arginine or a salt thereof;
  e) L-Glutamine or a salt thereof; and
  f) NAC or a salt thereof.

In some embodiments of any of the compositions or methods disclosed herein, the composition comprises:
  a) L-Leucine or a salt thereof,
  b) L-Isoleucine or a salt thereof,
  c) L-Valine or a salt thereof;
  d) L-Arginine or a salt thereof;
  e) L-Glutamine or a salt thereof;
  f) NAC or a salt thereof,
  g) L-Histidine or a salt thereof;
  h) L-Lysine or a salt thereof,
  i) L-Phenylalanine or a salt thereof,
  j) L-Threonine or a salt thereof.

In an embodiment, L-Leucine is provided as part of a dipeptide comprising L-Leucine, or a salt thereof, or a tripeptide comprising L-Leucine, or a salt thereof.

In an embodiment, L-Isoleucine is provided as part of a dipeptide comprising L-Isoleucine, or a salt thereof, or a tripeptide comprising L-Isoleucine, or a salt thereof.

In an embodiment, L-Valine is provided as part of a dipeptide comprising L-Valine, or a salt thereof, or a tripeptide comprising L-Valine, or a salt thereof.

In an embodiment, L-Arginine is provided as part of a dipeptide comprising L-Arginine, or a salt thereof, or a tripeptide comprising L-Arginine, or a salt thereof.

In an embodiment L-Glutamine is provided as part of a dipeptide comprising L-Glutamine, or a salt thereof, or a tripeptide comprising L-Glutamine, or a salt thereof.

In an embodiment NAC is provided as a part of a dipeptide comprising NAC, or a salt thereof, or a tripeptide comprising NAC, or a salt thereof.

In an embodiment, L-histidine is provided as part of a dipeptide comprising L-histidine, or a salt thereof, or a tripeptide comprising L-histidine, or a salt thereof.

In an embodiment, L-lysine is provided as part of a dipeptide comprising L-lysine, or a salt thereof, or a tripeptide comprising L-lysine, or a salt thereof.

In an embodiment, L-phenylalanine is provided as part of a dipeptide comprising L-phenylalanine, or a salt thereof, or a tripeptide comprising L-phenylalanine, or a salt thereof.

In an embodiment, L-threonine is provided as part of a dipeptide comprising L-threonine, or a salt thereof, or a tripeptide comprising L-threonine, or a salt thereof.

In some embodiments of any of the compositions or methods disclosed herein, the composition comprises a combination of 4 to 20 different amino acid entities, e.g., a combination of 5 to 15 different amino acid entities.

Another aspect of the invention features a method for improving one or more symptoms of post-acute sequelae of COVID-19, wherein the method comprises administering to a subject in need thereof an effective amount of a composition comprising:

a) a L-amino acid entity chosen from L-leucine or a salt thereof, or β-hydroxy-β-methylbutyrate (HMB) or a salt thereof, or a combination of L-leucine or a salt thereof and HMB or a salt thereof;

b) an R-amino acid entity chosen from: L-arginine or a salt thereof, ornithine or a salt thereof, or creatine or a salt thereof, or a combination of two or three of L-arginine or a salt thereof, ornithine or a salt thereof, or creatine or a salt thereof;

c) L-glutamine or a salt thereof; and d) N-acetylcysteine (NAC) or a salt thereof.

In an embodiment, L-Leucine is provided as part of a dipeptide comprising L-Leucine, or a salt thereof, or a tripeptide comprising L-Leucine, or a salt thereof.

In an embodiment, L-Arginine is provided as part of a dipeptide comprising L-Arginine, or a salt thereof, or a tripeptide comprising L-Arginine, or a salt thereof.

In an embodiment L-Glutamine is provided as part of a dipeptide comprising L-Glutamine, or a salt thereof, or a tripeptide comprising L-Glutamine, or a salt thereof.

In an embodiment NAC is provided as a part of a dipeptide comprising NAC, or a salt thereof, or a tripeptide comprising NAC, or a salt thereof.

Another aspect of the invention features a method for treating one or more symptoms or signs selected from the group consisting of anorexia, anxiety, arrhythmias, confusion ("brain fog"), dementia, depression, dyspnea, fatigue, hair loss, headache, heart failure, cardiomyopathy, angina, hepatic dysfunction, hyperglycemia, type 2 diabetes, increased heart rate, inflammation, loss of appetite, loss of memory, loss of smell, mood disorder, muscle weakness, myocardial ischemia, post-exertional malaise, diminished neurocognition, diminished sensory function, pulmonary infiltrates or fibrosis, postural orthostatic hypotension, renal dysfunction, and respiratory distress, wherein the method comprises administering to a subject in need thereof an effective amount of a composition comprising:

a) a L-amino acid entity chosen from L-leucine or a salt thereof, or β-hydroxy-β-methylbutyrate (HMB) or a salt thereof, or a combination of L-leucine or a salt thereof and HMB or a salt thereof;

b) an R-amino acid entity chosen from: L-arginine or a salt thereof, ornithine or a salt thereof, or creatine or a salt thereof, or a combination of two or three of L-arginine or a salt thereof, ornithine or a salt thereof, or creatine or a salt thereof;

c) L-glutamine or a salt thereof, and d) N-acetylcysteine (NAC) or a salt thereof.

In an embodiment, L-Leucine is provided as part of a dipeptide comprising L-Leucine, or a salt thereof, or a tripeptide comprising L-Leucine, or a salt thereof.

In an embodiment, L-Arginine is provided as part of a dipeptide comprising L-Arginine, or a salt thereof, or a tripeptide comprising L-Arginine, or a salt thereof.

In an embodiment L-Glutamine is provided as part of a dipeptide comprising L-Glutamine, or a salt thereof, or a tripeptide comprising L-Glutamine, or a salt thereof.

In an embodiment NAC is provided as a part of a dipeptide comprising NAC, or a salt thereof, or a tripeptide comprising NAC, or a salt thereof.

Another aspect of the invention features a method for treating post-acute sequelae of COVID-19, wherein the method comprises administering to a subject in need thereof an effective amount of a composition comprising:

a) a L-amino acid entity chosen from L-leucine or a salt thereof, or β-hydroxy-β-methylbutyrate (HMB) or a salt thereof, or a combination of L-leucine or a salt thereof and HMB or a salt thereof;

b) an R-amino acid entity chosen from: L-arginine or a salt thereof, ornithine or a salt thereof, or creatine or a salt thereof, or a combination of two or three of L-arginine or a salt thereof, ornithine or a salt thereof, or creatine or a salt thereof;

c) L-glutamine or a salt thereof, and d) N-acetylcysteine (NAC) or a salt thereof.

In an embodiment, L-Leucine is provided as part of a dipeptide comprising L-Leucine, or a salt thereof, or a tripeptide comprising L-Leucine, or a salt thereof.

In an embodiment, L-Arginine is provided as part of a dipeptide comprising L-Arginine, or a salt thereof, or a tripeptide comprising L-Arginine, or a salt thereof.

In an embodiment L-Glutamine is provided as part of a dipeptide comprising L-Glutamine, or a salt thereof, or a tripeptide comprising L-Glutamine, or a salt thereof.

In an embodiment NAC is provided as a part of a dipeptide comprising NAC, or a salt thereof, or a tripeptide comprising NAC, or a salt thereof.

In some embodiments of any of the compositions or methods disclosed herein, e.g., of any of the methods described herein, the subject has a disease or disorder selected from the group consisting of a mitochondrial disease or disorder, a musculoskeletal disease or disorder, a neurocognitive disease or disorder, or a pulmonary disease or disorder.

In some embodiments of any of the compositions or methods disclosed herein, e.g., of any of the methods described herein, the subject has myalgia, fibromyalgia, idiopathic pulmonary fibrosis, fatigue, muscle fatigue, mitochondrial dysfunction (e.g., increase lactic acid production), dyspnea after exertion, postural orthostatic tachycardia syndrome, tachycardia, mood disorders, or depression.

In some embodiments of any of the compositions or methods disclosed herein, e.g., of any of the methods described herein, the subject has immunologic symptoms or signs, metabolic symptoms or signs, and/or neurologic symptoms or signs. In some embodiments, an immunologic symptom or sign is selected from the group consisting of increased markers of inflammation (e.g., erythrocyte sedimentation rate, c reactive protein), increased proinflammatory cytokines (e.g., CRP, IL-1A, IL-17a, TNF-alpha), decreased cytotoxicity of natural killer cells, expression of cytolytic proteins, and production of cytokines, increased CD8+ cytotoxic T cells with CD38 activation antigen, T cell exhaustion, and increased autoantibodies, especially against targets in CNS and autonomic nervous system. In some embodiments, a metabolic symptom or sign is selected from the group consisting of increased lactic acid, reduced ATP generation from glucose by the tricarboxylic acid (TCA) cycle, reduced levels of fatty acids and of acyl-carnitine, reduced levels of amino acids via the urea cycle, impaired oxidative phosphorylation, redox imbalance (e.g., increased levels of oxidants, e.g., peroxides and superoxides, isoprostanes, at rest and/or after exercise or exertion; decreased levels of antioxidants, e.g., decreased levels of alpha-tocopherol, e.g., thiobarbituric acid reactive substances), increased inducible nitric oxide synthase (iNOS), increased NFκB, increased nitric oxide (NO), peroxynitrite, and/or nitrate (e.g., after exercise or exertion), elevated levels of brain ventricular lactic acid, and increased blood glucose (e.g., new onset diabetes). In some embodiments, a neurologic symptom or sign is selected from the group consisting of cognitive deficits (e.g., in attention and reaction time), impaired response to cognitive, motor, visual, and auditory challenges, abnormal nerve conduction studies, abnormal imaging of the brain, hypoperfusion and/or metabolic dysfunction of glial cells, neuroinflammation characterized by widespread activation of both astrocytes and microglia, downregulation of the hypothalamic-pituitary-adrenal (HPA) axis, impaired response of one region of the brain to signals from another region (impaired connectivity), disordered sympathetic and parasympathetic activity, increased levels of tissue repair-indicative proteins (e.g., alpha-2-macroglobulin, keratin 16, orosomucoid), autoantibodies targeting cholinergic, adrenergic, and muscarinic receptors, reduced anaerobic threshold and/or reduced peak work (e.g., after exercise or exertion), and increased lactic acid in muscle and the need to recruit additional brain regions to respond to cognitive challenges (by functional MRI) (e.g., following exertion).

In some embodiments of any of the compositions or methods disclosed herein, e.g., of any of the methods described herein, the subject has increased levels of inflammatory cytokines relative to a normal subject, e.g., the subject has increased levels of CRP or TNFα relative to a normal subject e.g., without the one or more symptoms or without post-acute sequelae of COVID-19.

In some embodiments, e.g., of any of the methods described herein, the subject exhibits muscle atrophy or has a decreased ratio of muscle tissue to adipose tissue relative to a normal subject, e.g., without the one or more symptoms or without post-acute sequelae of COVID-19.

In some embodiments, e.g., of any of the methods described herein, the subject exhibits brain fog or has a decreased neurocognitive function relative to a normal subject, e.g., without the one or more symptoms or without post-acute sequelae of COVID-19.

In some embodiments, e.g., of any of the methods described herein, the subject exhibits dyspnea or has a decreased pulmonary function relative to a normal subject, e.g., without the one or more symptoms or without post-acute sequelae of COVID-19.

In some embodiments, e.g., of any of the methods described herein, the subject exhibits decreased metabolic function relative to a normal subject, e.g., without the one or more symptoms or without post-acute sequelae of COVID-19.

In some embodiments, e.g., of any of the methods described herein, the subject exhibits abnormal (e.g., increased) immunologic function relative to a normal subject, e.g., without the one or more symptoms or without post-acute sequelae of COVID-19.

In some embodiments, e.g., of any of the methods described herein, the subject is treated with a composition, e.g., any composition as described herein. In some embodiments of any of the aspects described herein:
(i) an amino acid entity (e.g., at least one, two, or three of the amino acid entities) of
(a) is selected from Table 2; and/or
(ii) one or both of the R-amino acid entity and the Q-amino acid entity are present at a higher amount (wt. %) than the L-amino acid entity.

Use of a composition for the treatment of post-acute sequelae of COVID-19, the composition comprising:
a) a leucine (L)-amino acid entity;
b) an arginine (R)-amino acid entity;
c) a glutamine (Q)-amino acid entity; and
d) a N-acetylcysteine (NAC) entity, e.g., NAC.

Use of a composition for the treatment of one or more symptoms or signs selected from the group consisting of anorexia, anxiety, arrhythmias, confusion ("brain fog"), dementia, depression, dyspnea, fatigue, hair loss, headache, heart failure, cardiomyopathy, angina increased heart rate, loss of appetite, loss of memory, loss of smell, mood disorder, myocardial ischemia, post-exertional malaise, diminished neurocognition, diminished sensory function, pulmonary infiltrates or fibrosis, postural orthostatic hypotension, renal dysfunction, and respiratory distress, wherein the composition comprises:
a) a leucine (L)-amino acid entity;
b) an arginine (R)-amino acid entity;
c) a glutamine (Q)-amino acid entity; and
d) a N-acetylcysteine (NAC) entity, e.g., NAC.

Use of a composition for the treatment of one or more symptoms or signs selected from the group consisting of myalgia, fibromyalgia, idiopathic pulmonary fibrosis, fatigue, muscle fatigue, muscle dysfunction, mitochondrial dysfunction, dyspnea after exertion, postural orthostatic tachycardia syndrome, tachycardia, mood disorders, and depression, wherein the composition comprises:
a) a leucine (L)-amino acid entity;
b) an arginine (R)-amino acid entity;
c) a glutamine (Q)-amino acid entity; and
d) a N-acetylcysteine (NAC) entity, e.g., NAC.

Use of a composition for the treatment of myalgia, wherein the composition comprises:
a) a leucine (L)-amino acid entity;
b) an arginine (R)-amino acid entity;
c) a glutamine (Q)-amino acid entity; and
d) a N-acetylcysteine (NAC) entity, e.g., NAC.

Use of a composition for the treatment of idiopathic pulmonary fibrosis (IPF), wherein the composition comprises:
a) a leucine (L)-amino acid entity;
b) an arginine (R)-amino acid entity;
c) a glutamine (Q)-amino acid entity; and
d) a N-acetylcysteine (NAC) entity, e.g., NAC.

Use of a composition for the treatment of fatigue and/or muscle fatigue, wherein the composition comprises:
a) a leucine (L)-amino acid entity;
b) an arginine (R)-amino acid entity;
c) a glutamine (Q)-amino acid entity; and
d) a N-acetylcysteine (NAC) entity, e.g., NAC.

Use of a composition for the treatment of mitochondrial dysfunction, wherein the composition comprises:
a) a leucine (L)-amino acid entity;
b) an arginine (R)-amino acid entity;
c) a glutamine (Q)-amino acid entity; and
d) a N-acetylcysteine (NAC) entity, e.g., NAC.

Use of a composition for the treatment of dyspnea after exertion, wherein the composition comprises:
a) a leucine (L)-amino acid entity;
b) an arginine (R)-amino acid entity;
c) a glutamine (Q)-amino acid entity; and
d) a N-acetylcysteine (NAC) entity, e.g., NAC.

Use of a composition for the treatment of confusion, wherein the composition comprises:
a) a leucine (L)-amino acid entity;
b) an arginine (R)-amino acid entity;

c) a glutamine (Q)-amino acid entity; and
d) a N-acetylcysteine (NAC) entity, e.g., NAC.

Use of a composition for the treatment of myalgic encephalomyelitis/chronic fatigue syndrome (ME/CFS), wherein the composition comprises:
a) a leucine (L)-amino acid entity;
b) an arginine (R)-amino acid entity;
c) a glutamine (Q)-amino acid entity; and
d) a N-acetylcysteine (NAC) entity, e.g., NAC.

The use of a composition in the manufacture of a treatment for post-acute sequelae of COVID-19, the composition comprising:
a) a leucine (L)-amino acid entity;
b) an arginine (R)-amino acid entity;
c) a glutamine (Q)-amino acid entity; and
d) a N-acetylcysteine (NAC) entity, e.g., NAC.

The use of a composition in the manufacture of a treatment for one or more symptoms or signs selected from the group consisting of anorexia, anxiety, arrhythmias, confusion ("brain fog"), dementia, depression, dyspnea, fatigue, hair loss, headache, heart failure, cardiomyopathy, angina increased heart rate, loss of appetite, loss of memory, loss of smell, mood disorder, myocardial ischemia, post-exertional malaise, diminished neurocognition, diminished sensory function, pulmonary infiltrates or fibrosis, postural orthostatic hypotension, renal dysfunction, and respiratory distress, wherein the composition comprises:
a) a leucine (L)-amino acid entity;
b) an arginine (R)-amino acid entity;
c) a glutamine (Q)-amino acid entity; and
d) a N-acetylcysteine (NAC) entity, e.g., NAC.

The use of a composition in the manufacture of a treatment for one or more symptoms or signs selected from the group consisting of myalgia, fibromyalgia, idiopathic pulmonary fibrosis, fatigue, muscle fatigue, muscle dysfunction, mitochondrial dysfunction, dyspnea after exertion, postural orthostatic tachycardia syndrome, tachycardia, mood disorders, and depression, wherein the composition comprises:
a) a leucine (L)-amino acid entity;
b) an arginine (R)-amino acid entity;
c) a glutamine (Q)-amino acid entity; and
d) a N-acetylcysteine (NAC) entity, e.g., NAC.

The use of a composition in the manufacture of a treatment for myalgia, wherein the composition comprises:
a) a leucine (L)-amino acid entity;
b) an arginine (R)-amino acid entity;
c) a glutamine (Q)-amino acid entity; and
d) a N-acetylcysteine (NAC) entity, e.g., NAC.

The use of a composition in the manufacture of a treatment for idiopathic pulmonary fibrosis (IPF), wherein the composition comprises:
a) a leucine (L)-amino acid entity;
b) an arginine (R)-amino acid entity;
c) a glutamine (Q)-amino acid entity; and
d) a N-acetylcysteine (NAC) entity, e.g., NAC.

The use of a composition in the manufacture of a treatment for fatigue and/or muscle fatigue, wherein the composition comprises:
a) a leucine (L)-amino acid entity;
b) an arginine (R)-amino acid entity;
c) a glutamine (Q)-amino acid entity; and
d) a N-acetylcysteine (NAC) entity, e.g., NAC.

The use of a composition in the manufacture of a treatment for mitochondrial dysfunction, wherein the composition comprises:
a) a leucine (L)-amino acid entity;
b) an arginine (R)-amino acid entity;
c) a glutamine (Q)-amino acid entity; and
d) a N-acetylcysteine (NAC) entity, e.g., NAC.

The use of a composition in the manufacture of a treatment for dyspnea after exertion, wherein the composition comprises:
a) a leucine (L)-amino acid entity;
b) an arginine (R)-amino acid entity;
c) a glutamine (Q)-amino acid entity; and
d) a N-acetylcysteine (NAC) entity, e.g., NAC.

The use of a composition in the manufacture of a treatment for confusion, wherein the composition comprises:
a) a leucine (L)-amino acid entity;
b) an arginine (R)-amino acid entity;
c) a glutamine (Q)-amino acid entity; and
d) a N-acetylcysteine (NAC) entity, e.g., NAC.

The use of a composition in the manufacture of a treatment for myalgic encephalomyelitis/chronic fatigue syndrome (ME/CFS), wherein the composition comprises:
a) a leucine (L)-amino acid entity;
b) an arginine (R)-amino acid entity;
c) a glutamine (Q)-amino acid entity; and
d) a N-acetylcysteine (NAC) entity, e.g., NAC.

A composition for use in the treatment of post-acute sequelae of COVID-19, the composition comprising:
a) a leucine (L)-amino acid entity;
b) an arginine (R)-amino acid entity;
c) a glutamine (Q)-amino acid entity; and
d) a N-acetylcysteine (NAC) entity, e.g., NAC.

A composition for use in the treatment of one or more symptoms or signs selected from the group consisting of anorexia, anxiety, arrhythmias, confusion ("brain fog"), dementia, depression, dyspnea, fatigue, hair loss, headache, heart failure, cardiomyopathy, angina increased heart rate, loss of appetite, loss of memory, loss of smell, mood disorder, myocardial ischemia, post-exertional malaise, diminished neurocognition, diminished sensory function, pulmonary infiltrates or fibrosis, postural orthostatic hypotension, renal dysfunction, and respiratory distress, wherein the composition comprises:
a) a leucine (L)-amino acid entity;
b) an arginine (R)-amino acid entity;
c) a glutamine (Q)-amino acid entity; and
d) a N-acetylcysteine (NAC) entity, e.g., NAC.

A composition for use in the treatment of one or more symptoms or signs selected from the group consisting of myalgia, fibromyalgia, idiopathic pulmonary fibrosis, fatigue, muscle fatigue, muscle dysfunction, mitochondrial dysfunction, dyspnea after exertion, postural orthostatic tachycardia syndrome, tachycardia, mood disorders, and depression, wherein the composition comprises:
a) a leucine (L)-amino acid entity;
b) an arginine (R)-amino acid entity;
c) a glutamine (Q)-amino acid entity; and
d) a N-acetylcysteine (NAC) entity, e.g., NAC.

A composition for use in the treatment of myalgia, wherein the composition comprises:
a) a leucine (L)-amino acid entity;
b) an arginine (R)-amino acid entity;
c) a glutamine (Q)-amino acid entity; and
d) a N-acetylcysteine (NAC) entity, e.g., NAC.

A composition for use in the treatment of idiopathic pulmonary fibrosis (IPF), wherein the composition comprises:
- a) a leucine (L)-amino acid entity;
- b) an arginine (R)-amino acid entity;
- c) a glutamine (Q)-amino acid entity; and
- d) a N-acetylcysteine (NAC) entity, e.g., NAC.

A composition for use in the treatment of fatigue and/or muscle fatigue, wherein the composition comprises:
- a) a leucine (L)-amino acid entity;
- b) an arginine (R)-amino acid entity;
- c) a glutamine (Q)-amino acid entity; and
- d) a N-acetylcysteine (NAC) entity, e.g., NAC.

A composition for use in the treatment of mitochondrial dysfunction, wherein the composition comprises:
- a) a leucine (L)-amino acid entity;
- b) an arginine (R)-amino acid entity;
- c) a glutamine (Q)-amino acid entity; and
- d) a N-acetylcysteine (NAC) entity, e.g., NAC.

A composition for use in the treatment of dyspnea after exertion, wherein the composition comprises:
- a) a leucine (L)-amino acid entity;
- b) an arginine (R)-amino acid entity;
- c) a glutamine (Q)-amino acid entity; and
- d) a N-acetylcysteine (NAC) entity, e.g., NAC.

A composition for use in the treatment of confusion, wherein the composition comprises:
- a) a leucine (L)-amino acid entity;
- b) an arginine (R)-amino acid entity;
- c) a glutamine (Q)-amino acid entity; and
- d) a N-acetylcysteine (NAC) entity, e.g., NAC.

A composition for use in the treatment of myalgic encephalomyelitis/chronic fatigue syndrome (ME/CFS), wherein the composition comprises:
- a) a leucine (L)-amino acid entity;
- b) an arginine (R)-amino acid entity;
- c) a glutamine (Q)-amino acid entity; and
- d) a N-acetylcysteine (NAC) entity, e.g., NAC.

DETAILED DESCRIPTION

Figure 1:
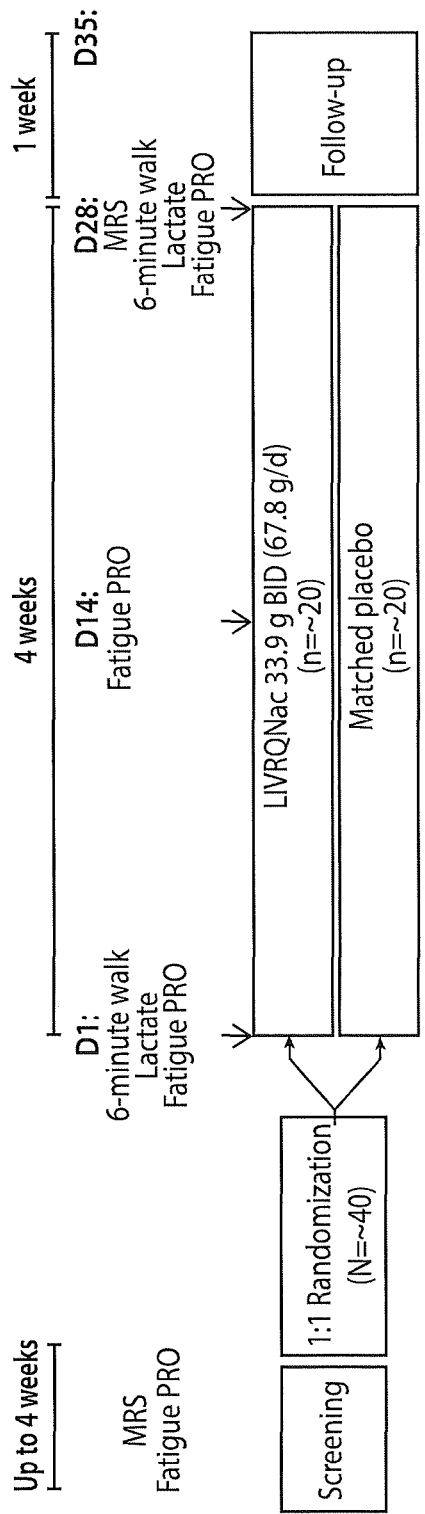
FIG. 1 is a schematic of the timeline for the study as described in Example 9.

The present invention provides, at least in part, methods and compositions comprising at least four different amino acid entities, and uses thereof for treating post-acute sequelae of COVID-19 (PASC). In some embodiments, the composition is capable of one or more of:
a) decreasing or preventing myalgia;
b) decreasing or preventing fibromyalgia;
c) decreasing or preventing idiopathic pulmonary fibrosis;
d) decreasing or preventing fatigue;
e) decreasing or preventing muscle fatigue;
f) decreasing or preventing muscle dysfunction;
g) decreasing or mitochondrial dysfunction;
h) decreasing or preventing dyspnea after exertion;
i) improving exercise tolerance or the ability to conduct activities of daily living;
j) decreasing or preventing postural orthostatic tachycardia syndrome; or
k) decreasing or preventing tachycardia;
l) improving mitochondrial function;
m) improving mitochondrial capacity or energetics (e.g., improvement in oxidative ATP synthesis, phosphocreatine [PCr] resynthesis following exercise or exertion);
n) reducing oxidative stress and/or reducing reactive oxygen species (ROS);
o) improving mood disorders and/or depression;
p) improving cognitive function;
q) increasing skeletal muscle or other organ vascular perfusion;
r) improving endothelial function;
s) decreasing or preventing diabetes (e.g., new onset diabetes); or
t) improving inflammation.

In some embodiments, the composition comprises a leucine (L)-amino acid entity, an arginine (R)-amino acid entity, a glutamine (Q)-amino acid entity; and an antioxidant or reactive oxygen species (ROS) scavenger (e.g., a N-acetylcysteine (NAC) entity, e.g., NAC).

The composition described herein can be administered to a subject to provide a beneficial effect in one or both of improving symptoms of or treating (e.g., reversing, reducing, ameliorating, or preventing) post-acute sequelae of COVID-19. A subject that may be treated with the composition include a subject having post-acute sequelae of COVID-19, such as mitochondrial dysfunction, metabolic dysfunction, musculoskeletal dysfunction, immunologic dysfunction, neurocognitive and sensory dysfunction, and pulmonary dysfunction. In particular, the subject may have one, two, or more (e.g., all) of myalgia, fibromyalgia, idiopathic pulmonary fibrosis, fatigue, muscle fatigue, mitochondrial dysfunction, dyspnea after exertion, postural orthostatic tachycardia syndrome, tachycardia, mood disorders, or depression.

The subject may exhibit an improvement in symptoms of post-acute sequelae of COVID-19 (e.g., improvement in mitochondrial, musculoskeletal, metabolic, immunologic, neurocognitive, and/or pulmonary function) after administration of a composition comprising a L-amino acid entity, a R-amino acid entity, a Q-amino acid entity; and an antioxidant or ROS scavenger, e.g., a NAC entity, e.g., NAC. For example, the amino acid entity composition may be administered to the subject for a treatment period of, e.g., two weeks, three weeks, four weeks, five weeks, six weeks, seven weeks, eight weeks, nine weeks, 10 weeks, 11 weeks, 12 weeks, 13 weeks, 14 weeks, 15 weeks, 16 weeks, or longer at a dose of about 15 total grams per day to about 90 total grams per day (e.g., a total of about 48 g or a total of about 72 g per day). In some embodiments, the composition is administered at a dose of about 30-40 g or 30-36 g, e.g., twice per day.

Treatment with the amino acid entity composition can result in improvement in PASC in a subject, e.g., by one, two, three, four, five, or more (e.g., all) of improved mitochondrial and/or muscle function (e.g. improved mitochondrial function via $^{31}$P MRS), improved functional capacity (e.g., improvement in distance walked in 6 minute walk), decreased fatigue, decreased serum lactate, improved phosphocreatine resynthesis after exercise or exertion, or improved mitochondrial capacity (Qmax, improved oxidative ATP synthesis).

In some embodiments, the composition is for use as a medicament in improving post-acute sequelae of COVID-19 in a subject. In some embodiments, the composition including amino acid entities is for use as a medicament in treating (e.g., reversing, reducing, ameliorating, or preventing) post-acute sequelae of COVID-19 in a subject.

In some embodiments, the composition is for use in the manufacture of a medicament for improving post-acute sequelae of COVID-19 in a subject. In some embodiments, the composition including amino acid entities is for use in the manufacture of a medicament for treating (e.g., reversing, reducing, ameliorating, or preventing) post-acute sequelae of COVID-19 in a subject.

Additionally, the compositions can be used in methods of dietary management of a subject (e.g., a subject with post-acute sequelae of COVID-19).

One embodiment provides a nutritional supplement, dietary formulation, functional food, medical food, food, or beverage comprising a composition described herein. Another embodiment provides a nutritional supplement, dietary formulation, functional food, medical food, food, or beverage comprising a composition described herein for use in the management of any of the diseases or disorders described herein.

One embodiment provides a method of maintaining or improving mitochondrial, musculoskeletal, metabolic, immunologic, neurocognitive, and/or pulmonary health comprising administering to a subject an effective amount of a composition described herein. Another embodiment provides a method of providing nutritional support or supplementation to a subject with post-acute sequelae of COVID-19 comprising administering to the subject an effective amount of a composition described herein. Yet another embodiment provides a method of providing nutritional supplementation that aids in the management of post-acute sequelae of COVID-19 comprising administering to the subject in need thereof an effective amount of a composition described herein.

Definitions

Terms used in the claims and specification are defined as set forth below unless otherwise specified.

It must be noted that, as used in the specification and the appended claims, the singular forms "a," "an" and "the" include plural referents unless the context clearly dictates otherwise.

As used herein, the term "amino acid entity" refers to a (L)-amino acid in free form or salt form (or both), the L-amino acid residue in a peptide smaller than 20 amino acid residues (e.g., oligopeptide, e.g., a dipeptide or a tripeptide), a derivative of the amino acid, a precursor of the amino acid, or a metabolite of the amino acid (see, e.g., Table 2). An amino acid entity includes a derivative of the amino acid, a precursor of the amino acid, a metabolite of the amino acid, or a salt form of the amino acid that is capable of effecting biological functionality of the free L-amino acid. An amino acid entity does not include a naturally occurring polypeptide or protein of greater than 20 amino acid residues, either in whole or modified form, e.g., hydrolyzed form.

As used herein the term "XXX amino acid entity" refers to an amino acid entity that if a free amino acid, comprises free XXX or XXX in salt form; if a peptide, refers to a peptide (e.g., a dipeptide or a tripeptide) comprising an XXX residue; if a derivative, refers to a derivative of XXX; if a precursor, refers to a precursor of XXX; and if a metabolite, refers to a XXX metabolite. For example, where XXX is leucine (L), then L-amino acid entity refers to free L or L in salt form, a peptide (e.g., a dipeptide or a tripeptide) comprising a L residue, a L derivative, a L precursor, or a metabolite of L; where XXX is arginine (R), then R-amino acid entity refers to free R or R in salt form, a peptide (e.g., a dipeptide or a tripeptide) comprising a R residue, a R derivative, a R precursor, or a metabolite of R; where XXX is glutamine (Q), then Q-amino acid entity refers to free Q or Q in salt form, a peptide (e.g., a dipeptide or a tripeptide) comprising a Q residue, a Q derivative, a Q precursor, or a metabolite of Q; and where XXX is N-acetylcysteine (NAC), then NAC entity refers to free NAC or NAC in salt form, a peptide (e.g., a dipeptide or a tripeptide) comprising a NAC residue, a NAC derivative, a NAC precursor, or a metabolite of NAC.

"About" and "approximately" shall generally mean an acceptable degree of error for the quantity measured given the nature or precision of the measurements. Exemplary degrees of error are within 20 percent (%), typically, within 15%, more typically, within 10%, and more typically, within 5% of a given value or range of values.

An "amino acid" refers to an organic compound having an amino group (—NH$_2$), a carboxylic acid group (—C(=O)OH), and a side chain bonded through a central carbon atom, and includes essential and non-essential amino acids, as well as natural and unnatural amino acids.

The proteogenic amino acids, shown below, are known by three- and one-letter abbreviations in addition to their full names. For a given amino acid, these abbreviations are used interchangeably herein. For example, Leu, L or leucine all refer to the amino acid leucine; Ile, I or isoleucine all refer to the amino acid isoleucine; Val, V or valine all refer to the amino acid valine; Arg, R or arginine all refer to the amino acid arginine; and Gln, Q or glutamine all refer to the amino acid glutamine.

Likewise, the non-natural amino acid derivative N-acetylcysteine may be referred to interchangeably by "NAC" or "N-acetylcysteine."

Amino acids may be present as D- or L-isomers. Unless otherwise indicated, amino acids referred to herein are L-isomers of amino acids.

TABLE 1

Amino acid names and abbreviations.

| Amino acid | Three-letter | One-letter |
|---|---|---|
| Alanine | Ala | A |
| Arginine | Arg | R |
| Asparagine | Asn | N |
| Aspartic acid | Asp | D |
| Cysteine | Cys | C |
| Glutamic acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The term "effective amount" as used herein means an amount of an amino acid, or pharmaceutical composition which is sufficient enough to significantly and positively modify the symptoms and/or conditions to be treated (e.g., to positively modify one, two, or more of a subject's symptoms, e.g., provide a positive clinical response). The effective amount of an active ingredient for use in a pharmaceutical composition will vary with the particular condition being treated, the severity of the condition, the duration of treatment, the nature of concurrent therapy, the particular active ingredient(s) being employed, the particular pharmaceutically-acceptable excipient(s) and/or carrier(s) utilized, and like factors with the knowledge and expertise of the attending physician.

A "pharmaceutical composition" described herein comprises at least one amino acid and a pharmaceutically acceptable carrier or excipient. In some embodiments, the pharmaceutical composition is used as a therapeutic, a nutraceutical, a medical food, or as a supplement.

The term "pharmaceutically acceptable" as used herein, refers to amino acids, materials, excipients, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. This may be a standard used by the pharmaceutical industry or by agencies or entities (e.g., government or trade agencies or entities) regulating the pharmaceutical industry to ensure one or more product quality parameters are within acceptable ranges for a medicine, pharmaceutical composition, treatment, or other therapeutic. A product quality parameter can be any parameter regulated by the pharmaceutical industry or by agencies or entities, e.g., government or trade agencies or entities, including but not limited to composition; composition uniformity; dosage; dosage uniformity; presence, absence, and/or level of contaminants or impurities; and level of sterility (e.g., the presence, absence and/or level of microbes). Exemplary government regulatory agencies include: Federal Drug Administration (FDA), European Medicines Agency (EMA), SwissMedic, China Food and Drug Administration (CFDA), or Japanese Pharmaceuticals and Medical Devices Agency (PMDA).

The term "post acute sequelae of COVID-19" or "PASC" as used herein, refers to symptoms experienced by a subject four or more weeks after initial infection with SARS-CoV-2. Other terms used to describe PASC include long COVID, long haul COVID, post-acute COVID, post-acute COVID syndrome (PACS) and/or chronic COVID.

A composition, formulation or product is "therapeutic" if it provides a beneficial clinical effect. A beneficial clinical effect can be shown by lessening the progression of a disease and/or alleviating one or more symptoms of the disease.

A "unit dose" or "unit dosage" as used herein means an amount or dose of medicine prepared in an individual packet or container for convenience, safety, or monitoring. A "unit dose" or "unit dosage" comprises the drug product or drug products in the form in which they are marketed for use, with a specific mixture of active ingredients and inactive components (excipients), in a particular configuration (such as a capsule shell, for example), and apportioned into a particular dose.

As used herein, the terms "treat," "treating," or "treatment" of PASC refer in one embodiment, to ameliorating PASC, (i.e., slowing or arresting or reducing the development of the disease or at least one of the clinical symptoms thereof). In another embodiment, "treat," "treating," or "treatment" refers to alleviating or ameliorating at least one physical parameter including those which may not be discernible by the patient. In yet another embodiment, "treat," "treating," or "treatment" refers to modulating a symptom of PASC, either physically, (e.g., stabilization of a discernible symptom), physiologically, (e.g., stabilization of a physical parameter), or both. In yet another embodiment, "treat," "treating," or "treatment" refers to preventing or delaying the onset or development or progression of PASC.

Determination of Amino Acid Weight Percent and Amino Acid Ratios in a Composition The weight ratio of a particular amino acid or particular amino acids in a composition or mixture of amino acids is the ratio of the weight of the particular amino acid or amino acids in the composition or mixture compared to the total weight of amino acids present in the composition or mixture. This value is calculated by dividing the weight of the particular amino acid or of the particular amino acids in the composition or mixture by the weight of all amino acids present in the composition or mixture. It is understood that NAC is considered to be an amino acid for the purpose of this calculation.

Compositions Comprising Amino Acid Entities

The present disclosure provides compositions, e.g., pharmaceutical compositions, comprising amino acid entities. These pharmaceutical compositions are made up of amino acid entities including amino acids in one or both of free form or salt form, amino acid residues of a peptide (e.g., of a dipeptide, oligopeptide, or polypeptide), derivatives of an amino acid, precursors of an amino acid, or metabolites of an amino acid. For example, the compositions can include a leucine (L)-amino acid entity, a arginine (R)-amino acid entity, a glutamine (Q)-amino acid entity; and an antioxidant or reactive oxygen species (ROS) scavenger, e.g., a N-acetylcysteine (NAC) entity, e.g., NAC (Table 2).

TABLE 2

Amino acid entities include amino acids, precursors, metabolites, and derivatives of the compositions described herein.

| | Exemplary Amino Acid | Precursors | Metabolites | Derivatives |
| --- | --- | --- | --- | --- |
| L | L-Leucine | Oxo-leucine | HMB (beta-hydroxy-beta-methylbutyrate); Oxo-leucine; Isovaleryl-CoA | N-Acetyl-Leucine |
| I | L-Isoleucine | 2-Oxo-3-methyl-valerate | 2-Oxo-3-methyl-valerate; Methylbutyryl-CoA | N-Acetyl-Isoleucine |
| V | L-Valine | 2-Oxo-valerate | Isobutyryl-CoA; 3-HIB-CoA; 3-HIB | N-Acetyl-Valine |
| R | L-Arginine | Argininosuccinate; Aspartate | Ornithine; Agmatine; Creatine | N-Acetyl-Arginine; |
| Q | L-Glutamine | Glutamate | Carbamoyl-P; Glutamate | N-Acetyl-Glutamine; |
| NAC | N-Acetylcysteine | Acetyl serine | Glutathione; Homocysteine; Methionine | L-Cysteine; Cystine; Cysteamine |
| G | Glycine | L-Serine | Glutathione; L-Serine | Sarcosine |
| H | L-Histidine | Histidinol; Histidinal; Ribose-5-phosphate | Carnosine; Histamine; Urocanate | N-Acetyl-Histidine |
| K | L-Lysine | Diaminopimelate | Trimethyllysine; Carnitine; Saccharopine | N-Acetyl-Lysine |
| F | L-Phenylalanine | Phenylpyruvate | Tyrosine | N-Acetyl-Phenylalanine |
| T | L-Threonine | Homoserine; O-phosphohomoserine | Oxobutyrate | N-Acetyl-Threonine |
| S | L-Serine | Phosphoserine, P-hydroxypyruvate | Phosphatidylserine | |

It is contemplated a composition described herein may comprise (e.g., as an alternative to serine), glycine, threonine, or a combination of serine and glycine (e.g., a 1:1 ratio of serine and glycine).

The individual amino acid entities are present in the composition, e.g., the amino acid composition, in various amounts or ratios, which can be presented as amount by weight (e.g., in grams), ratio by weight of amino acid entities to each other, amount by mole, amount by weight percent of the composition, amount by mole percent of the composition, caloric content, percent caloric contribution to the composition, etc. Generally, this disclosure will provide grams of an amino acid entity in a dosage form, i.e., the weight of an amino acid entity relative to the weight of the total composition to define the weight percent of the amino acid entity. In some embodiments, the amino acid composition, is provided as a pharmaceutically acceptable preparation (e.g., a pharmaceutical product).

In some embodiments, the total weight of the L-amino acid entity, R-amino acid entity, Q-amino acid entity; and ROS scavenger, e.g., a NAC entity, e.g., NAC, is greater than the total wt. of other amino acid entities in the composition. In certain embodiments, two, three, or more (e.g., all) of methionine (M), tryptophan (W), or valine (V) may be absent from the amino acid entity composition, or if present, are present at less than 2 weight (wt.) %.

In some embodiments, one or both of the R-amino acid entity and the Q-amino acid entity are present at a higher amount (wt. %) than the L-amino acid entity. The R-amino acid entity can be present, e.g., at an amount of at least 2 wt. %, at least 3 wt. %, at least 4 wt. %, at least 5 wt. %, at least 6 wt. %, at least 7 wt. %, or at least 8 wt. % greater than the L-amino acid entity. The Q-amino acid entity can be present, e.g., at an amount of at least 2 wt. %, at least 3 wt. %, at least 4 wt. %, or at least 5 wt. % greater than the L-amino acid entity.

In some embodiments, the L-amino acid entity is selected from the group consisting of a precursor, a metabolite, and a derivative. In certain embodiments, the L-amino acid entity is selected from the group consisting of L-leucine, β-hydroxy-β-methylbutyrate (HMB), oxo-leucine, isovaleryl-CoA, and N-acetylleucine. In one embodiment, the L-amino acid entity is L-leucine. In another embodiment, the L-amino acid entity is HMB.

In some embodiments, the R-amino acid entity is selected from the group consisting of a precursor, a metabolite, and a derivative. In certain embodiments, the R-amino acid entity is selected from the group consisting of L-arginine, ornithine, argininosuccinate, aspartate, agmatine, creatine, and N-acetyl-arginine. In one embodiment, the R-amino acid entity is L-arginine. In one embodiment, the R-amino acid entity is creatine. In another embodiment, the R-amino acid entity is ornithine.

In some embodiments, the Q-amino acid entity is selected from the group consisting of a precursor, a metabolite, and a derivative. In certain embodiments, the Q-amino acid entity is selected from the group consisting of L-glutamine, glutamate, carbamoyl-P, and N-acetylglutamine. In one embodiment, the Q-amino acid entity is L-glutamine.

In some embodiments, the NAC entity is selected from the group consisting of a precursor, a metabolite, and a derivative. In certain embodiments, the NAC entity is selected from the group consisting NAC, acetylserine, homocysteine, methionine, glutathione, cysteine, cystine, and L-cysteine. In one embodiment, the NAC entity is NAC. In one embodiment, the NAC entity is glutathione.

In various embodiments, the composition further comprises one or two additional branched-chain amino acid (BCAA)-entities, e.g., one or both of an isoleucine (I)-amino acid-entity and a valine (V)-amino acid-entity. In some embodiments, both the I-amino acid-entity and the V-amino acid-entity are present. In certain embodiments, the L-amino acid entity is present at a higher amount (% by weight) than one or both of the I-amino acid-entity and the V-amino acid-entity (e.g., the L-amino acid entity is present at an amount of at least 10 wt. %, at least 15 wt. %, at least 20 wt. %, at least 25 wt. %, at least 30 wt. %, at least 35 wt. %, at least 40 wt. %, at least 45 wt. %, or at least 50 wt. % greater than one or both of the I-amino acid-entity and the V-amino acid-entity).

In some embodiments, the I-amino acid entity is selected from the group consisting of a salt, a precursor, a metabolite, and a derivative. In certain embodiments, the I-amino acid entity is selected from the group consisting of L-isoleucine, 2-oxo-3-methyl-valerate, 2-oxo-3-methyl-valerate, methylbutyryl-CoA, and N-acetyl-isoleucine. In one embodiment, the I-amino acid entity is L-isoleucine.

In some embodiments, the V-amino acid entity is selected from the group consisting of a precursor, a metabolite, and a derivative. In certain embodiments, the V-amino acid entity is selected from the group consisting of L-valine, 2-oxo-valerate, isobutyryl-CoA, 3-HIB-CoA, 3-HIB, and N-acetyl-valine. In one embodiment, the V-amino acid entity is L-valine.

In some embodiments, the H-amino acid entity is selected from the group consisting of L-histidine, histidinol, histidinal, ribose-5-phosphate, carnosine, histamine, urocanate, and N-acetyl histidine, or a salt of any of the forgoing. In some embodiments, the H-amino acid entity is L-histidine or a salt thereof.

In some embodiments, the K-amino acid entity is selected from the group consisting of L-lysine, diaminopimelate, trimethyllysine, carnitine, saccharopine, and N-acetyl lysine, or a salt of any of the forgoing. In some embodiments, the K-amino acid entity is L-lysine or a salt thereof.

In some embodiments, the F-amino acid entity is selected from the group consisting of from L-phenylalanine, phenylpyruvate, tyrosine, and N-acetyl-phenylalanine, or a salt of any of the forgoing. In some embodiment, the F-amino acid entity is L-phenylalanine or a salt thereof.

In some embodiments, the T-amino acid entity is selected from the group consisting of L-threonine, homoserine, O-phosphohomoserine, oxobutyrate, and N-acetyl-threonine, or a salt of any of the forgoing. In some embodiments the T-amino acid entity is L-threonine or a salt thereof.

In some embodiments, the composition comprises L-leucine or a leucine metabolite (e.g., HMB), L-arginine or an L-arginine metabolite (e.g., creatine or ornithine), L-glutamine, and NAC or a NAC metabolite, e.g., glutathione. In one embodiment, the composition comprises L-leucine, L-arginine, L-glutamine, and NAC. In one embodiment, the composition comprises HMB, creatine, L-glutamine, and glutathione. In one embodiment, the composition comprises HMB, ornithine, L-glutamine, and glutathione. In one embodiment, the composition comprises HMB, L-arginine, L-glutamine, and NAC. In one embodiment, the composition comprises L-leucine, creatine, L-glutamine, and NAC. In one embodiment, the composition comprises L-leucine, ornithine, L-glutamine, and NAC. In one embodiment, the composition comprises L-leucine, L-arginine, L-glutamine, and glutathione.

In some embodiments, the weight (wt.) ratio of the L-amino acid entity, the R-amino acid entity, the Q-amino acid entity, and the NAC entity is about 0.5 to 3:0.5 to 4:1 to 4:0.1 to 2.5. In one embodiment, the wt. ratio of the L-amino acid entity, the R-amino acid entity, the Q-amino acid entity, and the NAC-entity is about 1:1.5:2:0.15. In one embodiment, the wt. ratio of the L-amino acid entity, the R-amino acid entity, the Q-amino acid entity, and the NAC entity is about 1:1.81:2:0.15. In one embodiment, the wt. ratio of the L-amino acid entity, the R-amino acid entity, the Q-amino acid entity, and the NAC entity is about 1:1.81:1.33:0.15.

In some embodiments, the wt. ratio of the L-amino acid entity, the I-amino acid entity, the V-amino acid entity, the R-amino acid entity, the Q-amino acid entity, and the NAC entity is about 0.5 to 2:0.1 to 1:0.1 to 1:0.5 to 3:0.5 to 4:0.1 to 0.5. In an embodiment, the wt. ratio of the L-amino acid entity, the I-amino acid entity, the V-amino acid entity, the R-amino acid entity, the Q-amino acid entity, and the NAC entity is about 1:0.5:0.5:1.5:2:0.15. In an embodiment, the wt. ratio of the L-amino acid entity, the I-amino acid entity, the V-amino acid entity, the R-amino acid entity, the Q-amino acid entity, and the NAC entity is about 1:0.5:0.5:1.81:2:0.15. In an embodiment, the wt. ratio of the L-amino acid entity, the I-amino acid entity, the V-amino acid entity, the R-amino acid entity, the Q-amino acid entity, and the NAC entity is about 1:0.5:0.5:1.81:1.33:0.15.

In various embodiments, the total wt. of amino acids present is about 2 g to about 60 g. In certain embodiments, the total wt. of amino acids present is about 6 g, about 12 g, about 18 g, about 24 g, or about 48 g. In one embodiment, the total wt. of amino acids present is about 6 g. In one embodiment, the total wt. of amino acids present is about 12 g. In one embodiment, the total wt. of amino acids present is about 18 g. In an embodiment, the total wt. of amino acids present is about 24 g. In one embodiment, the total wt. of amino acids present is about 48 g.

In some embodiments, the composition comprises about 0.5 g to about 10 g of the L-amino acid entity, about 0.25 g to about 5 g of the I-amino acid entity, about 0.25 g to about 5 g of the V-amino acid entity, about 1 g to about 20 g of the R-amino acid entity, about 1 g to about 20 g of the Q-amino acid entity, and about 0.1 g to about 5 g of the NAC entity. In an embodiment, the composition comprises about 1 g of the L-amino acid entity, about 0.5 g of the I-amino acid entity, about 0.5 g of V-amino acid entity, about 1.5 g of R-amino acid entity, about 2 g of Q-amino acid entity, and about 0.15 g of NAC entity. In an embodiment, the composition comprises about 2 g of the L-amino acid entity, about 1 g of the I-amino acid entity, about 1 g of the V-amino acid entity, about 3 g of the R-amino acid entity, about 4 g of the Q-amino acid entity, and about 0.3 g of the NAC entity. In an embodiment, the composition comprises about 4 g of the L-amino acid entity, about 2 g of the I-amino acid entity, about 2 g of the V-amino acid entity, about 6 g of the R-amino acid entity, about 8 g of the Q-amino acid entity, and about 0.6 g of the NAC entity.

In some embodiments, the amino acids comprise about 10 wt % to about 30 wt % leucine, about 5 wt % to about 15 wt % isoleucine, about 5 wt % to about 15 wt % valine, about 15 wt % to about 40 wt % arginine, about 20 wt % to about 50 wt % glutamine, and about 1 wt % to about 8 wt % n-acetylcysteine. In certain embodiments, the amino acids comprise about 16 wt % to about 18 wt % leucine, about 7 wt % to about 9 wt % isoleucine, about 7 wt % to about 9 wt % valine, about 28 wt % to about 32 wt % arginine, about 31 wt % to about 34 wt % glutamine, and about 1 wt % to about 5 wt % n-acetylcysteine. In an embodiment, the amino acids comprise about 16.8 wt % leucine, about 8.4 wt % isoleucine, about 8.4 wt % valine, about 30.4 wt % arginine, about 33.6 wt % glutamine, and about 2.5 wt % n-acetylcysteine.

In any of the foregoing embodiments, at least one amino acid entity is a free amino acid, e.g., one, two, three, or more (e.g., all) amino acid entities are a free amino acid. In some embodiments, the L-amino acid entity, the R-amino acid entity, the Q-amino acid entity, and the NAC entity is a free amino acid entity. In certain embodiment, the L-amino acid entity, the I-amino acid entity, the V-amino acid entity, the R-amino acid entity, the Q-amino acid entity, and the NAC entity a free amino acid.

In any of the foregoing embodiments, at least one amino acid entity is in a salt form, e.g., one, two, three, or more (e.g., all) of the amino acid entities is in a salt form. In some embodiments, wherein the L-amino acid entity, the R-amino acid entity, the Q-amino acid entity, and the NAC entity is in a salt form. In certain embodiments, the L-amino acid entity, the I-amino acid entity, the V-amino acid entity, the R-amino acid entity, the Q-amino acid entity, and the NAC entity is in a salt form.

In any of the foregoing embodiments, the composition comprises a combination of 2 to 20 different amino acid entities, e.g., 5 to 15 different amino acid entities.

In some embodiments, the NAC entity is more stable than cysteine. In certain embodiments, the NAC entity does not comprise cysteine.

In some embodiments, the composition further comprises one, two, three, four, five, six, seven, eight, nine, or more (e.g., all) or more of serine, glycine, glutamine, HMB, arginine, L-leucine, ornithine, L-cysteine, cystine, or glutathione.

In some embodiments, the composition further comprises serine.

In some embodiments, the composition further comprises glycine.

In some embodiments, the composition further comprises carnitine.

In some embodiments, the composition includes arginine, glutamine, N-acetylcysteine, and a branched-chain amino acid (BCAA) chosen from one, two, or all of leucine, isoleucine, and valine.

In some embodiments, the BCAA is leucine.
In some embodiments, the BCAA is isoleucine.
In some embodiments, the BCAA is valine.
In some embodiments, the BCAA is leucine and isoleucine.
In some embodiments, the BCAA is leucine and valine.
In some embodiments, the BCAA is isoleucine and valine.
In some embodiments, the BCAA is leucine, isoleucine, and valine.

In particular, the composition may consist of leucine, isoleucine, valine, arginine, glutamine, and N-acetylcysteine.

In some embodiments, the amino acids leucine, isoleucine, valine, arginine, glutamine and N-acetylcysteine are present in a weight ratio of about 1:0.5:0.5:1.5:2:0.1-0.3. In some embodiments, the amino acids leucine, isoleucine, valine, arginine, glutamine and N-acetylcysteine are present in a weight ratio of about 1:0.5:0.5:1.5:2:0.15. In some embodiments, the amino acids leucine, isoleucine, valine, arginine, glutamine and N-acetylcysteine are present in a weight ratio of about 1:0.5:0.5:1.5:2:0.25. In some embodiments, the amino acids leucine, isoleucine, valine, arginine (e.g., arginine HCl), glutamine and N-acetylcysteine are present in a weight ratio of about 1:0.5:0.5:1.81:2:0.15. In some embodiments, the amino acids leucine, isoleucine, valine, arginine, glutamine and N-acetylcysteine are present in a weight ratio of about 1:0.5:0.5:1.5:2:0.1-0.3. In some embodiments, the amino acids leucine, isoleucine, valine, arginine, glutamine and N-acetylcysteine are present in a weight ratio of about 1+/−15%:0.5+/−15%:0.5+/−15%: 1.5+/−15%:2+/−15%:0.15+/−15%. In some embodiments, the amino acids leucine, isoleucine, valine, arginine, glutamine and N-acetylcysteine are present in a weight ratio of about 1+/−15%:0.5+/−15%:0.5+/−15%:1.5+/−15%: 2+/−15%:0.25+/−15%. In some embodiments, the amino acids leucine, isoleucine, valine, arginine (e.g., arginine HCl), glutamine and N-acetylcysteine are present in a weight ratio of about 1+/−15%:0.5+/−15%:0.5+/−15%: 1.81+/−15%:2+/−15%:0.15+/−15%. In some embodiments, the amino acids leucine, isoleucine, valine, arginine, glutamine and N-acetylcysteine are present in a weight ratio of about 1+/−20%:0.5+/−20%:0.5+/−20%:1.5+/−20%: 2+/−20%:0.15+/−20%. In some embodiments, the amino acids leucine, isoleucine, valine, arginine, glutamine and N-acetylcysteine are present in a weight ratio of about 1+/−20%:0.5+/−20%:0.5+/−20%:1.5+/−20%:2+/−20%: 0.25+/−20%. In some embodiments, the amino acids leucine, isoleucine, valine, arginine (e.g., arginine HCl), glutamine and N-acetylcysteine are present in a weight ratio of about 1+/−20%:0.5+/−20%:0.5+/−20%:1.81+/−20%: 2+/−20%:0.15+/−20%. In some embodiments, the amino acids leucine, isoleucine, valine, arginine (e.g., arginine HCl), glutamine and N-acetylcysteine are present in a weight ratio of about 1+/−20%:0.5+/−20%:0.5+/−20%: 1.81+/−20%:1.333+/−20%:0.15+/−20%.

In some embodiments, the amino acids leucine, isoleucine, valine, arginine (e.g., arginine HCl), glutamine and N-acetylcysteine are present in a weight ratio of about 1:0.5:0.5:1.5-1.81:2:0.1-0.3. In some embodiments, the amino acids leucine, isoleucine, valine, arginine (e.g., arginine HCl), glutamine and N-acetylcysteine are present in a weight ratio of about 1:0.5:0.5:1.5-1.81:2:0.15. In some embodiments, the amino acids leucine, isoleucine, valine, arginine (e.g., arginine HCl), glutamine, and N-acetylcysteine are present in a weight ratio of about 1:0.5:0.5:1.5-1.81: 2:0.25.

In some embodiments, the amino acids leucine, isoleucine, valine, arginine (e.g., arginine HCl), glutamine and N-acetylcysteine are present in a weight ratio of about 1:0.5:0.5:1.81:2:0.1-0.3. In some embodiments, the amino acids leucine, isoleucine, valine, arginine (e.g., arginine HCl), glutamine and N-acetylcysteine are present in a weight ratio of about 1:0.5:0.5:1.81:2:0.15. In some embodiments, the amino acids leucine, isoleucine, valine, arginine (e.g., arginine HCl), glutamine, and N-acetylcysteine are present in a weight ratio of about 1:0.5:0.5:1.81:2:0.25. In some embodiments, the amino acids leucine, isoleucine, valine, arginine (e.g., arginine HCl), glutamine and N-acetylcysteine are present in a weight ratio of about 1+/−15%: 0.5+/−15%:0.5+/−15%:1.81+/−15%:2+/−15%:0.15+/−15%. In some embodiments, the amino acids leucine, isoleucine, valine, arginine (e.g., arginine HCl), glutamine, and N-acetylcysteine are present in a weight ratio of about 1+/−15%: 0.5+/−15%:0.5+/−15%:1.81+/−15%:2+/−15%:0.25+/−15%. In some embodiments, the amino acids leucine, isoleucine, valine, arginine (e.g., arginine HCl), glutamine and N-acetylcysteine are present in a weight ratio of about 1+/−20%: 0.5+/−20%:0.5+/−20%:1.81+/−20%:2+/−20%:0.15+/−20%. In some embodiments, the amino acids leucine, isoleucine, valine, arginine (e.g., arginine HCl), glutamine, and N-acetylcysteine are present in a weight ratio of about 1+/−20%: 0.5+/−20%:0.5+/−20%:1.81+/−20%:2+/−20%:0.25+/−20%.

In some embodiments, the amino acids leucine, isoleucine, valine, arginine (e.g., arginine HCl), glutamine and N-acetylcysteine are present in a weight ratio of about 1+/−15%: 0.5+/−15%:0.5+/−15%:1.81+/−15%:1.333+/−15%: 0.15+/−15%. In some embodiments, the amino acids leucine, isoleucine, valine, arginine (e.g., arginine HCl), glutamine, and N-acetylcysteine are present in a weight ratio of about 1+/−15%:0.5+/−15%:0.5+/−15%:1.81+/−15%: 1.333+/−15%:0.25+/−15%. In some embodiments, the amino acids leucine, isoleucine, valine, arginine (e.g., arginine HCl), glutamine and N-acetylcysteine are present in a weight ratio of about 1+/−20%:0.5+/−20%:0.5+/−20%: 1.81+/−20%:1.333+/−20%:0.15+/−20%. In some embodiments, the amino acids leucine, isoleucine, valine, arginine (e.g., arginine HCl), glutamine, and N-acetylcysteine are present in a weight ratio of about 1+/−20%:0.5+/−20%: 0.5+/−20%:1.81+/−20%:1.333+/−20%:0.25+/−20%.

In some embodiments, the amino acids leucine, isoleucine, valine, arginine HCl, glutamine and N-acetylcysteine are present in a weight ratio of about 1:0.5:0.5:1.5:2:0.1 to 0.3. In some embodiments, the amino acids leucine, isoleucine, valine, arginine HCl, glutamine and N-acetylcysteine are present in a weight ratio of about 1:0.5:0.5:1.5:2:0.25. In some embodiments, the amino acids leucine, isoleucine, valine, arginine HCl, glutamine and N-acetylcysteine are present in a weight ratio of 1:0.5:0.5:1.5:2:0.15. In some embodiments, the amino acids leucine, isoleucine, valine, arginine HCl, glutamine and N-acetylcysteine are present in a weight ratio of about 1:0.5:0.5:1.81:2:0.25. In some embodiments, the amino acids leucine, isoleucine, valine, arginine HCl, glutamine and N-acetylcysteine are present in a weight ratio of 1:0.5:0.5:1.81:2:0.15. In some embodiments, the amino acids leucine, isoleucine, valine, arginine HCl, glutamine and N-acetylcysteine are present in a weight ratio of about 1+/−15%:0.5+/−15%:0.5+/−15%:1.5+/−15%: 2+/−15%:0.25+/−15%. In some embodiments, the amino acids leucine, isoleucine, valine, arginine HCl, glutamine and N-acetylcysteine are present in a weight ratio of 1+/−15%:0.5+/−15%:0.5+/−15%:1.5+/−15%:2+/−15%: 0.15+/−15%. In some embodiments, the amino acids leucine, isoleucine, valine, arginine HCl, glutamine and N-acetylcysteine are present in a weight ratio of about 1+/−15%: 0.5+/−15%:0.5+/−15%:1.81+/−15%:2+/−15%:0.25+/−15%. In some embodiments, the amino acids leucine, isoleucine, valine, arginine HCl, glutamine and N-acetylcysteine are present in a weight ratio of 1+/−15%:0.5+/−15%: 0.5+/−15%:1.81+/−15%:2+/−15%:0.15+/−15%. In some embodiments, the amino acids leucine, isoleucine, valine, arginine HCl, glutamine and N-acetylcysteine are present in a weight ratio of about 1+/−20%:0.5+/−20%:0.5+/−20%: 1.5+/−20%:2+/−20%:0.25+/−20%. In some embodiments, the amino acids leucine, isoleucine, valine, arginine HCl, glutamine and N-acetylcysteine are present in a weight ratio of 1+/−20%:0.5+/−20%:0.5+/−20%:1.5+/−20%:2+/−20%: 0.15+/−20%. In some embodiments, the amino acids leucine, isoleucine, valine, arginine HCl, glutamine and N-acetylcysteine are present in a weight ratio of about 1+/−20%: 0.5+/−20%:0.5+/−20%:1.81+/−20%:2+/−20%:0.25+/−20%. In some embodiments, the amino acids leucine, isoleucine, valine, arginine HCl, glutamine and N-acetylcysteine are present in a weight ratio of 1+/−20%:0.5+/−20%: 0.5+/−20%:1.81+/−20%:2+/−20%:0.15+/−20%.

In some embodiments, the amino acids leucine, isoleucine, valine, arginine HCl, glutamine and N-acetylcysteine are present in a weight ratio of about 1:0.5:0.5:1.81:2:0.1 to 0.3. In some embodiments, the amino acids leucine, isoleucine, valine, arginine HCl, glutamine and N-acetylcysteine are present in a weight ratio of about 1:0.5:0.5:1.81:2:0.25. In some embodiments, the amino acids leucine, isoleucine, valine, arginine HCl, glutamine and N-acetylcysteine are present in a weight ratio of 1:0.5:0.5:1.81:2:0.15. In some embodiments, the amino acids leucine, isoleucine, valine, arginine HCl, glutamine and N-acetylcysteine are present in a weight ratio of 1:0.5:0.5:1.81:1.333:0.15. In some embodiments, the amino acids leucine, isoleucine, valine, arginine HCl, glutamine and N-acetylcysteine are present in a weight ratio of about 1+/−15%:0.5+/−15%:0.5+/−15%: 1.81+/−15%:2+/−15%:0.25+/−15%. In some embodiments, the amino acids leucine, isoleucine, valine, arginine HCl, glutamine and N-acetylcysteine are present in a weight ratio of 1+/−15%:0.5+/−15%:0.5+/−15%:1.81+/−15%:2+/−15%: 0.15+/−15%. In some embodiments, the amino acids leucine, isoleucine, valine, arginine HCl, glutamine and N-acetylcysteine are present in a weight ratio of about 1+/−20%: 0.5+/−20%:0.5+/−20%:1.81+/−20%:2+/−20%:0.25+/−20%. In some embodiments, the amino acids leucine, isoleucine, valine, arginine HCl, glutamine and N-acetylcysteine are present in a weight ratio of 1+/−20%:0.5+/−20%: 0.5+/−20%:1.81+/−20%:2+/−20%:0.15+/−20%.

In some embodiments, the amino acids leucine, isoleucine, valine, arginine HCl, glutamine and N-acetylcysteine are present in a weight ratio of about 1+/−15%:0.5+/−15%: 0.5+/−15%:1.81+/−15%:1.333+/−15%:0.25+/−15%. In some embodiments, the amino acids leucine, isoleucine, valine, arginine HCl, glutamine and N-acetylcysteine are present in a weight ratio of 1+/−15%:0.5+/−15%: 0.5+/−15%:1.81+/−15%:1.333+/−15%:0.15+/−15%. In some embodiments, the amino acids leucine, isoleucine, valine, arginine HCl, glutamine and N-acetylcysteine are present in a weight ratio of about 1+/−20%:0.5+/−20%: 0.5+/−20%:1.81+/−20%:1.333+/−20%:0.25+/−20%. In some embodiments, the amino acids leucine, isoleucine, valine, arginine HCl, glutamine and N-acetylcysteine are present in a weight ratio of 1+/−20%:0.5+/−20%: 0.5+/−20%:1.81+/−20%:1.333+/−20%:0.15+/−20%.

In some embodiments, the amino acids leucine, isoleucine, valine, arginine, glutamine and N-acetylcysteine are present in a weight ratio of about 1:0.5:0.5:1.81:2:0.1-0.3. In some embodiments, the amino acids leucine, isoleucine, valine, arginine, glutamine and N-acetylcysteine are present in a weight ratio of about 1:0.5:0.5:1.81:2:0.15. In some embodiments, the amino acids leucine, isoleucine, valine, arginine, glutamine, and N-acetylcysteine are present in a weight ratio of about 1:0.5:0.5:1.81:2:0.25. In some embodiments, the amino acids leucine, isoleucine, valine, arginine, glutamine and N-acetylcysteine are present in a weight ratio of about 1+/−15%:0.5+/−15%:0.5+/−15%:1.81+/−15%: 2+/−15%:0.15+/−15%. In some embodiments, the amino acids leucine, isoleucine, valine, arginine, glutamine, and N-acetylcysteine are present in a weight ratio of about 1+/−15%:0.5+/−15%:0.5+/−15%:1.81+/−15%:2+/−15%: 0.25+/−15%. In some embodiments, the amino acids leucine, isoleucine, valine, arginine, glutamine and N-acetylcysteine are present in a weight ratio of about 1+/−20%: 0.5+/−20%:0.5+/−20%:1.81+/−20%:2+/−20%:0.15+/−20%. In some embodiments, the amino acids leucine, isoleucine, valine, arginine, glutamine, and N-acetylcysteine are present in a weight ratio of about 1+/−20%:0.5+/−20%:0.5+/−20%: 1.81+/−20%:2+/−20%:0.25+/−20%. In some embodiments, the amino acids leucine, isoleucine, valine, arginine, glutamine and N-acetylcysteine are present in a weight ratio of about 1+/−15%:0.5+/−15%:0.5+/−15%:1.81+/−15%: 1.33+/−15%:0.15+/−15%. In some embodiments, the amino acids leucine, isoleucine, valine, arginine, glutamine, and N-acetylcysteine are present in a weight ratio of about 1+/−15%:0.5+/−15%:0.5+/−15%:1.81+/−15%:1.33+/−15%: 0.25+/−15%. In some embodiments, the amino acids leucine, isoleucine, valine, arginine, glutamine and N-acetylcysteine are present in a weight ratio of about 1+/−20%:0.5+/−20%:0.5+/−20%:1.81+/−20%:1.33+/−20%: 0.15+/−20%. In some embodiments, the amino acids leucine, isoleucine, valine, arginine, glutamine, and N-acetylcysteine are present in a weight ratio of about 1+/−20%:0.5+/−20%:0.5+/−20%:1.81+/−20%:1.33+/−20%: 0.25+/−20%.

In some embodiments, the amino acids leucine, isoleucine, valine, arginine, glutamine and N-acetylcysteine are present in a weight ratio of about 1:0.5:0.5:1.5 to 2:1 to 2:0.1 to 0.3. In some embodiments, the amino acids leucine, isoleucine, valine, arginine, glutamine and N-acetylcysteine are present in a weight ratio of about 1:0.5:0.5:1.5:2:0.1 to 0.3. In some embodiments, the amino acids leucine, isoleucine, valine, arginine, glutamine and N-acetylcysteine are present in a weight ratio of about 1:0.5:0.5:1.5:2:0.25. In some embodiments, the amino acids leucine, isoleucine, valine, arginine, glutamine and N-acetylcysteine are present in a weight ratio of 1:0.5:0.5:1.5:2:0.15. In some embodiments, the amino acids leucine, isoleucine, valine, arginine, glutamine and N-acetylcysteine are present in a weight ratio of about 1+/−15%:0.5+/−15%:0.5+/−15%:1.5+/−15%: 2+/−15%:0.25+/−15%. In some embodiments, the amino acids leucine, isoleucine, valine, arginine, glutamine and N-acetylcysteine are present in a weight ratio of 1+/−15%: 0.5+/−15%:0.5+/−15%:1.5+/−15%:2+/−15%:0.15+/−15%. In some embodiments, the amino acids leucine, isoleucine, valine, arginine, glutamine and N-acetylcysteine are present in a weight ratio of about 1+/−20%:0.5+/−20%:0.5+/−20%: 1.5+/−20%:2+/−20%:0.25+/−20%. In some embodiments, the amino acids leucine, isoleucine, valine, arginine, glutamine and N-acetylcysteine are present in a weight ratio of 1+/−20%:0.5+/−20%:0.5+/−20%:1.5+/−20%:2+/−20%: 0.15+/−20%.

In some embodiments, a total weight (wt) of the amino acids per dose is about 2 g to about 60 g.

In some embodiments, the total weight of amino acids present per dose is about 5 g, about 6 g, about 7 g, about 11 g, about 12 g, about 13 g, about 14 g, about 15 g, about 16 g, about 17 g, about 18 g, about 19 g, about 20 g, about 21 g, about 22 g, about 23 g, about 24 g, about 25 g, about 26 g, about 27 g, about 28 g, about 29 g, about 30 g, about 31 g, about 32 g, about 33 g, about 34 g, about 35 g, about 36 g, about 37 g, about 38 g, about 39 g, about 40 g, about 41 g, about 42 g, about 43 g, about 44 g, about 45 g, about 46 g, about 47 g, about 48 g, about 49 g, or about 50 g.

In some embodiments, the composition includes about 0.5 g to about 10 g of leucine, about 0.25 g to about 5 g of isoleucine, about 0.25 g to about 5 g of valine, about 1 g to about 20 g of arginine, about 1 g to about 20 g of glutamine, and about 0.1 g to about 5 g of N-acetylcysteine.

In some embodiments, the composition includes at least 1 g of leucine, at least 0.5 g of isoleucine, at least 0.5 g of valine, at least 1.5 g of arginine (or 1.81 g of arginine HCl), at least 2 g of glutamine, and at least 0.15 g of N-acetylcysteine.

In some embodiments, the composition includes about 1 g of leucine, about 0.5 g of isoleucine, about 0.5 g of valine, about 1.5 g of arginine (or 1.81 g of arginine HCl), about 2 g of glutamine, and about 0.15 g of N-acetylcysteine.

In some embodiments, the composition includes at least 2 g of leucine, at least 1 g of isoleucine, at least 1 g of valine, at least 3.0 g of arginine (or 3.62 g of arginine HCl), at least 4 g of glutamine, and at least 0.3 g of N-acetylcysteine.

In some embodiments, the composition includes about 2 g of leucine, about 1 g of isoleucine, about 1 g of valine, about 3.0 g of arginine (or 3.62 g of arginine HCl), about 4 g of glutamine, and about 0.3 g of N-acetylcysteine.

In some embodiments, the composition includes at least 4 g of leucine, at least 2 g of isoleucine, at least 2 g of valine, at least 6.0 g or arginine (or 7.24 g of arginine HCl), at least 8 g of glutamine, and at least 0.6 g of N-acetylcysteine.

In some embodiments, the composition includes about 4 g of leucine, about 2 g of isoleucine, about 2 g of valine, about 6.0 g or arginine (or 7.24 g of arginine HCl), about 8 g of glutamine, and about 0.6 g of N-acetylcysteine.

In some embodiments, the composition includes at least 1.0 g of leucine, at least 0.5 g of isoleucine, at least 0.5 g of valine, at least 1.5 g of arginine, at least 2.0 g of glutamine, or at least 0.15 g of N-acetylcysteine. In some embodiments, the composition includes about 1.0 g of leucine, about 0.5 g of isoleucine, about 0.5 g of valine, about 1.5 g of arginine, about 2.0 g of glutamine, or about 0.15 g of N-acetylcysteine.

In some embodiments, the composition includes at least 1.0 g of leucine, at least 0.5 g of isoleucine, at least 0.5 g of valine, at least 1.5 g of arginine, at least 2.0 g of glutamine, and at least 0.25 g of N-acetylcysteine. In some embodiments, the composition includes about 1.0 g of leucine, about 0.5 g of isoleucine, about 0.5 g of valine, about 1.5 g of arginine, about 2.0 g of glutamine, and about 0.25 g of N-acetylcysteine.

In some embodiments, the amino acids of the composition include about 10 wt % to about 30 wt % leucine, about 5 wt % to about 15 wt % isoleucine, about 5 wt % to about 15 wt % valine, about 15 wt % to about 40 wt % arginine, about 20 wt % to about 50 wt % glutamine, and about 1 wt % to about 8 wt % N-acetylcysteine.

In some embodiments, the amino acids of the composition include about 16 wt % to about 18 wt % leucine, about 7 wt % to about 9 wt % isoleucine, about 7 wt % to about 9 wt % valine, about 28 wt % to about 32 wt % arginine, about 31 wt % to about 34 wt % glutamine, and about 1 wt % to about 5 wt % N-acetylcysteine.

In some embodiments, the amino acids of the composition include about 16.8 wt % leucine, about 8.4 wt % isoleucine, about 8.4 wt % valine, about 30.4 wt % arginine, about 33.6 wt % glutamine, and about 2.5 wt % N-acetylcysteine.

In some embodiments, the composition comprises one or more excipients selected from the group consisting of: citric acid, lecithin, a sweetener, a dispersion enhancer, a flavoring, a bitterness masking agent, and a natural or artificial coloring.

In some embodiments, the composition comprises citric acid.

In some embodiments, the composition is in the form of a solid, powder, solution, or gel. In certain embodiments, the composition is in the form of a powder (e.g. in a packet).

In some embodiments, the composition includes one or more pharmaceutically acceptable excipients, wherein the amino acids comprise leucine, arginine, glutamine, and N-acetylcysteine. An aspect of the present disclosure provides a composition comprising free amino acids and one or more pharmaceutically acceptable excipients, wherein the amino acids consist of leucine, arginine, glutamine, and N-acetylcysteine. In some embodiments, the amino acids leucine, arginine, glutamine, N-acetylcysteine and glycine are present in a weight ratio of 1:1.5:2:0.15. In some embodiments, the composition comprises at least 1.0 g of leucine, at least 1.5 g of arginine, at least 2.0 g of glutamine, or at least 0.15 g of N-acetylcysteine. In some embodiments, the composition comprises at least 1.5 g of arginine and at least 2.0 g of glutamine. In some embodiments, the amino acids leucine, arginine, glutamine, and N-acetylcysteine are present in weight % of each compared to total amino acid weight of 20.4 to 22.6%, 30.6 to 33.9%, 40.9 to 45.2%, and 3.1 to 3.4%, respectively. In some embodiments, the amino acids leucine, arginine, glutamine, and N-acetylcysteine, are present in weight % of each compared to total amino acid weight of 21.5%, 32.3%, 43.0%, and 3.2%, respectively.

An exemplary Amino Acid Composition includes leucine, isoleucine, valine, arginine HCl, glutamine, and N-acetylcysteine as its amino acid entities in a wt. ratio of 1:0.5:0.5:1.81:2:0.15 (Table 3). An exemplary Amino Acid Composition includes leucine, isoleucine, valine, arginine, glutamine, and N-acetylcysteine as its amino acid entities in a wt. ratio of 1:0.5:0.5:1.5:2:0.15 (Table 4).

TABLE 3

Exemplary amino acid components of the composition including Arginine HCl.

| Amino acid | wt. ratio | wt. % | g/packet | g dose #1 | g dose #2 |
|---|---|---|---|---|---|
| Leucine | 1 | 16.78 | 1.00 g | 2 g | 4 g |
| Isoleucine | 0.5 | 8.39 | 0.50 g | 1 g | 2 g |
| Valine | 0.5 | 8.39 | 0.50 g | 1 g | 2 g |
| Arginine HCl | 1.81 | 30.37 | 1.81 g | 3.62 g | 7.24 g |
| Glutamine | 2 | 33.56 | 2.00 g | 4 g | 8 g |
| N-acetylcysteine | 0.15 | 2.52 | 0.15 g | 0.3 g | 0.6 g |
| Total amino acids | | | 5.96 g | ~12 g | ~24 g |

TABLE 4

Exemplary amino acid components of the composition including Arginine.

| Amino acid | wt. ratio | wt. % | g/packet | g dose #1 | g dose #2 |
|---|---|---|---|---|---|
| Leucine | 1 | 17.70 | 1.00 g | 2 | 4 |
| Isoleucine | 0.5 | 8.85 | 0.50 g | 1 | 2 |
| Valine | 0.5 | 8.85 | 0.50 g | 1 | 2 |
| Arginine | 1.5 | 26.55 | 15 g | 3 | 6 |
| Glutamine | 2 | 35.4 | 2.00 g | 4 | 8 |
| N-acetylcysteine | 0.15 | 2.65 | 0.15 g | 0.3 | 0.6 |
| Total amino acids | | | 5.65 g | 11.3 g | 22.6 g |

An exemplary Amino Acid Composition includes leucine, isoleucine, valine, arginine HCl, glutamine, and N-acetylcysteine as its amino acid entities in a wt. ratio of 1:0.5:0.5:0.905:2:0.15 (Table 5). An exemplary Amino Acid Composition includes leucine, isoleucine, valine, arginine, glutamine, and N-acetylcysteine as its amino acid entities in a wt. ratio of 1:0.5:0.5:0.75:2:0.15 (Table 6).

TABLE 5

Exemplary amino acid components of the composition including Arginine HCl.

| Amino acid | wt. ratio | wt. % | g/packet | g dose #1 | g dose #2 |
|---|---|---|---|---|---|
| Leucine | 1 | 19.78 | 1.00 g | 2 g | 4 g |
| Isoleucine | 0.5 | 9.89 | 0.50 g | 1 g | 2 g |
| Valine | 0.5 | 9.89 | 0.50 g | 1 g | 2 g |
| Arginine HCl | 0.905 | 17.90 | 0.905 g | 1.81 g | 3.62 g |

TABLE 5-continued

Exemplary amino acid components of the composition including Arginine HCl.

| Amino acid | wt. ratio | wt. % | g/packet | g dose #1 | g dose #2 |
|---|---|---|---|---|---|
| Glutamine | 2 | 39.56 | 2.00 g | 4 g | 8 g |
| N-acetylcysteine | 0.15 | 2.97 | 0.15 g | 0.3 g | 0.6 g |
| Total amino acids | | | 5.06 g | ~10 g | ~20 g |

TABLE 6

Exemplary amino acid components of the composition including Arginine.

| Amino acid | wt. ratio | wt. % | g/packet | g dose #1 | g dose #2 |
|---|---|---|---|---|---|
| Leucine | 1 | 20.41 | 1.00 g | 2 | 4 |
| Isoleucine | 0.5 | 10.20 | 0.50 g | 1 | 2 |
| Valine | 0.5 | 10.20 | 0.50 g | 1 | 2 |
| Arginine | 0.75 | 15.31 | 0.75 g | 1.5 | 3 |
| Glutamine | 2 | 40.82 | 2.00 g | 4 | 8 |
| N-acetylcysteine | 0.15 | 3.06 | 0.15 g | 0.3 | 0.6 |
| Total amino acids | | | 4.9 g | 9.8 g | 19.6 g |

An exemplary Amino Acid Composition includes leucine, isoleucine, valine, arginine HCl, glutamine, and N-acetylcysteine as its amino acid entities in a wt. ratio of 1:0.5:0.25:0.905:1:0.225 (Table 7). An exemplary Amino Acid Composition includes leucine, isoleucine, valine, arginine, glutamine, and N-acetylcysteine as its amino acid entities in a wt. ratio of 1:0.5:0.25:0.75:1:0.225 (Table 8).

TABLE 7

Exemplary amino acid components of the composition including Arginine HCl.

| Amino acid | wt. ratio | wt. % | g/packet | g dose #1 | g dose #2 |
|---|---|---|---|---|---|
| Leucine | 1 | 25.77 | 1.00 g | 2 g | 4 g |
| Isoleucine | 0.5 | 12.89 | 0.50 g | 1 g | 2 g |
| Valine | 0.25 | 6.44 | 0.25 g | 0.50 g | 1 g |
| Arginine HCl | 0.905 | 23.32 | 0.905 g | 1.81 g | 3.62 g |
| Glutamine | 1 | 25.77 | 1.00 g | 2 g | 4 g |
| N-acetylcysteine | 0.225 | 5.80 | 0.225 g | 0.45 g | 0.9 g |
| Total amino acids | | | 3.88 g | 7.76 g | 15.52 g |

TABLE 8

Exemplary amino acid components of the composition including Arginine.

| Amino acid | wt. ratio | wt. % | g/packet | g dose #1 | g dose #2 |
|---|---|---|---|---|---|
| Leucine | 1 | 26.85 | 1.00 g | 2 | 4 |
| Isoleucine | 0.5 | 13.42 | 0.50 g | 1 | 2 |
| Valine | 0.25 | 6.71 | 0.25 g | 0.5 | 1 |
| Arginine | 0.75 | 20.13 | 0.75 g | 1.5 | 3 |
| Glutamine | 1 | 26.85 | 1.00 g | 2 | 4 |
| N-acetylcysteine | 0.225 | 6.04 | 0.225 g | 0.45 | 0.9 |
| Total amino acids | | | 3.725 g | 7.45 g | 14.9 g |

The disclosure also provides a composition including at least four different amino acid entities (e.g., four, five, six, or more different amino acid entities), in which the composition is capable of one, two, three, four, five, six, seven, eight, nine, ten, eleven, twelve, thirteen, fourteen, fifteen, sixteen, seventeen, or all of:

a) one or both of decreasing or preventing myalgia;
b) one or both of decreasing or preventing fibromyalgia;
c) one or both of decreasing or preventing idiopathic pulmonary fibrosis;
d) one or both of decreasing or preventing fatigue;
e) one or both of decreasing or preventing muscle fatigue;
f) one or both of decreasing or preventing muscle dysfunction;
g) one or both of decreasing mitochondrial dysfunction;
h) one or both of decreasing or preventing dyspnea after exertion;
i) improving exercise tolerance or the ability to conduct activities of daily living;
j) one or both of decreasing or preventing postural orthostatic tachycardia syndrome;
k) one or both of decreasing or preventing tachycardia;
l) improving mitochondrial function;
m) improving mitochondrial capacity or energetics (e.g., improvement in oxidative ATP synthesis, phosphocreatine [PCr] resynthesis following exercise or exertion);
n) one or both of reducing oxidative stress and/or reducing reactive oxygen species (ROS);
o) improving mood disorders and/or depression;
p) improving cognitive function;
q) increasing skeletal muscle or other organ vascular perfusion;
r) improving endothelial function;
s) decreasing or preventing diabetes (e.g., new onset diabetes); or
t) improving inflammation.

In some embodiments, the composition includes at least four different amino acid entities (e.g., four, five, six, or more different amino acid entities) that decreases or prevents myalgia.

In some embodiments, the composition includes at least four different amino acid entities (e.g., four, five, six, or more different amino acid entities) that decreases or prevents fatigue.

In some embodiments, the composition includes at least four different amino acid entities (e.g., four, five, six, or more different amino acid entities) that decreases or prevents muscle fatigue.

In some embodiments, the composition includes at least four different amino acid entities (e.g., four, five, six, or more different amino acid entities) that decreases or prevents mitochondrial dysfunction.

In some embodiments, the composition includes at least four different amino acid entities (e.g., four, five, six, or more different amino acid entities) that decreases or prevents dyspnea after exertion.

In some embodiments, the composition includes at least four different amino acid entities (e.g., four, five, six, or more different amino acid entities) that improves exercise tolerance or the ability to conduct activities of daily living.

In some embodiments, the composition includes at least four different amino acid entities (e.g., four, five, six, or more different amino acid entities) that decreases or prevents postural orthostatic tachycardia syndrome.

In some embodiments, the composition includes at least four different amino acid entities (e.g., four, five, six, or more different amino acid entities) that decreases or prevents tachycardia.

In some embodiments, the composition includes at least four different amino acid entities (e.g., four, five, six, or more different amino acid entities) that improves mitochondrial function.

In some embodiments, the composition includes at least four different amino acid entities (e.g., four, five, six, or more different amino acid entities) that improves mitochondrial capacity.

In some embodiments, the composition includes at least four different amino acid entities (e.g., four, five, six, or more different amino acid entities) that improves mood disorders.

In some embodiments, the composition includes at least four different amino acid entities (e.g., four, five, six, or more different amino acid entities) that improves depression.

In some embodiments, the composition includes at least four different amino acid entities (e.g., four, five, six, or more different amino acid entities) that improves cognitive function.

In some embodiments, the composition includes at least four different amino acid entities (e.g., four, five, six, or more different amino acid entities) that increases skeletal muscle or other organ vascular perfusion.

In certain embodiments, the composition is capable of reducing, or reduces, myalgia by at least 5%, 10%, 15%, 20%, 20%, 30%, 40%, 45%, 50%, 55%, 60%, 65%, 70%, 75%, 80%, 85%, or 90% relative to a reference composition (e.g., a vehicle control; an amino acid composition comprising L-leucine, L-isoleucine, L-valine; an amino acid composition comprising L-arginine, L-glutamine, and NAC; an amino acid composition comprising L-leucine, L-isoleucine, L-valine, L-arginine, and L-glutamine; or NAC).

In certain embodiments, the composition is capable of reducing, or reduces, fibromyalgia by at least 5%, 10%, 15%, 20%, 20%, 30%, 40%, 45%, 50%, 55%, 60%, 65%, 70%, 75%, 80%, 85%, or 90% relative to a reference composition (e.g., a vehicle control; an amino acid composition comprising L-leucine, L-isoleucine, L-valine; an amino acid composition comprising L-arginine, L-glutamine, and NAC; an amino acid composition comprising L-leucine, L-isoleucine, L-valine, L-arginine, and L-glutamine; or NAC).

In certain embodiments, the composition is capable of reducing, or reduces, idiopathic pulmonary fibrosis by at least 5%10%, 15%, 20%, 20%, 30%, 40%, 45%, 50%, 55%, 60%, 65%, 70%, 75%, 80%, 85%, or 90% relative to a reference composition (e.g., a vehicle control; an amino acid composition comprising L-leucine, L-isoleucine, L-valine; an amino acid composition comprising L-arginine, L-glutamine, and NAC; an amino acid composition comprising L-leucine, L-isoleucine, L-valine, L-arginine, and L-glutamine; or NAC).

In certain embodiments, the composition is capable of reducing, or reduces, fatigue by at least 5%, 10%, 15%, 20%, 20%, 30%, 40%, 45%, 50%, 55%, 60%, 65%, 70%, 75%, 80%, 85%, or 90% relative to a reference composition (e.g., a vehicle control; an amino acid composition comprising L-leucine, L-isoleucine, L-valine; an amino acid composition comprising L-arginine, L-glutamine, and NAC; an amino acid composition comprising L-leucine, L-isoleucine, L-valine, L-arginine, and L-glutamine; or NAC).

In certain embodiments, the composition is capable of reducing, or reduces, muscle fatigue by at least 5%, 10%, 15%, 20%, 20%, 30%, 40%, 45%, 50%, 55%, 60%, 65%, 70%, 75%, 80%, 85%, or 90% relative to a reference composition (e.g., a vehicle control; an amino acid composition comprising L-leucine, L-isoleucine, L-valine; an amino acid composition comprising L-arginine, L-glutamine, and NAC; an amino acid composition comprising L-leucine, L-isoleucine, L-valine, L-arginine, and L-glutamine; or NAC).

In certain embodiments, the composition is capable of reducing, or reduces, mitochondrial dysfunction by at least 5%, 10%, 15%, 20%, 20%, 30%, 40%, 45%,50%, 55%, 60%, 65%, 70%, 75%, 80%, 85%, or 90% relative to a reference composition (e.g., a vehicle control; an amino acid composition comprising L-leucine, L-isoleucine, L-valine; an amino acid composition comprising L-arginine, L-glutamine, and NAC; an amino acid composition comprising L-leucine, L-isoleucine, L-valine, L-arginine, and L-glutamine; or NAC).

In certain embodiments, the composition is capable of reducing, or reduces, dyspnea after exertion by at least 5%10%, 15%, 20%, 20%, 30%, 40%, 45%, 50%, 55%, 60%, 65%, 70%, 75%, 80%, 85%, or 90% relative to a reference composition (e.g., a vehicle control; an amino acid composition comprising L-leucine, L-isoleucine, L-valine; an amino acid composition comprising L-arginine, L-glutamine, and NAC; an amino acid composition comprising L-leucine, L-isoleucine, L-valine, L-arginine, and L-glutamine; or NAC).

In certain embodiments, the composition is capable of reducing, or reduces, postural orthostatic tachycardia syndrome by at least 5%, 10%, 15%, 20%, 20%, 30%, 40%, 45%, 50%, 55%, 60%, 65%, 70%, 75%, 80%, 85%, or 90% relative to a reference composition (e.g., a vehicle control; an amino acid composition comprising L-leucine, L-isoleucine, L-valine; an amino acid composition comprising L-arginine, L-glutamine, and NAC; an amino acid composition comprising L-leucine, L-isoleucine, L-valine, L-arginine, and L-glutamine; or NAC).

In certain embodiments, the composition is capable of reducing, or reduces, tachycardia by at least 5%, 10%, 15%, 20%, 20%, 30%, 40%, 45%, 50%, 55%, 60%, 65%, 70%, 75%, 80%, 85%, or 90% relative to a reference composition (e.g., a vehicle control; an amino acid composition comprising L-leucine, L-isoleucine, L-valine; an amino acid composition comprising L-arginine, L-glutamine, and NAC; an amino acid composition comprising L-leucine, L-isoleucine, L-valine, L-arginine, and L-glutamine; or NAC).

In certain embodiments, the composition is capable of improving, or improves, mitochondrial function by at least 5%, 10%, 15%, 20%, 20%, 30%, 40%, 45%, 50%, 55%, 60%, 65%, 70%, 75%, 80%, 85%, or 90% relative to a reference composition (e.g., a vehicle control; an amino acid composition comprising L-leucine, L-isoleucine, L-valine; an amino acid composition comprising L-arginine, L-glutamine, and NAC; an amino acid composition comprising L-leucine, L-isoleucine, L-valine, L-arginine, and L-glutamine; or NAC).

In certain embodiments, the composition is capable of improving, or improves, exercise tolerance or the ability to conduct activities of daily living by at least 5%, 10%, 15%, 20%, 20%, 30%, 40%, 45%, 50%, 55%, 60%, 65%, 70%, 75%, 80%, 85%, or 90% relative to a reference composition (e.g., a vehicle control; an amino acid composition comprising L-leucine, L-isoleucine, L-valine; an amino acid composition comprising L-arginine, L-glutamine, and NAC; an amino acid composition comprising L-leucine, L-isoleucine, L-valine, L-arginine, and L-glutamine; or NAC).

In certain embodiments, the composition is capable of improving, or improves, mitochondrial capacity (e.g., improvement in oxidative ATP synthesis phosphocreatine [PCr] resynthesis following exercise or exertion) by at least 5%, 10%, 15%, 20%, 20%, 30%, 40%, 45%, 50%, 55%, 60%, 65%, 70%, 75%, 80%, 85%, or 90% relative to a reference composition (e.g., a vehicle control; an amino acid composition comprising L-leucine, L-isoleucine, L-valine;

an amino acid composition comprising L-arginine, L-glutamine, and NAC; an amino acid composition comprising L-leucine, L-isoleucine, L-valine, L-arginine, and L-glutamine; or NAC).

In certain embodiments, the composition is capable of improving, or improves, mood disorders and/or depression by at least 5%, 10%, 15%, 20%, 20%, 30%, 40%, 45%, 50%, 55%, 60%, 65%, 70%, 75%, 80%, 85%, or 90% relative to a reference composition (e.g., a vehicle control; an amino acid composition comprising L-leucine, L-isoleucine, L-valine; an amino acid composition comprising L-arginine, L-glutamine, and NAC; an amino acid composition comprising L-leucine, L-isoleucine, L-valine, L-arginine, and L-glutamine; or NAC).

In certain embodiments, the composition is capable of improving, or improves, cognitive function by at least 5%10%, 15%, 20%, 20%, 30%, 40%, 45%, 50%, 55%, 60%, 65%, 70%, 75%, 80%, 85%, or 90% relative to a reference composition (e.g., a vehicle control; an amino acid composition comprising L-leucine, L-isoleucine, L-valine; an amino acid composition comprising L-arginine, L-glutamine, and NAC; an amino acid composition comprising L-leucine, L-isoleucine, L-valine, L-arginine, and L-glutamine; or NAC).

In certain embodiments, the composition is capable of improving, or improves, skeletal muscle or other organ vascular perfusion by at least 5%, 10%, 15%, 20%, 20%, 30%, 40%, 45%, 50%, 55%, 60%, 65%, 70%, 75%, 80%, 85%, or 90% relative to a reference composition (e.g., a vehicle control; an amino acid composition comprising L-leucine, L-isoleucine, L-valine; an amino acid composition comprising L-arginine, L-glutamine, and NAC; an amino acid composition comprising L-leucine, L-isoleucine, L-valine, L-arginine, and L-glutamine; or NAC).

Amino Acid Compositions Comprising Ethylenediaminetetraacetic Acid (EDTA)

In some embodiments, an amino acid composition described herein, e.g., an amino composition for using in treating PASC, further comprises a chelating agent, e.g., EDTA or a pharmaceutically acceptable salt thereof. Without wishing to be bound by theory, in some embodiments, inclusion of the chelating agent such as EDTA promotes a reduction in Nac-Nac dimerization. In some embodiments, the EDTA salt comprises disodium EDTA. In some embodiments, a composition described herein comprises an amount of an EDTA or salt thereof (e.g., disodium EDTA) that is 0.1-1%, e.g., about 0.74% wt/wt of the composition in powder form.

In some aspects, the present disclosure provides a composition comprising:
a) a leucine (L)-amino acid entity;
b) an arginine (R)-amino acid entity;
c) a glutamine (Q)-amino acid entity;
d) a N-acetylcysteine (NAC) entity, e.g., NAC; and
e) a chelating agent, e.g., EDTA or a salt thereof or a pharmaceutically acceptable salt thereof.

In some embodiments, the composition comprising EDTA or a salt thereof is a composition according to Table 9 below.

TABLE 9

Exemplary amino acid composition

| Material | Mass (g) | % wt/wt |
| --- | --- | --- |
| L-Leucine | 2.0000 | 14.85 |
| L-Isoleucine | 1.0000 | 7.42 |

TABLE 9-continued

Exemplary amino acid composition

| Material | Mass (g) | % wt/wt |
| --- | --- | --- |
| L-Valine | 1.0000 | 7.42 |
| L-Arginine HCl [1] | 3.6280 | 26.94 |
| L-Glutamine | 4.0000 | 29.70 |
| N-Acetyl-L-cysteine | 0.3000 | 2.23 |
| Amino Acids (-HCl) | 11.3000 | 83.90 |
| Citric Acid | 0.4000 | 2.97 |
| Soybean Lecithin | 0.3000 | 2.23 |
| Xanthan Gum 180 | 0.2000 | 1.48 |
| Sucralose | 0.0300 | 0.22 |
| Orange Flavor | 0.2000 | 1.48 |
| N-C Custard Type Flavor | 0.0500 | 0.37 |
| FD&C Yellow No 6 | 0.0090 | 0.07 |
| Low-Substituted Hydroxypropyl Cellulose | 0.1000 | 0.74 |
| Silicon Dioxide | 0.1320 | 0.98 |
| Magnesium Stearate | 0.0200 | 0.15 |
| Disodium EDTA | 0.1000 | 0.74 |
| Total | 13.4690 | 100.00 |

[1] 3.6284 g of L-Arginine HCl is equivalent to 3.000 g of L-Arginine

In some embodiments, a composition described herein comprises an amount of citric acid that is about 0.4000 g or about 4.34% wt/wt of the composition in powder form. In some embodiments, a composition described herein comprises an amount of Soybean Lecithin that is about 0.3000 g or about 2.23% wt/wt of the composition in powder form. In some embodiments, a composition described herein comprises an amount of sucralose that is about 0.0300 g or about 0.22% wt/wt of the composition in powder form. In some embodiments, a composition described herein comprises an amount of orange flavor that is about 0.2000 g or about 1.48% wt/wt of the composition in powder form. In some embodiments, a composition described herein comprises an amount of N—C Custard Type Flavor that is about 0.0500 g or about 0.37% wt/wt of the composition in powder form. In some embodiments, a composition described herein comprises an amount of Silicon Dioxide that is about 0.1320 g or about 0.98% wt/wt of the composition in powder form. In some embodiments, a composition described herein comprises an amount of an EDTA or salt thereof (e.g., disodium EDTA) that is about 0.1000 g or about 0.74% wt/wt of the composition in powder form.

Production of the Amino Acid Compositions

Amino acids used to make the compositions may be agglomerated, and/or instantized to aid in dispersal and/or solubilization.

The amino acid compositions of the present disclosure may be made using amino acids and amino acid derivatives from the following sources, or other sources may be used: FUSI-BCAA™ Instantized Blend (L-Leucine, L-Isoleucine and L-Valine in 2:1:1 weight ratio), FUSIL™ Instantized L-Leucine, L-Arginine HCl, and L-Glutamine may be obtained from Ajinomoto Co., Inc; N-acetyl-cysteine may be obtained from Spectrum Chemical.

To produce the amino acid compositions of the instant disclosure, the following general steps may be used: the starting materials (individual amino acids and excipients) may be blended in a blending unit. Blending may be followed by verification of blend uniformity and amino acid content. The blended powder may be filled into stick packs or other unit dosage form. The content of stick packs or other unit dosage forms may be dispersed in water at time of use for oral administration.

Formulations

The pharmaceutical compositions of the present disclosure may be in a form suitable for oral use (for example as tablets, lozenges, hard or soft capsules, aqueous or oily suspensions, emulsions, dispersible powders or granules, syrups or elixirs, medical food products, nutraceuticals), for topical use (for example as creams, ointments, gels, or aqueous or oily solutions or suspensions), for administration by inhalation (for example as finely divided powder) or for parental administration (for example as a sterile aqueous or oily solution for intravenous, subcutaneous, intramuscular dosing or as a suppository for rectal dosing).

Excipients

The amino acid compositions of the present disclosure may be compounded or formulated with one or more excipients. Non-limiting examples of suitable excipients include a tastant, a flavorant, a buffering agent, a preservative, a stabilizer, a binder, a compaction agent, a lubricant, a dispersion enhancer, a disintegration agent, a flavoring agent, a sweetener, and a coloring agent.

In some embodiments, the excipient comprises a buffering agent. Non-limiting examples of suitable buffering agents include citric acid, sodium citrate, magnesium carbonate, magnesium bicarbonate, calcium carbonate, and calcium bicarbonate.

In some embodiments, the excipient comprises a preservative. Non-limiting examples of suitable preservatives include antioxidants, such as alpha-tocopherol and ascorbate, and antimicrobials, such as parabens, chlorobutanol, and phenol.

In some embodiments, the composition comprises a binder as an excipient. Non-limiting examples of suitable binders include starches, pregelatinized starches, gelatin, polyvinylpyrolidone, cellulose, methylcellulose, sodium carboxymethylcellulose, ethylcellulose, polyacrylamides, polyvinyloxoazolidone, polyvinylalcohols, C12-C18 fatty acid alcohol, polyethylene glycol, polyols, saccharides, oligosaccharides, and combinations thereof.

In some embodiments, the composition comprises a lubricant as an excipient. Non-limiting examples of suitable lubricants include magnesium stearate, calcium stearate, zinc stearate, hydrogenated vegetable oils, sterotex, polyoxyethylene monostearate, talc, polyethyleneglycol, sodium benzoate, sodium lauryl sulfate, magnesium lauryl sulfate, and light mineral oil.

In some embodiments, the composition comprises a dispersion enhancer as an excipient. Non-limiting examples of suitable dispersants include starch, alginic acid, polyvinylpyrrolidones, guar gum, kaolin, xanthan gum, bentonite, purified wood cellulose, sodium starch glycolate, isoamorphous silicate, and microcrystalline cellulose as high HLB emulsifier surfactants.

In some embodiments, the composition comprises a disintegrant as an excipient. In some embodiments, the disintegrant is a non-effervescent disintegrant. Non-limiting examples of suitable non-effervescent disintegrants include starches such as corn starch, potato starch, pregelatinized and modified starches thereof, sweeteners, clays, such as bentonite, microcrystalline cellulose, alginates, sodium starch glycolate, gums such as agar, guar, locust bean, karaya, pecitin, and tragacanth. In some embodiments, the disintegrant is an effervescent disintegrant. Non-limiting examples of suitable effervescent disintegrants include sodium bicarbonate in combination with citric acid, and sodium bicarbonate in combination with tartaric acid.

In some embodiments, the excipient comprises a chelating agent. The chelating agents may be, e.g., EDTA or a salt thereof (e.g., disodium EDTA).

In some embodiments, the excipient comprises a flavoring agent. Flavoring agents can be chosen from synthetic flavor oils and flavoring aromatics; natural oils; extracts from plants, leaves, flowers, and fruits; and combinations thereof. In some embodiments, the flavoring agent is selected from cinnamon oils; oil of wintergreen; peppermint oils; clover oil; hay oil; anise oil; eucalyptus; vanilla; citrus oil such as lemon oil, orange oil, grape and grapefruit oil; and fruit essences including apple, peach, pear, strawberry, raspberry, cherry, plum, pineapple, and apricot.

In some embodiments, the excipient comprises a sweetener. Non-limiting examples of suitable sweeteners include glucose (corn syrup), dextrose, invert sugar, fructose, and mixtures thereof (when not used as a carrier); saccharin and its various salts such as the sodium salt; dipeptide sweeteners such as aspartame; dihydrochalcone compounds, glycyrrhizin; *Stevia rebaudiana* (Stevioside); chloro derivatives of sucrose such as sucralose; and sugar alcohols such as sorbitol, mannitol, sylitol, and the like. Also contemplated are hydrogenated starch hydrolysates and the synthetic sweetener 3,6-dihydro-6-methyl-1,2,3-oxathiazin-4-one-2,2-dioxide, particularly the potassium salt (acesulfame-K), and sodium and calcium salts thereof.

In some embodiments, the composition comprises a coloring agent. Non-limiting examples of suitable color agents include food, drug and cosmetic colors (FD&C), drug and cosmetic colors (D&C), and external drug and cosmetic colors (Ext. D&C). The coloring agents can be used as dyes or their corresponding lakes.

Particular excipients may include one or more of: citric acid, lecithin, (e.g. Alcolec F100), sweeteners (e.g. sucralose, sucralose micronized NF, acesulfame potassium (e.g. Ace-K)), a dispersion enhancer (e.g. xanthan gum (e.g. Ticaxan Rapid-3)), flavorings (e.g. vanilla custard #4306, Nat Orange WONF #1326, lime 865.0032U, and lemon 862.2169U), a bitterness masking agent (e.g. 936.2160U), and natural or artificial colorings (e.g. FD&C Yellow 6).

Particular excipients may include one or more of: citric acid, lecithin (e.g. Alcolec F100), a dispersion enhancer (e.g. xanthan gum (e.g. Ticaxan Rapid-3)), a sweetener (e.g. sucralose), orange flavor (e.g., Nat Orange WONF #1326), custard flavor (e.g. vanilla custard #4306), coloring (e.g. FD&C Yellow 6), low substituted hydroxypropyl-cellulose (L-HPC), colloidal silicon dioxide, and magnesium stearate.

Methods of Treatment

The composition as described herein can be administered to improve mitochondrial, metabolic, immunologic, musculoskeletal, neurocognitive, and/or pulmonary function, e.g., in a patient with post-acute sequelae of COVID-19. The composition as described herein can also be administered to treat (e.g., reverse, reduce, ameliorate, or prevent) a disorder, e.g., post-acute sequelae of COVID-19 in a subject. The composition as described herein can also be administered to treat (e.g., reverse, reduce, ameliorate, or prevent) a disorder, e.g., myalgic encephalomyelitis/chronic fatigue syndrome (ME/CFS), post-infectious fatigue syndrome, post-critical illness syndrome, or post-intensive care unit syndrome, following illness or infection, e.g., related to post-acute sequelae of COVID-19 in a subject. The present disclosure provides methods of treating post-acute sequelae of COVID-19 selected from myalgia, fibromyalgia, idiopathic pulmonary fibrosis, fatigue, muscle fatigue, mitochondrial dysfunction, dyspnea after exertion, postural orthostatic tachycardia syndrome, and tachycardia. In particular, an effective amount of the composition can be administered (e.g., according to a dosage regimen described herein) to treat a subject with post-acute sequelae of COVID-19.

In some embodiments, a method of treating a subject having post-acute sequelae of COVID-19 comprises administering to a subject: a) a leucine (L)-amino acid entity; b) an arginine (R)-amino acid entity; and c) a glutamine (Q)-amino acid entity. In some embodiments, a method of treating a subject having post-acute sequelae of COVID-19 comprises administering to a subject: a) a leucine (L)-amino acid entity; b) an arginine (R)-amino acid entity; c) a glutamine (Q)-amino acid entity; d) a N-acetylcysteine (NAC) entity, e.g. NAC.

In some embodiments, a method of treating a subject having post-acute sequelae of COVID-19 comprises administering to a subject a composition comprising: a) a leucine (L)-amino acid entity, a arginine (R)-amino acid entity, and a glutamine (Q)-amino acid entity; and b) a N-acetylcysteine (NAC) entity, e.g., NAC; and optionally c) an essential amino acid (EAA)-entity chosen from a histidine (H)-amino acid-entity, a lysine (K)-amino acid-entity, a phenylalanine (F)-amino acid-entity, and a threonine (T)-amino acid-entity or a combination of two, three, or four of the EAAs.

In some embodiments, a method of treating a subject having post-acute sequelae of COVID-19 comprises administering to a subject in need thereof an effective amount of a composition comprising:

a) a L-amino acid entity chosen from L-leucine or a salt thereof, or β-hydroxy-β-methylbutyrate (HM41B) or a salt thereof;

b) an R-amino acid entity chosen from L-arginine or a salt thereof, ornithine or a salt thereof, or creatine or a salt thereof; and c) L-glutamine or a salt thereof;

d) N-acetylcysteine (NAC) or a salt thereof; and e) an EAA chosen from L-histidine or a salt thereof, L-lysine or a salt thereof, L-phenylalanine or a salt thereof, or L-threonine or a salt thereof or a combination of two, three, or four of the EAAs.

The present disclosure provides methods of treating one or more symptoms of post-acute sequelae of COVID-19. In some embodiments, the present disclosure provides a method for treating one or more symptoms selected from the group consisting of anorexia, anxiety, arrhythmias, confusion ("brain fog"), dementia, depression, dyspnea, fatigue, hair loss, headache, heart failure, cardiomyopathy, angina hepatic dysfunction, hyperglycemia, type 2 diabetes, increased heart rate, inflammation, loss of appetite, loss of memory, loss of smell, mood disorder, muscle weakness, myocardial ischemia, post-exertional malaise, diminished neurocognition, diminished sensory function, pulmonary fibrosis, postural orthostatic hypotension, renal dysfunction, and respiratory distress, wherein the method comprises administering to a subject an effective amount of: a) a leucine (L)-amino acid entity; b) an arginine (R)-amino acid entity; and c) a glutamine (Q)-amino acid entity. In some embodiments, the present disclosure provides a method for treating one or more symptoms selected from the group consisting of anorexia, anxiety, arrhythmias, confusion ("brain fog"), dementia, depression, dyspnea, fatigue, hair loss, headache, heart failure, cardiomyopathy, angina, hepatic dysfunction, hyperglycemia, type 2 diabetes, increased heart rate, inflammation, loss of appetite, loss of memory, loss of smell, mood disorder, muscle weakness, myocardial ischemia, post-exertional malaise, diminished neurocognition, diminished sensory function, pulmonary fibrosis, postural orthostatic hypotension, renal dysfunction, and respiratory distress, wherein the method comprises administering to a subject an effective amount of: a) a leucine (L)-amino acid entity; b) an arginine (R)-amino acid entity; c) a glutamine (Q)-amino acid entity; and d) a N-acetylcysteine (NAC) entity, e.g., NAC. In some embodiments, one or both of the R-amino acid entity and the Q-amino acid entity are present at a higher amount (wt. %) than the L-amino acid entity. In some embodiments, amino acid entities administered further comprises a glycine (G)-amino acid entity.

In some embodiments, the present disclosure provides a method for treating one or more symptoms or signs selected from immunologic symptoms or signs, metabolic symptoms or signs, and/or neurologic symptoms or signs. In some embodiments, an immunologic symptom or sign is selected from the group consisting of increased markers of inflammation (e.g., erythrocyte sedimentation rate, c reactive protein) increased proinflammatory cytokines (e.g., CRP, IL-1A, IL-17a, TNF-alpha), decreased cytotoxicity of natural killer cells, expression of cytolytic proteins, and production of cytokines, increased CD8+ cytotoxic T cells with CD38 activation antigen, T cell exhaustion, and increased autoantibodies, especially against targets in CNS and autonomic nervous system. In some embodiments, a metabolic symptom or sign is selected from the group consisting of increased lactic acid, reduced ATP generation from glucose by the tricarboxylic acid (TCA) cycle, reduced levels of fatty acids and of acyl-carnitine, reduced levels of amino acids via the urea cycle, impaired oxidative phosphorylation, redox imbalance (e.g., increased levels of oxidants, e.g., peroxides and superoxides, isoprostanes, at rest and/or after exercise or exertion; decreased levels of antioxidants, e.g., decreased levels of alpha-tocopherol, e.g., thiobarbituric acid reactive substances), increased inducible nitric oxide synthase (iNOS), increased NFκB, increased nitric oxide (NO), peroxynitrite, and/or nitrate (e.g., after exercise or exertion), and elevated levels of brain ventricular lactic acid. In some embodiments, a neurologic symptom or sign is selected from the group consisting of cognitive deficits (e.g., in attention and reaction time), impaired response to cognitive, motor, visual, and auditory challenges, abnormal nerve conduction studies, abnormal imaging of the brain, hypoperfusion and/or metabolic dysfunction of glial cells, neuroinflammation characterized by widespread activation of both astrocytes and microglia, downregulation of the hypothalamic-pituitary-adrenal (HPA) axis, impaired response of one region of the brain to signals from another region (impaired connectivity), disordered sympathetic and parasympathetic activity, increased levels of tissue repair-indicative proteins (e.g., alpha-2-macroglobulin, keratin 16, orosomucoid), autoantibodies targeting cholinergic, adrenergic, and muscarinic receptors, reduced anaerobic threshold and/or reduced peak work (e.g., after exercise or exertion), and increased lactic acid in muscle and the need to recruit additional brain regions to respond to cognitive challenges (by functional MRI) (e.g., following exertion).

In some embodiments, the present disclosure provides a method for treating one or more symptoms selected from the group consisting of anorexia, anxiety, arrhythmias, dementia, depression, fatigue, hair loss, headache, heart failure, cardiomyopathy, angina, loss of appetite, loss of memory, mood disorder, myocardial ischemia, post-exertional malaise, diminished neurocognition, diminished sensory function, pulmonary fibrosis, renal dysfunction, and respiratory distress, wherein the method comprises administering to a subject an effective amount of: a) a leucine (L)-amino acid entity; b) an arginine (R)-amino acid entity; and c) a glutamine (Q)-amino acid entity. In some embodiments, the present disclosure provides a method for treating one or more symptoms selected from the group consisting of anorexia, anxiety, arrhythmias, dementia, depression, fatigue, hair loss, headache, heart failure, loss of appetite, loss of memory, mood disorder, myocardial ischemia, post-exertional malaise, diminished neurocognition, diminished sensory function, pulmonary fibrosis, renal dysfunction, and respiratory distress, wherein the method comprises administering to a subject an effective amount of: a) a leucine (L)-amino acid entity; b) an arginine (R)-amino acid entity; c) a glutamine (Q)-amino acid entity; and d) a N-acetylcysteine (NAC) entity, e.g., NAC. In some embodiments, one or both of the R-amino acid entity and the Q-amino acid entity are present at a higher amount (wt. %) than the L-amino acid entity, or the amino acid entities administered further comprise a glycine (G)-amino acid entity.

In some embodiments, the present disclosure provides a method for treating one or more symptoms selected from the group consisting of myalgia, muscle fatigue, fatigue, dyspnea after exertion, postural orthostatic tachycardia syndrome, and tachycardia, wherein the method comprises administering to a subject an effective amount of: a) a leucine (L)-amino acid entity; b) an arginine (R)-amino acid entity; and c) a glutamine (Q)-amino acid entity. In some embodiments, the present disclosure provides a method for treating one or more symptoms selected from the group consisting of myalgia, fibromyalgia, idiopathic pulmonary fibrosis, fatigue, mitochondrial dysfunction, dyspnea after exertion, postural orthostatic tachycardia syndrome, tachycardia, mood disorders, and depression, wherein the method comprises administering to a subject an effective amount of: a) a leucine (L)-amino acid entity; b) an arginine (R)-amino acid entity; c) a glutamine (Q)-amino acid entity; and d) a N-acetylcysteine (NAC) entity, e.g., NAC. In some embodiments, one or both of the R-amino acid entity and the Q-amino acid entity are present at a higher amount (wt. %) than the L-amino acid entity. In some embodiments, amino acid entities administered further comprises a glycine (G)-amino acid entity.

Patients with Post-Acute Sequelae of COVID-19 (PASC)

In some embodiments, a subject has post-acute sequelae of COVID-19. In some embodiments, a subject has one or more symptoms selected from the group consisting of anorexia, anxiety, arrhythmias, confusion ("brain fog"), dementia, depression, dyspnea, fatigue, hair loss, headache, heart failure, cardiomyopathy, angina, hepatic dysfunction, hyperglycemia, type 2 diabetes, increased heart rate, inflammation, loss of appetite, loss of memory, loss of smell, mood disorder, muscle weakness, myocardial ischemia, post-exertional malaise, diminished neurocognition, diminished sensory function, pulmonary fibrosis, postural orthostatic hypotension, renal dysfunction, and respiratory distress. In some embodiments, a subject has one or more symptoms selected from the group consisting of myalgia, muscle fatigue, fatigue, dyspnea after exertion, postural orthostatic tachycardia syndrome, tachycardia, mood disorders, and depression. In some embodiments, the subject has been infected with a virus selected from the group consisting of SARS-CoV-1, SARS-CoV-2, MERS, influenza A or B, herpesviruses (Epstein-Barr virus, human cytomegalovirus, and human herpesviruses 6A and 6B), Ebola virus, West Nile virus, dengue virus, Ross river virus, enteroviruses, and human parvovirus B19. In some embodiments, a subject has been infected with a coronavirus (e.g., a human alpha coronavirus (e.g., HCoV-229E or HCoV-NL63), a human betacoronavirus (HCoV-OC43 or HKU1), SARS-CoV-1, SARS-CoV-2, and/or MERS).

In some embodiments, after administration, a subject experiences a reduction in fatigue on a CFQ-11 test. Unless otherwise specified, a reduction in fatigue on a CFQ-11 test refers to the overall CFQ-11 score which includes both a physical domain and a mental domain. In some embodiments, a subject having a reduction in fatigue on a CFQ-11 test has a reduction of fatigue in one or both of the physical domain and the mental domain of the CFQ-11 test.

In some embodiments, a subject has been hospitalized for acute COVID-19. In some embodiments, a subject has been hospitalized for one or more symptoms of post-acute sequelae of COVID-19. In some embodiments, a subject had not been vaccinated for COVID-19 prior to contracting COVID-19. In some embodiments, a subject had not been vaccinated (e.g., partially vaccinated or fully vaccinated) for COVID-19 prior to contracting COVID-19. In some embodiments, a subject had been vaccinated for COVID-19 after contracting COVID-19. In some embodiments, the subject tested positive for SARS-CoV-2 and developed symptoms consistent with infection. In some embodiments, the subject tested positive for SARS-CoV-2 and was asymptomatic, but later developed symptoms consistent with PASC. In some embodiments, the subject tested positive for SARS-COV-2, had symptoms of infection, became antibody negative or asymptomatic, and then was re-infected with another variant of SARS-CoV-2.

In some embodiments, a subject tested positive for COVID-19, e.g., about 1, 2, 3, or 4 weeks before administration. In some embodiments, a subject tested positive for COVID-19 at least twice over a period of time, e.g., at least 3 or 4 weeks, before administering a composition described herein. In some embodiments, a subject had acute COVID-19 for about 3, 4, 5, 6, 8, 10, or 12 weeks, before administering a composition described herein. In some embodiments, a subject had one or more symptoms of acute COVID-10 for at least 3 or 4 weeks, before administration of a composition described herein. In some embodiments, a subject is (e.g., is determined to be) negative for SARS-CoV-2 at the time of administration of a composition described herein. In some embodiments, at the time of administration of a composition described herein, the subject is (e.g., is determined to be) positive for SARS-CoV-2. In some embodiments, at the time of administration, the subject no longer has detectable SARS-CoV-2 in a nasal sample at the time they are administered the composition.

Fatigue Measurement

In some embodiments, a subject is evaluated for indicia of fatigue. In certain embodiments, the subject is evaluated for indicia of fatigue after having been diagnosed as having had or having an infection with SARS-CoV-2. In some embodiments, the subject is evaluated for indicia of fatigue prior to administration of (a)-(d). In some embodiments, the subject is evaluated for indicia of fatigue after administration of (a)-(d) (e.g., at least 1, 2, 3, 4, 5, 6, 7, 8, 9, 10, 11, 12, or more weeks after start of administration). In some embodiments, the subject is evaluated for indicia of fatigue prior to and after (e.g., at least 1, 2, 3, 4, 5, 6, 7, 8, 9, 10, 11, 12, or more weeks after the start) administration of (a)-(d). In some embodiments, the subject is evaluated for indicia of fatigue prior to administration of a composition comprising (a)-(d). In some embodiments, the subject is evaluated for indicia of fatigue after administration of a composition comprising (a)-(d). In some embodiments, the subject is evaluated for indicia of fatigue prior to and after (e.g., at least 1, 2, 3, 4, 5, 6, 7, 8, 9, 10, 11, 12, or more weeks after the start)

administration of a composition comprising (a)-(d). In some embodiments, the subject is evaluated for indicia of fatigue using a scale to measure fatigue.

Various self-administered scales to measure fatigue may be used. In some embodiments, a scale to measure fatigue is used, for example, in clinical trials, to select patients for treatment. In some embodiments, a scale to measure fatigue is used for diagnosis of fatigue after a viral infection. An exemplary scale to measure fatigue is the Chalder Fatigue Scale (CFQ or CFQ-11) or The Fatigue Scale, a self-administered questionnaire for measuring the extent and severity of fatigue within both clinical and non-clinical, epidemiological populations, which was initially developed to measure fatigue in chronic fatigue syndrome (CFS) patients. The CFQ offers both bimodal and Likert scoring. The Likert scoring system allows for means and distributions to be calculated for both the global total as well as the two sub-scales. The scoring systems utilized in the CFQ 11 are virtually identical to the concepts of caseness used in General Health Questionnaire (Jackson C A, 2007). Studies of CFS patients have shown high reliability coefficients for CFQ 11 (Morriss R K, 1998), ranging from 0.90 for the Likert scoring method and 0.83 for the binary scoring method (Loge J H, 1998). Another tool for measuring fatigue is the PROMIS Fatigue Short Form 7a (PROMIS F-SF). PROMIS F-SF is a seven-item questionnaire derived from the 95-item PROMIS Fatigue item bank that assesses both the experience of fatigue and the interference of fatigue on daily activities of a subject over the previous week. Clinical study findings support the reliability and validity of PROMIS F-SF as a measure of fatigue for ME/CFS and support the drug development tool submission for qualifying this measure to evaluate therapeutic effect in ME/CFS clinical trials. Correlation between the PROMIS F-SF and another scale, the MFSI-SF (Multidimensional Fatigue Symptom Inventory-Short Form), ranged from r=0.70 to 0.85, and between the PROMIS F-SF and the BFI (Brief Fatigue Inventory) ranged from r=0.60 to 0.85. Correlations between the PROMIS F-SF and the stress, PSS (Perceived Stress Scale) and depressive symptoms, CES-D (Center for Epidemiological Studies-Depression) ranged from r=0.37 to 0.62, and r=0.45 to 0.64 respectively. This tool consists of only seven items; therefore, patient burden to complete the tool is low as opposed to the MFSI-SF, which has 30 items. In addition, the PROMIS F-SF assesses fatigue over the prior week as compared to the BFI, which assesses fatigue over the prior 24 hours. The Functional Assessment of Chronic Illness Therapy (FACIT) measurement system is a comprehensive compilation of questions that measure health-related quality of life in patients with cancer and other chronic diseases. The FACIT fatigue questionnaire was developed to assess fatigue associated with anemia and has been validated in the general population and is a reliable and valid measure of fatigue in patients with cancer and in patients with RA (Rheumatoid Arthritis) and PsA (Psoriatic Arthritis). There was a good (negative) correlation between the FACIT fatigue and mFSS (modified Fatigue Severity Score) scores (r=−0.79, 95% CI −0.85 to −0.72). The negative sign reflects that higher score on the FACIT fatigue scale indicate less fatigue whereas higher scores on the mFSS scale indicate more fatigue. Results of clinical trials have shown that different fatigue measurement tools might perform differently with different diseases. Other self-reported scales are used to measure fatigue such as the 16-item Multidimensional Assessment of Fatigue (MAF) Scale, the Vitality Scale from the Medical Outcomes Study Short-Form 36 (SF-36), the Brief Fatigue Inventory, Visual Analog Scale (VAS) Fatigue Scale, Fatigue Severity Scale (FSS), and Fatigue Impact Scale. At the 90% sensitivity level for the Fatigue Scale (CFQ) (with a score ≥14.50), the PFRS fatigue scale (a score of ≥1.88), the MFTQ Energy Scale (a score of ≥18.75), MFTQ Brain Fog Scale (a score of ≥24.17), and the FSS (a score of ≥4.95), the specificity was found to be 0.61, 0.62, 0.71, 0.73, and 0.84, respectively. In other words, these scales or subscales can identify 90% of those individuals with CFS (chronic fatigue syndrome), which appears to be similar to post viral infection fatigue like Long COVID fatigue.

In a particular embodiment, both the CFQ (the Fatigue Scale) and the PROMIS F-SF as measures of fatigue associated with Long Covid.

Improvement in Symptoms of Post-Acute Sequelae of COVID-19

The composition as described herein can be administered to treat (e.g., reverse, reduce, ameliorate, or prevent) a subject (e.g., a human) with post-acute sequelae of COVID-19, thereby improving a symptom of post-acute sequelae of COVID-19 in the patient. In some embodiments, the composition is administered to a subject with post-acute sequelae of COVID-19.

In some embodiments, administration of a composition (e.g., at a dosage regimen described herein) results in an improvement in one or more symptoms of post-acute sequelae of COVID-19, e.g., a mitochondrial, metabolic, musculoskeletal, immunologic, neurocognitive, and/or pulmonary symptom of post-acute sequelae of COVID-19, in a subject.

In some embodiments, administration of the composition results in improved mitochondrial function in a subject with post-acute sequelae of COVID-19. In some embodiments, administration of the composition results in improved musculoskeletal function in a subject with post-acute sequelae of COVID-19. In some embodiments, administration of the composition results in improved neurocognitive function in a subject with post-acute sequelae of COVID-19. In some embodiments, administration of the composition results in improved pulmonary function in a subject with post-acute sequelae of COVID-19.

In some embodiments, administration of the composition results in decreased reactive oxygen species (ROS) in a subject with post-acute sequelae of COVID-19.

In some embodiments, administration of the composition results in decreased myalgia in a subject with post-acute sequelae of COVID-19.

In some embodiments, administration of the composition results in decreased fibromyalgia in a subject with post-acute sequelae of COVID-19.

In some embodiments, administration of the composition results in decreased idiopathic pulmonary fibrosis in a subject with post-acute sequelae of COVID-19.

In some embodiments, administration of the composition results in decreased fatigue in a subject with post-acute sequelae of COVID-19.

In some embodiments, administration of the composition results in decreased muscle fatigue in a subject with post-acute sequelae of COVID-19.

In some embodiments, administration of the composition results in decreased dyspnea after exertion in a subject with post-acute sequelae of COVID-19. In some embodiments, administration of the composition results in decreased postural orthostatic tachycardia syndrome in a subject with post-acute sequelae of COVID-19. In some embodiments, administration of the composition results in decreased tachycardia in a subject with post-acute sequelae of COVID-19.

In some embodiments, the composition reduces or inhibits myalgia in a subject with post-acute sequelae of COVID-19. In some embodiments, the composition reduces or inhibits fatigue in a subject with post-acute sequelae of COVID-19.

In some embodiments, the composition reduces muscle fatigue in a subject with post-acute sequelae of COVID-19. In some embodiments, the composition reduces dyspnea after exertion in a subject with post-acute sequelae of COVID-19. In some embodiments, the composition reduces mitochondrial dysfunction in a subject with post-acute sequelae of COVID-19. In some embodiments, the composition reduces postural orthostatic tachycardia syndrome in a subject with post-acute sequelae of COVID-19. In some embodiments, the composition reduces tachycardia in a subject with post-acute sequelae of COVID-19. In some embodiments, the composition decreases or prevents muscle dysfunction. In some embodiments, the composition improves mitochondrial function in a subject with post-acute sequelae of COVID-19. In some embodiments, the composition improves exercise tolerance or the ability to conduct activities of daily living in a subject with post-acute sequelae of COVID-19. In some embodiments, the composition improves mitochondrial capacity (e.g., improvement in oxidative ATP synthesis, phosphocreatine [PCr] resynthesis following exercise or exertion) in a subject with post-acute sequelae of COVID-19. In some embodiments, the composition reduces oxidative stress and/or reduces reactive oxygen species (ROS). In some embodiments, the composition improves mood disorders in a subject with post-acute sequelae of COVID-19. In some embodiments, the composition improves depression in a subject with post-acute sequelae of COVID-19. In some embodiments, the composition improves cognitive function in a subject with post-acute sequelae of COVID-19. In some embodiments, the composition increases skeletal muscle or other organ vascular perfusion in a subject with post-acute sequelae of COVID-19. In some embodiments, the composition improves endothelial function. In some embodiments, the composition improves (e.g., reduces) blood glucose levels (e.g., blood glucose levels due to new onset diabetes).

In some embodiments, administration of a composition (e.g., at a dosage regimen described herein) including amino acid entities results in an improvement in one or more symptoms of post-acute sequelae of COVID-19, e.g., a mitochondrial, metabolic, musculoskeletal, immunologic neurocognitive, and/or pulmonary symptom, in a subject.

Dosage Regimens

The composition can be administered according to a dosage regimen described herein to treat (e.g., inhibit, reduce, ameliorate, or prevent) a disorder, e.g., myalgic encephalomyelitis/chronic fatigue syndrome (ME/CFS), post-infectious fatigue syndrome, post-critical illness syndrome or post-intensive care unit syndrome, following illness or infection, e.g., related to post-acute sequelae of COVID-19 in a subject (e.g., a human). The composition can be administered according to a dosage regimen described herein to treat (e.g., inhibit, reduce, ameliorate, or prevent) a disorder, e.g., post-acute sequelae of COVID-19 in a subject (e.g., a human).

The composition can be provided to a patient with post-acute sequelae of COVID-19 in either a single or multiple dosage regimens. In some embodiments, doses are administered, e.g., twice daily, three times daily, four times daily, five times daily, six times daily, seven times daily, or more. In some embodiments, the composition is administered for at least 2 days, 3 days, 4 days, 5 days, 6 days, 7 days, or 2 weeks. In some embodiments, the composition is administered for at least 10 weeks, 11 weeks, 12 weeks, 13 weeks, 14 weeks, 15 weeks, 16 weeks, 17 weeks, 18 weeks, 19 weeks, 20 weeks, or longer. In some embodiments, the composition is administered chronically, e.g., more than 30 days, e.g., 31 days, 40 days, 50 days, 60 days, 3 months, 6 months, 9 months, one year, two years, or three years).

In some embodiments, the composition is administered at a dose of about 2 g to about 60 g total amino acids, e.g., once per day, twice per day, three times per day, four times per day, five times per day, or six times per day (e.g., three times per day). In some embodiments, the composition is administered at a dose of about 5 g to about 15 g, about 10 g to about 20 g, about 20 g to about 40 g, or about 30 g to about 50 g total amino acids, e.g., once per day, twice per day, three times per day, four times per day, five times per day, or six times per day (e.g., three times per day). In some embodiments, the composition is administered at a dose of about 30 g to about 40 g, about 30 g to about 36 g, e.g., once per day, twice per day, or three times per day. In some embodiments, the composition is administered at a dose of about 30 g to 31 g, about 31 g to about 32 g, about 32 g to about 33 g, about 33 to about 34 g, or about 34 g to about 35 g, twice per day.

In some embodiments, the composition is administered at a dose of about 5 g to about 10 g total amino acids, e.g., once per day, twice per day, three times per day, four times per day, five times per day, or six times per day (e.g., three times per day). In some embodiments, the composition is administered at a dose of about 6 g total amino acids, e.g., once per day, twice per day, three times per day, four times per day, five times per day, or six times per day (e.g., three times per day). In an embodiment, the composition is administered at a dose of about 6 g total amino acids three times per day.

In some embodiments, the composition is administered at a dose of about 10 g to about 20 g total amino acids, e.g., once per day, twice per day, three times per day, four times per day, five times per day, or six times per day (e.g., three times per day). In some embodiments, the composition is administered at a dose of about 12 g total amino acids, e.g., once per day, twice per day, three times per day, four times per day, five times per day, or six times per day (e.g., three times per day). In an embodiment, the composition is administered at a dose of about 12 g total amino acids three times per day.

In some embodiments, the composition is administered at a dose of about 20 g to about 40 g total amino acids, e.g., once per day, twice per day, three times per day, four times per day, five times per day, or six times per day (e.g., three times per day). In some embodiments, the composition is administered at a dose of about 18 g total amino acids, e.g., once per day, twice per day, three times per day, four times per day, five times per day, or six times per day (e.g., three times per day). In an embodiment, the composition is administered at a dose of about 18 g total amino acids three times per day.

In some embodiments, the composition is administered at a dose of about 20 g to about 40 g total amino acids, e.g., once per day, twice per day, three times per day, four times per day, five times per day, or six times per day (e.g., three times per day). In some embodiments, the composition is administered at a dose of about 24 g total amino acids, e.g., once per day, twice per day, three times per day, four times per day, five times per day, or six times per day (e.g., three times per day). In an embodiment, the composition is administered at a dose of about 24 g total amino acids three times per day.

In some embodiments, the composition is administered at a dose of about 30 g to about 50 g total amino acids, e.g., once per day, twice per day, three times per day, four times per day, five times per day, or six times per day (e.g., three times per day). In some embodiments, the composition is administered at a dose of about 48 g total amino acids, e.g., once per day, twice per day, three times per day, four times per day, five times per day, or six times per day (e.g., three times per day). In an embodiment, the composition is administered at a dose of about 48 g total amino acids three times per day.

In some embodiments, the composition is administered at a dose of about 5 grams, about 8 grams, about 9 grams, about 10 grams, about 11 grams, about 12 grams, about 13 grams, about 14 grams, about 15 grams, about 16 grams, about 17 grams, about 18 grams, about 19 about grams, about 20 grams, about 21 grams, about 22 grams, about 24 grams, about 25 grams, about 26 grams, about 27 grams, about 28 grams, about 29 grams, or about 30 grams total amino acids (e.g., about 12 g or about 24 g), e.g., once per day, twice per day, three times per day, four times per day, five times per day, or six times per day (e.g., three times per day).

In some embodiments, the composition is administered every 2 hours, every 3 hours, every 4 hours, every 5 hours, every 6 hours, every 7 hours, every 8 hours, every 9 hours, or every 10 hours to a subject with post-acute sequelae of COVID-19.

In some embodiments, amino acids of the composition are administered separately to a subject with post-acute sequelae of COVID-19. In some embodiments, amino acids of the composition are administered as an admixture to a subject with post-acute sequelae of COVID-19. In some embodiments, the composition is administered to a subject with post-acute sequelae of COVID-19 orally. In an embodiment, the composition is administered to a subject with post-acute sequelae of COVID-19 prior to a meal. In an embodiment, the composition is administered to a subject with post-acute sequelae of COVID-19 concurrent with a meal. In an embodiment, the composition is administered to a subject with post-acute sequelae of COVID-19 following a meal.

In some embodiments, the composition is in a solution or suspension. In some embodiments, the composition is contacted with a liquid (e.g., a beverage, e.g., water), thereby making a solution or suspension. In some embodiments, amino acids administered are in one or more compositions (e.g., one or more stick packs), optionally wherein the one or more compositions are contacted with a liquid. In some embodiments, the one or more compositions are contacted with the liquid simultaneously or sequentially. In some embodiments, one, two, or three, or more of amino acids administered are in a first composition, and the remaining one, two, or three, or more are in a second composition.

In an embodiment, the composition includes at least 2 g of leucine, at least 1 g of isoleucine, at least 1 g of valine, at least 1.5 g of arginine (or 1.81 g of arginine HCl), at least 4 g of glutamine, and at least 0.3 g of N-acetylcysteine for administration two times per day (e.g., a total of at least 34 g per day).

In an embodiment, the composition includes about 2 g of leucine, about 1 g of isoleucine, about 1 g of valine, about 1.5 g of arginine (or 1.81 g of arginine HCl), about 4 g of glutamine, and about 0.3 g of N-acetylcysteine for administration two times per day (e.g., a total of about 34 g per day).

In an embodiment, the composition includes at least 6 g of leucine, at least 3 g of isoleucine, at least 3 g of valine, at least 4.5 g of arginine (or 5.43 g of arginine HCl), at least 12 g of glutamine, and at least 0.9 g of N-acetylcysteine for administration two times per day (e.g., a total of at least 68 g per day).

In an embodiment, the composition includes about 6 g of leucine, about 3 g of isoleucine, about 3 g of valine, about 4.5 g of arginine (or 5.43 g of arginine HCl), about 12 g of glutamine, and about 0.9 g of N-acetylcysteine for administration two times per day (e.g., a total of about 68 g per day).

Secondary Agents

In some embodiments, the method further comprises administering a secondary agent prior to, concurrently with, or after administration of the amino acid composition. In some embodiments, a secondary agent is selected from an antidepressant, a pain reliever (e.g., acetaminophen or a NSAID), a beta-blocker, an anti-epileptic agent, an anti-arrhythmic agent, an anti-viral agent, and a vaccine.

Dietary Compositions

The composition including amino acid entities can be dietary compositions, e.g., chosen from a medical food, a functional food, or a supplement.

The composition including amino acid entities can be for use as a dietary composition, e.g., chosen from a medical food, a functional food, or a supplement. In some embodiments, the dietary composition is for use in a method comprising administering the composition to a subject.

In some embodiments, the subject has fatty liver disease.

In an embodiment, the subject has NASH.

In some embodiments, the subject has one, two, three, four, or more (e.g., all) of myalgia, muscle fatigue, fatigue, dyspnea after exertion, mitochondrial dysfunction, postural orthostatic tachycardia syndrome, tachycardia, mood disorders or depression.

Methods of Providing an Amino Acid to a Subject

The present disclosure features a method of providing amino acid entities to a subject comprising administering to the subject an effective amount of a composition described herein, e.g., a composition comprising a leucine (L)-amino acid entity, a arginine (R)-amino acid entity, a glutamine (Q)-amino acid entity; and an antioxidant or reactive oxygen species (ROS) scavenger, e.g., a N-acetylcysteine (NAC) entity, e.g., NAC.

The present disclosure also features a method of increasing one, two, three, or more (e.g., all) amino acid entities in a subject comprising administering to the subject an effective amount of the composition described herein. In some embodiments, administration of the composition results in an increase in the amino acid entities in one, two, or more (e.g., all) of blood, plasma, or serum of the subject, e.g., in a blood, plasma, or serum sample from the subject.

Biomarkers

Any of the methods disclosed herein can include evaluating or monitoring the effectiveness of administering a composition including amino acid entities to a subject with a PASC. In some embodiments, a composition described herein results in an improvement in one or more biomarkers described herein. In some embodiments, a method described herein comprises measuring one or more biomarkers described herein.

MOTs-C

MOTS-c (Human Mitochondrial Open Reading Frame Of The 12S rRNA-c) is a recently discovered mitochondrially-encoded signaling peptide that primarily targets skeletal muscle and contributes to metabolic homeostasis (Lee et al., ("The mitochondrial-derived peptide MOTS-c promotes metabolic homeostasis and reduces obesity and insulin resistance." Cell Metab 21(3): 443-454, 2015)). MOTS-c exerts its activities by modulating the folate-methionine cycle leading to an accumulation of AICAR, increased NAD+ levels and AMPK activation (Lee et al., ("MOTS-c: A novel mitochondrial-derived peptide regulating muscle and fat metabolism." Free Radic Biol Med 100:182-187, 2016)). Metabolic and oxidative stress stimulate translocation of MOTS-c to the nucleus where it modulates gene expression to restore homeostasis by improving glucose and lipid metabolism and reducing oxidative stress and inflammation (Benayoun and Lee, ("MOTS-c: A Mitochondrial-Encoded Regulator of the Nucleus." Bioessays 41(9): e1900046, 2019); Rochette et al., ("Mitochondrial-derived peptides: New markers for cardiometabolic dysfunction." Arch Cardiovasc Dis 115(1): 48-56, 2021); Yoon et al., ("Exercise, Mitohormesis, and Mitochondrial ORF of the 12S rRNA Type-C (MOTS-c)." Diabetes Metab J 46(3): 402-413, 2022)). Decreased circulating MOTS-c concentrations are associated with metabolic diseases and aging, whereas exercise induces upregulation of MOTS-c in skeletal muscle and the systemic circulation (Merry et al., ("Mitochondrial-derived peptides in energy metabolism." Am J Physiol Endocrinol Metab 319(4): E659-E666, 2020); Miller et al., ("Peptides derived from small mitochondrial open reading frames: Genomic, biological, and therapeutic implications." Exp Cell Res 393(2): 112056, 2021); Reynolds et al., ("MOTS-c is an exercise-induced mitochondrial-encoded regulator of age-dependent physical decline and muscle homeostasis." Nat Commun 12(1): 470, 2021); Yoon et al., 2022, supra). Administration of exogenous MOTS-c in preclinical models promotes improvement in metabolic disorders including obesity, diabetes and cardiovascular disease, as well as age-related physical decline (Merry et al., 2020, supra; Dabravolski et al., ("The Role of Mitochondria-Derived Peptides in Cardiovascular Diseases and Their Potential as Therapeutic Targets." Int J Mol Sci 22(16), 2021); Reynolds et al., 2021, supra). Within skeletal muscle, MOTS-c has been shown to improve metabolism, promote resistance of myoblasts to metabolic stress (Reynolds et al., 2020), reduce myostatin expression and inhibit atrophic signaling pathways resulting from a high-fat diet (Reynolds et al., 2021, supra).

Although MOTS-c remains insufficiently studied in the context of SARS-Cov-2 induced pathophysiology, significantly reduced levels of MOTS-c and another mitochondrial peptide, humanin, were recently described in neuronal and astrocyte-derived extracellular vesicles (EV) of Long COVID patients with neuropsychiatric manifestations (Peluso et al., ("SARS-CoV-2 and Mitochondrial Proteins in Neural-Derived Exosomes of COVID-19." Ann Neurol 91(6): 772-781, 2022)). In contrast, the SARS-Cov-2 S1 subunit and nucleocapsid (N) proteins were elevated in EVs, indicating that S1, N, humanin and MOTS-c might serve as diagnostic biomarkers for Long COVID and efficacy markers for novel Long-COVID therapeutics.

In some embodiments, the biomarker comprises circulating mitochondrial peptides (e.g., MOTS-c). Without wishing to be bound by theory, in some embodiments, in response to metabolic stress, MOTS-c translocates to the nucleus where it binds to antioxidant response elements (ARE) present in the promoter regions of a number of genes. In some embodiments, translocation of MOTS-c to the nucleus results in increased mitochondrial respiration, mTORC2 activity, stimulation of glucose uptake, and promotion muscle growth. In some embodiments, MOTS-c exhibits decreased levels in CFS/QFS. In some embodiments, MOTS-c levels are increased in a subject treated with a composition described herein.

$CO_2$ and Bicarbonate $CO_2$ is a byproduct of metabolic processes involved in ATP production. Blood delivers oxygen to tissues to support ATP production and removes $CO_2$; $CO_2$ is then exhaled through the lungs during respiration. $CO_2$ is often measured clinically as part of a basic metabolic or electrolyte panel. Abnormal $CO_2$ values might represent lung or kidney dysfunction or indicate a wide range of conditions including metabolic disease.

In some embodiments, the biomarker comprises bicarbonate. Without wishing to be bound by theory, bicarbonate is an electrolyte that is used by the body to help maintain the body's pH balance. In some embodiments, a test for bicarbonate levels comprises measuring the total amount of carbon dioxide ($CO_2$) in the blood, which occurs mostly in the form of bicarbonate ($HCO_3^-$). The $CO_2$ is mainly a by-product of various metabolic processes. Measuring bicarbonate as part of an electrolyte or metabolic panel may help diagnose an electrolyte imbalance or acidosis or alkalosis. Acidosis and alkalosis describe the abnormal conditions that result from an imbalance in the pH of the blood caused by an excess of acid or alkali (base). This imbalance is typically caused by some underlying condition or disease. The lungs and kidneys are the major organs involved in regulating blood pH through the removal of excess bicarbonate. The lungs flush acid out of the body by exhaling $CO_2$. Any disease or condition that affects the lungs, kidneys, metabolism, or breathing has the potential to cause acidosis or alkalosis. In some embodiments, bicarbonate levels in the blood are decreased in a subject treated with a composition described herein.

Vascular Cell Adhesion Molecule 1 (VCAM-1)

Vascular cell adhesion molecule 1 (VCAM-1) is expressed on the surface of endothelial cells and facilitates adhesion of inflammatory cells through interaction with leukocyte integrins (Smadja et al., ("COVID-19 is a systemic vascular hemopathy: insight for mechanistic and clinical aspects." Angiogenesis 24(4): 755-788, 2021). Constitutive expression of VCAM-1 is low in healthy individuals but upregulated on the cell surface in response to inflammatory conditions, including COVID-19 (Ambrosino et al., ("Endothelial Dysfunction in COVID-19: A Unifying Mechanism and a Potential Therapeutic Target." Biomedicines 10(4), 2022)). Increases in circulating VCAM-1 (soluble VCAM-1; sVCAM-1) is a marker of vascular inflammation and endothelial activation. In COVID-19 patients, elevated sVCAM-1 levels are associated with higher viral load, greater disease severity and increased mortality (Bermejo-Martin et al., ("Viral RNA load in plasma is associated with critical illness and a dysregulated host response in COVID-19." Crit Care 24(1): 691, 2020); Tong et al., ("Elevated Expression of Serum Endothelial Cell Adhesion Molecules in COVID-19 Patients." J Infect Dis 222(6): 894-898, 2020); Birnhuber et al., ("Between inflammation and thrombosis: endothelial cells in COVID-19." Eur Respir J 58(3), 2021); Spadaro et al., ("Markers of endothelial and epithelial pulmonary injury in mechanically ventilated COVID-19 ICU patients." Crit Care 25(1): 74, 2021); Vieceli Dalla Sega et al., ("Time course of endothelial dysfunction markers and mortality in COVID-19 patients: A pilot study." Clin Transl Med 11(3): e283, 2021)). Recently, platelet-derived and endothelial-cell-derived microparticles from intubated COVID-19 patients have been shown to induce VCAM-1 expression and apoptosis in in vitro cultured endothelial cells (Garnier et al., ("Plasma microparticles of intubated COVID-19 patients cause endothelial cell death, neutrophil adhesion and netosis, in a phosphatidylserine-dependent manner." Br J Haematol 196 (5): 1159-1169, 2021)).

In some embodiments, the biomarker is Vascular cell adhesion molecule 1 (VCAM-1). Without wishing to be bound by theory, VCAM-1 is expressed on the surface of endothelial cells and facilitates adhesion of inflammatory cells through interaction with leukocyte integrins. Without wishing to be bound by theory, increases in circulating VCAM-1 (soluble VCAM-1; sVCAM-1) is a marker of vascular inflammation and endothelial activation. In some embodiments, a test for VCAM-1 levels comprises measuring the amount of VCAM-1 in the blood (e.g., serum). In some embodiments, VCAM-1 is measured by electrochemiluminescence immunoassay (ECLIA). Measuring VCAM-1 as part of an ECLIA may help diagnose an inflammatory condition. Constitutive expression of VCAM-1 is low in healthy individuals but upregulated on the cell surface in response to inflammatory conditions, including COVID-19. In COVID-19 patients, elevated sVCAM-1 levels are associated with higher viral load, greater disease severity and increased mortality (Bermejo-Martin et al., 2020, supra; Tong et al., 2020, supra; Birnhuber et al., 2021, supra; Spadaro et al., 2021, supra; Vieceli Dalla Sega et al., 2021, supra). Recently, platelet-derived and endothelial-cell-derived microparticles from intubated COVID-19 patients have been shown to induce VCAM-1 expression and apoptosis in in vitro cultured endothelial cells (Garnier et al., 2021, supra). In some embodiments, VCAM-1 (e.g., sVCAM-1) levels in the serum are decreased in a subject treated with a composition described herein. In some embodiments, VCAM-1 (e.g., sVCAM-1) levels in the serum are decreased in a subject treated with a composition described herein compared to a control (e.g., a subject not treated with a composition described herein).

In embodiments, the value of effectiveness to the composition in treating a subject with a PASC comprises a measure of one, two, three, four, five, six, seven, eight, nine, ten, eleven, twelve, thirteen, fourteen, fifteen, sixteen, seventeen, or more (e.g., all) of the following:
a) growth differentiation factor-15 (GDF-15);
b) SIRT1;
c) SIRT3;
d) COXII;
e) COXIV;
f) SHLP1-6;
g) Humanin;
h) carnosine;
i) acetyl carnitines;
j) phosphocreatine;
k) creatine;
l) taurine;
m) glycogen;
n) IL-6;
o) C-reactive protein (CRP)
p) FGF-21;
q) MOTS-c; or
r) serum lactate.

In some embodiments of any of the methods disclosed herein, the measure of one or more of a)-r) is obtained from a sample acquired from the subject with PASC. In some embodiments, the sample is chosen from a blood sample (e.g., a plasma sample).

In some embodiments, the subject is evaluated prior to receiving, during, or after receiving, a composition including amino acid entities.

In some embodiments, administration of the composition including amino acid entities (e.g., at a dose of about 2 g to about 60 g total amino acids, e.g., about 6 g, about 12 g, about 18 g, about 24 g, or about 48 g), results in an improvement in one, two, three, four, five, six, seven, eight, nine, ten, eleven, twelve, thirteen, fourteen, fifteen, sixteen, seventeen, or more (e.g., all) of the following:
a) growth differentiation factor-15 (GDF-15);
b) SIRT1;
c) SIRT3;
d) COXII;
e) COXIV;
f) SHLP1-6;
g) Humanin;
h) carnosine;
i) acetyl carnitines;
j) phosphocreatine;
k) creatine;
l) taurine;
m) glycogen;
n) IL-6;
o) C-reactive protein (CRP)
p) FGF-21;
q) MOTS-c; or
r) serum lactate.

In some embodiments, administration of the composition including amino acid entities (e.g., at a dose of about 2 g to about 60 g total amino acids, e.g., about 6 g, about 12 g, about 18 g, about 24 g, or about 48 g three times daily), results in an improvement in one, two, three, four, five, six, seven, eight, nine, ten, or more (e.g., all) of a)-r) after a treatment period of, about 24 hours, about 72 hours, about 1 week, about 2 weeks, about 3 weeks, about 4 weeks, about 5 weeks, about 6 weeks, about 7 weeks, about 8 weeks, about 9 weeks, about 10 weeks, about 11 weeks, or 12 weeks. In certain embodiments, administration of the composition results in an improvement in one, two, three, four, five, or more (e.g., all) of a)-r) after a treatment period of about 2 weeks.

EXAMPLES

The Example below is set forth to aid in the understanding of the inventions, but is not intended to, and should not be construed to, limit its scope in any way.

Example 1: Method of Producing the Amino Acid Compositions

The amino acid compositions of the instant disclosure and formulations thereof may be made according to methods known in the art. They may also be made by the methods described below.

The starting materials (individual amino acids and excipients) are blended and sieved to generate a powder blend, which is filled into stick packs or sachets. The contents of the stick packs or sachets are dispersed in water at time of use for oral administration. Examples of the sachet formulations made thereby, are provided below in Tables 10 and 11.

TABLE 10

Exemplary composition comprising amino acids

| Ingredient | Sachet Dry Weight (g) | Dry Weight (% w/w) | Single Dose Dry Weight (g) | Max Daily Dose Dry Weight (g) | Single Dose Concentration (g/L) in 6 oz.* |
|---|---|---|---|---|---|
| L-Leucine | 2.0000 | 13.01 | 2.0000 | 12.0000 | 11.27 |
| L-Isoleucine | 1.0000 | 6.51 | 1.0000 | 6.0000 | 5.64 |
| L-Valine | 1.0000 | 6.51 | 1.0000 | 6.0000 | 5.64 |
| L-Arginine HCl | 3.6280 | 23.61 | 3.6280 | 21.7680 | 20.45 |
| L-Glutamine | 4.0000 | 26.03 | 4.0000 | 24.0000 | 22.54 |
| N-Acetyl-L-cysteine (NAC) | 0.3000 | 1.95 | 0.3000 | 1.8000 | 1.69 |
| Citric Acid | 0.6667 | 4.34 | 0.6667 | 4.0002 | 3.76 |
| Lecithin | 1.6666 | 10.85 | 1.6666 | 9.9996 | 9.36 |
| Xanthan Gum | 0.2000 | 1.30 | 0.2000 | 1.2000 | 1.13 |
| Sucralose | 0.0667 | 0.43 | 0.0667 | 0.4002 | 0.38 |
| Orange (Nat + WONF) | 0.3500 | 2.28 | 0.3500 | 2.1000 | 1.97 |
| Vanilla Custard (Art) | 0.0600 | 0.39 | 0.0600 | 0.3600 | 0.34 |
| FD&C Yellow 6 | 0.0090 | 0.06 | 0.0090 | 0.0540 | 0.05 |
| L-HPC (low substituted hydroxypropyl-cellulose) | 0.1000 | 0.65 | 0.1000 | 0.6000 | 0.56 |
| Colloidal SiO$_2$ | 0.3000 | 1.95 | 0.3000 | 1.8000 | 1.69 |
| Magnesium Stearate | 0.0200 | 0.13 | 0.0200 | 0.1200 | 0.11 |
| AMINO ACIDS (-HCL) | 11.3000 | 73.53 | 11.3000 | 67.8000 | 63.68 |
| TOTAL | 15.3670 | 100.00 | 15.3670 | 92.2020 | 86.60 |

*1 sachet is used to form a suspension in 6 oz. of water

TABLE 11

Exemplary composition comprising amino acids

| Ingredient | Sachet Dry Weight (g) | Dry Weight (% w/w) | Single Dose Dry Weight (g) | Max Daily Dose Dry Weight (g) | Single Dose Concentration (g/L) in 6 oz.* |
|---|---|---|---|---|---|
| L-Leucine | 2.0000 | 15.15 | 2.0000 | 12.0000 | 16.91 |
| L-Isoleucine | 1.0000 | 7.58 | 1.0000 | 6.0000 | 8.45 |
| L-Valine | 1.0000 | 7.58 | 1.0000 | 6.0000 | 8.45 |
| L-Arginine HCl | 3.6280 | 27.49 | 3.6280 | 21.7680 | 30.67 |
| L-Glutamine | 4.0000 | 30.31 | 4.0000 | 24.0000 | 33.81 |
| N-Acetyl-L-cysteine (NAC) | 0.3000 | 2.27 | 0.3000 | 1.8000 | 2.54 |
| Citric Acid | 0.2000 | 1.52 | 0.2000 | 1.2000 | 1.69 |
| Lecithin | 0.1600 | 1.21 | 0.1600 | 0.9600 | 1.35 |
| Xanthan Gum | 0.2000 | 1.52 | 0.2000 | 1.2000 | 1.69 |
| Sucralose | 0.0300 | 0.23 | 0.0300 | 0.1800 | 0.25 |
| Orange (Nat + WONF) | 0.2000 | 1.52 | 0.2000 | 1.2000 | 1.69 |
| Vanilla Custard (Art) | 0.0500 | 0.38 | 0.0500 | 0.3000 | 0.42 |
| FD&C Yellow 6 | 0.0020 | 0.02 | 0.0020 | 0.0120 | 0.02 |
| L-HPC (low substituted hydroxypropyl-cellulose) | 0.2640 | 2.00 | 0.2640 | 1.5840 | 2.23 |
| Colloidal SiO$_2$ | 0.1320 | 1.00 | 0.1320 | 0.7920 | 1.12 |
| Magnesium Stearate | 0.0330 | 0.25 | 0.0330 | 0.1980 | 0.28 |
| AMINO ACIDS (-HCL) | 11.3000 | 85.61 | 11.3000 | 67.8000 | 95.52 |
| TOTAL | 13.1990 | 100.00 | 13.1990 | 79.1940 | 111.58 |

*1 sachet is used to form a suspension in 6 oz. of water

Example 2: Hepatocyte Model for Steatosis and Inflammation

Hepatocyte lipotoxicity appears to be a central driver of hepatic cellular injury via oxidative stress and endoplasmic reticulum (ER) stress. The ability of amino acids to influence steatosis (lipid accumulation) and inflammation in hepatocytes was assessed using human primary hepatocytes (Lonza, TRL).

Cell Seeding and Maintenance

Primary hepatocytes lot nos. from two healthy human donors were seeded on day 0 at density of 6e04 cells in 96 well optical microplates (Thermofisher) in hepatocyte plating media (William's E medium (Gibco) supplemented with 10% heat-inactivated FBS (Atlanta Bio), 2 mM Glutamax (Gibco), 1×ITS plus (R&D systems), and 0.2% Primocin (InVivoGen) and incubated for 6 hours at 37° C., 5% CO$_2$. After 6 hours, cells were washed twice with 150 µl William's E medium and incubated overnight at 37° C., 5% CO$_2$ with serum-free hepatocytes culture media (Hepatocytes defined medium (Corning)) supplemented with 5 µg human recombinant EGF (Corning), 2 mM Glutamax (Gibco), and 1× Penicillin/Streptomycin. On day 1, cells were washed twice with 150 µL per well William's E medium (Gibco) and incubated for 24 h in the hepatocyte culture media in the same conditions described above.

Amino Acids Pre-Treatment

On day 2, cells were washed twice with 150 µl DPBS 1× (Gibco) and maintained in amino acid-free WEM (US Biologicals) containing a defined custom amino acid concentration based on the mean physiological concentrations in blood. The values are published in the Human Metabolome Database (Wishart D S, Tzur D, Knox C, et al., *HMDB: the Human Metabolome Database*. Nucleic Acids Res. 2007 January; 35(Database issue):D521-6. 17202168; which is hereby incorporated by reference in its entirety). This custom media is supplemented with 11 mM Glucose, 0.272 mM Sodium Pyruvate, and a dose curve of defined amino acid compositions (i.e., vehicle, LIVRQ+N-acetylcysteine, LIVRQ, RQ+N-acetylcysteine, N-acetylcysteine alone, LIV, or individually with L-Leucine, L-Isoleucine, L-Valine, L-Arginine, L-Glutamine, and L-Cysteine) at various ranges of concentrations (1× is L-Leucine: 152.7 µM; L-Isoleucine: 66.4 µM; L-Valine: 234.2 µM; L-Arginine: 108.8 µM; L-Glutamine: 562.1 µM; N-acetylcysteine: 250 µM [not endogenous]). Cells were maintained in this defined media for 24 hours at 37° C., 5% $CO_2$.

Co-Treatment with Free Fatty Acids and Different Amino Acids Combination

After pre-treatment, cells were exposed to free fatty acids (FFA) at 250 µM with a ratio of 2:1 (Oleate:Palmitate) supplemented with TNF-α (Thermofisher) at 1 ng/ml or vehicle. Cells were incubated with the FFAs mixture and the different amino acids combinations for 24 hours at 37° C., 5% C02. After 24 hours incubation, media was removed for cytokine analysis and replaced by fresh media containing the same stimulus conditions and amino acid concentrations. Cells were incubated for an additional 48 hours for a total of 72 hours of FFA and TNFα stimulation.

Cytokine Analysis after 24 h by ELISA

Human CCL2 (MCP-1) was measured by ELISA (Human CCK2/MCP-1 DuoSet ELISA, R&D Systems) at 1/5 or 1/10 dilution in 1× Reagent Diluent (Reagent Ancillary Kit 2, R&D Systems). Data were normalized to the specific per well cell density determined by nuclei count stained by Hoechst 3342 (Life technologies) in the fluorescence microscopy described below.

Intracellular Lipid Accumulation Analysis after 72 h by Fluorescence Microscopy

After 72 hours, cells were washed twice in 100 µl PBS 1× (Gibco), fixed with 4% Paraformaldehyde, and washed twice with PBS 1× (100 l). After fixation, lipids were stained with HCS LipidTOX Red Neutral (Thermofisher Scientific) diluted 1000× and nuclei were stained with Hoechst 3342 (Life Technologies) diluted to 4 µg/ml. The LipidTOX™ neutral lipid stain has an extremely high affinity for neutral lipid droplets that was detected by fluorescence microscopy using a high content imager (Molecular Devices).

Results

Lipid Accumulation and Steatosis Phenotypes

Primary human hepatocytes from healthy donors were found to have low levels of lipid accumulation. Treatment of the cells with free fatty acids (FF)+TNFα induced lipid accumulation with a macro-steatosis phenotype. Treatment with LIVRQNAC changed the hepatocyte phenotypes from macro-steatosis to micro-steatosis.

MCP1/CCL2 Secretion

Tables 12-15 show the baseline subtracted secretion of MCP1/CCL2 in primary human hepatocytes cells from two healthy donors (donor 1 for Tables 12 or 13, and donor 2 for Tables 14 and 15). LIVRQNAC, LIVRQNAC+G, LIVRQNAC+S, LIVRQ and RQNAC significantly decreased MCP1/CCL2 secretion in both donors. The combination LIV, however, significantly increased MCP1/CCL2 secretion only in one of the donors. The addition of arginine (R) and glutamine (Q) to a combination of LIV decreased the secretion of MCP1/CCL2 in both donors compared to LIV alone. Individually, N-acetyl cysteine and glutamine are shown to significantly decrease MCP1/CCL2 secretion, while arginine increased MCP1 secretion. Isoleucine, Leucine and Valine did not have an effect on MCP1/CCL2 secretion.

TABLE 12

Changes in MCP1 expression for donor 1 upon administration of amino acid compositions MCP1 expression relative to Control—Donor 1

| Amino Acid Supplement | Conc. (X) | Mean | Std. Deviation | Number of values | P-value* | Significance |
|---|---|---|---|---|---|---|
| LIVRQNAC | 40 | −24.1616 | 0.032252 | 3 | 0.0001 | **** |
| LIVRQNAC | 30 | −22.2916 | 2.119583 | 3 | 0.0001 | **** |
| LIVRQNAC | 20 | −18.4363 | 0.850597 | 3 | 0.0005 | *** |
| LIVRQNAC | 10 | −14.3383 | 1.854977 | 3 | 0.0074 | ** |
| LIVRQNAC | 1 | 0 | 1.048045 | 3 | | |
| LIVRQNAC+G | 40 | −22.0824 | 0.873105 | 3 | 0.0001 | **** |
| LIVRQNAC+G | 30 | −19.2605 | 1.611788 | 3 | 0.0003 | *** |
| LIVRQNAC+G | 20 | −17.5807 | 2.893835 | 3 | 0.0009 | *** |
| LIVRQNAC+G | 10 | −13.7521 | 3.068991 | 3 | 0.0106 | * |
| LIVRQNAC+G | 1 | 0 | 1.682719 | 3 | | |
| LIVRQNAC+S | 40 | −32.4703 | 0.340537 | 3 | 0.0001 | **** |
| LIVRQNAC+S | 30 | −30.768 | 1.339048 | 3 | 0.0001 | **** |
| LIVRQNAC+S | 20 | −25.5964 | 1.854519 | 3 | 0.0001 | **** |
| LIVRQNAC+S | 10 | −17.8326 | 1.974033 | 3 | 0.0008 | *** |
| LIVRQNAC+S | 1 | 2.37E−15 | 18.41384 | 3 | | |
| LIV | 40 | 15.52052 | 6.323205 | 3 | 0.0094 | ** |
| LIV | 30 | 12.3111 | 10.02706 | 3 | 0.0475 | * |
| LIV | 20 | 12.6686 | 4.109608 | 3 | 0.0401 | * |
| LIV | 10 | −5.18869 | 1.579468 | 3 | 0.6477 | ns |
| LIV | 1 | −1.2E−15 | 8.178943 | 3 | | |
| LIVRQ | 40 | −25.9576 | 0.484283 | 3 | 0.0028 | ** |
| LIVRQ | 30 | −23.6562 | 2.599721 | 3 | 0.0099 | ** |
| LIVRQ | 20 | −13.4723 | 3.427666 | 3 | 0.6401 | ns |
| LIVRQ | 10 | −9.22141 | 7.599407 | 3 | 0.9986 | ns |
| LIVRQ | 1 | −8.23198 | 5.80889 | 3 | | |
| RQNAC | 40 | −21.4681 | 2.903892 | 3 | 0.0003 | *** |

TABLE 12-continued

Changes in MCP1 expression for donor 1 upon administration of amino acid compositions

| | | MCP1 expression relative to Control—Donor 1 | | | | |
|---|---|---|---|---|---|---|
| Amino Acid Supplement | Conc. (X) | Mean | Std. Deviation | Number of values | P-value* | Significance |
| RQNAC | 30 | −17.1873 | 5.202568 | 3 | 0.0038 | ** |
| RQNAC | 20 | −12.1782 | 2.907484 | 3 | 0.0506 | ns |
| RQNAC | 10 | −8.89378 | 4.748653 | 3 | 0.206 | ns |
| RQNAC | 1 | 1.18E-15 | 10.02527 | 3 | | |
| N-Acetyl Cysteine | 40 | −17.6065 | 1.211739 | 3 | 0.0009 | *** |
| N-Acetyl Cysteine | 20 | −10.8919 | 2.27818 | 3 | 0.0545 | ns |
| N-Acetyl Cysteine | 10 | −2.49755 | 8.795693 | 3 | 0.9424 | ns |
| N-Acetyl Cysteine | 5 | −0.76286 | 7.457085 | 3 | 0.9991 | ns |
| N-Acetyl Cysteine | 0 | 0 | 6.716428 | 3 | | |

TABLE 13

Changes in MCP1 expression for donor 1 upon administration of single amino acid compositions

| | | MCP1 expression relative to Control-Donor 1 | | | | |
|---|---|---|---|---|---|---|
| Amino Acid Supplement | Conc. (μM) | Mean | Std. Deviation | Number of values | P-value* | Significance |
| Valine | 23420 | 14.16805 | 19.23365 | 3 | 0.6777 | ns |
| Valine | 11710 | 77.73396 | 137.82 | 3 | 0.9998 | ns |
| Valine | 4684 | 23.6867 | 46.48697 | 3 | 0.2502 | ns |
| Valine | 234 | −2.4E-15 | 13.86902 | 3 | | |
| Arginine | 5440 | 10.9386 | 4.79774 | 3 | 0.0057 | ** |
| Arginine | 2720 | 6.526801 | 4.266971 | 3 | 0.1517 | ns |
| Arginine | 1088 | 5.114414 | 4.685563 | 3 | 0.3321 | ns |
| Arginine | 109 | 2.37E-15 | 0.666016 | 3 | | |
| Glutamine | 22484 | −21.8392 | 1.113443 | 3 | 0.0004 | *** |
| Glutamine | 11242 | −9.00139 | 1.68951 | 3 | 0.2459 | ns |
| Glutamine | 3747 | −0.89805 | 6.374471 | 3 | 0.9991 | ns |
| Glutamine | 749 | 0 | 9.549143 | 3 | | |
| Isoleucine | 6639 | −0.205 | 2.292188 | 3 | 0.9998 | ns |
| Isoleucine | 3320 | −2.41722 | 2.382379 | 3 | 0.4907 | ns |
| Isoleucine | 1328 | −0.30729 | 2.409691 | 3 | 0.9992 | ns |
| Isoleucine | 66 | −1.2E-15 | 3.163838 | 3 | | |
| Leucine | 15270 | −1.36762 | 3.37035 | 3 | 0.8675 | ns |
| Leucine | 7635 | 1.895506 | 3.757642 | 3 | 0.6872 | ns |
| Leucine | 3054 | 3.340489 | 3.016641 | 3 | 0.2201 | ns |
| Leucine | 153 | 5.92E-16 | 3.132507 | 3 | | |
| N-Acetyl Cysteine | 10000 | −17.6065 | 1.211739 | 3 | 0.0009 | *** |
| N-Acetyl Cysteine | 5000 | −10.8919 | 2.27818 | 3 | 0.0545 | ns |
| N-Acetyl Cysteine | 2500 | −2.49755 | 8.795693 | 3 | 0.9424 | ns |
| N-Acetyl Cysteine | 1000 | −0.76286 | 7.457085 | 3 | 0.9991 | ns |
| N-Acetyl Cysteine | 0 | 0 | 6.716428 | 3 | | |

TABLE 14

Changes in MCP1 expression for donor 2 upon administration of amino acid compositions

| | | MCP1 expression relative to Control—Donor 2 | | | | |
|---|---|---|---|---|---|---|
| Amino Acid Supplement | Conc. (X) | Mean | Std. Deviation | Number of values | P-value* | Significance |
| LIVRQNAC | 40 | −24.5376 | 1.632923 | 3 | 0.0001 | **** |
| LIVRQNAC | 30 | −13.6824 | 2.562571 | 3 | 0.0001 | **** |
| LIVRQNAC | 20 | −8.42053 | 1.545343 | 3 | 0.0001 | **** |
| LIVRQNAC | 10 | 2.126223 | 0.453924 | 3 | 0.0007 | *** |
| LIVRQNAC | 1 | −4.7E-15 | 0.412226 | 3 | | |
| LIVRQNAC + G | 40 | −35.3651 | 2.08381 | 3 | 0.0007 | *** |

TABLE 14-continued

Changes in MCP1 expression for donor 2 upon administration of amino acid compositions

| | | MCP1 expression relative to Control—Donor 2 | | | | |
|---|---|---|---|---|---|---|
| Amino Acid Supplement | Conc. (X) | Mean | Std. Deviation | Number of values | P-value* | Significance |
| LIVRQNAC + G | 30 | −30.3247 | 5.225183 | 3 | 0.001 | *** |
| LIVRQNAC + G | 20 | −17.0719 | 4.522244 | 3 | 0.0119 | * |
| LIVRQNAC + G | 10 | −14.2586 | 2.767898 | 3 | 0.049 | * |
| LIVRQNAC + G | 1 | −7.1E−15 | 7.613666 | 3 | | |
| LIVRQNAC + S | 40 | −35.8381 | 1.404782 | 3 | 0.0001 | **** |
| LIVRQNAC + S | 30 | −30.9946 | 2.372062 | 3 | 0.0001 | **** |
| LIVRQNAC + S | 20 | −16.8831 | 3.223007 | 3 | 0.0004 | *** |
| LIVRQNAC + S | 10 | −5.60595 | 10.2119 | 3 | 0.1887 | |
| LIVRQNAC + S | 1 | 2.37E−15 | 4.4168 | 3 | | |
| LIV | 40 | −46.7898 | 8.664441 | 3 | 0.3692 | ns |
| LIV | 30 | −34.5953 | 16.84743 | 3 | 0.6246 | ns |
| LIV | 20 | −28.0851 | 31.84348 | 3 | 0.7684 | ns |
| LIV | 10 | −11.0006 | 72.74556 | 3 | 0.9889 | ns |
| LIV | 1 | 9.47E−15 | 60.93638 | 3 | | |
| LIVRQ | 40 | −129.802 | 7.067989 | 3 | 0.0008 | *** |
| LIVRQ | 30 | −110.034 | 4.53852 | 3 | 0.0042 | ** |
| LIVRQ | 20 | −33.3611 | 31.87706 | 3 | 0.6524 | |
| LIVRQ | 10 | −3.30904 | 71.03267 | 3 | 0.9999 | |
| LIVRQ | 1 | −4.7E−15 | 46.12987 | 3 | | |
| RQNAC | 40 | −133.48 | 1.908424 | 3 | 0.0006 | *** |
| RQNAC | 30 | −123.712 | 1.043889 | 3 | 0.0013 | ** |
| RQNAC | 20 | −109.575 | 5.533323 | 3 | 0.0044 | ** |
| RQNAC | 10 | −55.8583 | 22.72309 | 3 | 0.2273 | |
| RQNAC | 1 | 1.42E−14 | 43.79031 | 3 | | |
| N-Acetyl Cysteine | 10000 | −28.4419 | 1.694 | 3 | 0.0001 | *** |
| N-Acetyl Cysteine | 5000 | −10.5725 | 4.362178 | 3 | 0.0012 | ** |
| N-Acetyl Cysteine | 2500 | −4.0591 | 5.600773 | 3 | 0.0572 | ns |
| N-Acetyl Cysteine | 1000 | 1.602474 | 3.423109 | 3 | 0.0001 | **** |
| N-Acetyl Cysteine | 0 | 0 | 2.068861 | 3 | | |

TABLE 15

Changes in MCP1 expression for donor 2 upon administration of single amino acid compositions

| | | MCP1 expression relative to Control—Donor 2 | | | | |
|---|---|---|---|---|---|---|
| Amino Acid Supplement | Conc. (µM) | Mean | Std. Deviation | Number of values | P-value* | Significance |
| Valine | 23420 | −30.7921 | 22.55378 | 3 | 0.6118 | ns |
| Valine | 11710 | 38.24762 | 28.44112 | 3 | 0.4268 | ns |
| Valine | 4684 | 10.79011 | 51.87642 | 3 | 0.9835 | ns |
| Valine | 234 | −1.4E−14 | 30.91388 | 3 | | |
| Arginine | 5440 | 8.493664 | 22.98385 | 3 | 0.9913 | ns |
| Arginine | 2720 | 24.06261 | 63.49489 | 3 | 0.7429 | ns |
| Arginine | 1088 | 24.95224 | 52.94171 | 3 | 0.7192 | ns |
| Arginine | 109 | −4.7E−15 | 11.27976 | 3 | | |
| Glutamine | 22484 | −138.873 | 10.74317 | 3 | 0.0001 | **** |
| Glutamine | 11242 | −90.6558 | 15.43989 | 3 | 0.0037 | ** |
| Glutamine | 3747 | −45.0574 | 41.63249 | 3 | 0.2474 | ns |
| Glutamine | 749 | 2.84E−14 | 59.86955 | 3 | 0.7631 | |
| Isoleucine | 6639 | 18.62132 | 26.01824 | 3 | 0.5663 | ns |
| Isoleucine | 3320 | −5.64461 | 7.719105 | 3 | 0.9882 | ns |
| Isoleucine | 1328 | 26.62309 | 5.65413 | 3 | 0.2613 | ns |
| Isoleucine | 66 | 0 | 4.245462 | 3 | | |
| Leucine | 15270 | −26.6436 | 10.08177 | 3 | 0.2607 | ns |
| Leucine | 7635 | −2.98815 | 21.00205 | 3 | 0.9989 | ns |
| Leucine | 3054 | 16.11014 | 8.662188 | 3 | 0.68 | ns |
| Leucine | 153 | −4.7E−15 | 7.63396 | 3 | | |
| N-Acetyl Cysteine | 10000 | −28.4419 | 1.694 | 3 | 0.0001 | *** |

TABLE 15-continued

Changes in MCP1 expression for donor 2 upon administration of single amino acid compositions

| | | MCP1 expression relative to Control—Donor 2 | | | | |
|---|---|---|---|---|---|---|
| Amino Acid Supplement | Conc. (µM) | Mean | Std. Deviation | Number of values | P-value* | Significance |
| N-Acetyl Cysteine | 5000 | −10.5725 | 4.362178 | 3 | 0.0012 | ** |
| N-Acetyl Cysteine | 2500 | −4.0591 | 5.600773 | 3 | 0.0572 | ns |
| N-Acetyl Cysteine | 1000 | 1.602474 | 3.423109 | 3 | 0.0001 | **** |
| N-Acetyl Cysteine | 0 | 0 | 2.068861 | 3 | | |

Example 3: Hepatic Stellate Cell—TNFα Inflammatory Response

Methods

Primary human hepatic stellate cells were obtained from Samsara Sciences based on the following criteria for selecting donors: adult age (between 18 and 50 years), normal BMI (>18.5 and <25), and absence of confounding liver disease. Primary human hepatic stellate cells grown in Complete HSC Medium to ~80% confluence in T75 or T150 flasks below passage 10 were seeded into sterile, collagen I coated, 96-well optical plastic microplates (ThermoScientific, 152036) at 4000 cells per well (~1250 cells per cm²) and incubated for 6 hours at 37° C., 5% $CO_2$ in a humidified incubator.

After 6 hours, plates were removed from the incubator and the medium gently pipetted off and washed once with 150 µL per well DPBS. The DPBS was removed and the pretreatment medium (± single amino acid dropout, 1×HMDB DMEM+3% dialyzed FBS+0.2% Primocin, ± Supplemental amino acid dose at multiples of 1×HMDB [L-Leucine: 152.7 µM; L-Isoleucine: 66.4 µM; L-Valine: 234.2 µM; L-Arginine: 108.8 µM; L-Glutamine: 562.1 µM; N-acetylcysteine: 250 µM (not endogenous)]; see experiment for medium composition) was applied to the cells at 150 µL per well. Plates were returned to the incubator overnight, ~14-15 hours.

After overnight pretreatment, the medium was removed from the cells, and the same pretreatment medium, now supplemented with 3 ng/mL TNFα is applied. Each plate contained 3 ng/mL TNFα in 1× human plasma amino acid (HMDB or PAA) concentration medium, 0 ng/mL in 1×HMDB, and 3 ng/mL TNFα+50 nM Bengamide in 1×HMDB to serve as controls. Plates were incubated for 12 hours at 37° C., 5% $CO_2$.

After 12 hour stimulus with TNFα, supernatant was removed and frozen at −80° C. in two separate aliquots. Plates were washed gently once with DPBS and 100 µL per well of 1×HMDB DMEM+3% dialyzed FBS+0.2% Primocin+10% CCK-8 viability reagent (Dojindo). Plates were incubated for 1 hour at 37° C., 5% $CO_2$.

After 1 hour of incubation, viability was measured on the Synergy plate reader (Absorbance at 977 (test), 900 (reference), and 450 (CCK8) nm). Immediately, the medium was removed and the plates were fixed with 70 µL per well 4% paraformaldehyde in PBS at room temperature for 20 minutes, followed by two 150 µL PBS washes, and stored with 100 µL per well PBS at 4° C. until immunofluorescence staining.

Human CCL2/MCP1 and Human IL-6 were measured by ELISA (Human CCK2/MCP-1 DuoSet ELISA, R&D Systems; Human IL-6 DuoSet ELISA, R&D Systems) at 1/5 and 1/20 dilution in 1× Reagent Diluent (Reagent Ancillary Kit 2, R&D Systems). Data were normalized to the specific per well cell density determined by Hoechst stained nuclei count.

Results

Pro-Inflammatory MCP-1 Chemokine Secretion

Tables 16-19 show per-cell normalized MCP-1 chemokine secretion in primary human hepatic stellate cells from two donors as a fold change from the plasma amino acid background. Statistical significance calculated by one-way ANOVA with Dunnett's multiple comparison test within each treatment group. LIVRQNAC+G and RQNAC significantly decrease MCP-1 secretion in both donors. LIVRQNAC, LIVRQNAC+S reduced MCP1 secretion and was statistically significant in one of two donors. Individually, each of valine, arginine, and leucine had no significant impact on MCP-1 secretion. Glutamine reduced MCP1 secretion in both donors but was only statistically significant in one of two donors. N-acetyl cysteine significantly reduced MCP-1 secretion in both donors.

TABLE 16

Changes in MCP1 secretion for donor 3 upon administration of amino acid compositions

| | | Fold Change MCP1 Secretion Normalized Per Cell | | | | |
|---|---|---|---|---|---|---|
| Amino Acid Supplement | Conc. (X) | Mean | Std. Deviation | Number of values | Significance | P-value |
| LIVRQNAC | 40 | 0.6237 | 0.2500 | 3 | ns | 0.2763 |
| LIVRQNAC | 30 | 0.6180 | 0.2436 | 3 | ns | 0.2657 |
| LIVRQNAC | 20 | 0.5679 | 0.1728 | 3 | ns | 0.1863 |
| LIVRQNAC | 10 | 0.5548 | 0.2139 | 3 | ns | 0.1694 |
| LIVRQNAC | 1 | 1.0000 | 0.3619 | 3 | | |

TABLE 16-continued

Changes in MCP1 secretion for donor 3 upon administration of amino acid compositions

| | | Fold Change MCP1 Secretion Normalized Per Cell | | | | |
|---|---|---|---|---|---|---|
| Amino Acid Supplement | Conc. (X) | Mean | Std. Deviation | Number of values | Significance | P-value |
| LIVRQNAC + G | 40 | 0.6216 | 0.0903 | 3 | ** | 0.0036 |
| LIVRQNAC + G | 30 | 0.6742 | 0.0549 | 3 | ** | 0.0095 |
| LIVRQNAC + G | 20 | 0.6373 | 0.0888 | 3 | ** | 0.0047 |
| LIVRQNAC + G | 10 | 0.7075 | 0.0610 | 3 | * | 0.0179 |
| LIVRQNAC + G | 1 | 1.0000 | 0.1704 | 3 | | |
| LIVRQNAC + S | 40 | 0.5911 | 0.1451 | 3 | ns | 0.2045 |
| LIVRQNAC + S | 30 | 0.5932 | 0.1943 | 3 | ns | 0.2077 |
| LIVRQNAC + S | 20 | 0.5760 | 0.1681 | 3 | ns | 0.1828 |
| LIVRQNAC + S | 10 | 0.6820 | 0.2396 | 3 | ns | 0.3845 |
| LIVRQNAC + S | 1 | 1.0000 | 0.4098 | 3 | | |
| LIV | 40 | 1.2677 | 0.5786 | 3 | ns | 0.7802 |
| LIV | 30 | 1.3632 | 0.5837 | 3 | ns | 0.8368 |
| LIV | 20 | 1.3336 | 0.4754 | 3 | ns | 0.7964 |
| LIV | 10 | 1.3745 | 0.5427 | 3 | ns | 0.9132 |
| LIV | 1 | 1.0000 | 0.3186 | 3 | | |
| LIVRQ | 40 | 1.3042 | 0.4140 | 3 | ns | 0.7695 |
| LIVRQ | 30 | 1.2208 | 0.4403 | 3 | ns | 0.9036 |
| LIVRQ | 20 | 0.9915 | 0.3521 | 3 | ns | 0.9999 |
| LIVRQ | 10 | 0.9968 | 0.3907 | 3 | ns | 0.9999 |
| LIVRQ | 1 | 1.0000 | 0.4257 | 3 | | |
| RQNAC | 40 | 0.3220 | 0.0282 | 3 | **** | 0.0001 |
| RQNAC | 30 | 0.4353 | 0.0941 | 3 | **** | 0.0001 |
| RQNAC | 20 | 0.4629 | 0.0998 | 3 | *** | 0.0001 |
| RQNAC | 10 | 0.6513 | 0.0925 | 3 | ** | 0.0028 |
| RQNAC | 1 | 1.0000 | 0.1132 | 3 | | |
| N-Acetyl Cysteine | 40 | 0.4485 | 0.0587 | 3 | *** | 0.0002 |
| N-Acetyl Cysteine | 20 | 0.5413 | 0.1018 | 3 | *** | 0.0009 |
| N-Acetyl Cysteine | 10 | 0.6565 | 0.0502 | 3 | ** | 0.007 |
| N-Acetyl Cysteine | 5 | 0.8492 | 0.1515 | 3 | ns | 0.2738 |
| N-Acetyl Cysteine | 0 | 1.0000 | 0.1142 | 3 | | |

TABLE 17

Changes in MCP1 secretion for donor 3 upon administration of single amino acid compositions

| | | Fold Change MCP1 Secretion Normalized Per Cell | | | | |
|---|---|---|---|---|---|---|
| Amino Acid Supplement | Conc. (μM) | Mean | Std. Deviation | Number of values | Significance | P-value |
| Valine | 23420 | 1.2651 | 0.1295 | 3 | ns | 0.1126 |
| Valine | 11710 | 1.0204 | 0.1126 | 3 | ns | 0.9956 |
| Valine | 4684 | 1.0630 | 0.0878 | 3 | ns | 0.8999 |
| Valine | 234 | 1.0000 | 0.2008 | 3 | | |
| Arginine | 5440 | 0.7840 | 0.2753 | 3 | ns | 0.7069 |
| Arginine | 2720 | 0.8821 | 0.2249 | 3 | ns | 0.9264 |
| Arginine | 1088 | 0.9435 | 0.3221 | 3 | ns | 0.9903 |
| Arginine | 109 | 1.0000 | 0.3404 | 3 | | |
| Glutamine | 22484 | 0.6212 | 0.1952 | 3 | ns | 0.2465 |
| Glutamine | 11242 | 0.6106 | 0.2085 | 3 | ns | 0.226 |
| Glutamine | 3747 | 0.6036 | 0.2596 | 3 | ns | 0.2135 |
| Glutamine | 749 | 0.7048 | 0.2473 | 3 | ns | 0.4593 |
| Glutamine | 562 | 1.0000 | 0.2185 | 3 | | |
| Isoleucine | 6639 | 1.2084 | 0.1334 | 3 | ns | 0.284 |
| Isoleucine | 3320 | 1.2169 | 0.0589 | 3 | ns | 0.2565 |
| Isoleucine | 1328 | 1.5550 | 0.2070 | 3 | ** | 0.0038 |
| Isoleucine | 66 | 1.0000 | 0.1188 | 3 | | |
| Leucine | 15270 | 1.1808 | 0.2601 | 3 | ns | 0.5156 |
| Leucine | 7635 | 1.3054 | 0.1748 | 3 | ns | 0.1491 |
| Leucine | 3054 | 1.1479 | 0.0605 | 3 | ns | 0.6605 |
| Leucine | 153 | 1.0000 | 0.0784 | 3 | | |

TABLE 17-continued

Changes in MCP1 secretion for donor 3 upon administration of single amino acid compositions

| Amino Acid Supplement | Conc. (µM) | Mean | Std. Deviation | Number of values | Significance | P-value |
|---|---|---|---|---|---|---|
| N-Acetyl Cysteine | 10000 | 0.4485 | 0.0587 | 3 | *** | 0.0002 |
| N-Acetyl Cysteine | 5000 | 0.5413 | 0.1018 | 3 | *** | 0.0009 |
| N-Acetyl Cysteine | 2500 | 0.6565 | 0.0502 | 3 | ** | 0.007 |
| N-Acetyl Cysteine | 1000 | 0.8492 | 0.1515 | 3 | ns | 0.2738 |
| N-Acetyl Cysteine | 0 | 1.0000 | 0.1142 | 3 | | |

TABLE 18

Changes in MCP1 secretion for donor 4 upon administration of amino acid compositions Fold Change MCP1 Secretion Normalized Per Cell

| Amino Acid Supplement | Conc. (X) | Mean | Std. Deviation | Number of values | Significance | P-value |
|---|---|---|---|---|---|---|
| LIVRQNAC | 40 | 0.7791 | 0.0740 | 3 | ns | 0.1328 |
| LIVRQNAC | 30 | 0.6333 | 0.1114 | 3 | * | 0.0116 |
| LIVRQNAC | 20 | 0.6997 | 0.1013 | 3 | * | 0.0352 |
| LIVRQNAC | 10 | 0.8114 | 0.1271 | 3 | ns | 0.2216 |
| LIVRQNAC | 1 | 1.0000 | 0.1607 | 3 | | |
| LIVRQNAC + G | 40 | 0.6738 | 0.0979 | 3 | * | 0.0454 |
| LIVRQNAC + G | 30 | 0.7117 | 0.0783 | 3 | ns | 0.0794 |
| LIVRQNAC + G | 20 | 0.6735 | 0.1127 | 3 | * | 0.0452 |
| LIVRQNAC + G | 10 | 0.7682 | 0.0563 | 3 | ns | 0.1778 |
| LIVRQNAC + G | 1 | 1.0000 | 0.2452 | 3 | | |
| LIVRQNAC + S | 40 | 0.5780 | 0.0781 | 3 | ** | 0.0025 |
| LIVRQNAC + S | 30 | 0.5393 | 0.1185 | 3 | ** | 0.0013 |
| LIVRQNAC + S | 20 | 0.6487 | 0.0732 | 3 | ** | 0.0085 |
| LIVRQNAC + S | 10 | 0.6872 | 0.0118 | 3 | * | 0.017 |
| LIVRQNAC + S | 1 | 1.0000 | 0.1803 | 3 | | |
| LIV | 40 | 0.7010 | 0.1399 | 3 | ** | 0.0059 |
| LIV | 30 | 0.8883 | 0.0530 | 3 | ns | 0.3745 |
| LIV | 20 | 0.9284 | 0.0579 | 3 | ns | 0.7114 |
| LIV | 10 | 0.8663 | 0.0569 | 3 | ns | 0.2428 |
| LIV | 1 | 1.0000 | 0.0928 | 3 | | |
| LIVRQ | 40 | 1.2235 | 0.0592 | 3 | ns | 0.4365 |
| LIVRQ | 30 | 1.1653 | 0.0558 | 3 | ns | 0.6679 |
| LIVRQ | 20 | 0.8845 | 0.2698 | 3 | ns | 0.862 |
| LIVRQ | 10 | 1.0110 | 0.0738 | 3 | ns | 0.9999 |
| LIVRQ | 1 | 1.0000 | 0.3016 | 3 | | |
| RQNAC | 40 | 0.4312 | 0.0994 | 3 | *** | 0.0006 |
| RQNAC | 30 | 0.3910 | 0.0649 | 3 | *** | 0.0003 |
| RQNAC | 20 | 0.5579 | 0.2079 | 3 | ** | 0.0037 |
| RQNAC | 10 | 0.5545 | 0.0663 | 3 | ** | 0.0035 |
| RQNAC | 1 | 1.0000 | 0.0987 | 3 | | |
| N-Acetyl Cysteine | 40 | 0.5011 | 0.0756 | 3 | *** | 0.0001 |
| N-Acetyl Cysteine | 20 | 0.6728 | 0.1024 | 3 | ** | 0.003 |
| N-Acetyl Cysteine | 10 | 0.8033 | 0.1101 | 3 | ns | 0.058 |
| N-Acetyl Cysteine | 5 | 0.6437 | 0.0648 | 3 | ** | 0.0017 |
| N-Acetyl Cysteine | 0 | 1.0000 | 0.0673 | 3 | | |

TABLE 19

Changes in MCP1 secretion for donor 4 upon administration of single amino acid compositions Fold Change MCP1 Secretion Normalized Per Cell

| Amino Acid Supplement | Conc. (µM) | Mean | Std. Deviation | Number of values | Significance | P-value |
|---|---|---|---|---|---|---|
| Valine | 23420 | 1.1525 | 0.0406 | 3 | ns | 0.9999 |
| Valine | 11710 | 1.1544 | 0.1743 | 3 | ns | 0.8877 |
| Valine | 4684 | 1.0942 | 0.0846 | 3 | ns | 0.3545 |
| Valine | 234 | 1.0000 | 0.1464 | 3 | | |
| Arginine | 5440 | 0.9456 | 0.0639 | 3 | ns | 0.9076 |
| Arginine | 2720 | 1.0446 | 0.0741 | 3 | ns | 0.9449 |
| Arginine | 1088 | 1.0453 | 0.1733 | 3 | ns | 0.9423 |
| Arginine | 109 | 1.0000 | 0.1486 | 3 | | |
| Glutamine | 22484 | 0.7039 | 0.0544 | 3 | ** | 0.0065 |
| Glutamine | 11242 | 0.7129 | 0.2237 | 3 | ** | 0.0077 |
| Glutamine | 3747 | 0.6639 | 0.0467 | 3 | ** | 0.0027 |
| Glutamine | 749 | 0.7782 | 0.0860 | 3 | * | 0.0452 |
| Glutamine | 562 | 1.0000 | 0.0709 | 6 | | |
| Isoleucine | 6639 | 0.9103 | 0.0536 | 3 | ns | 0.5597 |
| Isoleucine | 3320 | 0.8830 | 0.0872 | 3 | ns | 0.3538 |
| Isoleucine | 1328 | 1.3338 | 0.1099 | 3 | ** | 0.0044 |
| Isoleucine | 66 | 1.0000 | 0.0853 | 3 | | |
| Leucine | 15270 | 1.5745 | 0.0844 | 3 | ns | 0.1886 |
| Leucine | 7635 | 1.7129 | 0.6026 | 3 | ns | 0.0885 |
| Leucine | 3054 | 1.5342 | 0.1746 | 3 | ns | 0.2332 |
| Leucine | 153 | 1.0000 | 0.2040 | 3 | | |
| N-Acetyl Cysteine | 10000 | 0.5011 | 0.0756 | 3 | *** | 0.0001 |
| N-Acetyl Cysteine | 5000 | 0.6728 | 0.1024 | 3 | ** | 0.003 |
| N-Acetyl Cysteine | 2500 | 0.8033 | 0.1101 | 3 | ns | 0.058 |
| N-Acetyl Cysteine | 1000 | 0.6437 | 0.0648 | 3 | ** | 0.0017 |
| N-Acetyl Cysteine | 0 | 1.0000 | 0.0673 | 3 | | |

IL-6 Cytokine Secretion

Tables 20-23 show per-cell normalized IL-6 cytokine secretion in primary human hepatic stellate cells from two donors as a fold change from the plasma amino acid background. Statistical significance calculated by one-way ANOVA with Dunnett's multiple comparison test within each treatment group. LIVRQNAC, LIVRQNAC+S and RQNAC significantly reduced IL-6 secretion in one of two donors. LIVRQNAC+G, LIVRQNAC+S and RQNAC decreased IL-6 secretion in both donors. LIV and LIVRQ did not have a significant impact on IL-6 secretion in either donor. Individually, valine, arginine, isoleucine, and leucine had no significant effect on IL-6 secretion. N-acetyl cysteine reduced IL-6 secretion in both donors but was only statistically significant in one of two donors. Glutamine significantly reduced IL-6 secretion in both donors.

TABLE 20

Changes in IL-6 cytokine secretion for donor 1 upon administration of amino acid compositions

| Amino Acid Supplement | Conc. (X) | Fold Change IL-6 Secretion Normalized Per Cell | | Number of values | Signifi-cance | P-value |
|---|---|---|---|---|---|---|
| | | Mean | Std. Deviation | | | |
| LIVRQNAC | 40 | 0.4857 | 0.0915 | 3 | *** | 0.0004 |
| LIVRQNAC | 30 | 0.5667 | 0.0941 | 3 | ** | 0.0014 |
| LIVRQNAC | 20 | 0.6671 | 0.0431 | 3 | ** | 0.0088 |
| LIVRQNAC | 10 | 0.6579 | 0.1231 | 3 | ** | 0.0074 |
| LIVRQNAC | 1 | 1.0000 | 0.1361 | 3 | | |
| LIVRQNAC + G | 40 | 0.4995 | 0.1427 | 3 | ns | 0.0949 |
| LIVRQNAC + G | 30 | 0.5722 | 0.2185 | 3 | ns | 0.1679 |
| LIVRQNAC + G | 20 | 0.6185 | 0.1769 | 3 | ns | 0.2376 |
| LIVRQNAC + G | 10 | 0.7040 | 0.2809 | 3 | ns | 0.4276 |
| LIVRQNAC + G | 1 | 1.0000 | 0.3513 | 3 | | |
| LIVRQNAC + S | 40 | 0.5397 | 0.1569 | 3 | * | 0.0105 |
| LIVRQNAC + S | 30 | 0.5513 | 0.1190 | 3 | * | 0.0122 |
| LIVRQNAC + S | 20 | 0.6264 | 0.1593 | 3 | * | 0.0338 |
| LIVRQNAC + S | 10 | 0.6799 | 0.1218 | 3 | ns | 0.0703 |
| LIVRQNAC + S | 1 | 1.0000 | 0.1671 | 3 | | |
| LIV | 40 | 1.3536 | 0.4767 | 3 | ns | 0.6216 |
| LIV | 30 | 1.2423 | 0.3135 | 3 | ns | 0.8437 |
| LIV | 20 | 1.2321 | 0.4818 | 3 | ns | 0.8611 |
| LIV | 10 | 1.1421 | 0.3489 | 3 | ns | 0.9704 |
| LIV | 1 | 1.0000 | 0.1647 | 3 | | |
| LIVRQ | 40 | 0.8274 | 0.2003 | 3 | ns | 0.7863 |
| LIVRQ | 30 | 0.8880 | 0.2175 | 3 | ns | 0.938 |
| LIVRQ | 20 | 0.8468 | 0.1100 | 3 | ns | 0.8431 |
| LIVRQ | 10 | 0.9247 | 0.2696 | 3 | ns | 0.984 |
| LIVRQ | 1 | 1.0000 | 0.3311 | 3 | | |
| RQNAC | 40 | 0.3958 | 0.0947 | 3 | * | 0.0109 |
| RQNAC | 30 | 0.4433 | 0.1317 | 3 | * | 0.0177 |
| RQNAC | 20 | 0.4936 | 0.1079 | 3 | * | 0.0297 |
| RQNAC | 10 | 0.5729 | 0.1741 | 3 | ns | 0.0674 |
| RQNAC | 1 | 1.0000 | 0.3440 | 3 | | |
| N-Acetyl Cysteine | 40 | 0.5716 | 0.2306 | 3 | ns | 0.2067 |
| N-Acetyl Cysteine | 20 | 0.6121 | 0.1718 | 3 | ns | 0.2729 |
| N-Acetyl Cysteine | 10 | 0.7354 | 0.2816 | 3 | ns | 0.5703 |
| N-Acetyl Cysteine | 5 | 0.7141 | 0.2509 | 3 | ns | 0.5098 |
| N-Acetyl Cysteine | 0 | 1.0000 | 0.3472 | 3 | | |

TABLE 21

Changes in IL-6 cytokine secretion for donor 1 upon administration of single amino acid compositions

| Amino Acid Supplement | Conc. (µM) | Fold Change IL-6 Secretion Normalized Per Cell | | Number of values | Signifi-cance | P-value |
|---|---|---|---|---|---|---|
| | | Mean | Std. Deviation | | | |
| Valine | 23420 | 1.0404 | 0.2175 | 3 | ns | 0.9949 |
| Valine | 11710 | 0.9562 | 0.3332 | 3 | ns | 0.9935 |
| Valine | 4684 | 0.9790 | 0.1777 | 3 | ns | 0.9993 |
| Valine | 234 | 1.0000 | 0.2868 | 3 | | |
| Arginine | 5440 | 0.7776 | 0.1994 | 3 | ns | 0.6927 |
| Arginine | 2720 | 1.0231 | 0.4381 | 3 | ns | 0.9993 |
| Arginine | 1088 | 0.9828 | 0.2957 | 3 | ns | 0.9997 |
| Arginine | 109 | 1.0000 | 0.1728 | 3 | | |
| Glutamine | 22484 | 0.5138 | 0.0818 | 3 | ** | 0.0046 |
| Glutamine | 11242 | 0.5136 | 0.1189 | 3 | ** | 0.0046 |
| Glutamine | 3747 | 0.5460 | 0.0891 | 3 | ** | 0.0072 |
| Glutamine | 749 | 0.6320 | 0.1181 | 3 | * | 0.0249 |
| Glutamine | 562 | 1.0000 | 0.2226 | 3 | | |
| Isoleucine | 6639 | 1.0859 | 0.1489 | 3 | ns | 0.764 |
| Isoleucine | 3320 | 1.1156 | 0.0776 | 3 | ns | 0.5903 |
| Isoleucine | 1328 | 1.0233 | 0.1536 | 3 | ns | 0.9922 |
| Isoleucine | 66 | 1.0000 | 0.1276 | 3 | | |
| Leucine | 15270 | 1.0767 | 0.0246 | 3 | ns | 0.853 |
| Leucine | 7635 | 1.1215 | 0.0872 | 3 | ns | 0.6249 |
| Leucine | 3054 | 1.1762 | 0.2273 | 3 | ns | 0.3655 |
| Leucine | 153 | 1.0000 | 0.1535 | 3 | | |
| N-Acetyl Cysteine | 10000 | 0.5716 | 0.2306 | 3 | ns | 0.2067 |
| N-Acetyl Cysteine | 5000 | 0.6121 | 0.1718 | 3 | ns | 0.2729 |
| N-Acetyl Cysteine | 2500 | 0.7354 | 0.2816 | 3 | ns | 0.5703 |
| N-Acetyl Cysteine | 1000 | 0.7141 | 0.2509 | 3 | ns | 0.5098 |
| N-Acetyl Cysteine | 0 | 1.0000 | 0.3472 | 3 | | |

TABLE 22

Changes in IL-6 cytokine secretion for donor 2 upon administration of amino acid compositions

| Amino Acid Supplement | Conc. (X) | Fold Change IL-6 Secretion Normalized Per Cell | | Number of values | Signifi-cance | P-value |
|---|---|---|---|---|---|---|
| | | Mean | Std. Deviation | | | |
| LIVRQNAC | 40 | 0.9911 | 0.1150 | 3 | ns | 0.9998 |
| LIVRQNAC | 30 | 0.9560 | 0.0473 | 3 | ns | 0.9404 |
| LIVRQNAC | 20 | 1.0008 | 0.1450 | 3 | ns | 0.9999 |
| LIVRQNAC | 10 | 1.0845 | 0.0707 | 3 | ns | 0.6567 |
| LIVRQNAC | 1 | 1.0000 | 0.0553 | 3 | | |
| LIVRQNAC + G | 40 | 0.8055 | 0.1705 | 3 | ns | 0.4153 |
| LIVRQNAC + G | 30 | 0.8218 | 0.1567 | 3 | ns | 0.4855 |
| LIVRQNAC + G | 20 | 0.9236 | 0.1642 | 3 | ns | 0.9342 |
| LIVRQNAC + G | 10 | 1.1076 | 0.2097 | 3 | ns | 0.8216 |
| LIVRQNAC + G | 1 | 1.0000 | 0.0416 | 3 | | |
| LIVRQNAC + S | 40 | 0.9508 | 0.0933 | 3 | ns | 0.967 |
| LIVRQNAC + S | 30 | 0.8581 | 0.0364 | 3 | ns | 0.4836 |
| LIVRQNAC + S | 20 | 0.8289 | 0.0765 | 3 | ns | 0.3356 |
| LIVRQNAC + S | 10 | 0.8487 | 0.1018 | 3 | ns | 0.432 |
| LIVRQNAC + S | 1 | 1.0000 | 0.2312 | 3 | | |
| LIV | 40 | 0.9122 | 0.0773 | 3 | ns | 0.8233 |
| LIV | 30 | 1.0994 | 0.0987 | 3 | ns | 0.7586 |
| LIV | 20 | 1.0400 | 0.2330 | 3 | ns | 0.9857 |
| LIV | 10 | 0.9579 | 0.1077 | 3 | ns | 0.9828 |
| LIV | 1 | 1.0000 | 0.0540 | 3 | | |
| LIVRQ | 40 | 0.9327 | 0.0639 | 3 | ns | 0.8313 |
| LIVRQ | 30 | 0.8421 | 0.1125 | 3 | ns | 0.2361 |
| LIVRQ | 20 | 0.7871 | 0.0932 | 3 | ns | 0.0841 |
| LIVRQ | 10 | 0.8693 | 0.0750 | 3 | ns | 0.3744 |
| LIVRQ | 1 | 1.0000 | 0.1428 | 3 | | |
| RQNAC | 40 | 0.8711 | 0.0816 | 3 | ns | 0.5267 |
| RQNAC | 30 | 0.7460 | 0.1133 | 3 | ns | 0.0843 |
| RQNAC | 20 | 0.7838 | 0.0708 | 3 | ns | 0.1544 |
| RQNAC | 10 | 0.8781 | 0.1566 | 3 | ns | 0.5705 |
| RQNAC | 1 | 1.0000 | 0.1557 | 3 | | |
| N-Acetyl Cysteine | 40 | 0.7064 | 0.0418 | 3 | ns | 0.0508 |
| N-Acetyl Cysteine | 20 | 0.8111 | 0.1049 | 3 | ns | 0.2549 |
| N-Acetyl Cysteine | 10 | 0.9180 | 0.2230 | 3 | ns | 0.8353 |
| N-Acetyl Cysteine | 5 | 0.9161 | 0.1067 | 3 | ns | 0.8252 |
| N-Acetyl Cysteine | 0 | 1.0000 | 0.0632 | 3 | | |

TABLE 23

Changes in IL-6 cytokine secretion for donor 2 upon administration of single amino acid compositions

| Amino Acid Supplement | Conc. (µM) | Mean | Std. Deviation | Number of values | Significance | P-value |
|---|---|---|---|---|---|---|
| Valine | 23420 | 0.9015 | 0.0930 | 3 | ns | 0.4967 |
| Valine | 11710 | 0.9218 | 0.1179 | 3 | ns | 0.6516 |
| Valine | 4684 | 1.0383 | 0.1014 | 3 | ns | 0.9291 |
| Valine | 234 | 1.0000 | 0.0696 | 3 | | |
| Arginine | 5440 | 0.8895 | 0.0897 | 3 | ns | 0.547 |
| Arginine | 2720 | 0.9401 | 0.1611 | 3 | ns | 0.8654 |
| Arginine | 1088 | 0.9924 | 0.0692 | 3 | ns | 0.9996 |
| Arginine | 109 | 1.0000 | 0.1263 | 3 | | |
| Glutamine | 22484 | 0.5993 | 0.0611 | 3 | **** | 0.0001 |
| Glutamine | 11242 | 0.6478 | 0.0371 | 3 | **** | 0.0001 |
| Glutamine | 3747 | 0.7100 | 0.0356 | 3 | *** | 0.0003 |
| Glutamine | 749 | 0.7673 | 0.0222 | 3 | ** | 0.0017 |
| Glutamine | 562 | 1.0000 | 0.1027 | 6 | | |
| Isoleucine | 6639 | 1.1648 | 0.1125 | 3 | ns | 0.1448 |
| Isoleucine | 3320 | 0.9096 | 0.0916 | 3 | ns | 0.5304 |
| Isoleucine | 1328 | 1.1020 | 0.0987 | 3 | ns | 0.4446 |
| Isoleucine | 66 | 1.0000 | 0.0641 | 3 | | |
| Leucine | 15270 | 1.0183 | 0.1155 | 3 | ns | 0.9795 |
| Leucine | 7635 | 0.9574 | 0.0590 | 3 | ns | 0.8187 |
| Leucine | 3054 | 1.0011 | 0.0618 | 3 | ns | 0.9999 |
| Leucine | 153 | 1.0000 | 0.0277 | 3 | | |
| N-Acetyl Cysteine | 10000 | 0.7064 | 0.0418 | 3 | ns | 0.0508 |
| N-Acetyl Cysteine | 5000 | 0.8111 | 0.1049 | 3 | ns | 0.2549 |
| N-Acetyl Cysteine | 2500 | 0.9180 | 0.2230 | 3 | ns | 0.8353 |
| N-Acetyl Cysteine | 1000 | 0.9161 | 0.1067 | 3 | ns | 0.8252 |
| N-Acetyl Cysteine | 0 | 1.0000 | 0.0632 | 3 | | |

Example 4: TGFβ1 Fibrogenic Gene Expression of Hepatic Stellate Cell

Primary human hepatic stellate cells were obtained from Samsara Sciences based on the following criteria for selecting donors: adult age (between 18 and 50 years), normal BMI (>18.5 and <25), and absence of confounding liver disease. Cells grown in Complete HSC Medium to ~80% confluence in T75 or T150 flasks below passage 10 were seeded into sterile, collagen I coated, 96-well optical plastic microplates (ThermoScientific, 152036) at 6000 cells per well (~1250 cells per cm2) and incubated overnight at 37° C., 5% $CO_2$ in a humidified incubator in DMEM with 2% Fetal Bovine Serum and 1% Antibiotic-Antimycotic.

After the overnight incubation, plates were removed from the incubator and the medium was gently pipetted off and washed twice with 150 µL per well DPBS. The DPBS was removed and the pretreatment medium (±single amino acid dropout, 1×HMDB DMEM+1% Antibiotic-Antimycotic, 10 mM HEPES, ±supplemental amino acid dose; Amino acids in supplemental AA dose were at multiples of 1×HMDB: L-Leucine: 152.7 µM; L-Isoleucine: 66.4 µM; L-Valine: 234.2 µM; L-Arginine: 108.8 µM; L-Glutamine: 562.1 µM; N-acetylcysteine: 250 µM [not endogenous]J see experiment for medium composition) was applied to the cells at 150 µL per well. Plates were returned to the incubator for 10.5 hours.

After 10.5 hour pretreatment, the medium was removed from the cells, and the same pretreatment medium, now supplemented with 3 ng/mL TGFβ1, was applied. Each plate contained 3 ng/mL TGFβ1 in 1× human plasma amino acid (HMDB or PAA) concentration medium, 0 ng/mL in 1×HMDB, and 3 ng/mL TGFβ1+20 µM Silybin in 1×HMDB to serve as controls. Plates were then incubated for 24 hours at 37° C., 5% CO2.

After 24 hour stimulus, supernatant was removed and frozen at −80° C. in two separate aliquots. The cells were then washed with 125 µL per well Buffer FCW (FastLane Cell Multiplex NR Kit, Qiagen, 216713). The wash buffer was immediately removed and 50 µL of Cell Processing Mix (containing genomic DNA Wipeout buffer) was applied to lyse cells, incubating for 10 minutes at room temperature. RNA lysate was then transferred to 96-well qPCR plates, sealed, and gDNA was digested on thermal cycler at 75° C. for 5 minutes. RNA lysate was frozen at −80° C.

Each 20 µL one-step RT-qPCR reaction contained 4 µL of RNA lysate. Gene expression of Col1a1, Timp2, and Gapdh were multiplexed using the HEX, Cy5, and FAM fluorescent channels, respectively, with commercially available primer-probe mixes (the Human Col1a1 Primer-Probe Set, HEX; the Human Timp2 Primer-Probe Set, Cy5; and the Human Gapdh Primer-Probe Set, FAM from IDT). Gene expression was evaluated using the ΔΔCq method within each single amino acid dropout and supplementation by normalizing to its own 1× HMDB concentration.

Human Procollagen Iα1 was measured from the supernatant by ELISA (Human Pro-Collagen I alpha 1 DuoSet ELISA, R&D Systems) at 1/100 dilution in 1× Reagent Diluent (Reagent Ancillary Kit 2, R&D Systems).

Results

Col1a1 Gene Expression

Tables 24-29 show the mean fold change in Col1a1 gene expression in primary human hepatic stellate cells from three different healthy donors. LIVRQNAC and LIVRQNAC+S showed significantly decreased Col1a1 gene expression in two of three donors. LIVRQNAC+G and RQNAC showed significantly decreased Col1a1 expression in all three donors. LIVRQ showed a significant change in Col1a1 gene expression in only one donor. LIV alone did not significantly change Col1a1 gene expression.

Each of leucine, isoleucine, valine, and arginine did not significantly change Col1a1 gene expression in any donor when the amino acid was administered alone. Glutamine decreased Col1a1 gene expression in two of three donors. N-acetyl cysteine significantly reduced Col1a1 gene expression in all three donors.

TABLE 24

Fold change of Col1a1 gene expression after administration of an amino acid composition, normalized to Gapdh expression in a first donor

| | | Col1a1 Fold Expression Relative to Control | | | | |
|---|---|---|---|---|---|---|
| Amino Acid Supplement | Conc. (X) | Mean | Std. Deviation | Number of values | P-value* | Significance |
| LIVRQNAC | 40 | 0.91 | 0.08 | 4 | ns | 0.401 |
| LIVRQNAC | 30 | 0.87 | 0.10 | 4 | ns | 0.1073 |
| LIVRQNAC | 20 | 0.88 | 0.04 | 4 | ns | 0.1483 |
| LIVRQNAC | 10 | 0.90 | 0.08 | 4 | ns | 0.3035 |
| LIVRQNAC | 1 | 1.00 | 0.10 | 4 | | |
| LIVRQNAC + G | 40 | 0.73 | 0.15 | 4 | ** | 0.0053 |
| LIVRQNAC + G | 30 | 0.79 | 0.08 | 4 | * | 0.0252 |
| LIVRQNAC + G | 20 | 0.84 | 0.08 | 4 | ns | 0.1181 |
| LIVRQNAC + G | 10 | 0.79 | 0.11 | 4 | * | 0.0286 |
| LIVRQNAC + G | 1 | 1.00 | 0.03 | 4 | | |
| LIVRQNAC + S | 40 | 0.79 | 0.05 | 4 | * | 0.0325 |
| LIVRQNAC + S | 30 | 0.86 | 0.13 | 4 | ns | 0.1848 |
| LIVRQNAC + S | 20 | 0.96 | 0.10 | 4 | ns | 0.9287 |
| LIVRQNAC + S | 10 | 0.85 | 0.12 | 4 | ns | 0.1566 |
| LIVRQNAC + S | 1 | 1.00 | 0.10 | 4 | | |
| LIV | 40 | 0.93 | 0.03 | 4 | ns | 0.5561 |
| LIV | 30 | 1.04 | 0.07 | 4 | ns | 0.8872 |

TABLE 24-continued

Fold change of Col1a1 gene expression after administration of an amino acid composition, normalized to Gapdh expression in a first donor

| | | Col1a1 Fold Expression Relative to Control | | | |
|---|---|---|---|---|---|
| Amino Acid Supplement | Conc. (X) | Mean | Std. Deviation | Number of values | P-value* | Significance |
| LIV | 20 | 1.04 | 0.09 | 4 | ns | 0.9069 |
| LIV | 10 | 1.05 | 0.10 | 4 | ns | 0.8156 |
| LIV | 1 | 1.00 | 0.07 | 4 | | |
| LIVRQ | 40 | 0.75 | 0.03 | 4 | *** | 0.001 |
| LIVRQ | 30 | 0.73 | 0.05 | 4 | *** | 0.0004 |
| LIVRQ | 20 | 0.80 | 0.03 | 4 | ** | 0.0054 |
| LIVRQ | 10 | 0.84 | 0.08 | 4 | * | 0.0208 |
| LIVRQ | 1 | 1.01 | 0.13 | 4 | | |
| RQNAC | 40 | 0.51 | 0.07 | 4 | **** | 0.0001 |
| RQNAC | 30 | 0.49 | 0.02 | 4 | **** | 0.0001 |
| RQNAC | 20 | 0.59 | 0.04 | 4 | **** | 0.0001 |
| RQNAC | 10 | 0.68 | 0.07 | 4 | **** | 0.0001 |
| RQNAC | 1 | 1.00 | 0.11 | 4 | | |
| N-Acetyl Cysteine | 40 | 0.76 | 0.06 | 4 | ** | 0.0011 |
| N-Acetyl Cysteine | 20 | 1.02 | 0.08 | 4 | ns | 0.9921 |
| N-Acetyl Cysteine | 10 | 1.07 | 0.08 | 4 | ns | 0.5517 |
| N-Acetyl Cysteine | 5 | 1.00 | 0.08 | 4 | ns | 0.9999 |
| N-Acetyl Cysteine | 0 | 1.00 | 0.06 | 4 | | |

TABLE 25

Fold change of Col1a1 gene expression after administration of a single amino acid composition, normalized to Gapdh expression in the first donor

| | | Col1a1 Fold Expression Relative to Control | | | | |
|---|---|---|---|---|---|---|
| Amino Acid Supplement | Conc. (μM) | Mean | Std. Deviation | Number of values | P-value* | Significance |
| Valine | 23420 | 1.00 | 0.05 | 4 | ns | 0.9996 |
| Valine | 11710 | 1.09 | 0.17 | 4 | ns | 0.5528 |
| Valine | 4684 | 1.05 | 0.11 | 4 | ns | 0.8851 |
| Valine | 234 | 1.00 | 0.08 | 4 | | |
| Arginine | 5440 | 1.12 | 0.18 | 4 | ns | 0.2151 |
| Arginine | 2720 | 1.03 | 0.03 | 4 | ns | 0.9625 |
| Arginine | 1088 | 0.99 | 0.06 | 4 | ns | 0.9989 |
| Arginine | 109 | 1.00 | 0.03 | 4 | | |
| Glutamine | 22484 | 0.53 | 0.01 | 4 | **** | 0.0001 |
| Glutamine | 11242 | 0.62 | 0.05 | 4 | **** | 0.0001 |
| Glutamine | 3747 | 0.70 | 0.03 | 3 | **** | 0.0001 |
| Glutamine | 749 | 1.00 | 0.07 | 4 | ns | 0.9999 |
| Glutamine | 562 | 1.00 | 0.07 | 3 | | |
| Isoleucine | 6639 | 1.11 | 0.07 | 4 | ns | 0.7553 |
| Isoleucine | 3320 | 1.10 | 0.14 | 4 | ns | 0.7944 |
| Isoleucine | 1328 | 1.05 | 0.22 | 4 | ns | 0.9831 |
| Isoleucine | 66 | 1.01 | 0.21 | 4 | | |
| Leucine | 15270 | 0.99 | 0.10 | 4 | ns | 0.994 |
| Leucine | 7635 | 1.12 | 0.16 | 4 | ns | 0.5049 |
| Leucine | 3054 | 1.11 | 0.15 | 4 | ns | 0.5499 |
| Leucine | 153 | 1.00 | 0.11 | 4 | | |
| N-Acetyl Cysteine | 10000 | 0.76 | 0.06 | 4 | ** | 0.0011 |
| N-Acetyl Cysteine | 5000 | 1.02 | 0.08 | 4 | ns | 0.9921 |
| N-Acetyl Cysteine | 2500 | 1.07 | 0.08 | 4 | ns | 0.5517 |
| N-Acetyl Cysteine | 1000 | 1.00 | 0.08 | 4 | ns | 0.9999 |
| N-Acetyl Cysteine | 0 | 1.00 | 0.06 | 4 | | |

TABLE 26

Fold change of Col1a1 gene expression after administration of an amino acid composition, normalized to Gapdh expression in second donor.

| | | Col1a1 Fold Expression Relative to Control | | | | |
|---|---|---|---|---|---|---|
| Amino Acid Supplement | Conc. (X) | Mean | Std. Deviation | Number of values | P-value* | Significance |
| LIVRQNAC | 40 | 0.72 | 0.05 | 4 | **** | 0.0001 |
| LIVRQNAC | 30 | 0.72 | 0.02 | 4 | **** | 0.0001 |
| LIVRQNAC | 20 | 0.70 | 0.03 | 4 | **** | 0.0001 |
| LIVRQNAC | 10 | 0.71 | 0.08 | 4 | **** | 0.0001 |
| LIVRQNAC | 1 | 1.00 | 0.02 | 4 | | |
| LIVRQNAC + G | 40 | 0.60 | 0.09 | 4 | **** | 0.0001 |
| LIVRQNAC + G | 30 | 0.68 | 0.07 | 4 | *** | 0.0001 |
| LIVRQNAC + G | 20 | 0.71 | 0.09 | 4 | *** | 0.0003 |
| LIVRQNAC + G | 10 | 0.69 | 0.06 | 4 | *** | 0.0002 |
| LIVRQNAC + G | 1 | 1.00 | 0.07 | 4 | | |
| LIVRQNAC + S | 40 | 0.66 | 0.02 | 4 | **** | 0.0001 |
| LIVRQNAC + S | 30 | 0.69 | 0.06 | 4 | **** | 0.0001 |
| LIVRQNAC + S | 20 | 0.76 | 0.05 | 4 | *** | 0.0002 |
| LIVRQNAC + S | 10 | 0.77 | 0.04 | 4 | *** | 0.0003 |
| LIVRQNAC + S | 1 | 1.00 | 0.11 | 4 | | |
| LIV | 40 | 1.20 | 0.21 | 4 | ns | 0.1032 |
| LIV | 30 | 1.10 | 0.09 | 4 | ns | 0.6074 |
| LIV | 20 | 1.10 | 0.04 | 4 | ns | 0.6031 |
| LIV | 10 | 1.02 | 0.08 | 4 | ns | 0.9981 |
| LIV | 1 | 1.00 | 0.11 | 4 | | |
| LIVRQ | 40 | 1.23 | 0.13 | 4 | ns | 0.1945 |
| LIVRQ | 30 | 1.12 | 0.13 | 4 | ns | 0.7176 |
| LIVRQ | 20 | 1.08 | 0.24 | 4 | ns | 0.8874 |
| LIVRQ | 10 | 1.14 | 0.16 | 4 | ns | 0.5632 |
| LIVRQ | 1 | 1.00 | 0.11 | 4 | | |
| RQNAC | 40 | 0.54 | 0.03 | 4 | **** | 0.0001 |
| RQNAC | 30 | 0.55 | 0.06 | 4 | **** | 0.0001 |
| RQNAC | 20 | 0.58 | 0.04 | 4 | **** | 0.0001 |
| RQNAC | 10 | 0.73 | 0.04 | 4 | *** | 0.0007 |
| RQNAC | 1 | 1.01 | 0.16 | 4 | | |
| N-Acetyl Cysteine | 40 | 0.57 | 0.06 | 4 | **** | 0.0001 |
| N-Acetyl Cysteine | 20 | 0.69 | 0.06 | 4 | **** | 0.0001 |
| N-Acetyl Cysteine | 10 | 0.69 | 0.09 | 4 | *** | 0.0001 |
| N-Acetyl Cysteine | 5 | 0.69 | 0.05 | 4 | *** | 0.0001 |
| N-Acetyl Cysteine | 0 | 1.00 | 0.10 | 4 | | |

TABLE 27

Fold change of Col1a1 gene expression after administration of a single amino acid composition, normalized to Gapdh expression in second donor.

| | | Col1a1 Fold Expression Relative to Control | | | | |
|---|---|---|---|---|---|---|
| Amino Acid Supplement | Conc. (μM) | Mean | Std. Deviation | Number of values | P-value* | Significance |
| Valine | 23420 | 1.05 | 0.03 | 4 | ns | 0.9194 |
| Valine | 11710 | 0.98 | 0.11 | 4 | ns | 0.9827 |
| Valine | 4684 | 1.05 | 0.18 | 4 | ns | 0.8893 |
| Valine | 234 | 1.00 | 0.11 | 4 | | |
| Arginine | 5440 | 1.15 | 0.10 | 4 | ns | 0.2773 |
| Arginine | 2720 | 1.15 | 0.14 | 4 | ns | 0.2759 |
| Arginine | 1088 | 0.99 | 0.15 | 4 | ns | 0.9938 |
| Arginine | 109 | 1.00 | 0.12 | 4 | | |
| Glutamine | 22484 | 0.86 | 0.07 | 4 | ns | 0.1411 |
| Glutamine | 11242 | 0.91 | 0.09 | 4 | ns | 0.4365 |
| Glutamine | 3747 | 1.04 | 0.14 | 4 | ns | 0.9811 |
| Glutamine | 749 | 1.02 | 0.13 | 4 | ns | 0.9988 |
| Glutamine | 562 | 1.01 | 0.12 | 8 | | |
| Isoleucine | 6639 | 1.03 | 0.07 | 4 | ns | 0.8931 |
| Isoleucine | 3320 | 0.99 | 0.08 | 4 | ns | 0.9841 |
| Isoleucine | 1328 | 0.97 | 0.10 | 4 | ns | 0.9157 |
| Isoleucine | 66 | 1.00 | 0.02 | 4 | | |
| Leucine | 15270 | 1.13 | 0.14 | 4 | ns | 0.0811 |
| Leucine | 7635 | 1.05 | 0.05 | 4 | ns | 0.7277 |

TABLE 27-continued

Fold change of Col1a1 gene expression after administration of a single amino acid composition, normalized to Gapdh expression in second donor.

| | | Col1a1 Fold Expression Relative to Control | | | |
|---|---|---|---|---|---|
| Amino Acid Supplement | Conc. (µM) | Mean | Std. Deviation | Number of values | P-value* | Significance |
| Leucine | 3054 | 1.06 | 0.03 | 4 | ns | 0.5342 |
| Leucine | 153 | 1.00 | 0.03 | 4 | | |
| N-Acetyl Cysteine | 10000 | 0.57 | 0.06 | 4 | **** | 0.0001 |
| N-Acetyl Cysteine | 5000 | 0.69 | 0.06 | 4 | **** | 0.0001 |
| N-Acetyl Cysteine | 2500 | 0.69 | 0.09 | 4 | *** | 0.0001 |
| N-Acetyl Cysteine | 1000 | 0.69 | 0.05 | 4 | *** | 0.0001 |
| N-Acetyl Cysteine | 0 | 1.00 | 0.10 | 4 | | |

TABLE 28

Fold change of Col1a1 gene expression after administration of an amino acid composition, normalized to Gapdh expression in third donor.

| | | Col1a1 Fold Expression Relative to Control | | | |
|---|---|---|---|---|---|
| Amino Acid Supplement | Conc. (X) | Mean | Std. Deviation | Number of values | P-value* | Significance |
| LIVRQNAC | 40 | 0.81 | 0.09 | 4 | ** | 0.008 |
| LIVRQNAC | 30 | 0.70 | 0.06 | 4 | *** | 0.0001 |
| LIVRQNAC | 20 | 0.79 | 0.08 | 4 | ** | 0.0035 |
| LIVRQNAC | 10 | 0.79 | 0.07 | 4 | ** | 0.0039 |
| LIVRQNAC | 1 | 1.00 | 0.06 | 4 | | |
| LIVRQNAC + G | 40 | 0.63 | 0.10 | 4 | *** | 0.0002 |
| LIVRQNAC + G | 30 | 0.64 | 0.02 | 4 | *** | 0.0003 |
| LIVRQNAC + G | 20 | 0.75 | 0.14 | 4 | ** | 0.005 |
| LIVRQNAC + G | 10 | 0.71 | 0.11 | 4 | ** | 0.0017 |
| LIVRQNAC + G | 1 | 1.00 | 0.03 | 4 | | |
| LIVRQNAC + S | 40 | 0.79 | 0.11 | 4 | * | 0.0316 |
| LIVRQNAC + S | 30 | 0.79 | 0.04 | 4 | * | 0.0309 |
| LIVRQNAC + S | 20 | 0.77 | 0.09 | 4 | * | 0.0208 |
| LIVRQNAC + S | 10 | 0.85 | 0.09 | 4 | ns | 0.1434 |
| LIVRQNAC + S | 1 | 1.01 | 0.16 | 4 | | |
| LIV | 40 | 1.00 | 0.16 | 4 | ns | 0.9999 |
| LIV | 30 | 0.94 | 0.16 | 4 | ns | 0.8685 |
| LIV | 20 | 1.08 | 0.08 | 4 | ns | 0.6767 |
| LIV | 10 | 0.93 | 0.04 | 4 | ns | 0.7713 |
| LIV | 1 | 1.00 | 0.05 | 4 | | |
| LIVRQ | 40 | 1.00 | 0.16 | 4 | ns | 0.9999 |
| LIVRQ | 30 | 1.07 | 0.13 | 4 | ns | 0.8753 |
| LIVRQ | 20 | 1.10 | 0.13 | 4 | ns | 0.6983 |
| LIVRQ | 10 | 1.05 | 0.21 | 4 | ns | 0.9641 |
| LIVRQ | 1 | 1.00 | 0.07 | 4 | | |
| RQNAC | 40 | 0.64 | 0.05 | 4 | *** | 0.0003 |
| RQNAC | 30 | 0.70 | 0.13 | 4 | ** | 0.0018 |
| RQNAC | 20 | 0.66 | 0.05 | 4 | *** | 0.0005 |
| RQNAC | 10 | 0.87 | 0.15 | 4 | ns | 0.2175 |
| RQNAC | 1 | 1.00 | 0.04 | 4 | | |
| N-Acetyl Cysteine | 40 | 0.62 | 0.01 | 4 | *** | 0.0005 |
| N-Acetyl Cysteine | 20 | 0.73 | 0.10 | 4 | ** | 0.0083 |
| N-Acetyl Cysteine | 10 | 0.82 | 0.09 | 4 | ns | 0.0909 |
| N-Acetyl Cysteine | 5 | 0.91 | 0.12 | 4 | ns | 0.4954 |
| N-Acetyl Cysteine | 0 | 1.01 | 0.16 | 4 | | |

TABLE 29

Fold change of Col1a1 gene expression after administration of a single amino acid composition, normalized to Gapdh expression in second donor.

| | | Col1a1 Fold Expression Relative to Control | | | |
|---|---|---|---|---|---|
| Amino Acid Supplement | Conc. (µM) | Mean | Std. Deviation | Number of values | P-value* | Significance |
| Valine | 23420 | 1.13 | 0.12 | 4 | ns | 0.7199 |
| Valine | 11710 | 1.27 | 0.31 | 4 | ns | 0.1735 |
| Valine | 4684 | 1.22 | 0.16 | 4 | ns | 0.3247 |
| Valine | 234 | 1.01 | 0.13 | 4 | | |
| Arginine | 5440 | 1.02 | 0.09 | 4 | ns | 0.9702 |
| Arginine | 2720 | 0.99 | 0.09 | 4 | ns | 0.9973 |
| Arginine | 1088 | 0.95 | 0.02 | 4 | ns | 0.5384 |
| Arginine | 109 | 1.00 | 0.05 | 4 | | |
| Glutamine | 22484 | 0.81 | 0.11 | 4 | * | 0.0113 |
| Glutamine | 11242 | 0.81 | 0.11 | 4 | ** | 0.0087 |
| Glutamine | 3747 | 1.00 | 0.03 | 4 | ns | 0.9999 |
| Glutamine | 749 | 0.96 | 0.07 | 4 | ns | 0.8697 |
| Glutamine | 562 | 1.00 | 0.10 | 8 | | |
| Isoleucine | 6639 | 1.03 | 0.04 | 4 | ns | 0.9974 |
| Isoleucine | 3320 | 0.94 | 0.13 | 4 | ns | 0.8329 |
| Isoleucine | 1328 | 0.94 | 0.17 | 4 | ns | 0.7947 |
| Isoleucine | 66 | 1.02 | 0.20 | 4 | | |
| Leucine | 15270 | 1.07 | 0.12 | 4 | ns | 0.9535 |
| Leucine | 7635 | 1.00 | 0.16 | 4 | ns | 0.998 |
| Leucine | 3054 | 1.08 | 0.23 | 4 | ns | 0.9185 |
| Leucine | 153 | 1.01 | 0.19 | 4 | | |
| N-Acetyl Cysteine | 10000 | 0.62 | 0.01 | 4 | *** | 0.0005 |
| N-Acetyl Cysteine | 5000 | 0.73 | 0.10 | 4 | ** | 0.0083 |
| N-Acetyl Cysteine | 2500 | 0.82 | 0.09 | 4 | ns | 0.0909 |
| N-Acetyl Cysteine | 1000 | 0.91 | 0.12 | 4 | ns | 0.4954 |
| N-Acetyl Cysteine | 0 | 1.01 | 0.16 | 4 | | |

Procollagen Iα1 Secretion

Tables 30-35 show the fold change in procollagen Iα1 in primary human hepatic stellate cells from three different healthy donors normalized to their respective baseline amino acid conditions. Statistical significance calculated by one-way ANOVA with Dunnett's multiple comparison test within each treatment group. The combination LIV significantly increased procollagen Iα1 secretion in all three donors. The addition of arginine (R) and glutamine (Q) to a combination of LIV counteracted the profibrogenic effect of LIV alone. LIVRQNAC, LIVRQNAC+G, LIVRQNAC+S and RQNAC significantly decreased procollagen Iα1 secretion in all three donors. Individually, N-acetyl cysteine was shown to significantly decrease procollagen Iα1 secretion in two of the three donors. Valine significantly increased procollagen Iα1 secretion in only one of two donors, while isoleucine and arginine significantly increased procollagen Iα1 secretion in two of three donors. In other words, glutamine administered individually did not have a significant impact on procollagen Iα1 secretion. As such, the reduction of the profibrogenic effect of LIV with arginine and glutamine relative to that of LIV alone would not have been expected based on the effect of individual amino acid treatments.

TABLE 30

Fold change of procollagen 1α1 secretion after administration of an amino acid composition in a first donor

| Amino Acid Supplement | Conc. (X) | Procollagen 1α1 Secretion (Fold Change of 1X) | | | | |
|---|---|---|---|---|---|---|
| | | Mean | Std. Deviation | Number of values | P-value* | Significance |
| LIVRQNAC | 40 | 0.6283 | 0.0585 | 3 | *** | 0.0001 |
| LIVRQNAC | 30 | 0.5975 | 0.0709 | 3 | **** | 0.0001 |
| LIVRQNAC | 20 | 0.6504 | 0.0622 | 4 | *** | 0.0001 |
| LIVRQNAC | 10 | 0.8287 | 0.0936 | 4 | * | 0.0277 |
| LIVRQNAC | 1 | 1.0000 | 0.0908 | 4 | | |
| LIVRQNAC + G | 40 | 0.5288 | 0.0402 | 3 | *** | 0.0006 |
| LIVRQNAC + G | 30 | 0.6297 | 0.0200 | 3 | ** | 0.0042 |
| LIVRQNAC + G | 20 | 0.5926 | 0.0634 | 4 | ** | 0.001 |
| LIVRQNAC + G | 10 | 0.7404 | 0.0920 | 4 | * | 0.0267 |
| LIVRQNAC + G | 1 | 1.0000 | 0.2151 | 4 | | |
| LIVRQNAC + S | 40 | 0.5900 | 0.0450 | 3 | *** | 0.0003 |
| LIVRQNAC + S | 30 | 0.5562 | 0.1242 | 3 | *** | 0.0002 |
| LIVRQNAC + S | 20 | 0.6844 | 0.0638 | 3 | ** | 0.0022 |
| LIVRQNAC + S | 10 | 0.7003 | 0.0946 | 3 | ** | 0.0032 |
| LIVRQNAC + S | 1 | 1.0000 | 0.0311 | 3 | | |
| LIV | 40 | 1.3017 | 0.1474 | 3 | ns | 0.0518 |
| LIV | 30 | 1.3358 | 0.1922 | 3 | * | 0.0305 |
| LIV | 20 | 1.2592 | 0.0747 | 3 | ns | 0.0997 |
| LIV | 10 | 1.0149 | 0.1089 | 3 | ns | 0.9997 |
| LIV | 1 | 1.0000 | 0.0828 | 3 | | |
| LIVRQ | 40 | 1.0070 | 0.1716 | 3 | ns | 0.9999 |
| LIVRQ | 30 | 1.0190 | 0.1103 | 3 | ns | 0.9983 |
| LIVRQ | 20 | 1.1403 | 0.0516 | 3 | ns | 0.3875 |
| LIVRQ | 10 | 1.0454 | 0.0908 | 3 | ns | 0.9609 |
| LIVRQ | 1 | 1.0000 | 0.0935 | 3 | | |
| RQNAC | 40 | 0.3622 | 0.0166 | 3 | **** | 0.0001 |
| RQNAC | 30 | 0.4232 | 0.0819 | 3 | **** | 0.0001 |
| RQNAC | 20 | 0.5819 | 0.0574 | 3 | *** | 0.0001 |
| RQNAC | 10 | 0.8181 | 0.0703 | 3 | * | 0.0313 |
| RQNAC | 1 | 1.0000 | 0.0967 | 3 | | |
| N-Acetyl Cysteine | 40 | 0.5076 | 0.0154 | 3 | **** | 0.0001 |
| N-Acetyl Cysteine | 20 | 0.6593 | 0.0914 | 3 | *** | 0.0003 |
| N-Acetyl Cysteine | 10 | 0.7939 | 0.0715 | 3 | ** | 0.01 |
| N-Acetyl Cysteine | 5 | 0.9175 | 0.0519 | 3 | ns | 0.3855 |
| N-Acetyl Cysteine | 0 | 1.0000 | 0.0686 | 3 | | |

TABLE 31

Fold change of procollagen 1α1 secretion after administration of a single amino acid composition in the first donor

| Amino Acid Supplement | Conc. (μM) | Procollagen 1α1 Secretion (Fold Change of 1X) | | | | |
|---|---|---|---|---|---|---|
| | | Mean | Std. Deviation | Number of values | P-value* | Significance |
| Valine | 23420 | 1.2139 | 0.0544 | 3 | ns | 0.1392 |
| Valine | 11710 | 1.2069 | 0.0881 | 3 | ns | 0.155 |
| Valine | 4684 | 1.1203 | 0.1908 | 3 | ns | 0.5111 |
| Valine | 234 | 1.0000 | 0.1389 | 4 | | |
| Arginine | 5440 | 1.0646 | 0.0939 | 3 | ns | 0.4155 |
| Arginine | 2720 | 1.1757 | 0.0466 | 3 | * | 0.01 |
| Arginine | 1088 | 1.0291 | 0.0615 | 4 | ns | 0.8428 |
| Arginine | 109 | 1.0000 | 0.0389 | 4 | | |
| Glutamine | 22484 | 1.0564 | 0.1293 | 3 | ns | 0.8468 |
| Glutamine | 11242 | 1.0888 | 0.0261 | 3 | ns | 0.5648 |
| Glutamine | 3747 | 1.0757 | 0.1003 | 4 | ns | 0.6356 |
| Glutamine | 749 | 0.9790 | 0.0836 | 4 | ns | 0.993 |
| Glutamine | 562 | 1.0000 | 0.0596 | 3 | | |
| Isoleucine | 6639 | 1.2144 | 0.1129 | 3 | ns | 0.0537 |
| Isoleucine | 3320 | 1.1366 | 0.0938 | 3 | ns | 0.2411 |
| Isoleucine | 1328 | 0.9229 | 0.0614 | 3 | ns | 0.6321 |
| Isoleucine | 66 | 1.0000 | 0.0953 | 3 | | |
| Leucine | 15270 | 1.1710 | 0.1043 | 3 | ns | 0.094 |
| Leucine | 7635 | 1.0915 | 0.0832 | 3 | ns | 0.4736 |
| Leucine | 3054 | 1.1410 | 0.1245 | 4 | ns | 0.1424 |
| Leucine | 153 | 1.0000 | 0.0481 | 4 | | |

TABLE 32

Fold change of procollagen 1α1 secretion after administration of an amino acid composition in the second donor

| Amino Acid Supplement | Conc. (X) | Procollagen 1α1 Secretion (Fold Change of 1X) | | | | |
|---|---|---|---|---|---|---|
| | | Mean | Std. Deviation | Number of values | P-value* | Significance |
| LIVRQNAC | 40 | 0.7465 | 0.0551 | 3 | ** | 0.0041 |
| LIVRQNAC | 30 | 0.6829 | 0.0991 | 3 | *** | 0.0007 |
| LIVRQNAC | 20 | 0.6922 | 0.0281 | 4 | *** | 0.0004 |
| LIVRQNAC | 10 | 0.7879 | 0.0748 | 4 | ** | 0.0085 |
| LIVRQNAC | 1 | 1.0000 | 0.1141 | 4 | | |
| LIVRQNAC + G | 40 | 0.6372 | 0.0267 | 3 | **** | 0.0001 |
| LIVRQNAC + G | 30 | 0.7347 | 0.0324 | 3 | **** | 0.0001 |
| LIVRQNAC + G | 20 | 0.6716 | 0.0552 | 4 | **** | 0.0001 |
| LIVRQNAC + G | 10 | 0.7823 | 0.0579 | 4 | *** | 0.0001 |
| LIVRQNAC + G | 1 | 1.0000 | 0.0580 | 4 | | |
| LIVRQNAC + S | 40 | 0.8756 | 0.0372 | 3 | ns | 0.1229 |
| LIVRQNAC + S | 30 | 0.7340 | 0.0432 | 3 | ** | 0.0019 |
| LIVRQNAC + S | 20 | 0.7405 | 0.0491 | 3 | ** | 0.0022 |
| LIVRQNAC + S | 10 | 0.7472 | 0.0710 | 3 | ** | 0.0027 |
| LIVRQNAC + S | 1 | 1.0000 | 0.1031 | 3 | | |
| LIV | 40 | 1.4409 | 0.0697 | 3 | **** | 0.0001 |
| LIV | 30 | 1.3679 | 0.0156 | 3 | *** | 0.0001 |
| LIV | 20 | 1.3418 | 0.1090 | 3 | *** | 0.0002 |
| LIV | 10 | 1.2176 | 0.0343 | 3 | ** | 0.0057 |
| LIV | 1 | 1.0000 | 0.0396 | 3 | | |
| LIVRQ | 40 | 0.9851 | 0.0534 | 3 | ns | 0.9965 |
| LIVRQ | 30 | 1.0185 | 0.0735 | 3 | ns | 0.9921 |
| LIVRQ | 20 | 0.9212 | 0.0215 | 3 | ns | 0.4893 |
| LIVRQ | 10 | 0.9558 | 0.0580 | 3 | ns | 0.8556 |
| LIVRQ | 1 | 1.0000 | 0.1134 | 3 | | |
| RQNAC | 40 | 0.6363 | 0.0432 | 3 | *** | 0.0002 |
| RQNAC | 30 | 0.6154 | 0.0196 | 3 | *** | 0.0001 |
| RQNAC | 20 | 0.7060 | 0.0851 | 3 | *** | 0.0009 |
| RQNAC | 10 | 0.8385 | 0.0248 | 3 | * | 0.041 |
| RQNAC | 1 | 1.0000 | 0.1071 | 3 | | |
| N-Acetyl Cysteine | 40 | 0.8383 | 0.0378 | 3 | s | 0.4053 |
| N-Acetyl Cysteine | 20 | 0.7378 | 0.1347 | 3 | ns | 0.1002 |
| N-Acetyl Cysteine | 10 | 0.8877 | 0.2282 | 3 | ns | 0.6842 |
| N-Acetyl Cysteine | 5 | 0.8387 | 0.832 | 3 | ns | 0.407 |
| N-Acetyl Cysteine | 0 | 1.0000 | 0.0808 | 3 | | |

TABLE 33

Fold change of procollagen 1α1 secretion after administration of a single amino acid composition in the second donor Procollagen Iα1 Secretion (Fold Change of 1x)

| Amino Acid Supplement | Conc. (μM) | Mean | Std. Deviation | Number of values | P-value* | Significance |
|---|---|---|---|---|---|---|
| Valine | 23420 | 1.3068 | 0.0963 | 3 | ** | 0.0019 |
| Valine | 11710 | 1.2877 | 0.1122 | 3 | ** | 0.0029 |
| Valine | 4684 | 1.2865 | 0.0717 | 4 | ** | 0.0018 |
| Valine | 234 | 1.0000 | 0.0589 | 4 | | |
| Arginine | 5440 | 1.1304 | 0.0187 | 3 | ns | 0.0937 |
| Arginine | 2720 | 1.0722 | 0.0791 | 3 | ns | 0.4483 |
| Arginine | 1088 | 1.0126 | 0.0822 | 4 | ns | 0.989 |
| Arginine | 109 | 1.0000 | 0.0778 | 4 | | |
| Glutamine | 22484 | 0.7143 | 0.0566 | 3 | ** | 0.0058 |
| Glutamine | 11242 | 0.7080 | 0.0246 | 3 | ** | 0.005 |
| Glutamine | 3747 | 0.7541 | 0.0860 | 4 | * | 0.0102 |
| Glutamine | 749 | 0.9191 | 0.1171 | 4 | ns | 0.5776 |
| Glutamine | 562 | 1.0000 | 0.1003 | 3 | | |
| Isoleucine | 6639 | 1.5423 | 0.1489 | 3 | ** | 0.006 |
| Isoleucine | 3320 | 1.4940 | 0.0238 | 3 | * | 0.0102 |
| Isoleucine | 1328 | 1.4811 | 0.2307 | 3 | * | 0.0117 |
| Isoleucine | 66 | 1.0000 | 0.1264 | 3 | | |
| Leucine | 15270 | 0.9518 | 0.0406 | 3 | ns | 0.9292 |
| Leucine | 7635 | 1.2628 | 0.1763 | 3 | ns | 0.0607 |
| Leucine | 3054 | 1.0781 | 0.1735 | 4 | ns | 0.7374 |
| Leucine | 153 | 1.0000 | 0.0681 | 4 | | |

TABLE 34

Fold change of procollagen 1α1 secretion after administration of an amino acid composition in the third donor Procollagen Iα1 Secretion (Fold Change of 1x)

| Amino Acid Supplement | Conc. (X) | Mean | Std. Deviation | Number of values | P-value* | Significance |
|---|---|---|---|---|---|---|
| LIVRQNAC | 40 | 0.9052 | 0.0344 | 3 | ns | 0.5685 |
| LIVRQNAC | 30 | 0.7456 | 0.0895 | 3 | * | 0.0192 |
| LIVRQNAC | 20 | 0.7817 | 0.0680 | 4 | * | 0.03 |
| LIVRQNAC | 10 | 0.9774 | 0.1451 | 4 | ns | 0.9927 |
| LIVRQNAC | 1 | 1.0000 | 0.1116 | 4 | | |
| LIVRQNAC + G | 40 | 0.7040 | 0.0080 | 3 | ** | 0.002 |
| LIVRQNAC + G | 30 | 0.6249 | 0.0819 | 3 | *** | 0.0003 |
| LIVRQNAC + G | 20 | 0.6863 | 0.1334 | 4 | *** | 0.0006 |
| LIVRQNAC + G | 10 | 1.0068 | 0.0642 | 4 | ns | 0.9998 |
| LIVRQNAC + G | 1 | 1.0000 | 0.0724 | 4 | | |
| LIVRQNAC + S | 40 | 0.9190 | 0.0772 | 3 | ns | 0.3351 |
| LIVRQNAC + S | 30 | 0.8107 | 0.0596 | 3 | * | 0.0101 |
| LIVRQNAC + S | 20 | 0.8878 | 0.0129 | 3 | ns | 0.1296 |
| LIVRQNAC + S | 10 | 0.9814 | 0.0458 | 3 | ns | 0.9852 |
| LIVRQNAC + S | 1 | 1.0000 | 0.0780 | 3 | | |
| LIV | 40 | 1.3233 | 0.0667 | 3 | ** | 0.0024 |
| LIV | 30 | 1.2510 | 0.1070 | 3 | * | 0.0125 |
| LIV | 20 | 1.2702 | 0.0639 | 3 | ** | 0.0079 |
| LIV | 10 | 1.1912 | 0.1049 | 3 | ns | 0.0532 |
| LIV | 1 | 1.0000 | 0.0521 | 3 | | |
| LIVRQ | 40 | 1.2020 | 0.1119 | 3 | ns | 0.1081 |
| LIVRQ | 30 | 1.1380 | 0.0955 | 3 | ns | 0.3407 |
| LIVRQ | 20 | 0.9489 | 0.1179 | 3 | ns | 0.9263 |
| LIVRQ | 10 | 1.0786 | 0.0764 | 3 | ns | 0.7564 |
| LIVRQ | 1 | 1.0000 | 0.1056 | 3 | | |
| RQNAC | 40 | 0.6590 | 0.0860 | 3 | ** | 0.0012 |
| RQNAC | 30 | 0.6708 | 0.0407 | 3 | ** | 0.0016 |
| RQNAC | 20 | 0.9135 | 0.1192 | 3 | ns | 0.5063 |
| RQNAC | 10 | 0.8783 | 0.0515 | 3 | ns | 0.245 |
| RQNAC | 1 | 1.0000 | 0.0740 | 3 | | |
| N-Acetyl Cysteine | 40 | 0.6962 | 0.0189 | 3 | * | 0.0125 |
| N-Acetyl Cysteine | 20 | 0.8521 | 0.0709 | 3 | ns | 0.2666 |
| N-Acetyl Cysteine | 10 | 0.9391 | 0.1250 | 3 | ns | 0.8641 |
| N-Acetyl Cysteine | 5 | 1.0897 | 0.1245 | 3 | ns | 0.6511 |
| N-Acetyl Cysteine | 0 | 1.0000 | 0.1133 | 3 | | |

TABLE 35

Fold change of procollagen 1α1 secretion after administration of a single amino acid composition in the third donor

| Amino Acid Supplement | Conc. (μM) | Procollagen Iα1 Secretion (Fold Change of 1×) | | | | |
|---|---|---|---|---|---|---|
| | | Mean | Std. Deviation | Number of values | P-value* | Significance |
| Valine | 23420 | 1.1139 | 0.1077 | 3 | ns | 0.5315 |
| Valine | 11710 | 1.0498 | 0.1773 | 3 | ns | 0.918 |
| Valine | 4684 | 1.0428 | 0.1036 | 4 | ns | 0.9323 |
| Valine | 234 | 1.0000 | 0.1203 | 4 | | |
| Arginine | 5440 | 1.2125 | 0.0862 | 3 | * | 0.0112 |
| Arginine | 2720 | 1.1314 | 0.0820 | 3 | ns | 0.1114 |
| Arginine | 1088 | 1.0623 | 0.0629 | 4 | ns | 0.5378 |
| Arginine | 109 | 1.0000 | 0.0760 | 4 | | |
| Glutamine | 22484 | 1.0121 | 0.0730 | 3 | ns | 0.9989 |
| Glutamine | 11242 | 1.1204 | 0.1056 | 3 | ns | 0.2356 |
| Glutamine | 3747 | 0.9734 | 0.0900 | 4 | ns | 0.9747 |
| Glutamine | 749 | 1.0317 | 0.0644 | 4 | ns | 0.9538 |
| Glutamine | 562 | 1.0000 | 0.0447 | 3 | | |
| Isoleucine | 6639 | 1.4465 | 0.0958 | 3 | ** | 0.0014 |
| Isoleucine | 3320 | 1.2703 | 0.0352 | 3 | * | 0.024 |
| Isoleucine | 1328 | 1.2687 | 0.0374 | 3 | * | 0.0247 |
| Isoleucine | 66 | 1.0000 | 0.1629 | 3 | | |
| Leucine | 15270 | 0.9892 | 0.0260 | 3 | ns | 0.9979 |
| Leucine | 7635 | 1.2027 | 0.0693 | 3 | ns | 0.0638 |
| Leucine | 3054 | 1.1399 | 0.1385 | 4 | ns | 0.1844 |
| Leucine | 153 | 1.0000 | 0.1077 | 4 | | |

Example 5: Cytokine Secretion in Primary Human Macrophages

Isolation of Peripheral Blood Mononuclear Cell (PBMC) Unpurified buffy coats (Research Blood Components) were carefully poured into 50 mL centrifuge tubes and diluted with room temperature Dulbecco's Phosphate Buffered Saline (dPBS) with Calcium and Magnesium (Gibco). Diluted buffy coats were further divided into four total 50 mL centrifuge tubes at 20 mL per tube. Lymphocyte Separation Medium (Corning) was carefully pipetted to the bottom of each centrifuge tube. Mixtures were centrifuged at 850×g for 32 minutes at 20° C. with 0 deceleration and acceleration.

The PBMC layer was separated from other components after centrifugation and added to new 50 mL centrifuge tube containing 25 mL dPBS. Total volume was brought up to 50 mL with dPBS and centrifuged at 600×g for 10 minutes at 20° C. with acceleration of 9, deceleration of 5. Supernatant was carefully removed from cell pellets. The cell pellets were resuspended using 10 mL dPBS. Total volume was then brought up to 50 mL using dPBS and centrifuged at 450×g for 5 min at 20° C. with acceleration of 9, deceleration of 9. The supernatant removal and cell pellet resuspension was repeated again.

The supernatant was then carefully removed from cell pellets. Cell pellets were resuspended in 10 mL dPBS without calcium or magnesium and filtered through a 70 μM cell strainer. The total PBMC number was determined using a Cellometer K2 automated cell counter. A total of 5E6 cells were saved for flow cytometric analysis. Remaining cells were centrifuged at 490×g for 5 minutes at 20° C. with acceleration of 9, deceleration of 9.

CD14+ Cell Selection

CD14+ cells were selected using EasySep™ Human CD14 Positive Selection Kit II (STEMCELL Technologies). Cells were resuspended in cold EasySep™ Buffer (STEMCELL Technologies) at 1×10⁸ cells/mL. A total of 100 μL/mL EasySep™ Human CD14 Positive Selection Cocktail II was added to the cell suspension, mixed, and incubated at room temperature for 10 minutes. A total of 100 μL/mL RapidSpheres were added to the mixture and incubated at room temperature for 3 minutes after mixing, then RoboSep buffer was added to bring up the total volume to 10 mL. The mixture in a 15 mL tube was placed in magnet and incubated at room temperature for 3 minutes. Supernatant was discarded and 10 mL fresh EasySep™ buffer was added to 15 mL tube. The addition of RoboSep buffer, mixing, and discarding of supernatant was repeated two more times.

Negative and positive fractions were centrifuged at 490×g for 5 minutes at 20° C. with acceleration of 9, deceleration of 9, and resuspended in DMEM (Gibco) and 10% Heat Inactivated Fetal Bovine Serum (Atlanta Bio) and Penicillin/Streptomycin. Cells were counted and centrifuged again at 490×g for 5 minutes at 20° C. with acceleration of 9, deceleration of 9. After centrifugation, cell were resuspended in DMEM (Gibco) and 10% Heat Inactivated Fetal Bovine Serum (Atlanta Bio) and Penicillin/Streptomycin containing 500 U/mL GM- and plated at 1-2×10⁶ cells/mL on 10 cm tissue culture plates. Cells were kept in 37° C., 5% CO2 in between feedings/harvest.

CD14+ Cell Feeding

Cells were fed every 3-4 days by removing media and unattached cells, centrifuging at 490×g for 5 minutes at 20° C. with acceleration of 9, deceleration of 9, and resuspending in fresh DMEM (Gibco) and 10% Heat Inactivated Fetal Bovine Serum (Atlanta Bio) and Penicillin/Streptomycin containing 500 U/mL GM-CSF. Resuspended cells were seeded back onto 10 cm tissue culture plates and incubated at 37° C., 5% CO2.

Macrophage Harvest

After complete cell attachment, culture supernatant was removed and cultures were washed 1× with 5 mL PBS. A total of 3 mL room temperature Cellstripper was added and cultures were incubated at 37° C., 5% CO2 for approximately 10 minutes until cells were rounded and beginning to detach. Cell scraper was used to completely detach cells from plate. Collected cell were spun down at 490 g for 5 min at room temperature and resuspended in 10% DMSO in Heat Inactivated Fetal Bovine Serum and immediately frozen in −80° C.

Screen

Primary human PMBC derived macrophages were seeded on day 0 at 3.0E4 cells per well in 96-well microplates (ThermoFisher) in Dulbecco's Modified Eagle Medium (DMEM) (Gibco) supplemented with penicillin-streptomycin (Hyclone) and 10% heat inactivated fetal bovine serum (HI-FBS) (Atlanta Bio) and incubated overnight at 37° C., 5% CO2. On day 1, cells were washed once with 150 μL per well DPBS (Gibco) and treated with 75 μL of:
  a. Amino acid free DMEM (US Biologicals) containing a defined custom amino acid concentration based on the mean physiological concentrations in blood based on values published in the Human Metabolome Database (HMDB), with 6 mM glucose, 1 mM sodium pyruvate, 10 mM HEPES, 0.2% primocin (InVivoGen); or
  b. The same medium described above with one amino acid at various concentrations including complete drop-out. (1× is L-Leucine: 152.7 μM; L-Isoleucine: 66.4 μM; L-Valine: 234.2 μM; L-Arginine: 1088 μM; L-Glutamine: 562.1 μM; L-Glycine 251.3 μM; L-Serine 141.5 μM; N-acetylcysteine: 250 μM [not endogenous]).

On day 2, cells were treated with 75 μL of the same mediums described above supplemented with 0.30 ng/mL lipopolysaccharide (LPS) (Sigma) for a final concentration of 0.15 ng/mL LPS. Control wells were treated with 1 μM BX-795 (Tocis), 1 μM TAK242 (Sigma), 0.15 ng/mL LPS, or phosphate buffered saline (PBS).

On day 3, the supernatant was collected and immediately frozen in −80° C. freezer. Cells were washed once with 150 μL DPBS and viability was assessed using the WST-8 Cell Proliferation Cytotoxicity Assay (Dojindo). Following the assay, cells were washed twice with 150 μL PBS and fixed with 400 paraformaldehyde for 5 min followed by two additional washes with 150 μL PBS. Protein levels in supernatant samples were analyzed by ELISA for IL-6 and TNF-α using commercially available kits (R&D Systems) according to manufacturer-supplied protocols. Results are shown in Tables 36-41, below.

TABLE 36

IL-6 Measurements: Donor 1

| Amino Acid Supplement | Conc. (X) | Mean | Std. Deviation | Number of values | P-value* | Significance |
|---|---|---|---|---|---|---|
| LIVRQNAC | 40 | −619.787 | 114.1592 | 3 | 0.0001 | **** |
| LIVRQNAC | 30 | −525.849 | 63.87122 | 3 | 0.0001 | **** |
| LIVRQNAC | 20 | −290.199 | 33.5584 | 3 | 0.0092 | ** |
| LIVRQNAC | 10 | 51.81434 | 183.3933 | 3 | 0.9479 | ns |
| LIVRQNAC | 1 | 0 | 148.7761 | 3 | na | na |
| LIVRQNAC + G | 40 | −1099.11 | 44.1139 | 3 | 0.0001 | **** |
| LIVRQNAC + G | 30 | −903.836 | 107.7113 | 3 | 0.0001 | **** |
| LIVRQNAC + G | 20 | −616.626 | 114.7826 | 3 | 0.0001 | **** |
| LIVRQNAC + G | 10 | −367.918 | 98.44611 | 3 | 0.0007 | *** |
| LIVRQNAC + G | 1 | 0 | 172.9553 | 3 | na | na |
| LIVRQNAC + S | 40 | −968.997 | 90.53282 | 3 | 0.0001 | **** |
| LIVRQNAC + S | 30 | −798.326 | 52.89122 | 3 | 0.0001 | **** |
| LIVRQNAC + S | 20 | −506.804 | 63.85224 | 3 | 0.0001 | **** |
| LIVRQNAC + S | 10 | −243.259 | 114.742 | 3 | 0.0365 | * |
| LIVRQNAC + S | 1 | 0 | 259.8506 | 3 | na | na |
| LIV | 40 | 4.918642 | 62.7077 | 3 | 0.9999 | ns |
| LIV | 30 | 86.01907 | 128.1151 | 3 | 0.7604 | ns |
| LIV | 20 | 112.1501 | 83.62436 | 3 | 0.564 | ns |
| LIV | 10 | 54.22668 | 63.10515 | 3 | 0.9392 | ns |
| LIV | 1 | 0 | 75.98804 | 3 | na | na |
| LIVRQ | 40 | 322.0706 | 73.87715 | 3 | 0.0033 | ** |
| LIVRQ | 30 | 297.8004 | 34.60168 | 3 | 0.0072 | ** |
| LIVRQ | 20 | 604.021 | 203.8836 | 3 | 0.0001 | **** |
| LIVRQ | 10 | 289.1798 | 57.78952 | 3 | 0.0095 | ** |
| LIVRQ | 1 | 0 | 93.58494 | 3 | na | na |
| RQNAC | 40 | −911.011 | 12.65475 | 3 | 0.0001 | **** |
| RQNAC | 30 | −766.912 | 26.23659 | 3 | 0.0001 | **** |
| RQNAC | 20 | −511.403 | 32.15983 | 3 | 0.0001 | **** |
| RQNAC | 10 | −201.63 | 6.477522 | 3 | 0.1054 | ns |
| RQNAC | 1 | 0 | 174.9658 | 3 | na | na |
| N-Acetyl Cysteine | 40 | −914.194 | 56.77271 | 3 | 0.0001 | **** |
| N-Acetyl Cysteine | 20 | −553.802 | 85.27013 | 3 | 0.0001 | **** |
| N-Acetyl Cysteine | 10 | −121.142 | 53.05191 | 3 | 0.4973 | ns |
| N-Acetyl Cysteine | 5 | 308.1772 | 263.4651 | 3 | 0.0052 | ** |
| N-Acetyl Cysteine | 0 | 0 | 45.08485 | 3 | na | na |

| Amino Acid Supplement | Conc. (μM) | Mean | Std. Deviation | Number of values | P-value* | Significance |
|---|---|---|---|---|---|---|
| | | Donor 1 IL-6 Measurements | | | | |
| Valine | 23420 | −106.268 | 155.3559 | 3 | 0.7885 | ns |
| Valine | 11710 | −97.25 | 77.26313 | 3 | 0.8339 | ns |
| Valine | 4684 | −85.9843 | 74.99317 | 3 | 0.8841 | ns |
| Valine | 234 | 0 | 124.8497 | 3 | na | na |
| Arginine | 5440 | 357.4394 | 154.8508 | 3 | 0.0159 | * |

TABLE 36-continued

IL-6 Measurements: Donor 1

| Arginine | 2720 | −186.57 | 85.86105 | 3 | 0.3477 | ns |
|---|---|---|---|---|---|---|
| Arginine | 1088 | −181.36 | 131.6475 | 3 | 0.3722 | ns |
| Arginine | 109 | 0 | 282.0306 | 3 | na | na |
| Glutamine | 22484 | 440.1437 | 114.443 | 3 | 0.0022 | ** |
| Glutamine | 11242 | 397.1745 | 23.36272 | 3 | 0.0064 | ** |
| Glutamine | 3747 | 291.5443 | 81.30853 | 3 | 0.0623 | ns |
| Glutamine | 749 | 0 | 73.06692 | 3 | na | na |
| Isoleucine | 6639 | −218.332 | 146.5098 | 3 | 0.221 | ns |
| Isoleucine | 3320 | −15.8843 | 89.88616 | 3 | 0.9998 | ns |
| Isoleucine | 1328 | 25.98372 | 323.6109 | 3 | 0.9984 | ns |
| Isoleucine | 66 | 0 | 48.21125 | 3 | na | na |
| Leucine | 15270 | 84.46122 | 68.15253 | 3 | 0.8902 | ns |
| Leucine | 7635 | −69.9873 | 99.00843 | 3 | 0.9398 | ns |
| Leucine | 3054 | 244.9743 | 355.6551 | 3 | 0.1442 | ns |
| Leucine | 153 | 0 | 61.85589 | 3 | na | na |

Treatment with LIVRQNAC, LIVRQNAC+G, LIVRQNAC+S, RQNAC, and NAC significantly reduced LPS-induced IL-6 secretion in primary human monocyte-derived macrophages. Treatment with LIVRQ significantly increased IL-6 secretion, while LIV had no effect. Arginine and glutamine administered alone increased IL-6 secretion while other amino acids alone did not affect IL-6 secretion. Two Way ANOVA Dunnett Multiple Comparisons was performed for statistical analysis. Mean values represented as baseline subtracted values.

TABLE 37

IL-6 Measurements: Donor 2

| Amino Acid Supplement | Conc. (X) | Mean | Std. Deviation | Number of values | P-value* | Significance |
|---|---|---|---|---|---|---|
| LIVRQNAC | 40 | −27.1916 | 1.853569 | 3 | 0.0003 | *** |
| LIVRQNAC | 30 | −21.5766 | 1.709414 | 3 | 0.0045 | ** |
| LIVRQNAC | 20 | −8.20655 | 8.458638 | 3 | 0.5143 | ns |
| LIVRQNAC | 10 | −1.71581 | 6.104437 | 3 | 0.9965 | ns |
| LIVRQNAC | 1 | −2.4E−15 | 11.85079 | 3 | | |
| LIVRQNAC + G | 40 | −33.2001 | 3.55425 | 3 | 0.0001 | **** |
| LIVRQNAC + G | 30 | −30.8468 | 0.854995 | 3 | 0.0001 | **** |
| LIVRQNAC + G | 20 | −18.4318 | 4.870421 | 3 | 0.0187 | * |
| LIVRQNAC + G | 10 | 14.63551 | 21.82024 | 3 | 0.0824 | ns |
| LIVRQNAC + G | 1 | 2.37E−15 | 8.607557 | 3 | | |
| LIVRQNAC + S | 40 | −26.5993 | 2.963677 | 3 | 0.0004 | *** |
| LIVRQNAC + S | 30 | −14.2166 | 1.460268 | 3 | 0.0954 | ns |
| LIVRQNAC + S | 20 | −8.2522 | 2.917345 | 3 | 0.5095 | ns |
| LIVRQNAC + S | 10 | 8.127841 | 1.783214 | 3 | 0.5227 | ns |
| LIVRQNAC + S | 1 | 0 | 6.232673 | 3 | | |
| LIV | 40 | 34.10306 | 1.950493 | 3 | 0.0001 | **** |
| LIV | 30 | 31.10835 | 9.757211 | 3 | 0.0001 | **** |
| LIV | 20 | 20.32684 | 3.17293 | 3 | 0.0081 | ** |
| LIV | 10 | 15.10204 | 9.179111 | 3 | 0.0697 | ns |
| LIV | 1 | −7.1E−15 | 4.738966 | 3 | | |
| LIVRQ | 40 | 49.62156 | 17.37012 | 3 | 0.0001 | **** |
| LIVRQ | 30 | 42.9625 | 7.798872 | 3 | 0.0001 | **** |
| LIVRQ | 20 | 48.38603 | 13.08566 | 3 | 0.0001 | **** |
| LIVRQ | 10 | 45.99191 | 15.19687 | 3 | 0.0001 | **** |
| LIVRQ | 1 | 1.18E−15 | 6.324379 | 3 | | |
| RQNAC | 40 | −36.5521 | 1.877658 | 3 | 0.0001 | **** |
| RQNAC | 30 | −26.3768 | 0.744676 | 3 | 0.0004 | *** |
| RQNAC | 20 | −18.7428 | 1.353649 | 3 | 0.0164 | * |
| RQNAC | 10 | −3.74427 | 4.74578 | 3 | 0.9393 | ns |
| RQNAC | 1 | 2.37E−15 | 12.26314 | 3 | | |
| N-Acetyl Cysteine | 40 | −33.7585 | 0.895842 | 3 | 0.0001 | **** |
| N-Acetyl Cysteine | 20 | −24.9999 | 1.083467 | 3 | 0.0008 | *** |
| N-Acetyl Cysteine | 10 | −9.75111 | 2.381012 | 3 | 0.3617 | ns |
| N-Acetyl Cysteine | 5 | −0.79458 | 5.988677 | 3 | 0.9998 | ns |
| N-Acetyl Cysteine | 0 | −2.4E−15 | 1.900091 | 3 | | |

| Amino Acid Supplement | Conc. (μM) | Mean | Std. Deviation | Number of values | P-value* | Significance |
|---|---|---|---|---|---|---|
| Valine | 23420 | 4.395899 | 10.35903 | 3 | 0.973 | ns |
| Valine | 11710 | −1.19605 | 7.303571 | 3 | 0.9998 | ns |
| Valine | 4684 | −4.52846 | 4.069907 | 3 | 0.97 | ns |

TABLE 37-continued

IL-6 Measurements: Donor 2

| | | | | | | |
|---|---|---|---|---|---|---|
| Valine | 234 | −4.7E−15 | 9.361734 | 3 | | |
| Arginine | 5440 | −12.4164 | 0.292618 | 3 | 0.5017 | ns |
| Arginine | 2720 | −13.6102 | 2.1177 | 3 | 0.4207 | ns |
| Arginine | 1088 | −9.70116 | 9.286942 | 3 | 0.6995 | ns |
| Arginine | 109 | 2.37E−15 | 14.30728 | 3 | | |
| Glutamine | 22484 | 34.38845 | 7.467725 | 3 | 0.0026 | ** |
| Glutamine | 11242 | 63.31441 | 35.02748 | 3 | 0.0001 | **** |
| Glutamine | 3747 | 22.51543 | 9.686139 | 3 | 0.0721 | ns |
| Glutamine | 749 | 2.37E−15 | 2.203881 | 3 | | |
| Isoleucine | 6639 | −1.77438 | 10.22772 | 3 | 0.999 | ns |
| Isoleucine | 3320 | 2.305485 | 1.328015 | 3 | 0.9975 | ns |
| Isoleucine | 1328 | −2.31776 | 9.121049 | 3 | 0.9974 | ns |
| Isoleucine | 66 | 0 | 12.3413 | 3 | | |
| Leucine | 15270 | 47.59735 | 16.64049 | 3 | 0.0001 | **** |
| Leucine | 7635 | 30.46065 | 7.144005 | 3 | 0.0087 | ** |
| Leucine | 3054 | 29.60609 | 13.39676 | 3 | 0.0111 | * |
| Leucine | 153 | 7.11E−15 | 6.308577 | 3 | | |

Treatment with LIVRQNAC, LIVRQNAC+G, LIVRQNAC+S, RQNAC, and NAC significantly reduced LPS-induced IL-6 secretion in primary human monocyte-derived macrophages. Treatment with LIVRQ and LIV significantly increased IL-6 secretion. Glutamine and leucine administered alone increased IL-6 secretion, while the other amino acids alone had no effect. Two Way ANOVA Dunnett Multiple Comparisons was performed for statistical analysis. Mean values represented as baseline subtracted values.

TABLE 38

IL-6 Measurements: Donor 3

| Amino Acid Supplement | Conc. (X) | Mean | Std. Deviation | Number of values | P-value* | Significance |
|---|---|---|---|---|---|---|
| LIVRQNAC | 40 | −18.2445 | 4.129349 | 3 | 0.7529 | ns |
| LIVRQNAC | 30 | −16.8219 | 1.366045 | 3 | 0.8001 | ns |
| LIVRQNAC | 20 | −13.4826 | 12.48206 | 3 | 0.8948 | ns |
| LIVRQNAC | 10 | −34.4539 | 37.38053 | 3 | 0.2356 | ns |
| LIVRQNAC | 1 | −1.4E−14 | 14.03982 | 3 | | |
| LIVRQNAC + G | 40 | −54.4799 | 5.467815 | 3 | 0.0228 | * |
| LIVRQNAC + G | 30 | −48.3118 | 1.960574 | 3 | 0.0513 | ns |
| LIVRQNAC + G | 20 | −55.792 | 7.763897 | 3 | 0.019 | * |
| LIVRQNAC + G | 10 | −44.8309 | 14.34972 | 3 | 0.0783 | ns |
| LIVRQNAC + G | 1 | 0 | 26.01471 | 3 | | |
| LIVRQNAC + S | 40 | −14.5337 | 15.82418 | 3 | 0.868 | ns |
| LIVRQNAC + S | 30 | −25.9127 | 10.00119 | 3 | 0.479 | ns |
| LIVRQNAC + S | 20 | −25.8862 | 21.61536 | 3 | 0.48 | ns |
| LIVRQNAC + S | 10 | −11.9742 | 10.3333 | 3 | 0.9277 | ns |
| LIVRQNAC + S | 1 | −4.3E−14 | 15.34164 | 3 | | |
| LIV | 40 | 10.21257 | 37.58938 | 3 | 0.9576 | ns |
| LIV | 30 | −32.6891 | 24.862 | 3 | 0.2771 | ns |
| LIV | 20 | 27.66715 | 39.40901 | 3 | 0.4207 | ns |
| LIV | 10 | 9.44789 | 71.20002 | 3 | 0.9677 | ns |
| LIV | 1 | −4.7E−14 | 27.50075 | 3 | | |
| LIVRQ | 40 | 74.9145 | 12.55033 | 3 | 0.001 | *** |
| LIVRQ | 30 | 120.1764 | 20.21514 | 3 | 0.0001 | **** |
| LIVRQ | 20 | 77.12007 | 11.45452 | 3 | 0.0007 | *** |
| LIVRQ | 10 | 67.95483 | 43.58345 | 3 | 0.003 | ** |
| LIVRQ | 1 | −2.4E−14 | 27.62048 | 3 | | |
| RQNAC | 40 | −45.9765 | 5.740028 | 3 | 0.0683 | ns |
| RQNAC | 30 | −53.3845 | 16.45009 | 3 | 0.0265 | * |
| RQNAC | 20 | −65.6761 | 3.400465 | 3 | 0.0044 | ** |
| RQNAC | 10 | −32.8776 | 33.99103 | 3 | 0.2724 | ns |
| RQNAC | 1 | −2.8E−14 | 23.14404 | 3 | | |
| N-Acetyl Cysteine | 40 | −140.851 | 4.662272 | 3 | 0.0001 | **** |
| N-Acetyl Cysteine | 20 | −122.656 | 8.219985 | 3 | 0.0001 | **** |
| N-Acetyl Cysteine | 10 | −103.586 | 28.4385 | 3 | 0.0001 | **** |
| N-Acetyl Cysteine | 5 | −70.3269 | 8.563896 | 3 | 0.0021 | ** |
| N-Acetyl Cysteine | 0 | −9.5E−15 | 11.75797 | 3 | | |

TABLE 38-continued

IL-6 Measurements: Donor 3

| Amino Acid Supplement | Conc. (μM) | Donor 3 IL-6 Measurements | | | | |
|---|---|---|---|---|---|---|
| | | Mean | Std. Deviation | Number of values | P-value* | Significance |
| Valine | 23420 | −29.2004 | 25.98066 | 3 | 0.4329 | ns |
| Valine | 11710 | −43.8022 | 8.331697 | 3 | 0.1239 | ns |
| Valine | 4684 | −30.0609 | 8.478329 | 3 | 0.4072 | ns |
| Valine | 234 | 4.26E−14 | 17.2027 | 3 | | |
| Arginine | 5440 | −6.80983 | 0.643932 | 3 | 0.9922 | ns |
| Arginine | 2720 | −7.50318 | 22.06663 | 3 | 0.9888 | ns |
| Arginine | 1088 | 31.5786 | 70.48311 | 3 | 0.3642 | ns |
| Arginine | 109 | 0 | 17.26952 | 3 | | |
| Glutamine | 22484 | 108.5158 | 55.59202 | 3 | 0.0001 | **** |
| Glutamine | 11242 | 98.4903 | 58.37 | 3 | 0.0001 | **** |
| Glutamine | 3747 | 25.35457 | 16.40416 | 3 | 0.556 | ns |
| Glutamine | 749 | 3.79E−14 | 16.54987 | 3 | | |
| Isoleucine | 6639 | −16.3663 | 8.09174 | 3 | 0.9718 | ns |
| Isoleucine | 3320 | 0 | 19.80362 | 3 | 0.9928 | ns |
| Isoleucine | 1328 | −28.9897 | 13.10903 | 3 | 0.6593 | ns |
| Isoleucine | 66 | −6.69039 | 13.72995 | 3 | | |
| Leucine | 15270 | # | # | 3 | # | # |
| Leucine | 7635 | # | # | 3 | # | # |
| Leucine | 3054 | # | # | 3 | # | # |
| Leucine | 153 | # | # | 3 | # | # |

Leucine was not measured in Exp3 due to technical error

Treatment with LIVRQNAC+G, LIVRQNAC+S, RQNAC, and NAC significantly reduced LPS-induced IL-6 secretion in primary human monocyte-derived macrophages. Treatment with LIVRQ increased IL-6 secretion, while LIV and LIVRQNAC had no statistically significant effects on IL-6 secretion. Glutamine administered alone significantly increased IL-6 secretion, while other amino acids alone had no effect. Two Way ANOVA Dunnett Multiple Comparisons was performed for statistical analysis. Mean values represented as baseline subtracted values.

TABLE 39

TNF-α Measurements: Donor 1

| Amino Acid Supplement | Conc. (X) | Donor 1 TNF-α Measurements | | | | |
|---|---|---|---|---|---|---|
| | | Mean | Std. Deviation | Number of values | P-value* | Significance |
| LIVRQNAC | 40 | −422.74 | 4.347575 | 3 | 0.0001 | **** |
| LIVRQNAC | 30 | −389.74 | 1.004633 | 3 | 0.0001 | **** |
| LIVRQNAC | 20 | −336.69 | 3.007435 | 3 | 0.0001 | **** |
| LIVRQNAC | 10 | −246.04 | 27.61929 | 3 | 0.0001 | **** |
| LIVRQNAC | 1 | 0 | 36.31082 | 3 | | |
| LIVRQNAC + G | 40 | −490.92 | 4.427614 | 3 | 0.0001 | **** |
| LIVRQNAC + G | 30 | −447.73 | 9.819865 | 3 | 0.0001 | **** |
| LIVRQNAC + G | 20 | −377.32 | 5.837159 | 3 | 0.0001 | **** |
| LIVRQNAC + G | 10 | −268.29 | 9.642365 | 3 | 0.0001 | **** |
| LIVRQNAC + G | 1 | 0 | 37.44353 | 3 | | |
| LIVRQNAC + S | 40 | −415.03 | 4.800449 | 3 | 0.0001 | **** |
| LIVRQNAC + S | 30 | −379.44 | 4.694868 | 3 | 0.0001 | **** |
| LIVRQNAC + S | 20 | −323.77 | 7.971135 | 3 | 0.0001 | **** |
| LIVRQNAC + S | 10 | −209.59 | 21.15676 | 3 | 0.0001 | **** |
| LIVRQNAC + S | 1 | 0 | 30.0492 | 3 | | |
| LIV | 40 | 60.37 | 20.26331 | 3 | 0.0065 | ** |
| LIV | 30 | 42.09 | 22.95664 | 3 | 0.0865 | ns |
| LIV | 20 | 63.37 | 37.24144 | 3 | 0.004 | ** |
| LIV | 10 | 45.61 | 44.71078 | 3 | 0.0556 | ns |
| LIV | 1 | 0 | 10.49958 | 3 | | |
| LIVRQ | 40 | 6.38 | 17.1283 | 3 | 0.9909 | ns |
| LIVRQ | 30 | −6.72 | 18.9622 | 3 | 0.989 | ns |
| LIVRQ | 20 | 38.38 | 39.85515 | 3 | 0.1333 | ns |
| LIVRQ | 10 | −18.95 | 10.84371 | 3 | 0.6982 | ns |
| LIVRQ | 1 | 0 | 36.96184 | 3 | | |
| RQNAC | 40 | −408.44 | 1.179877 | 3 | 0.0001 | **** |
| RQNAC | 30 | −390.41 | 1.341282 | 3 | 0.0001 | **** |
| RQNAC | 20 | −338.2 | 3.284307 | 3 | 0.0001 | **** |
| RQNAC | 10 | −251.35 | 4.121085 | 3 | 0.0001 | **** |
| RQNAC | 1 | 0 | 51.06933 | 3 | | |
| N-Acetyl Cysteine | 40 | −644.49 | 2.42197 | 3 | 0.0001 | **** |
| N-Acetyl Cysteine | 20 | −561.33 | 8.435064 | 3 | 0.0001 | **** |
| N-Acetyl Cysteine | 10 | −446.88 | 12.22132 | 3 | 0.0001 | **** |

TABLE 39-continued

TNF-α Measurements: Donor 1

| Amino Acid Supplement | Conc. (μM) | Mean | Std. Deviation | Number of values | P-value* | Significance |
|---|---|---|---|---|---|---|
| N-Acetyl Cysteine | 5 | −326.24 | 11.10173 | 3 | 0.0001 | **** |
| N-Acetyl Cysteine | 0 | 0 | 42.00516 | 3 | | |

Donor 1 TNF-α Measurements

| Amino Acid Supplement | Conc. (μM) | Mean | Std. Deviation | Number of values | P-value* | Significance |
|---|---|---|---|---|---|---|
| Valine | 23420 | −14.98 | 20.86784 | 3 | 0.9928 | ns |
| Valine | 11710 | −41.77 | 36.61662 | 3 | 0.7784 | ns |
| Valine | 4684 | −40.37 | 32.31016 | 3 | 0.7974 | ns |
| Valine | 234 | 0 | 24.8661 | 3 | | |
| Arginine | 5440 | 62.06 | 48.80326 | 3 | 0.4786 | ns |
| Arginine | 2720 | 5.12 | 15.47951 | 3 | 0.9998 | ns |
| Arginine | 1088 | −24.33 | 17.74317 | 3 | 0.9577 | ns |
| Arginine | 109 | 0 | 18.5366 | 3 | | |
| Glutamine | 22484 | −103.07 | 27.02483 | 3 | 0.0985 | ns |
| Glutamine | 11242 | −65.24 | 23.02631 | 3 | 0.4346 | ns |
| Glutamine | 3747 | −45.7 | 28.56445 | 3 | 0.7222 | ns |
| Glutamine | 749 | 0 | 30.75138 | 3 | | |
| Isoleucine | 6639 | −40.95 | 78.56369 | 3 | 0.7896 | ns |
| Isoleucine | 3320 | −96.3 | 45.66981 | 3 | 0.1339 | ns |
| Isoleucine | 1328 | −42.68 | 21.07739 | 3 | 0.7657 | ns |
| Isoleucine | 66 | 0 | 115.9559 | 3 | | |
| Leucine | 15270 | −46.21 | 29.00402 | 3 | 0.7148 | ns |
| Leucine | 7635 | −23.04 | 40.08864 | 3 | 0.965 | ns |
| Leucine | 3054 | 42.04 | 77.19161 | 3 | 0.7746 | ns |
| Leucine | 153 | 0 | 157.6578 | 3 | | |

Treatment with LIVRQNAC, LIVRQNAC+G, LIVRQNAC+S, RQNAC, and NAC significantly reduced LPS-induced TNF-α secretion in primary human monocyte-derived macrophages. Treatment with LIV increased TNF-α secretion, while LIVRQ had no significant effects on TNF-α secretion. None of the individually administered amino acids had an effect on TNF-α secretion. Two Way ANOVA Dunnett Multiple Comparisons was performed for statistical analysis. Mean values represented as baseline subtracted values.

TABLE 40

TNF-α Measurements: Donor 2

Donor 2 TNF-α Measurements

| Amino Acid Supplement | Conc. (X) | Mean | Std. Deviation | Number of values | P-value* | Significance |
|---|---|---|---|---|---|---|
| LIVRQNAC | 40 | −98.1341 | 2.118962 | 3 | 0.0001 | **** |
| LIVRQNAC | 30 | −85.1019 | 1.385677 | 3 | 0.0001 | **** |
| LIVRQNAC | 20 | −64.3364 | 10.07525 | 3 | 0.0001 | **** |
| LIVRQNAC | 10 | −38.3512 | 5.120689 | 3 | 0.0001 | **** |
| LIVRQNAC | 1 | 0 | 5.45587 | 3 | | |
| LIVRQNAC + G | 40 | −91.3454 | 5.994009 | 3 | 0.0001 | **** |
| LIVRQNAC + G | 30 | −82.4397 | 4.200763 | 3 | 0.0001 | **** |
| LIVRQNAC + G | 20 | −61.247 | 8.702492 | 3 | 0.0001 | **** |
| LIVRQNAC + G | 10 | −23.9913 | 7.471422 | 3 | 0.008 | ** |
| LIVRQNAC + G | 1 | −4.7E−15 | 4.578295 | 3 | | |
| LIVRQNAC + S | 40 | −74.1572 | 4.163823 | 3 | 0.0001 | **** |
| LIVRQNAC + S | 30 | −64.0016 | 5.549308 | 3 | 0.0001 | **** |
| LIVRQNAC + S | 20 | −47.5673 | 3.970363 | 3 | 0.0001 | **** |
| LIVRQNAC + S | 10 | −28.635 | 7.390447 | 3 | 0.0012 | ** |
| LIVRQNAC + S | 1 | −4.7E−15 | 7.564883 | 3 | | |
| LIV | 40 | 49.84155 | 4.092799 | 3 | **** | 0.0001 |
| LIV | 30 | 29.1118 | 14.72509 | 3 | *** | 0.001 |
| LIV | 20 | 30.17595 | 5.797518 | 3 | *** | 0.0006 |
| LIV | 10 | 16.68974 | 10.85983 | 3 | ns | 0.0974 |
| LIV | 1 | 0 | 10.41523 | 3 | | |
| LIVRQ | 40 | 64.1705 | 27.82953 | 3 | **** | 0.0001 |
| LIVRQ | 30 | 50.92104 | 6.955429 | 3 | **** | 0.0001 |
| LIVRQ | 20 | 45.65882 | 19.0128 | 3 | **** | 0.0001 |
| LIVRQ | 10 | 32.37038 | 19.44425 | 3 | *** | 0.0002 |
| LIVRQ | 1 | −4.7E−15 | 5.942707 | 3 | | |
| RQNAC | 40 | −84.147 | 5.821583 | 3 | **** | 0.0001 |
| RQNAC | 30 | −77.9626 | 1.626776 | 3 | **** | 0.0001 |
| RQNAC | 20 | −63.3754 | 3.494595 | 3 | **** | 0.0001 |
| RQNAC | 10 | −37.6072 | 1.88043 | 3 | **** | 0.0001 |
| RQNAC | 1 | −9.5E−15 | 4.727924 | 3 | | |
| N-Acetyl Cysteine | 40 | −103.984 | 0.720962 | 3 | 0.0001 | **** |

TABLE 40-continued

| | | TNF-α Measurements: Donor 2 | | | | |
|---|---|---|---|---|---|---|
| N-Acetyl Cysteine | 20 | −88.6528 | 0.668195 | 3 | 0.0001 | **** |
| N-Acetyl Cysteine | 10 | −70.8382 | 12.08717 | 3 | 0.0001 | **** |
| N-Acetyl Cysteine | 5 | −54.1596 | 11.06287 | 3 | 0.0001 | **** |
| N-Acetyl Cysteine | 0 | 9.47E−15 | 2.926881 | 3 | | |

| | | Donor 2 TNF-α Measurements | | | | |
|---|---|---|---|---|---|---|
| Amino Acid Supplement | Conc. (μM) | Mean | Std. Deviation | Number of values | P-value* | Significance |
| Valine | 23420 | −1.25079 | 12.85688 | 3 | 0.9991 | ns |
| Valine | 11710 | −0.83505 | 8.524018 | 3 | 0.9998 | ns |
| Valine | 4684 | −0.00221 | 5.127759 | 3 | 0.9999 | ns |
| Valine | 234 | −4.7E−15 | 8.717375 | 3 | | |
| Arginine | 5440 | −0.57378 | 8.672536 | 3 | 0.9999 | ns |
| Arginine | 2720 | −3.76334 | 2.467885 | 3 | 0.9594 | ns |
| Arginine | 1088 | −12.7222 | 4.764842 | 3 | 0.2488 | ns |
| Arginine | 109 | 1.42E−14 | 3.511446 | 3 | | |
| Glutamine | 22484 | 11.50181 | 6.216029 | 3 | 0.3311 | ns |
| Glutamine | 11242 | 20.03996 | 11.90208 | 3 | 0.0279 | * |
| Glutamine | 3747 | 9.338214 | 9.748253 | 3 | 0.5134 | ns |
| Glutamine | 749 | −9.5E−15 | 7.275868 | 3 | | |
| Isoleucine | 6639 | 19.25756 | 5.097831 | 3 | 0.0365 | * |
| Isoleucine | 3320 | 10.26061 | 7.861148 | 3 | 0.4307 | ns |
| Isoleucine | 1328 | 2.918887 | 1.921961 | 3 | 0.9836 | ns |
| Isoleucine | 66 | 4.74E−15 | 6.264135 | 3 | | |
| Leucine | 15270 | 46.68507 | 11.63209 | 3 | 0.0001 | **** |
| Leucine | 7635 | 41.97528 | 6.512087 | 3 | 0.0001 | **** |
| Leucine | 3054 | 31.74019 | 11.56537 | 3 | 0.0002 | *** |
| Leucine | 153 | 0 | 0.482598 | 3 | | |

Treatment with LIVRQNAC, LIVRQNAC+G, LIVRQNAC+S, RQNAC, and NAC significantly reduced LPS-induced TNF-α secretion in primary human monocyte-derived macrophages. Treatment with LIV and LIVRQ increased TNF-α secretion. Leucine, isoleucine, and glutamine administered individually increased TNF-α secretion, while the other amino acids had no effect. Two Way ANOVA Dunnett Multiple Comparisons was performed for statistical analysis. Mean values represented as baseline subtracted values.

TABLE 41

| | | TNF-α Measurements: Donor 3 | | | | |
|---|---|---|---|---|---|---|
| | | Donor 3 TNF-α Measurements | | | | |
| Amino Acid Supplement | Conc. (X) | Mean | Std. Deviation | Number of values | P-value* | Significance |
| LIVRQNAC | 40 | −18.7507 | 2.487301 | 3 | 0.0001 | **** |
| LIVRQNAC | 30 | −15.5979 | 0.932399 | 3 | 0.0006 | *** |
| LIVRQNAC | 20 | −10.7042 | 3.013527 | 3 | 0.026 | * |
| LIVRQNAC | 10 | −8.49034 | 2.434812 | 3 | 0.1029 | ns |
| LIVRQNAC | 1 | 0 | 4.067982 | 3 | | |
| LIVRQNAC + G | 40 | −14.6552 | 3.149813 | 3 | 0.0013 | ** |
| LIVRQNAC + G | 30 | −11.6973 | 2.026588 | 3 | 0.0129 | * |
| LIVRQNAC + G | 20 | −8.0218 | 0.671662 | 3 | 0.1331 | ns |
| LIVRQNAC + G | 10 | −4.8035 | 1.658348 | 3 | 0.5453 | ns |
| LIVRQNAC + G | 1 | −2.4E−15 | 5.625453 | 3 | | |
| LIVRQNAC + S | 40 | −14.247 | 1.800575 | 3 | 0.0018 | ** |
| LIVRQNAC + S | 30 | −15.1388 | 1.568817 | 3 | 0.0009 | *** |
| LIVRQNAC + S | 20 | −12.4722 | 3.334857 | 3 | 0.0073 | ** |
| LIVRQNAC + S | 10 | −6.72057 | 1.833554 | 3 | 0.2549 | ns |
| LIVRQNAC + S | 1 | 0 | 4.171555 | 3 | | |
| LIV | 40 | 14.07984 | 11.14252 | 3 | 0.002 | ** |
| LIV | 30 | 1.759786 | 1.102706 | 3 | 0.9748 | ns |
| LIV | 20 | 14.51396 | 10.41503 | 3 | 0.0014 | ** |
| LIV | 10 | 8.560957 | 12.86074 | 3 | 0.0989 | ns |
| LIV | 1 | 2.37E−15 | 3.660423 | 3 | | |
| LIVRQ | 40 | 25.84453 | 0.659584 | 3 | 0.0001 | **** |
| LIVRQ | 30 | 33.74883 | 5.974096 | 3 | 0.0001 | **** |
| LIVRQ | 20 | 20.94481 | 2.163828 | 3 | 0.0001 | **** |
| LIVRQ | 10 | 15.45187 | 3.942596 | 3 | 0.0007 | *** |
| LIVRQ | 1 | 0 | 4.575346 | 3 | | |
| RQNAC | 40 | −21.5102 | 1.191926 | 3 | 0.0001 | **** |
| RQNAC | 30 | −20.8898 | 2.622446 | 3 | 0.0001 | **** |
| RQNAC | 20 | −19.9558 | 3.302225 | 3 | 0.0001 | **** |
| RQNAC | 10 | −9.09425 | 5.483242 | 3 | 0.0725 | ns |

TABLE 41-continued

| | | TNF-α Measurements: Donor 3 | | | | |
|---|---|---|---|---|---|---|
| RQNAC | 1 | 0 | 6.189505 | 3 | | |
| N-Acetyl Cysteine | 40 | −55.3093 | 0.809363 | 3 | 0.0001 | **** |
| N-Acetyl Cysteine | 20 | −48.4373 | 1.563179 | 3 | 0.0001 | **** |
| N-Acetyl Cysteine | 10 | −41.7266 | 3.533914 | 3 | 0.0001 | **** |
| N-Acetyl Cysteine | 5 | −33.6246 | 0.253484 | 3 | 0.0001 | **** |
| N-Acetyl Cysteine | 0 | 4.74E−15 | 8.55997 | 3 | | |

| | | Donor 3 TNF-α Measurements | | | | |
|---|---|---|---|---|---|---|
| Amino Acid Supplement | Conc. (μM) | Mean | Std. Deviation | Number of values | P-value* | Significance |
| Valine | 23420 | 3.688279 | 7.532913 | 3 | 0.8962 | ns |
| Valine | 11710 | −2.59866 | 2.586099 | 3 | 0.9674 | ns |
| Valine | 4684 | 0.126 | 0.903014 | 3 | 0.9999 | ns |
| Valine | 234 | −2.4E−15 | 2.731283 | 3 | | |
| Arginine | 5440 | −1.76662 | 4.067694 | 3 | 0.992 | ns |
| Arginine | 2720 | −0.96691 | 4.86075 | 3 | 0.9991 | ns |
| Arginine | 1088 | 3.131153 | 10.346 | 3 | 0.9384 | ns |
| Arginine | 109 | 3.55E−15 | 4.325877 | 3 | | |
| Glutamine | 22484 | 29.14034 | 17.71417 | 3 | 0.0001 | **** |
| Glutamine | 11242 | 18.00238 | 14.58602 | 3 | 0.0061 | ** |
| Glutamine | 3747 | 1.935546 | 2.127977 | 3 | 0.9887 | ns |
| Glutamine | 749 | 0 | 5.196592 | 3 | | |
| Isoleucine | 6639 | −1.66019 | 4.262718 | 3 | 0.9938 | ns |
| Isoleucine | 3320 | 3.308901 | 3.745411 | 3 | 0.9262 | ns |
| Isoleucine | 1328 | −6.22991 | 0.48195 | 3 | 0.5976 | ns |
| Isoleucine | 66 | −2.4E−15 | 3.844593 | 3 | | |
| Leucine | 15270 | # | # | 3 | # | # |
| Leucine | 7635 | # | # | 3 | # | # |
| Leucine | 3054 | # | # | 3 | # | # |
| Leucine | 153 | # | # | 3 | # | # |

Leucine was not measured in Exp3 due to technical error

Treatment with LIVRQNAC, LIVRQNAC+G, LIVRQNAC+S, RQNAC, and NAC significantly reduced LPS-induced TNF-α secretion in primary human monocyte-derived macrophages. Treatment with LIV and LIVRQ increased TNF-α secretion. Individually administered amino acids had no significant effect on TNF-α secretion, except for glutamine which increased TNF-α secretion. Two Way ANOVA Dunnett Multiple Comparisons was performed for statistical analysis. Mean values represented as baseline subtracted values.

Example 6: ATP Production Rates in Primary Human M1 Macrophages

Activation of macrophages induces a metabolic switch from oxidative phosphorylation to glycolysis. This activation leads to increases in glycolysis, lactate production and glycolytic ATP levels, as well as reduction in mitochondrial ATP (with increases in TCA cycle substrates succinate and citrate) and increases in inflammatory cytokines and reactive oxygen species. Such metabolic changes in macrophages can contribute to promotion of NAFLD progression. Effects of the amino acids combination L-leucine, L-isoleucine, L-valine, L-arginine, L-glutamine, and N-acetylcysteine (LIVRQNAC) on M1 macrophage metabolism were assessed using a real-time ATP rate assay.

Primary human PMBC derived macrophages were seeded on day 0 at 2.0E4 cells per well in a Seahorse X96 Cell Culture Microplate V3-PS TC-Treated plate (Agilent) coated with 0.1 mg/mL Poly-D-Lysine (Trevigen) in Dulbecco's Modified Eagle Medium (DMEM) (Gibco) supplemented with penicillin-streptomycin (Gibco) and 10% heat inactivated fetal bovine serum (HI-FBS) (Atlanta Bio) and incubated overnight at 37° C., 5% CO2. On day 1, cells were washed once with 150 μL per well DPBS (Gibco) and treated with 100 μL of:

a. Amino acid free DMEM (US Biologicals) containing a defined custom amino acid concentration based on the mean physiological concentrations in blood based on values published in the Human Metabolome Database (HMDB), with 6 mM glucose, 1 mM sodium pyruvate, 10 mM HEPES (Sigma), and penicillin-streptomycin (Gibco); or b. The same medium described above with LIVRQNAC at 15× or 30×HMDB (1× is L-Leucine: 152.7 μM; L-Isoleucine: 66.4 μM; L-Valine: 234.2 PM; L-Arginine: 108.8 μM; L-Glutamine: 562.1 μM [below plasma level]; N-acetylcysteine: 250 M [not endogenous]).

On day 2, cells were treated with 100 uL of the same media described above supplemented with 0.15 ng/mL lipopolysaccharide (LPS) (Sigma). Control wells were treated with 0.15 ng/mL LPS, or phosphate buffered saline (PBS).

On day 3, the supernatant was collected and immediately frozen in −80° C. freezer. Cells were analyzed for total ATP production rate, glycolytic ATP production rate, and mitochondrial ATP production rate using a commercially available kit (Agilent Seahorse XF Real-Time ATP Rate Assay Kit) according to manufacturer-supplied protocol on a Seahorse XFe instrument. A custom assay medium (amino acid free DMEM/F12 without phenol red or sodium bicarbonate (US Biologicals) containing a defined custom amino acid concentration based on the mean physiological concentrations in blood based on values published in the Human Metabolome Database (HMDB), with 10 mM XF glucose (Agilent), 1 mM XF pyruvate (Agilent), and 5 mM HEPES (Sigma) was used. Buffer factor for the custom assay medium was determined according to manufacturer-supplied protocol. Following the assay, cells were washed twice with PBS and fixed with 400 paraformaldehyde. Data was normalized to the specific per well cell density determined by nuclei counts stained with using Hoechst 3342 (Life Technologies). Results are shown in Tables 42-44, below.

TABLE 42

Total ATP Production Rate Results

Total ATP Measurements

| Amino Acid Supplement | Conc. (X) | Mean Rate (pmol/min) | Std. Deviation | Number of values | P-Value | Significance |
|---|---|---|---|---|---|---|
| LIVRQNAC | 30 | 65.31 | 19.59 | 5 | 0.5528 | ns |
| LIVRQNAC | 15 | 74.32 | 21.47 | 5 | 0.7562 | ns |
| LPS, No AA Supplement | n/a | 71.08 | 7.03 | 5 | n/a | n/a |

TABLE 43

Glycolytic ATP Measurements

Glycolytic ATP Measurements

| Amino Acid Supplement | Conc. (X) | Mean Rate (pmol/min) | Std. Deviation | Number of values | P-Value | Significance |
|---|---|---|---|---|---|---|
| LIVRQNAC | 30 | 0.63 | 3.06 | 5 | <0.0001 | **** |
| LIVRQNAC | 15 | 5.95 | 3.12 | 5 | 0.0004 | *** |
| LPS, No AA Supplement | n/a | 16.80 | 2.75 | 5 | n/a | n/a |

TABLE 44

Mitochondrial ATP Measurements

Mitochondrial ATP Measurements

| Amino Acid Supplement | Conc. (X) | Mean Rate (pmol/min) | Std. Deviation | Number of values | P-Value | Significance |
|---|---|---|---|---|---|---|
| LIVRQNAC | 30 | 64.68 | 18.36 | 5 | 0.1456 | ns |
| LIVRQNAC | 15 | 68.38 | 18.80 | 5 | 0.2590 | ns |

TABLE 44-continued

Mitochondrial ATP Measurements

Mitochondrial ATP Measurements

| Amino Acid Supplement | Conc. (X) | Mean Rate (pmol/min) | Std. Deviation | Number of values | P-Value | Significance |
|---|---|---|---|---|---|---|
| LPS, No AA Supplement | n/a | 54.28 | 5.38 | 5 | n/a | n/a |

Tables 42-44 show the normalized ATP production rates with and without treatment with 30× and 15×LIVRQNAC in picomole per minute. As shown in Table 42, LIVRQNAC at 30× and 15× did not significantly affect total ATP production rate. However, the glycolytic ATP production rate (Table 43) was significantly decreased with LIVRQNAC treatment at both tested concentrations. The mitochondrial ATP production rate (Table 44) was increased, however did not reach statistical significance. P-value was calculated by t-test.

Example 7: Treatment of Immobilization in Subjects with an Amino Acid Composition not Only Reduces Loss of Muscle Mass and Function, but Reduces Fat Infiltration The study described herein features the administration of a composition including amino acids to healthy subjects undergoing unilateral knee immobilization. The goal of this study was to determine the impact of an amino acid composition on muscle atrophy after 7 days of single leg immobilization and 14 days of recovery post-immobilization. The composition included about 1 g of L-leucine, about 0.5 g of L-isoleucine, about 0.5 g of L-valine, about 1.5 g of L-arginine (or 1.81 g of L-arginine HCl), about 1.33 g of L-glutamine, about 0.15 g of N-acetylcysteine, about 0.08 g of L-histidine, about 0.35 g of L-lysine, about 0.08 g of L-phenylalanine, and about 0.17 g of L-threonine per stick packet for administration in four stick packs three times per day (e.g., a total of about 68 or 72 g per day, or about 23 g or 24 g three times per day). The composition also included excipients as shown in Table 45.

TABLE 45

Ingredient contents in each stick pack.

| INGREDIENT | GRADE | FUNCTION | GRAMS | SOURCE; COMMENT |
|---|---|---|---|---|
| Amino Acids | USP | Active Pharmaceutical Ingredient (API) | 6 | Various sources; Non-instantized form (MFG scale) |
| Citric Acid | USP | pH, Flavor | 0.67 | Spectrum Chems; f(volume) ≤ 1.0% w/v |
| Acesulfame K | NF | Sweetness (rapid onset) | 0.05 | Spectrum Chems; Target 1 Sweetener |
| Sucralose | NF | Sweetness (slow onset) | 0.03 | Spectrum Chems; WHO ADI ≤ 15 mg/kg |
| Lecithin (Alecolec Fl 00) | FCC | Wetting Agent | 0.83 | American Lecithin Company |
| Xanthan Gum | FCC | Stabilizer/Thickener | 0.24 | TIC Gums; f(volume) ≤ 0.5% w/v |
| Vanilla Custard (Art) | GRAS | Taste/Aroma | 0.06 | David Michael; Mask sulfur |
| Orange (Natural and WONF) | GRAS | 1° flavor | 0.36 | David Michael; Citrus profile matches low pH |
| Lime (Natural and WONF) | GRAS | 2° flavor | 0.05 | FONA; Single flavor supplier |
| Lemon (Natural and artificial) | GRAS | 2° flavor | 0.05 | FONA; Single flavor supplier |
| Taste Modifier | GRAS | Bitterness masking | 0.12 | FONA; Useful at low volume |

TABLE 45-continued

Ingredient contents in each stick pack.

| INGREDIENT | GRADE | FUNCTION | GRAMS | SOURCE; COMMENT |
|---|---|---|---|---|
| FD&C Yellow No.6 | USP | Color | 0.009 | Sensient; Match flavor profile |

In the study, subjects received the amino acid composition three times daily for 28 days. Amino acids were provided in powder form to be dissolved in 8 oz. of water. Participants underwent single-leg immobilization for 7 days (days 8-15) during the 28-day study period. An immobilization device was used for 7 days of single-leg immobilization of the dominant knee (based on maximal isometric leg strength) with a knee brace worn in a fixed flexion position at 1400 (e.g., a Breg brace).

Control subjects received placebo three times daily for 28 days. Placebo consisted of an amount of maltodextrin (NF grade) equivalent in caloric content to the amount of amino acids administered, with the same excipients, dissolved in 8 oz. of water.

The primary outcome measure of this study was safety and tolerability. In addition, muscle disuse atrophy, in particular, the impact of the amino acid formulation on muscle atrophy after 7 days of single leg immobilization was studied. The secondary outcome measures included muscle function based on knee strength, muscle cross-section area and volume, muscle fiber quality, and lean muscle mass. The percentage change in lean muscle mass in the subjects was determined using dual-energy x-ray absorptiometry (DEXA). The percentage change in maximum torque as measured using a BioDex machine (measured in Newton-meters) and percentage change in the time to maximum torque (measured in seconds) were also assessed. Muscle biopsies were performed to determine muscle fiber cross-sectional area (CSA). Muscle size was assessed via MRI. Muscle health was assessed by electrical impedance myography (EIM) measurements. Assessments were performed at baseline (day 1), pre-immobilization (day 8), post-immobilization (day 15), and recovery (day 28).

More specifically, MRIs were performed at Days 1, 8, 15, and 28. Axial (transverse) images were obtained from both thighs from the distal end of the femur to the greater trochanter using GE high fidelity 3T magnet. A fast-recovery, fast spin echo pulse sequence was used, along with IDEAL (iterative decomposition of water and fat with echo asymmetry and least-squares estimation) post-processing to obtain water-only, fat-only, in-phase and out-of-phase images of the thighs. The following parameters were used: TR=2000 msec, TE=30 msec, refocusing flip angle=111 degrees, echo train length=6, ASSET (parallel imaging factor)=2, field of view=42×21 cm, acquisition matrix=512× 256, 3-mm slice thickness, 0-mm slice gap. A total of approximately 160 slices were acquired, but varied depending on length of the thigh. The acquisition was done in two sections, a lower stage, and an upper stage. Total scan time for both stages was approximately 11 minutes. The scans were uploaded onto Analyze Pro software. The 50% region between the greater trochanter of the hip and lateral epicondyle of the knee were used for analysis. The segmentation features of the software were used to differentiate between the bone, fat, right muscle, right quadriceps, left muscle and left quadriceps. Then every third slice in the 50% region was manually traced for the quadriceps muscles of both legs. The highest number from these measurements was taken as the peak quadriceps cross-sectional area. The software was then able to take every third slice that was manually measured and extrapolate that data for every slice in the 50% region to get an estimate of quadriceps volume. CSA was expressed in $mm^2$ and muscle volume in $mm^3$. Protocol adapted from Reeder et al., 2005.

To obtain independent verification of the imaging data, DIXON sequences of the upper and lower thighs were securely transferred to the Image Analysis Group (IAG, London, UK) for whole muscle volume analysis and an additional analysis to measure intramuscular fat fraction. Given the water and fat images it is possible to generate a Fat Fraction (FF) image as:

$$FF=F/(W+F), \text{ where } F=\text{fat, and } W=\text{water.}$$

IAG calculated these images and added them to the individual DICOM studies. As the base images can give spurious regions of high fat fraction due to noise, a thresholding filter was used to reduce these small peripheral artefacts and minimize noise in regions where both the fat and water signals are small. Segmentations were carried out on the upper thigh FF images. The segmentation was from the middle of the thigh towards the pelvis for 20 slices. The segmentation was carried out manually from each sequence. Once segmented, the slice ROIs were grouped to form a volume ROI and the statistics automatically calculated.

Key criteria for selecting subjects included the following: 1) generally healthy, non-smoking; 2) willing and able to provide informed consent; 3) men age 20-45 years; and 4) BMI between 25 and 35 $kg/m^2$. Exclusion Criteria included the following: 1) smokers; 2) subject has any concurrent medical, orthopedic, or psychiatric condition that, in the opinion of the investigator, would compromise his/her ability to comply with the study requirements; 3) history of cancer within the last 5 years, except basal cell carcinoma, non-squamous skin carcinoma, prostate cancer, or carcinoma in situ with no significant progression over the past 2 years; 4) significant orthopedic, cardiovascular, pulmonary, renal, liver, infectious disease, immune disorder (requiring ongoing medical care), or metabolic/endocrine disorder (e.g., diabetes, high cholesterol, elevated fasting blood sugar) or other disease that would preclude oral protein supplement ingestion and/or assessment of safety and study objectives; 5) any cachexia-related condition (e.g., relating to cancer, tuberculosis, or human immunodeficiency virus infection and acquired immune deficiency syndrome) or any genetic muscle diseases or disorders; 6) current illnesses that could interfere with the study (e.g. prolonged severe diarrhea, regurgitation, or difficulty swallowing); 7) subject participated in a study of an investigational product less than 60 days or 5 half-lives of the investigational product, whichever is longer, before enrollment in this study; 8) hypersensitivity to any of the components of the test product; 9) excessive alcohol consumption (>21 units/week); 10) known sensitivity or allergy to amino acids or any ingredient in the test formulations; 11) prior gastrointestinal bypass surgery (e.g., lapband surgery), irritable bowel disease, or irritable bowel syndrome; 12) history of bleeding diathesis, platelet or coagulation disorders, or antiplatelet/anticoagulation therapy (up to 81 mg of baby aspirin per day taken as a prophylactic is permitted); 13) personal or family history of clotting disorder or deep vein thrombosis; 14) concomitant use of corticosteroids, testosterone replacement therapy (ingestion, injection, or transdermal), any anabolic steroid, creatine, whey protein supplements, casein, or branched-chain amino acids (BCAAs) within 45 days prior to screening; 15) contraindications to an MRI scan (e.g. subjects with non-removable ferromagnetic implants, pacemakers, aneurysm clips or other foreign bodies, or subjects with claustrophobic symptoms that would contraindicate an MRI scan); 16) hemoglobin less than 11.5 mg/dl at screening; or 17) platelets less than 150,000/µL (150×109/L) at screening.

The findings from this study suggest that the decline in lean leg mass as a result of unilateral limb immobilization (i.e. disuse atrophy), including reduction in fat infiltration into the muscle, was attenuated in those that received the LIVRQNacHKFT amino acid combination, as compared to those that received placebo. These results in subjects undergoing a unilateral limb immobilization suggest that the amino acid combination attenuated this decline in lean mass of the immobilized leg, while preserving muscle strength. The immobilized leg in the placebo administered groups did not recover their lean mass to the post-immobilized or the pre-immobilized state during the two week recovery period. By contrast, administration of the amino acid combination maintained and/or improved the lean leg mass within this two week recovery period to that of the post and pre-immobilization. The decline in muscle strength seen after a week of unilateral limb immobilization in the placebo group was also attenuated by the amino acid combination. The non-immobilized leg in either the Placebo or the LIVRQNacHKFT amino acid administered group did not appear to lose their lean leg mass nor their muscle strength to the same extent as the corresponding immobilized leg during the knee brace period, as expected of an appropriate control.

CSA of specific fibers within the vastus lateralis was preserved during immobilization with LIVRQNacHKFT vs. Pbo administration. One week of immobilization led to a 2.2% (±4.0) decrease in fiber CSA. Consistent with the existing literature, in the Pbo group, muscle disuse tended to result in a preferential loss of Type II vs. Type I fibers (4.5±4.8% loss for Type II vs. no change for Type I). By contrast, LIVRQNacHKFT administration preserved the cross-sectional area of both fiber types during immobilization. Quantification of CSA, with the following changes observed between LIVRQNacHKFT and Pbo: increase of 4.1-fold for total fibers; 1.7-fold for Type II fibers; 12-fold for Type I fibers (P=0.08). Of note, LIVRQNacHKFT had a particularly pronounced effect on the slow twitch type I fibers, in not only preserving them, but tended to induce their growth (13.3±7.4% increase in Type I fiber CSA from Day 8 to Day 15).

The observation of LIVRQNacHKFT's effect on the oxidative, slow twitch Type I fibers could suggest an impact on insulin sensitization, and the latter has been closely associated with muscle fat infiltration (Albu et al. 2005). Consistent with this effect on Type I muscle fibers, LIVRQNacHKFT administration significantly attenuated muscle fat infiltration during limb immobilization. Representative images depicting fat fraction (FF) changes show that in a subject administered Pbo, the non-immobilized leg had no change in FF, while the immobilized leg had increased FF and decreased muscle mass between Day 8 and 15. By contrast, in a subject administered LIVRQNacHKFT, the immobilized leg had lower fat fraction, and a higher muscle content following immobilization, illustrating LIVRQNacHKFT anti-atrophic effects. These FF changes were quantified across all subjects. Percent change in quadriceps muscle fat fraction on Day 15 vs. Day 8 was +12.8±6.1% in Pbo vs. −0.41±3.07% in LIVRQNacHKFT (P=0.018) in the immobilized leg. As expected, the non-immobilized leg had significantly less to no muscle fat infiltration: 1.76±2.6% (Pbo) vs. −2.05±2.4% (LIVRQNacHKFT), with no statistical difference between the groups (P=0.479).

Consistent with the literature (Tarulli et al. 2009), we observed decreases in phase, maximum reactance, and reactance slope (these parameters are considered to be reflective of muscle health, Rutkove 2009) during limb immobilization (i.e. from Day 8 to 15) in the Pbo group.

By contrast, LIVRQNacHKFT administration resulted in the attenuation, if not a numerical increase in these parameters during immobilization (with relative differences versus Pbo ranging from 115% to 155%). During the recovery phase, these parameters returned to pre-immobilization levels in both groups (Day 28 vs. Day 8), but these parameters tended to be higher in the LIVRQNacHKFT group compared to Pbo, with relative differences of 56%, 60%, and 70% for phase, max reactance, and reactance slope, respectively.

Example 8: Evaluation of LIVRQNac in Subjects With PASC

Objectives:
The primary objective is, in subjects with fatigue-predominant post acute sequalae of SARS-CoV2 infection (PASC):
  To assess the safety and tolerability of LIVRQNac vs placebo.
The key secondary objectives are:
  To assess the potential impact of LIVRQNac on muscle mitochondrial function compared to placebo
  To assess the impact of LIVRQNac on functional status compared to placebo.
The exploratory objectives are:
  To obtain additional insights into the mechanism of action of LIVRQNac
  To assess changes in health-related quality of life (HR-QoL) and fatigue as measured by CFQ-11 following treatment with LIVRQNac compared with placebo
  To determine baseline amino acid profile in subjects with PASC.

Study Endpoints:
Efficacy Endpoints
  The primary (key secondary) efficacy endpoints are:
  The proportion of subjects with improvement from baseline in PCr recovery following moderate exercise based on $^{31}$P-MRS
  The difference in rate of PCr recovery between drug and placebo
  The proportion of subjects with a decrease from baseline in serum lactate level after a 6 minute walk
  The proportion of subjects with an improvement in fatigue by CFQ-11 (items 1-7, 8-11, and 1-11 by both Likert and Bimodal Scoring) before and after 6 minute walk
  The difference in change in fatigue from baseline between LIVRQNac and placebo groups
  The proportion of subjects with serum lactate level ≤3 after 6 minute walk The change in serum lactate level after 6 minute walk Increase from baseline in distance traveled during 6 minute walk The exploratory efficacy endpoints are:

Change in circulating mitochondrial peptides (e.g., Mots-C), metabolomics, mitochondrial energetics in PBMCs (via Seahorse XF analysis), muscle injury biomarkers (e.g. troponins, creatine kinase, FGF-21, etc.) and predictors of response; and Pre-dose and post-dose plasma concentrations of amino acids Safety and Tolerability Endpoints The safety and tolerability of LIVRQNac will be assessed throughout the study. The safety and tolerability endpoints are:

Adverse events (AEs) and serious AEs;

Physical examination findings, including vital signs and body weight;

Clinical laboratory assessments (chemistry, hematology, coagulation, and urinalysis).

Study Design:

This is a single-center, randomized, double-blind, placebo-controlled, Phase 2a clinical study in subjects with fatigue-predominant PASC.

Subjects participate for up to 9 weeks. The study comprises a Screening Period of up to 8 weeks, a Treatment Period of 4 weeks, and a Follow-Up Period of 1 week.

Upon successful screening, including fatigue-predominant PASC at least 3 months after diagnosis of COVID-19 infection and a baseline abnormality suggestive of mitochondrial dysfunction on $^{31}$P-MRS and evidence of significant fatigue on a validated patient reported outcome (PRO) measure. Subjects are then randomized to 1 of the 2 daily oral treatment arms at an allocation ratio of 1:1:

33.9 g BID LIVRQNac (e.g., a composition comprising 33.9 g of the amino acids); or Placebo BID.

The first dose of study drug (LIVRQNac or placebo) is self-administered on Day 1 of the study after all Day 1 procedures have been completed. Subjects receive the randomized study drug BID for 4 weeks.

As this is a PoC study, the primary endpoint is safety, and the key efficacy endpoints include changes in PCr recovery time after moderate exercise by $^{31}$P-MRS and muscle metabolism, which is assessed by $^{31}$P-MRS at Week 4 (End of Treatment [EOT]), as well as additional endpoints including improvement in fatigue score by CFQ-11 before and after 6 minute walk, increase in distance walked during 6-minute walk, improvement in functional status by CFQ-11, and reduction in serum lactate after 6 minute walk. Additionally, a number of laboratory tests are assessed for potential improvements in mitochondrial function including, but not limited to, improvement in serum lactic acid post exercise.

Details of randomization will be provided in the Randomization Plan and Interactive Response Technology (IRT) system. Following the fasted blood draw, subjects are administered LIVRQNac or placebo BID. At baseline (Visit 2), 2 weeks (V3) and 4 weeks (V4), blood samples are collected, and $^{31}$P-MRS and 6-minute walk are repeated after 4 weeks (V4).

Subjects are adults under age 65 that have been diagnosed with COVID-19 infection (by RT-PCR) at least 3 months prior to screening, and are diagnosed with fatigue-predominant PASC±"brain fog" and have some evidence of reduced mitochondrial oxidative phosphorylation confirmed by PCr recovery constant of >40-50 seconds as assessed by P-MRS. This does not apply to the healthy control group.

LIVRQNac Dose, and Mode of Administration:

LIVRQNac active pharmaceutical ingredients and excipients are compounded to produce a uniform dry powder blend for suspension and is provided as a unit dose sachet containing 11.3 g AAs.

Subjects randomized to the active arm receive LIVRQNac as detailed below:

33.9 g LIVRQNac (e.g., according to Table 55 of Example 12): Subjects receive 3 sachets of LIVRQNac per dose, BID.

The sachets (LIVRQNac or placebo) are constituted in ~6 fluid oz (~180 mL) of potable water to form a uniformly dispersed suspension and self-administered orally as an orange-flavored drink, taken BID with or without food. Administration around mealtimes is recommended to promote compliance with the BID regimen and should occur at least 4 hours apart. The full dose needs to be taken within 30 minutes from constitution of the study drug.

Placebo, Dose, and Mode of Administration:

The placebo, which is used as a control, is formulated as a dry powder that has excipient and calorie content similar to LIVRQNac. The placebo closely matches the aroma, appearance, color, and taste profile of LIVRQNac. The total number of sachets, packaging, constitution, and administration of placebo mirrors LIVRQNac to maintain double blinding during the study.

Subjects randomized to the placebo arm receive 3 sachets of placebo per dose, BID.

The sachets (placebo) are constituted in ~6 fluid oz (~180 mL) of potable water to form a uniformly dispersed suspension and self-administered BID as an orange-flavored drink, taken BID with or without food. Administration around mealtimes is recommended to promote compliance with the BID regimen and should occur at least 4 hours apart. The full dose needs to be taken within 30 minutes from constitution of the study drug.

Duration of Study Drug Exposure:

Each subject (except for the healthy control group) receives the study drug (LIVRQNac and/or placebo) BID for up to 4 weeks.

Results:

In some embodiments, one or more of: reduction of elevated serum lactate from baseline (e.g. after 6 minute walk), improvement of fatigue PRO score or functional status (e.g. by CFQ-11) after 6 minute walk, increase in distance walked in 6 minute walk, improvement in phosphocreatine (PCr) recovery time constant following exercise, and/or improvement in oxidative ATP synthesis by LIVRQNac (compared to placebo) will indicate that LIVRQNac treats PASC in human subjects and/or improves quality of life in subjects having PASC, and reflect improvements in muscle 'mitochondrial capacity' or mitochondrial and/or muscle structure and function as a result of LIVRQNac administration.

Example 9: Evaluation of LIVRQNac in Subjects With PASC

Study Objectives

Primary Objective

The primary objective is to:

Assess the impact of LIVRQNac on muscle function (metabolism) following exercise Secondary Objective The secondary objectives are to:

Assess the relationship between LIVRQNac and functional status

Assess the safety and tolerability of LIVRQNac

Exploratory Objectives

The exploratory objectives are to:

Obtain additional insights into the mechanism of action of LIVRQNac

Obtain baseline AA profile in subjects with PASC

Study Endpoints

Efficacy Endpoints

Primary Efficacy Endpoint

The primary efficacy endpoint is:

The mean change from baseline at Week 4 in the phosphocreatine (PCr) recovery rate following moderate exercise, as assessed by $^{31}$P-magnetic resonance spectroscopy (MRS)

Secondary Efficacy Endpoints

The secondary efficacy endpoints are:

Absolute and relative change from baseline in PCr recovery rate as assessed by phosphorus magnetic resonance spectroscopy ($^{31}$P-MRS) at Week 4

The proportion of subjects with improvement in PCr recovery rate at Week 4

Absolute and relative change from baseline in serum lactate level after a 6 MWT at Week 4

The proportion of subjects with serum lactate level ≤3 mmol/L after a 6 MWT at Week 4

The proportion of subjects with a decrease in venous serum lactate level from baseline after a 6 MWT at Week 4

Change from baseline in distance traveled during a 6 MWT at Week 4

Change from baseline in subjects' fatigue score as assessed by Chalder Fatigue Questionnaire (CFQ)-11 (by Bimodal Scoring) before and after a 6 MWT at Week 4 and at Day 14 (without 6 MWT)

The proportion of subjects with an improvement in fatigue score as assessed by CFQ-11 before and after a 6 MWT at Week 4

Exploratory Efficacy Endpoints

The exploratory efficacy endpoints are:

Change from baseline in circulating mitochondrial peptides (e.g., Mots-C), metabolomics, proteomics; plasma biomarkers of inflammation, adhesion markers, muscle injury (e.g., troponins, creatine kinase, fibroblast growth factor-21) biomarkers, and mitochondrial function/metabolism (~1.5 mL total); nitric oxide biology; immune profiling, and metabolism/phenotypic extracellular acidification rate and oxygen consumption rate at Week 4

The mean change from baseline in energetically active metabolites measured using proton magnetic resonance spectroscopy ($^{1}$H-MRS; i.e., creatine, intramyocellular lipids, acetyl-carnitine, and carnosine) at Week 4

Change from baseline in predose plasma concentrations of amino acids at Week 4

The mean change from baseline in minimal intramuscular pH after exercise, initial PCr recovery rate, adenosine diphosphate (ADP) concentration at the end of exercise, maximal mitochondrial capacity, and other parameters measured using dynamic $^{31}$P-MRS at Week 4

Change from baseline in markers of mitochondrial function at 4 weeks such as growth and differentiation factor-15 (GDF-15), neurofilament light chain (NF-L). alpha lipoic acid (ALA), lipid peroxide (PerOx), total plasma antioxidant capacity (TAC), serum cytochrome c, danger-associated molecular patterns (DAMPs), i.e., self molecules present in inappropriate compartments due to cell destruction such as mtDNA, N-formyl peptides (FPs), novel cell free circulating-mtDNA (ccf-mtDNA).

Safety and Tolerability Endpoints

The safety and tolerability endpoints are:

AEs and serious adverse events (SAEs)

Physical examination findings, including vital signs (sitting systolic and diastolic blood pressure, heart rate, respiratory rate, body temperature, resting 02 saturation) and body weight Change in clinical laboratory assessments, including chemistry, hematology, and urinalysis Study Design Overall Study Design This is a single-center, randomized, double-blind, placebo-controlled, pilot clinical study in the United Kingdom (FIG. 1). The study will evaluate the efficacy and safety of LIVRQNac in subjects with fatigue-predominant PASC (>12 weeks after initial infection).

The total study duration for each subject will be approximately 9 weeks. This study will comprise a Screening Period of up to 4 weeks, a Treatment Period of up to 4 weeks, and a Follow-up Period of 1 week.

After obtaining informed consent, subjects will be screened, and approximately 40 eligible subjects (approximately 20 subjects per arm) will be randomized in a 1:1 ratio to receive BID oral administration of 33.9 g LIVRQNac or a placebo. Doses will be self-administered on Days 1 to 28, inclusive. Subjects will have clinic visits on Day 1 and Day 28, as well as telephone visits on Day 14 and 1 week after completion of study product administration. Doses may be self-administered at the clinic visit on Day 1 and Day 28 or End of Treatment (EOT)/Early Termination (ET).

The primary efficacy endpoint is the mean change from baseline at Week 4 in the PCr recovery rate following moderate exercise, as assessed by $^{31}$P-MRS, which will be evaluated at Screening and EOT/ET (Visit 4). Additional endpoints for assessment of muscle function, safety, tolerability, and exploratory efficacy endpoints will be assessed during the study.

Details of randomization will be provided in the Randomization Plan and Interactive Response Technology (IRT) system.

BID=twice daily; D=Day; MRS=magnetic resonance spectroscopy; PRO=patient-reported outcomes.

Scientific Rationale for Study Design

This pilot study is designed to assess LIVRQNac dosed for up to 4 weeks in subjects with PASC. The primary objective is to assess the impact LIVRQNac on muscle function (metabolism) following exercise. Key secondary objectives include assessment of the relationship between LIVRQNac and functional status and assessment of the safety and tolerability of LIVRQNac in subjects with PASC.

This study is designed to characterize to what degree the administration of LIVRQNac for up to 4 weeks in subjects with PASC will have an impact on muscle bioenergetics and consequently muscle function. $^{31}$P-MRS, 6 MWT, and CFQ-11 are utilized as appropriate scales for the assessment of the study endpoints. Accordingly, the mean change from baseline at Week 4 in PCr recovery rate following moderate exercise, as assessed by $^{31}$P-MRS, was chosen as the primary endpoint for the study. With relatively rapid time resolution (<8 seconds) and certain assumptions, a range of bioenergetic indexes will be determined from the metabolic changes. In particular, a functional estimate of mitochondrial oxidative capacity can be calculated from the kinetics of PCr recovery.

Additional biomarkers will be evaluated as exploratory endpoints to provide additional information about the full mechanism of action of LIVRQNac and to assist in the design of the future development program.

A sample size of approximately 40 subjects (20 subjects per arm) will be enrolled in the study. In order to detect a meaningful treatment difference of 10 second improvement, approximately 32 subjects will provide 80% power at a 2-sided, 5% significance level, in addition to approximately 20% dropout rate.

This sample size will also allow for a general assessment of safety and tolerability of LIVRQNac in this population.

Study Duration

Subjects will participate for up to 9 weeks. The study will comprise a Screening Period of up to 4 weeks, a Treatment Period of 4 weeks, and a Follow-up Period of 1 week.

Example 10—the Effect of LIVRONac on Substrate Oxidation and ATP Production Studied in the Seahorse Assay in Primary Human Hepatocytes Objectives:
  Investigate dose-dependent effects of LIVRQNac on ATP production rates in the presence of a lipotoxic insult (0.25 mM saturated free fatty acids (2:1 oleate:palmitate) plus 1 ng/mL tumor necrosis factor alpha)
  Investigate dose-dependent effects of LIVRQNac on substrate preference (glucose, glutamine, and long chain fatty acid) in the presence of a lipotoxic insult
Test Systems: Primary human hepatocytes (PHHs)
Test Article: LIVRQNac (e.g., according to Table 55 of Example 12)
Methods: A substrate oxidation mitochondrial stress test was performed (using substrate inhibitors etomoxir, BPTES or UK5099). The effect of up to 3 concentrations of LIVRQNac (5×, 15×, and 30×) plus cotreatment with a lipotoxic insult on oxygen consumption rate, extracellular acidification rate, and ATP production rate were assessed. The following experiments were conducted using PHH Donors HC10-3 and/or Donor HUM4218:
  Substrate oxidation stress test: vehicle plus lipotoxic insult.
  Substrate oxidation stress test: lipotoxic insult with 3 concentrations of LIVRQNac.
  Substrate oxidation stress test: addition of 3 metabolic pathway-specific inhibitors (etomoxir, UK5099, or BPTES) of long-chain fatty acids, glucose/pyruvate, and glutamine pathways, respectively, to measure the acute response for each pathway; 24 hours of cotreatment using lipotoxic insult with 3 concentrations of LIVRQNac.
Results:
  Basal respiration was increased with LIVRQNac treatment. All substrates tested (e.g., glucose, glutamine, and fatty acids) were utilized and contributed to this increase; however, the utilization proportions were not affected.
  There was a dose-dependent increase in mitochondrial-derived ATP and a reduction in glycolysis-generated ATPs.
Conclusion:
  A modulation of ATP production pathways and an increase in basal respiration were seen with LIVRQNac treatment. Acute COVID 19 literature suggests that energetic dysregulation and impact on mitochondrial metabolism can possibly persist beyond the acute phase. Thus, the results of studies shown here may support the bioenergetic benefit of LIVRQNac composition.

Introduction

According to the Centers for Disease Control and Prevention (CDC), some patients hospitalized for COVID-19 have had increased levels of liver enzymes such as alanine aminotransferase (ALT) and aspartate aminotransferase (AST), which point to abnormal liver function (CDC, What to know about liver disease and COVID-19, 2021; Marjot et al, *Nat. Rev. Gastroenterology & Hepatology* 18:348-364, 2021). Among other biochemical alterations are dysregulated fatty acid oxidation (FAO) and oxidative phosphorylation (Nie et al, *Cell* 184(3):775-791, 2021).

LIVRQNac is a composition of 5 specific AAs and an AA derivative (leucine [Leu], isoleucine [Ile], valine [Val], arginine [Arg], glutamine [Gln], and N-acetylcysteine [Nac]).

This study was conducted in a primary human hepatocyte (PHH) lipotoxicity model using a lipotoxic insult (0.25 mM saturated free fatty acids [2:1 oleate:palmitate] plus 1 ng/mL tumor necrosis factor alpha [TNF-α]) and LIVRQNac treatment. The results presented in the current study report using the PHH model suggest LIVRQNac has the potential to increase ATP production from oxidative phosphorylation while down-regulating glycolysis. Acute COVID-19 literature suggests energetic dysregulation and an impact on mitochondrial metabolism (Junfang et al, *Biosci. Rep.* 41(3), 2021; Sullivan et al, *Cell Rep.* 36(7):109527, 2021), which could possibly persist beyond the acute COVID phase. Thus, studies shown here may support the bioenergetic benefit of LIVRQNac composition.

Objectives

The objectives of this study were as follows:
1. Investigate dose-dependent effects of LIVRQNac on ATP production rates in the presence of a lipotoxic insult
2. Investigate dose-dependent effects of LIVRQNac on substrate preference (glucose, glutamine, and long-chain fatty acid) in the presence of a lipotoxic insult Test Systems PHHs from 2 healthy human donors were used in these studies (HC10-3, Xenotech, LLC; HUM4218, Lonza). PHHs were screened and tested to select donors that met the following quality control criteria: 1) post-thaw viability greater than 80%, 2) polarized morphology, and 3) stable albumin secretion rate for 8 to 10 days.

Test Article
  Test article: LIVRQNac
  Composition: Leu, Ile, Val, Arg (HCl), Gln, and Nac.
Control Article
  Control article: vehicle, phosphate buffered saline (PBS)
Lipotoxic Insult
  Lipotoxic insult: (0.25 mM saturated FFA [2:1 oleate:palmitate] plus 1 ng/mL TNF-α)
Inhibitors
  Etomoxir; FAO pathway inhibitor
  BPTES: bis-2-(5-phenylacetamido-1,3,4-thiadiazol-2-yl) ethyl sulfide; glutamine pathway inhibitor
  UK5099: acyano-(1-phenylindol-3-yl)-acrylate; glucose pathway inhibitor
Test Article Preparation
  For these studies, LIVRQNac was added at specified fold concentrations above plasma (5×, 15×, and 30×; 1× is L-Leucine: 152.7 µM; L-Isoleucine: 66.4 µM; L-Valine: 234.2 PM; L-Arginine: 108.8 µM; L-Glutamine: 46.8 µM [below plasma level]; N-acetylcysteine: 250 µM [not endogenous]), where 1× concentration matches the mean physiological level of AAs found in human plasma (values published in the HMDB [Wishart et al, *Nucleic Acids Research*, 35(Database Issue): D521-526, 2007]).

Increasing the fold concentrations of AAs in these studies was used to model relevant AA exposures while maintaining overall cell health.

Seahorse Methods
Collagen Coating 96-well Seahorse Assay plates were coated with collagen by first diluting collagen 1 stock (Corning) with 0.02 N acetic acid (cell culture grade water [Sigma], glacial acetic acid [Fisher]). A volume of 20 µL of the diluted collagen 1 was added to each well of the plate and incubated for 1 hour at room temperature. The remaining solution was aspirated, and wells were washed twice with phosphate-buffered saline (PBS; Gibco). Coated plates were stored at 4° C. until use.

PHH Culture and Treatment

PHHs from 2 healthy human donors were used in these studies. PHHs were screened and tested to select donors that met the following quality control criteria: 1) post-thaw viability greater than 80%, 2) polarized morphology, and 3) stable albumin secretion rate for 8 to 10 days, as described above.

Qualified PHHs were thawed and plated in PHH plating media (William's E medium [WEM, Gibco] supplemented with 10% heat-inactivated fetal bovine serum [FBS, Atlanta Bio], 2 mM glutamax [Gibco], and 0.2% primocin [InVivoGen]) on Day 1, at a density of 25,000 cells/well in 96-well Seahorse Assay plates (Agilent) coated with collagen as detailed above. Throughout the studies, cells were incubated at 37° C. with 5% $CO_2$. Following plating, PHHs were allowed to attach for 6 hours prior to washing them twice and incubating overnight in PHH plating media.

On Day 2, PHHs were washed twice and incubated for 24 hours in complete hepatocyte-defined medium supplemented with epidermal growth factor (EGF), (Corning), 2 mM glutamax (Gibco), and 1× penicillin/streptomycin (Gibco).

On Day 3, cells were washed twice with DPBS 1× (Gibco) then switched to an AA-free WEM (US Biologicals) containing defined custom AA concentrations that matched those found in healthy human plasma (values published in the HMDB [Wishart et al, 2007, supra], WEM 1×HMDB), and a lipotoxic insult was added as appropriate. This custom media was supplemented as needed with either PBS (vehicle) or the constituent AAs of LIVRQNac added at specified fold concentrations above plasma level (up to 30×; Nac is not endogenous in plasma and was proportionally scaled between 1.25 to 7.5 mM). Increasing the fold concentration of AAs in these studies was used to model relevant AA exposures while maintaining overall cell health. After 24 hours of treatment, the Seahorse Assay was performed as described below. After the assay, cells were fixed and stained as described below.

PHH media baseline AA concentrations (1×) match mean physiological levels found in human plasma (values published in the Human Metabolome Database; [Wishart et al 2007]). LIVRQNac constituents were added at specified fold concentrations above plasma level (up to 30×; Nac is not endogenous in plasma and was proportionally scaled between 1.25 to 7.5 mM; glutamine was added at 0.234, 0.702, and 1.404 mM).

Seahorse Assay—Substrate Oxidation Mitochondrial Stress Test

Substrate Oxidation Mitochondrial Stress Test was performed following manufacturer protocols. One day prior to the assay being performed, the assay cartridge was rehydrated in sterile water (Sigma) at 37° C. On the day of the assay, the cartridge was transferred to XF calibrant (Agilent) for 1 hour. Seahorse XF Dulbecco's modified eagle medium media (DMEM, Agilent) was prepared to manufacturer specifications with 10 mM Seahorse XF glucose (Agilent), 1 mM Seahorse XF pyruvate (Agilent), and 2 mM Seahorse XF L-glutamine (Agilent). 1 hour prior to assay, cells were switched from the treatment media to prepared Seahorse XF media and incubated at 37° C./5% $CO_2$. The 4-Port Cartridge was prepared with appropriate substrate inhibitor for each well as described in manufacturer protocol:

Port A—40 µM etomoxir/3 µM BPTES/4 µM UK5099
Port B—1.5 µM oligomycin;
Port C—0.75 µM carbonyl cyanide-p-trifluoromethoxy phenylhydrazone (FCCP)
Port D—1 µM rotenone+antimycin A).

The assay was run using Agilent Seahorse 96-XF machine (Agilent) and Wave software (Agilent). After the assay was complete, cells were fixed and stained for nuclei as described below.

Fixation and Nuclei Staining

Prior to staining, PHHs were washed with 1×PBS (Gibco) and fixed with 4% paraformaldehyde (PFA, Invitrogen). All cells were labeled with Hoechst 33342 (Invitrogen) at 4 µg/mL for nuclei stain and cells were imaged using ImageXpress micro confocal high-content imager (Molecular Devices). Nuclei labeled with Hoechst 33342 were detected in the DAPI channel. Image analysis was performed using MetaXpress version 6.2.3.733 software (Molecular Devices). Nuclei were counted for normalization of results only; the data are not presented in this report.

Data Analysis

Results are processed in GraphPad Prism and expressed as mean percent changes±standard error of the mean for each group. Results are considered significant when $p<0.05$.

Results
Substrate Oxidation Mitochondrial Stress Test
Substrate Preference

The purpose of the experiment was to assess substrate preference (glucose, glutamine, or palmitate) in PHHs, and how this preference is affected by addition of lipotoxic insult versus vehicle.

It was found that administration of lipotoxic insult does not considerably affect preference of any substrate.

Figure 2:
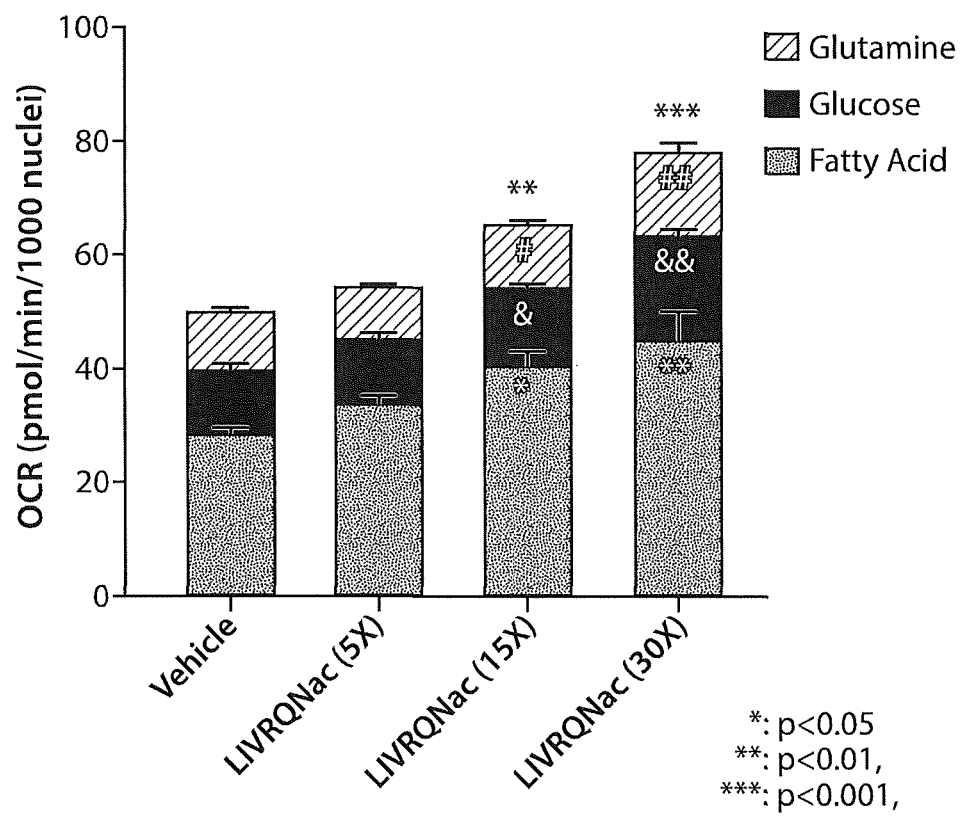
FIG. 2 is a bar graph depicting oxygen consumption rate (OCR) in lipotoxically-insulted PHHs treated with 5×, 15×, and 30×LIVRQNac compared to a control (vehicle). The bar graph shows acute response in primary human hepatocyte (PHH) donors HC10-3 and the effect of inhibitors of glutamine (GLN), glucose (GLC), and fatty acid oxidation (FAO) pathways. The study was performed as described in Example 10.

FIG. 2 and Table 46 demonstrate that while the proportions of utilized substrates remained the same, cotreatment of lipotoxic insult plus different doses of LIVRQNac was found to significantly increase utilization of all 3 substrates when compared to lipotoxic insult plus vehicle:

$p<0.05$ for LIVRQNac 5× and 30×
$p<0.01$ for LIVRQNac 15× compared to lipotoxic insult, FAO pathway
$p<0.01$ and $p<0.001$ for LIVRQNac 15× and 30×, respectively, glucose pathway
$p<0.05$ for LIVRQNac 30×, glutamine pathway), Substrate Preference in Presence of Metabolic Inhibitors The effect of cotreatment of lipotoxic insult with 3 concentrations of LIVRQNac on the oxygen consumption rate (OCR) in 2 PHH donors (HC10-3 and HUM4218) was assessed. The addition of 3 different metabolic pathway-specific inhibitors (etomoxir, UK5099, and BPTES for long-chain fatty acids, glucose/pyruvate, and glutamine pathways, respectively) enabled measurement of the acute response for each pathway. The assay is performed with saturating concentrations of glucose, pyruvate, and glutamine, while endogenous lipid/long-chain fatty acid cellular stores provide the substrate. The LIVRQNac dose-dependent increase in acute response after addition of inhibitors for the FAO, glucose (GLC), and glutamine (GLN) pathways, indicative of substrate preference, in PHHs from Donor HC10-3 are shown in FIG. 2 and Table 46.

LIVRQNac dose-dependently increased demand for all 3 substrates. PHH have the greatest mitochondrial substrate demand for fatty acids; however, the dynamic range of the data was narrower in PHH Donor HUM4218 compared to Donor HC10-3. The GLC OCR was greater in PHH Donor HUM4218 as compared to the results of Donor HC10-3. In both donors, LIVRQNac addition increased basal respiration (FAO), especially as seen in the results for Donor HC10-3 on the left.

This method provides information on the effect of lipotoxic insult plus LIVRQNac treatment on basal respiration, specific metabolic substrate dependence, and the impact of pathway inhibition in PHH.

Basal Respiration

The effect of cotreatment of lipotoxic insult with 3 concentrations of LIVRQNac on the OCR of basal respiration was assessed in 2 donors. The cotreatment of lipotoxic insult with increasing concentrations of LIVRQNac increased the OCR from basal respiration in a dose-dependent manner, consistent with the increasing preference for all 3 metabolic pathways with LIVRQNac treatment.

There was a more significant increase in basal respiration with the PHH from Donor HC10-3:
  $p<0.05$ for LIVRQNac 5× compared to the lipotoxic insult alone
  $p<0.01$ for the LIVRQNac 15×
  $p<0.001$ for the LIVRQNac 30×

Maximal respiration was increased as well, but since the spare respiratory capacity remained unchanged, it is likely that it was driven by the increase in basal respiration.

TABLE 46

Lipotoxic Insult plus LIVRQNac: Acute Response in PHH Donors HC10-3 and the Effect of Inhibitors of GLN, GLC, and FAO Metabolic Pathways

|  |  |  |  |  |  |  | avg | stdev | SEM |
|---|---|---|---|---|---|---|---|---|---|
| Fatty Acid OCR (pmol/min/1000 nuclei) | | | | | | | | | |
| Vehicle | 29.23 | 29.78 | 27.66 | 26.29 | 30.64 | 28.72 | 1.555545 | 0.695661 |
| LIVRQNac (5×) | 37.98 | 31.08 | 32.69 | 28.49 | 37.41 | 33.53 | 3.659689 | 1.636662 |
| LIVRQNac (15×) | 49.87 | 35.79 | 41.11 | 34.75 | 40.76 | 40.456 | 5.356744 | 2.395609 |
| LIVRQNac (30×) | 49.55 | 29.65 | 35.86 | 56.27 | 53.58 | 44.982 | 10.39704 | 4.649698 |
| Glucose OCR (pmol/min/1000 nuclei) | | | | | | | | | |
| Vehicle | 9.6 | 11.48 | 12.17 | 10.26 | 13.36 | 11.374 | 1.339934 | 0.599237 |
| LIVRQNac (5×) | 10.58 | 12.31 | 12.44 | 14.38 | 11.64 | 12.27 | 1.243833 | 0.556259 |
| LIVRQNac (15×) | 14.34 | 13.27 | 14.34 | 14.58 | 15.15 | 14.336 | 0.609675 | 0.272655 |
| LIVRQNac (30×) | 17.73 | 18.13 | 17.65 | 20.98 | 19.31 | 18.76 | 1.258634 | 0.562878 |
| Glutamine OCR (pmol/min/1000 nuclei) | | | | | | | | | |
| Vehicle | 10.37 | 11.25 | 10.94 | 7.48 | 9.75 | 9.958 | 1.340677 | 0.599569 |
| LIVRQNac (5×) | 9.53 | 9.57 | 9.18 | 8.52 | 6.85 | 8.73 | 1.012581 | 0.45284 |
| LIVRQNac (15×) | 10.36 | 9.58 | 10.17 | 9.69 | 12.77 | 10.514 | 1.164725 | 0.520881 |
| LIVRQNac (30×) | 11.56 | 16.89 | 19.22 | 14.8 | 10.66 | 14.626 | 3.205942 | 1.433741 |

(stdev is standard deviation. SEM is standard error of the mean.)

ATP Production Rate Assay

Figure 3:
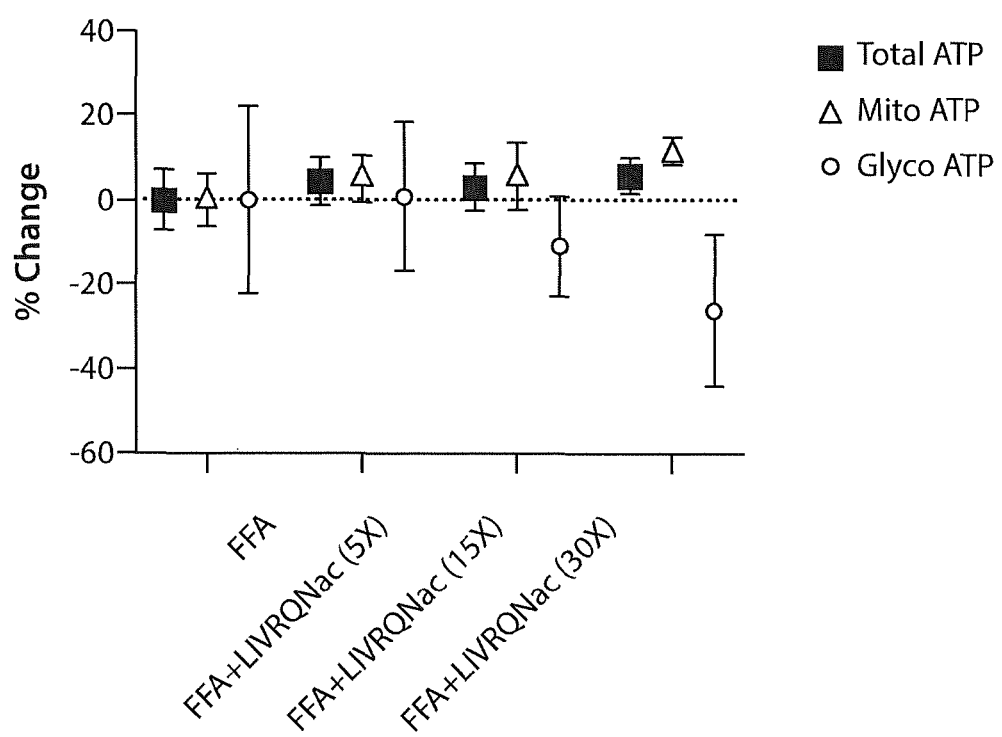
FIG. 3 is a scatterplot depicting ATP production after cotreatment of lipotoxic insult with LIVRQNac in PHH donor HC10-3. The study was performed as described in Example 10.

The effect of cotreatment of PHH cells with lipotoxic insult and LIVRQNac on ATP production, OCR, and extracellular acidification rate (ECAR) was assessed, and the results are shown in FIG. 3 and tables 47 and 48. In PHH from Donor HC10-3, LIVRQNac treatment resulted in a dose-dependent increase in mitochondrial-derived ATP, and there was a dose-dependent reduction in glycolysis-generated ATP. In addition, increased basal respiration and reduced glycolysis were observed phenotypically in this PHH donor. These single-donor PHH data show that LIVRQNac modulates glycolytic versus oxidative ATP production.

TABLE 47

Effect on basal rates of ATP production, percent glycolysis, and percent oxidative phosphorylation of lipotoxic insult and LIVRQNac cotreatment

| | Basal Rates (Average) | | | | | | | | | | | |
|---|---|---|---|---|---|---|---|---|---|---|---|---|
| | glycoATP Production Rate (pmol/min) | | mitoATP Production Rate (pmol/min) | | Total ATP Production Rate (pmol/min) | | XF ATP Rate Index | | % Glycolysis | | % Oxidative Phosphorylation | |
| Groups | Average | StDev | Average | StDev | Average | StDev | Average | StDev | Average | StDev | Average | StDev |
| FFA | 12.3 | 2.7 | 67.7 | 4.3 | 80.0 | 5.8 | 5.8 | 1.7 | 15.3 | 2.9 | 84.7 | 2.9 |
| FFA + LIVRQNac 15× | 11.0 | 1.5 | 71.7 | 5.5 | 82.7 | 4.5 | 6.7 | 1.3 | 13.4 | 2.2 | 86.6 | 2.2 |

TABLE 47-continued

Effect on basal rates of ATP production, percent glycolysis, and percent oxidative phosphorylation of lipotoxic insult and LIVRQNac cotreatment

| | Basal Rates (Average) | | | | | | | | | | | |
|---|---|---|---|---|---|---|---|---|---|---|---|---|
| | glycoATP Production Rate (pmol/min) | | mitoATP Production Rate (pmol/min) | | Total ATP Production Rate (pmol/min) | | XF ATP Rate Index | | % Glycolysis | | % Oxidative Phosphorylation | |
| Groups | Average | StDev | Average | StDev | Average | StDev | Average | StDev | Average | StDev | Average | StDev |
| FFA + LIVRQNac 30× | 9.1 | 2.2 | 75.6 | 2.1 | 84.7 | 3.3 | 8.8 | 2.6 | 10.7 | 2.3 | 89.3 | 2.3 |
| FFA + LIVRQNac 5× | 12.4 | 2.2 | 71.2 | 3.8 | 83.6 | 4.6 | 5.9 | 1.3 | 14.8 | 2.3 | 85.2 | 2.3 |
| Veh | 12.3 | 2.6 | 66.0 | 4.4 | 78.3 | 4.9 | 5.6 | 1.8 | 15.7 | 3.0 | 84.3 | 3.0 |
| Veh + LIVRQNac 15× | 10.8 | 2.8 | 73.9 | 4.9 | 84.7 | 6.2 | 7.4 | 2.5 | 12.6 | 2.8 | 87.4 | 2.8 |
| Veh + LIVRQNac 30× | 6.9 | 1.8 | 76.6 | 3.6 | 83.5 | 4.0 | 11.7 | 2.6 | 8.2 | 2.0 | 91.8 | 2.0 |
| Veh + LIVRQNac 5× | 11.6 | 3.0 | 77.7 | 5.4 | 89.3 | 4.3 | 7.3 | 2.8 | 13.0 | 3.4 | 87.0 | 3.4 |

TABLE 48

Effect of LIVRQNac treatment on percent change in ATP production in lipotoxically-insulted PHH

| | Total ATP | | Mito ATP | | Glyco ATP | |
|---|---|---|---|---|---|---|
| | % change | Std Dev | % change | Std Dev | % change | Std Dev |
| FFA | 0.00 | 7.27 | 0.00 | 6.31 | 0.00 | 22.24 |
| FFA + LIVRQNac (5×) | 4.46 | 5.77 | 5.10 | 5.61 | 0.92 | 17.65 |
| FFA + LIVRQNac (15×) | 3.25 | 5.65 | 5.82 | 8.07 | −10.86 | 11.79 |
| FFA + LIVRQNac (30×) | 5.84 | 4.18 | 11.65 | 3.08 | −26.08 | 17.97 |

(stdev is standard deviation)

Conclusion

The present study has shown an increased basal respiration with LIVRQNac treatment. All substrates tested (glucose, glutamine, and fatty acids) were utilized and contributed to this increase; however, the utilization proportions were not affected.

There was a dose-dependent increase in mitochondrial-derived ATP and a reduction in glycolysis-generated ATP, indicating that LIVRQNac modulates glycolytic versus oxidative ATP production.

Modulation of ATP production pathways and the increased basal respiration were seen with LIVRQNac treatment.

Acute COVID-19 literature suggests energetic dysregulation and an impact on mitochondrial metabolism (Junfang et al, 2021, supra; Sullivan et al, 2021, supra), which could possibly persist beyond the acute COVID phase. Thus, the studies shown here may support the bioenergetic benefit of LIVRQNac composition.

Example 11—The Effect of LIVRONac on Fatty Acid Oxidation in Primary Human Hepatocytes Objective(s): Investigate the dose-dependent effects of LIVRQNac on fatty acid oxidation (FAO) in primary human hepatocytes (PHH) in the presence of a lipotoxic insult using stable-labeled palmitate tracer.

Test Systems: Primary human hepatocytes (PHHs)

Test Article(s): LIVRQNac.

Methods: LIVRQNac at 10× and 30× concentrations, where 1× concentration matches the mean physiological level found in human plasma (values published in the Human Metabolome Database [Wishart et al, 2007, supra]) except for glutamine and Nac (1× is L-Leucine: 152.7 μM; L-Isoleucine: 66.4 μM; L-Valine: 234.2 μM; L-Arginine: 108.8 PM; L-Glutamine: 46.8 μM [below plasma level]; N-acetylcysteine: 250 μM [not endogenous]).), were added to cultures of PHH donor HC10-3 together with lipotoxic insult (0.25 mM saturated free fatty acids (2:1 oleate: palmitate) plus 1 ng/mL tumor necrosis factor alpha [TNF-α]), for 24 hours. Control cultures contained lipotoxic insult with high (11 mM) or low (5.5 mM) glucose concentrations and vehicle. Three biological replicates were used for each treatment. After 24 hours of treatment, lipotoxic insult containing a [U $^{13}$C]-palmitate tracer was added to cultures for an additional 1 hour. Levels of tracer incorporation and total quantities of acylcarnitines, acetyl-coenzyme A (acetyl CoA), the ketone body β-hydroxybutyrate (BHB), tricarboxylic acid cycle (TCA) intermediates, and amino acids were determined with liquid chromatography tandem mass spectrometry (LC MS/MS) and gas chromatography-mass spectrometry (GC-MS). Statistical differences between treatment groups were determined by ANOVA. Differences were considered statistically significant when p≤0.05.

Results: The results of the metabolic tracer studies in PHH showed LIVRQNac dose-dependently increased labeling of acylcarnitines, including palmitoylcarnitine (M16) and acetylcarnitine (M2), compared to vehicle treated cells using an endpoint measurement after 24 hours of treatment plus 1 hour of labeling. LIVRQNac also dose-dependently increased labeling of acetyl-CoA (M2) and the ketone body BHB (M2). The pool size, or combined concentration of unlabeled and labeled acetyl-CoA and BHB, end products of FAO and ketogenesis, respectively, remained the same for acetyl-CoA or increased for BHB with LIVRQNac treatment compared to vehicle. Increased labeling of select TCA cycle intermediates (malate M2, succinate M2) and amino acids (glutamate M2, aspartate M2) were also observed with LIVRQNac treatment compared to vehicle.

Conclusion: The present study was designed to explore mechanisms of the changes in lipid metabolism in PHH in response to lipotoxic insult plus LIVRQNac compared to lipotoxic insult alone. Increased labeling of palmitoylcarnitine with LIVRQNac treatment provides evidence for increased initiation of FAO. Increased labeling as well as unchanged or increased pool size for the products of FAO and ketogenesis, acetyl-CoA and BHB, respectively, provide evidence that LIVRQNac increases flux through these pathways from long-chain fatty acids (e.g., palmitate). Increased labeling of TCA cycle intermediates supports the flux of fatty acid-derived carbon into these metabolite pools. In sum, metabolic tracer studies using [U $^{13}$C] palmitate support a conclusion that LIVRQNac treatment increases FAO and ketogenesis in the presence of lipotoxic insult in PHH.

Introduction

LIVRQNac is a composition of 5 specific AAs and an AA derivative (Leucine [Leu], Isoleucine [Ile], Valine [Val], Arginine [Arg], Glutamine [Gln], and N-acetylcysteine [Nac]). The liver fat-lowering activity of LIVRQNac has been previously reported (Harrison et al, *Journal of Hepatology*, 73:S123, 2020; Harrison et al, *The American J of Gastroenterology*, 10.14309/ajg.0000000000001375, 2021). An analogous decrease in primary human hepatocyte (PHH) triglyceride accumulation as well as a change in imaged neutral lipid phenotype was observed (Daou et al, *Scientific Reports*, 11(1):11861, 2021) using LIVRQNac, containing: Leu, Ile, Val, Arg, Gln, Nac added at specified-fold concentrations above plasma (ex: 10×, 20×, 30×), where 1× concentration matches the mean physiological level found in human plasma (values published in the Human Metabolome Database [Wishart et al, 2007, supra]). A decrease in de novo lipogenesis (DNL), an increase in fatty acid oxidation (FAO), an increase in lipolysis, or a combination of these pathways could underlie LIVRQNac-dependent depletion of intracellular lipid stores in humans and PHH, respectively.

Stable-labeled isotope tracer methods paired with chromatography and mass spectrometry provide a means to investigate the contribution of potentially involved metabolic pathways to LIVRQNac effects on lipid metabolism in PHH. The studies described herein explore the mechanism of action of LIVRQNac and its effect on FAO for long-chain fatty acids (LCFA) using an isotopically labeled palmitate tracer ([U-$^{13}$C]-palmitate). Label incorporation into long-chain acylcarnitines/CoA is representative of initiation of FAO, while incorporation into acetylcarnitine/CoA is representative of overall beta-oxidation. Metabolite pool sizes of combined unlabeled and labeled metabolites can also provide insight into cellular metabolism Objective(s)

The objective of this study was as follows:
Investigate the dose-dependent effects of LIVRQNac on FAO in PHH in the presence of a lipotoxic insult using stable-labeled palmitate tracer.

Test Systems

PHHs from Donor HC10-3 were used in this study (Sekuisui XenoTech, LLC). PHHs were screened and tested in order to select donors that met the following quality control criteria: 1) post-thaw viability greater than 80%, 2) polarized morphology, and 3) stable albumin secretion rate for 8 to 10 days.

Test Article

Test articles: LIVRQNac
LIVRQNac cultures contained lipotoxic insult with high (11 mM) glucose Control Articles Control article: vehicle, phosphate-buffered saline (PBS)
Control cultures contained vehicle plus lipotoxic insult with high (11 mM) or low (5.5 mM) glucose concentrations Lipotoxic Insult lipotoxic insult, unlabeled: 0.25 mM saturated free fatty acids (sFFA) [2:1 oleate:palmitate] plus 1 ng/mL TNF-α, dissolved in water
lipotoxic insult, labeled: 0.25 mM sFFA (2:1 oleate:[U-$^{13}$C]-palmitate) plus 1 ng/mL TNF-α, dissolved in water Test Article Preparation LIVRQNac was added at specified-fold concentrations above plasma (10× and 30×; (1× is L-Leucine: 152.7 µM; L-Isoleucine: 66.4 µM; L-Valine: 234.2 PM; L-Arginine: 108.8 µM; L-Glutamine: 46.8 µM [below plasma level]; N-acetylcysteine: 250 µM [not endogenous]).), where 1× concentration matches the mean physiological level found in human plasma (values published in the Human Metabolome Database [Wishart et al, 2007, supra]). Increasing the fold concentrations of AAs in this study was used to model relevant AA exposures while maintaining overall cell health. AAs were added to appropriate media on the day of treatment, mixed, and added to PHH after washing twice with DPBS.

PHH Culture and Treatment

PHHs from one healthy human donor were used in this study. PHHs were screened and tested to select donors that met the following quality control criteria: 1) post-thaw viability greater than 80%, 2) polarized morphology, and 3) stable albumin secretion rate for 8 to 10 days.

Qualified PHHs were thawed and plated in PHH plating media (William's E medium [WEM, Gibco] supplemented with 10% heat-inactivated fetal bovine serum [HI FBS, Atlanta Bio], 2 mM glutamax [Gibco], and 0.2% primocin [InvivoGen]) on Day 1 at a density of 700,000 cells/well in 12-well collagen I-coated plates (Corning). Throughout the studies, cells were incubated at 37° C. with 5% $CO_2$. Following plating, PHHs were allowed to attach for 6 hours prior to washing them twice and incubating overnight in PHH plating media.

On Day 2, PHHs were washed twice and incubated for 24 hours in complete hepatocyte-defined medium (cHDM) (Corning) supplemented with epidermal growth factor (EGF), (Corning), 2 mM glutamax (Gibco), and 1× penicillin/streptomycin (Gibco).

On Day 3, cells were washed twice with DPBS 1× (Gibco) then switched to an AA-free WEM (US Biologicals) containing 500 µM carnitine, 10 µg/mL insulin, EGF, 1 µM dexamethasone, and defined custom AA concentrations that matched those found in healthy human plasma (values published in the Human Metabolome Database (Wishart et al, 2007, supra), (WEM 1×HMDB). A lipotoxic insult consisting of 0.25 mM sFFA (2:1 oleate:palmitate) and TNF-α (ThermoFisher) at 1 ng/mL was added as appropriate. This custom media was supplemented as needed with either PBS vehicle, or the constituent AAs of LIVRQNac added at specified-fold concentrations above plasma level (10× or 30×; (1× is L-Leucine: 152.7 µM; L-Isoleucine: 66.4 µM; L-Valine: 234.2 µM; L-Arginine: 108.8 µM; L-Glutamine: 46.8 µM [below plasma level]; N-acetylcysteine: 250 µM [not endogenous]).). Treatment groups are presented in Table 49. Increasing the fold concentration of AAs in these studies was used to model relevant AA exposures while maintaining overall cell health.

PHH media baseline amino acid concentrations (1×HMDB) match mean physiological levels found in human plasma (values published in the Human Metabolome Database, HMDB [Wishart et al, 2007, supra]). LIVRQNac constituents were added at specified-fold concentrations above plasma level (10× or 30× for LIVR; Nac was added at 2.5 or 7.5 mM; glutamine was added at 0.468 and 1.404 mM).

After 24 hours of treatment, medium was removed and replaced with medium containing the lipotoxic insult with [U-$^{13}$C]-labeled palmitate tracer, prepared as described below. Cells were harvested after 1 hour of incubation with labeled palmitate media as described below.

TABLE 49

Treatment Groups Used in the Study

| # | Treatment |
|---|---|
| 1 | Lipotoxic insult, High Glucose (11 mM) + Vehicle (DPBS) |
| 2 | Lipotoxic insult, Low Glucose (5.5 mM) + Vehicle (DPBS) |
| 1 | Lipotoxic insult, High Glucose (11 mM) + Vehicle (DPBS) |
| 3 | Lipotoxic insult, High Glucose (11 mM) + LIVRQNac (10×) |
| 4 | Lipotoxic insult, High Glucose (11 mM) + LIVRQNac (30×) |

DPBS = Dulbecco's phosphate-buffered saline.

[U-$^{13}$C]-Palmitate Labeling Preparation

Labeled palmitate media was prepared by adding 2 mM palmitic acid-$^{13}$C16 Labeled (Sigma) to AA-free WEM (US Biologicals) containing additives described below plus defined custom AA concentrations that matched those found in healthy human plasma (values published in the Human Metabolome Database (Wishart et al, 2007, supra), WEM 1×HMDB). The labeled lipotoxic insult comprised 0.25 mM sFFA (2:1 oleate:[U-$^{13}$C]-palmitate) and TNF-α (ThermoFisher) at 1 ng/mL. This custom labeled palmitate media was supplemented as needed with either PBS (vehicle) or the constituent AAs of LIVRQNac added at specified-fold concentrations above plasma level (10× or 30× 1× is L-Leucine: 152.7 µM; L-Isoleucine: 66.4 µM; L-Valine: 234.2 µM; L-Arginine: 108.8 µM; L-Glutamine: 46.8 µM [below plasma level]; N-acetylcysteine: 250 µM [not endogenous]).

Labeling Procedure and Sample Extraction

After cells had been treated in unlabeled custom WEM 1×HMDB media supplemented as needed with either PBS (vehicle) or LIVRQNac for 24 hours, the media was removed, and cells were incubated in labeled media described above and supplemented with the same LIVRQNac treatments for 1 hour. After 1 hour, media was removed, and cells were washed with 1 mL of 1×PBS (Gibco). The wash was discarded, and 0.333 mL of extraction buffer consisting of 80:20 methanol (Fisher):water with internal standards added (10 µM Isovaleryl-L-carnitine d9 [Sigma]; 10 µM Carnitine d9 [Sigma]) was added to each well. Wells were scraped, and triplicate wells were pooled. Pooled samples were centrifuged at 13000×g for 8 minutes to remove debris. Clear supernatant was transferred to a clean tube and stored at −80° C. Samples were dried by vacuum evaporation and then submitted for analysis.

Analysis

Acylcarnitines were analyzed by Sciex LC-QTRAP 6500+-MS/MS. The dried extracts were derivatized with 100 µl 3 M HCl methanol solution at 50° C. for 20 minutes. The derivatized samples were completely dried again by N2 gas and resuspended in 20 µl methanol followed by 80 µl water for Sciex LC-QTRAP 6500+-MS/MS analysis (Millington and Stevens, *Methods in Molecular Biology*, 708:55-72, 2011).

Acetyl-coenzyme A (Acetyl-CoA) was analyzed by Sciex LC-QTRAP 6500+-MS/MS. The dried extracts were resuspended in 1 ml methanol:water (1:1 volume ratio) containing 5% acetic acid. The sample was spiked with 0.1 nmol D9 pentanoyl-CoA as an internal standard and purified with solid phase extraction (SPE). The acetyl-CoA eluent collected from SPE was dried completely under N2 gas. The dried sample was resuspended in 60 µl water for liquid chromatography-tandem mass spectrometry (LC-MS/MS) analysis (Li et al, *Journal of Lipid Research*, 5(3):592-602, 2014).

Other metabolites were analyzed by Agilent gas chromatography-mass spectrometry (GC-MS). The dried samples were resuspended in 200 µl methanol and spiked with 0.5 nmol norvaline as an internal standard. Samples were dried by N2 gas completely and derivatized with 35 µl of 2% methooxyamine HCl in pyridine at 40° C. for 90 minutes followed by a second derivatization with 25 µl butyldimethylsilyl chloride (TBDMS) at 60° C. for 30 minutes. The derivatized samples were transferred to GC vials for GC-MS analysis (Zhang et al, *Cell Metabolism*, 33(4):804-814, 2021).

Mass isotopomers were designated as M0, M1, M2, . . . , where the number represents the number of heavy atoms in the molecule. Stable isotope enrichment of analytes is defined as the net increase in isotopomer labeling subtracted from the background of natural isotopomer distribution. Matrix calculation was employed to calculate stable isotope enrichment. The detailed calculation has been described in published papers (Fernandez et al, *Journal of Mass Spectrometry*, 31(3):255-262, 1996; Tomcik et al, *Analytical Biochemistry*, 410(1):110-117, 2011).

Data Analysis

Data generated from labeled and unlabeled analyte quantification by LC-MS/MS and GC-MS was analyzed in GraphPad Prism. Statistical analysis included ordinary one-way ANOVA with adjustment for multiple comparisons using Dunnett's multiple comparisons test. Treatment groups (e.g., LIVRQNac 10× and LIVRQNac 30×; see Table 9 for group descriptions) were compared with the lipotoxic insult high glucose (11 mM)+vehicle group, which contained an equivalent concentration of glucose. The lipotoxic insult low glucose (5.5 mM) group was not compared because of few differences in metabolite concentration or labeling observed between it and the high glucose group. Differences between data groups were considered significant when adjusted p≤0.05.

Results

The Effect of LIVRQNac Treatment on Acylcarnitines

Figure 4:
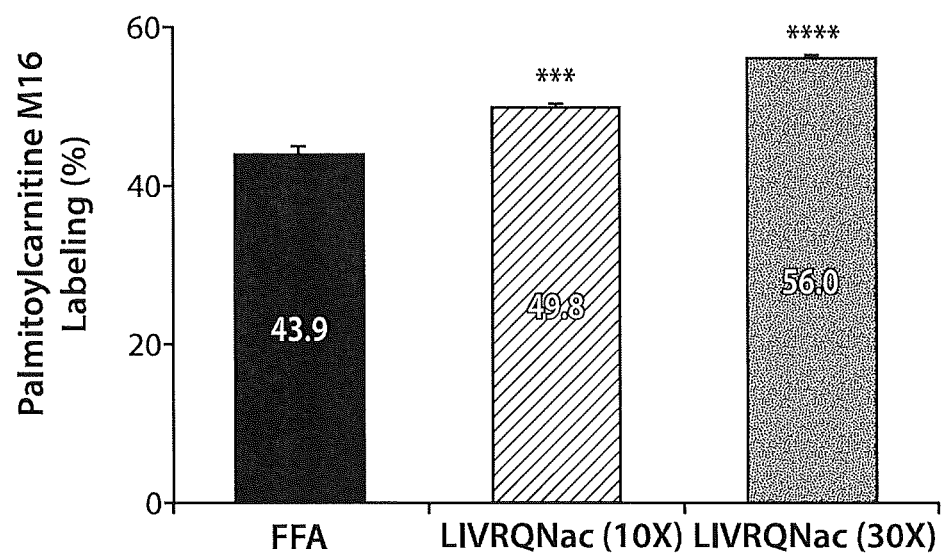
FIG. 4 is a bar graph showing an increase in the percentage of label incorporation from U $^{13}$C Palmitate in most acylcarnitine species after LIVRQNac administration. FFA=high glucose lipotoxic, *p<0.001, **p<0.0001. The bars represent the standard deviation. The study was performed as described in Example 11.

There was a dose-dependent increase in the percentage of acylcarnitines containing labeled carbon atoms (derived from [U-$^{13}$C]-palmitate tracer) in PHH treated with LIVRQNac plus lipotoxic insult compared to cultures treated with lipotoxic insult alone (FIG. 4). An increased percentage of fully labeled (M16) palmitoylcarnitine likely represents an effect of LIVRQNac to stimulate the initiation of FAO. Another possible but less likely explanation for increased palmitoylcarnitine labeling could be less dilution of labeled fatty acid by unlabeled fatty acid derived from lipolysis or DNL when LIVRQNac is present (FIG. 4 and Table 50, see Table 49 for group descriptions).

Few differences in metabolite concentrations or labeling were observed between the lipotoxic insult conditions containing high (11 mM) and low (5.5 mM) glucose. Throughout this report, the low glucose condition is not shown, and the treatment groups were compared with the high glucose control condition, matching the glucose concentration of LIVRQNac treatment conditions.

TABLE 50

Palmitoylcarnitine M16 Labeling %

|  | FFA | LIVRQNac 10X | LIVRQNac (3 OX) |
| --- | --- | --- | --- |
| Avg | 43.9 | 49.8 | 56 |
| SD | 1.61 | 0.50 | 0.62 |

The Effect of LIVRQNac Treatment on Acetyl-CoA and BHB

Figure 5:
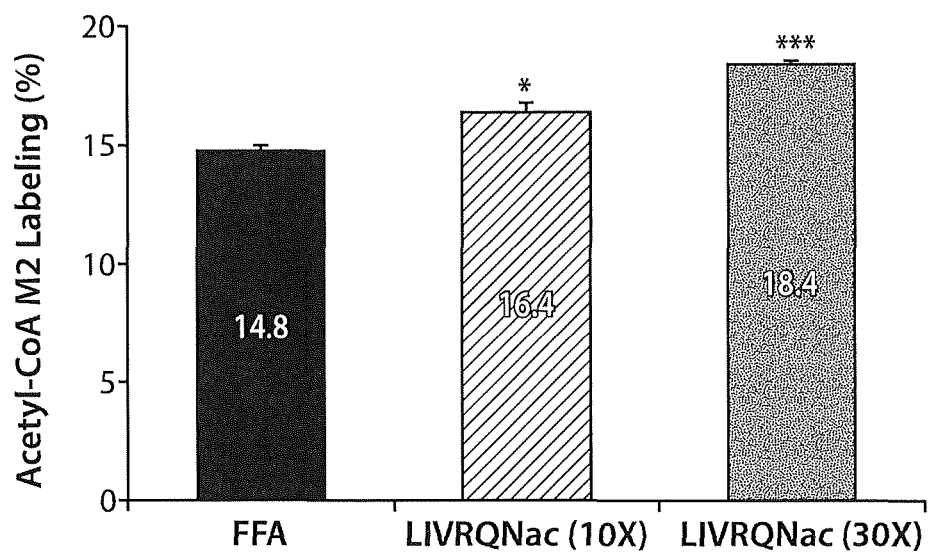
FIG. 5 is a bar graph showing an increase in the percentage of label incorporation from U $^{13}$C Palmitate in acetyl-CoA without a change in its overall levels after LIVRQNac administration. FFA=high glucose lipotoxic, *p<0.01, ***p<0.001. The bars represent the standard deviation. The study was performed as described in Example 11.

An increased percentage of labeled acetyl-CoA (M2) was found; the effect was dose-dependent with LIVRQNac (FIG. 5 and Table 51). The overall quantity of acetyl-CoA was not significantly changed by LIVRQNac treatments. Increased percentage of labeled acetylcarnitine (FIG. 4 and Table 50) and acetyl-CoA (FIG. 5 and table 51) is representative of an increase in beta-oxidation, during which successive 2-carbon units are cleaved from acyl-CoA chains as end-product acetyl-CoA, in equilibrium with acetylcarnitine. The unchanged pool of acetyl-CoA with increased labeling percentage represents increased flux through FAO to acetyl-CoA with LIVRQNac treatment compared to vehicle.

Figure 6A:
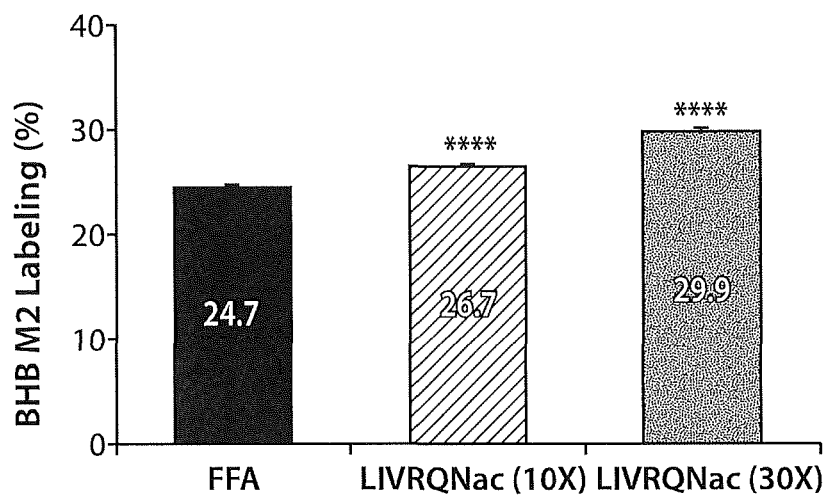
FIGS. 6A and 6B are bar graphs showing an increase in the percentage of label incorporation from U $^{13}$C Palmitate in the ketone body β-hydroxybutyrate (BHB) (FIG. 6A) and its overall levels (FIG. 6B). BHB M2 labeling (%) means the percentage of increase in incorporation of labeled carbon atoms (e.g., exogenous [U-$^{13}$C]-palmitate utilization). The bars represent standard deviation. ****p<0.0001. The study was performed as described in Example 11.
Figure 6B:
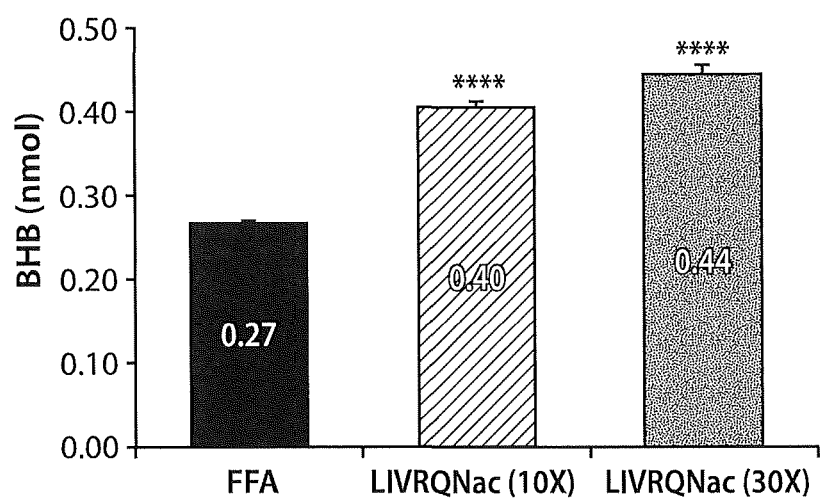
Figure 7:
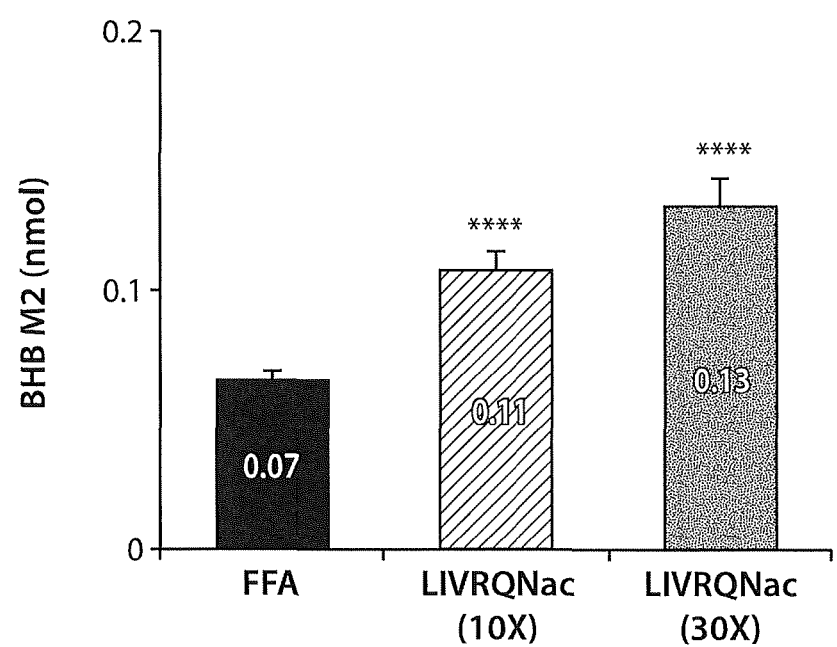
FIG. 7 is a bar graph showing an increase in the percentage of label incorporation from U $^{13}$C Palmitate in terminal FAO product β-hydroxybutyrate (BHB) and doubles the amount of M2 BHB derived from [U-$^{13}$C]-Palmitate. The bars represent standard deviation. *p<0.05; *p<0.001; **p<0.0001. The study was performed as described in Example 11.

Similarly, the ketone body BHB showed an increased percentage of label incorporation (M2) from [U-$^{13}$C]-palmitate tracer, and the effect was dose-dependent (FIG. 6A and Table 52). The overall levels of BHB were also significantly increased with LIVRQNac compared to the group treated with lipotoxic insult alone (ANOVA, $p<0.0001$ for all groups, FIG. 6B and Table 52). Whereas acetyl-CoA is an intermediate product utilized in the TCA cycle and other metabolic pathways, β-hydroxybutyrate is a terminal metabolite of [U-$^{13}$C]-palmitate oxidation and therefore, increases in both labeling and pool size are indicative of the dose-dependent increase in FAO with LIVRQNac. Treatment-induced doubling of M2 BHB, labeled from [U-$^{13}$C]-palmitate, is representative of FAO increase. A 102% Increase in M2 labeled BHB (nmol) from [U-$^{13}$C]-palmitate was observed with LIVRQNac (30×) treatment (FIG. 7 and Table 53).

Hence the BHB results reported here further support that LIVRQNac activates FAO and ketogenesis.

TABLE 51

Acetyl-CoA M2 Labeling (%)

Acetyl-CoA M2 Labeling %

|  | FFA | LIVRQNac 10X | LIVRQNac (3 OX) |
| --- | --- | --- | --- |
| Avg | 14.8 | 16.38 | 18.41 |
| SD | 0.31 | 0.77 | 0.25 |

TABLE 52

BHB M2 Labeling (%) and BHB (nmol)

|  | FFA | LIVRQNac 10X | LIVRQNac (3 OX) |
| --- | --- | --- | --- |
| BHB M2 Labeling % | | | |
| Avg | 24.7 | 26.70 | 29.9 |
| SD | 0.18 | 0.13 | 0.31 |
| BHB (nmol) | | | |
| Avg | 0.27 | 0.4 | 0.44 |
| SD | 0.01 | 0.01 | 0.02 |

TABLE 53

BHB M2 Labeling (%) multiplied by BHB (nmol)

M2 BHB (% x nmol)

|  | FFA | LIVRQNac 10X | LIVRQNac (3 OX) |
| --- | --- | --- | --- |
|  | 0.065 | 0.107 | 0.125 |
|  | 0.068 | 0.112 | 0.136 |
|  | 0.065 | 0.105 | 0.138 |
| Avg | 0.066 | 0.108 | 0.133 |
| SD | 0.002 | 0.004 | 0.007 |
| n (SQRT(3)) | 1.732 | 1.732 | 1.732 |
| SEM | 0.001 | 0.002 | 0.004 |

The Effect of LIVRQNac Treatment on TCA Cycle Intermediates

Figure 8:
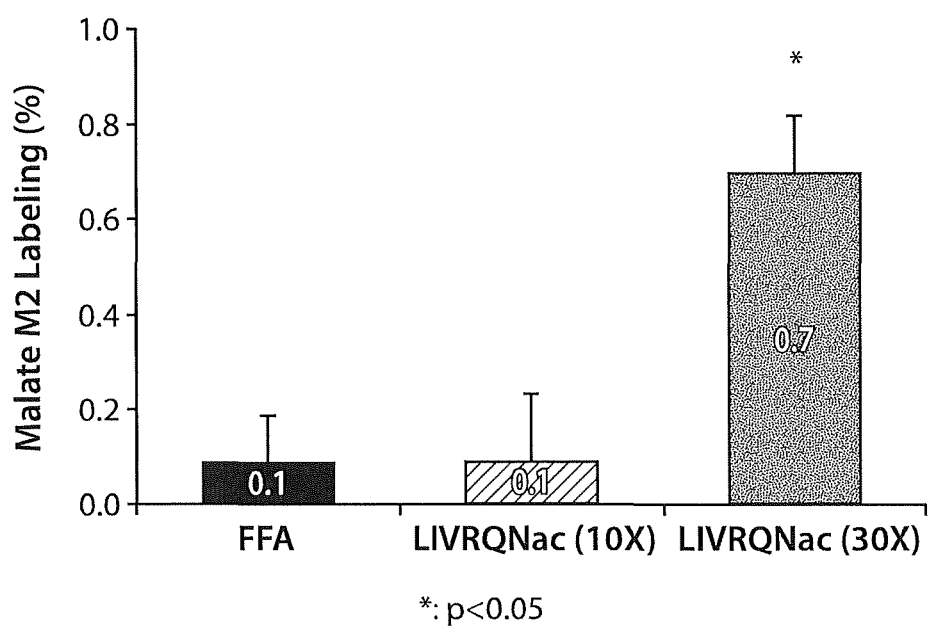
FIG. 8 is a bar graph showing an increase in the percentage of label incorporation from U $^{13}$C Palmitate in the citric acid cycle (TCA) cycle intermediate Malate after LIVRQNac administration. Succinate M2 labeling (%) means the percentage of increase in incorporation of labeled carbon atoms (e.g., exogenous [U-$^{13}$C]-palmitate utilization). The bars represent standard deviation. *p<0.05. The study was performed as described in Example 11.

LIVRQNac treatment caused an increase in the percentage of label incorporation for TCA cycle intermediate malate (FIG. 8 and Table 54). Combined, these results demonstrate flux of labeled carbon from [U-$^{13}$C]-palmitate tracer through the TCA cycle and into amino acid metabolite pools.

TABLE 54

Malate M2 Labeling (%)

Malate M2 Labeling %

|  | FFA | LIVRQNac 10X | LIVRQNac (3 OX) |
| --- | --- | --- | --- |
| Avg | 0.09 | 0.09 | 0.70 |
| SD | 0.18 | 0.25 | 0.21 |

Conclusion

PHHs treated with lipotoxic insult plus LIVRQNac had an increased percentage of label incorporation from [U-$^{13}$C]-palmitate tracer into acetylcarnitine and acetyl-CoA, the end products of FAO, compared with vehicle-treated controls. This provides evidence of increased FAO resulting from LIVRQNac treatment. Additionally, there was an increased percentage of label incorporation into the ketone body BHB, as well as increased total intracellular BHB concentration, both of which are consistent with increased FAO and ketogenesis. The percentage of label incorporation into palmitoylcarnitine and TCA cycle metabolites was increased in the presence of lipotoxic insult plus LIVRQNac treatment compared with lipotoxic insult alone, suggesting increased flux from LCFAs. The observed increased label incorporation into palmitoylcarnitine is likely explained by increased FAO initiation. The increase in labeling could also have been the result of less dilution of labeled fatty acid by unlabeled pools from DNL or lipolysis. This is viewed as a possible but unlikely explanation. While other areas of lipid metabolism will be the subject of separate studies, the totality of the present evidence supports that LIVRQNac plus lipotoxic insult induces remodeling of intracellular lipid metabolism in PHHs by increasing FAO.

LIVRQNac was previously found to upregulate PPARα genes, which play a major role in FAO processes, including induction of expression of genes encoding enzymes of FAO (see a review by Grygiel-Górniak B, *Nutrition Journal*, 13:17, 2014). This suggests a potential mechanism contributing to the increased rate of FAO in this experimental paradigm.

It has previously been reported that LIVRQNac has an impact on lowering liver fat in humans (Harrison et al, 2020, supra; Harrison et al, 2021, supra), and in cells, LIVRQNac impacts phenotypes related to lipid metabolism in PHH (Daou et al, 2021, supra). The present report provides direct evidence in support of the effect of LIVRQNac to increase FAO based on labeling of FAO-pathway products upon administration of stable-labeled tracer $[U-^{13}C]$-palmitate as measured by LC-MS/MS and GC-MS.

Acute COVID-19 literature suggests energetic dysregulation and an impact on mitochondrial metabolism (Junfang et al, 2021, supra; Sullivan et al, 2021, supra), which could possibly persist beyond the acute COVID phase. Thus, the studies shown here may support the bioenergetic benefit of LIVRQNac composition. LIVRQNac may increase fatty acid oxidation and improve cellular respiration in the context of PASC. The LIVRQNac-induced increase in PHH FAO, described herein, may lead to release into systemic circulation of terminal metabolites of FAO, such as the ketone body BHB, which may support muscle physiologic demands.

Example 12—Evaluation of LIVRONac in Subjects with Long COVID Fatigue

Long COVID-19 with Fatigue is a Serious Condition with Urgent Unmet Medical Need:

Long COVID-19 is a chronic, multi-organ disease predominantly characterized by fatigue and muscle weakness (Lopez Leon et al (More than 50 long-term effects of COVID-19: a systematic review and meta-analysis. *Sci Rep.* 2021 Aug. 9; 11(1):16144. doi: 10.1038/s41598-021-95565-8. PMID: 34373540; PMCID: PMC8352980)). Although many patients recover from COVID-19 within several weeks, a substantial proportion of patients exhibit persistent or new symptoms more than 4 weeks after being diagnosed (Sigfrid et al (Long Covid in adults discharged from UK hospitals after Covid-19: A prospective, multicentre cohort study using the ISARIC WHO Clinical Characterisation Protocol. Lancet Reg Health Eur. 2021 September; 8:100186. doi: 10.1016/j.lanepe.2021.100186. Epub 2021 Aug. 6. PMID: 34386785; PMCID: PMC8343377)). These patients with persistent post-acute COVID (PASC) symptoms are often referred to as suffering from long COVID. It is estimated that long COVID affects 20% to 70% of the survivors of acute infection. Many cross-sectional and cohort studies report that chronic fatigue is the most frequently reported symptom following recovery from acute COVID-19 (Evans et al. (Physical, cognitive, and mental health impacts of COVID-19 after hospitalisation (PHOSP-COVID): a UK multicentre, prospective cohort study. Lancet Respir Med. 2021 November; 9(11):1275-1287. doi: 10.1016/S2213-2600(21)00383-0. Epub 2021 Oct. 7. Erratum in: Lancet Respir Med. 2022 January; 10(1):e9. PMID: 34627560; PMCID: PMC8497028); Crook et al. (Long covid-mechanisms, risk factors, and management. BMJ. 2021 Jul. 26; 374:n1648. doi: 10.1136/bmj.n1648. Erratum in: BMJ. 2021 Aug. 3; 374:n1944. PMID: 34312178)). A recent large database of nearly 2 million individuals diagnosed with COVID-19 estimated that 23.2% of patients report at least 1 post-COVID-19 condition, and fatigue is among the 3 most common complaints, typically reported in more than half of subjects with persistent symptoms. Reports of fatigue are independent of the severity of initial illness (Townsend, et al. (Persistent poor health after COVID-19 is not associated with respiratory complications or initial disease severity. *Ann Am Thorac Soc.* 2021; 18(6): 997-1003); Augustin, et al. (Post-COVID syndrome in non-hospitalized patients with COVID-19: a longitudinal prospective cohort study. Lancet Reg Health Eur. 2021 July; 6:100122. doi: 10.1016/j.lanepe.2021.100122. Epub 2021 May 18. PMID: 34027514; PMCID: PMC8129613). There is evidence of substantial negative impact on quality of life (QoL) (Halpin et al. (Postdischarge symptoms and rehabilitation needs in survivors of COVID-19 infection: a cross-sectional evaluation. *J Med Virol.* 2020)), and given the large number of survivors with long COVID, it is reasonable to assume that there will be substantial long-term effects not only on individuals but also on the health care system. In a study that examined 1-year outcomes in hospital survivors with COVID-19, only 76% had returned to a pre-COVID-19 level of employment, with 32% of individuals attributing this to decreased physical function (Huang, et al. (1-year outcomes in hospital survivors with COVID-19: a longitudinal cohort study. Lancet. 2021; 398(10302):747-758)). Thus, long COVID-19 with fatigue is a serious disease, with the potential to substantially impair QoL and lead to increased health risks and costs and impairment of the ability to work.

Clinical STUDY for Long COVID-19

A randomized, double-blind, placebo-controlled Phase 2a trial was conducted to evaluate the efficacy and safety of a LIVRQNac Test Article in patients with moderate to severe fatigue related to long COVID (>12 weeks after initial infection). Enrollment in the study has been completed, with 41 patients randomized evenly to receive either 67.8 grams per day of LIVRQNac or a matched placebo in two divided doses for 28 days, with a one-week safety follow-up period. The total study duration for each subject is approximately 9 weeks and comprising of a Screening Period of up to 4 weeks, a Treatment Period of up to 4 weeks, and a Follow-up Period of 1 week (FIG. 1).

The primary efficacy endpoint is the mean change from baseline at Week 4 in the phosphocreatine (PCr) recovery rate following moderate exercise, as assessed by phosphorus magnetic resonance spectroscopy ($^{31}$P-MRS), which is evaluated at Screening and End of Trial (EOT) (visit 4). To assess fatigue, 6-minute walk test (6 MWT) and Chalder Fatigue scale, which have been successfully validated and used in previous studies on chronic fatigue syndrome (Mantha 2020) were utilized.

An analysis of the results from the first 20 subjects has been conducted, with the results presented here. Top line results with the 41 subjects enrolled in the study are expected to be available in the near future.

Description of Study Test Article

The LIVRQNac Test Article is an orally active mixture of 5 specific AAs (leucine, isoleucine, valine, arginine, glutamine), and N-acetylcysteine (Nac) as presented in Table 55.

TABLE 55

Amino Acid and Excipient Composition Within LIVRQNac Test Article

| Amino Acid Composition | Unit Dosage Dry Weight (g) | Percent (%) in Unit Dosage | Total Maximal Daily Dose (g) |
|---|---|---|---|
| L-Leucine | 2.000 | 13.01 | 12.000 |
| L-Isoleucine | 1.000 | 6.51 | 6.000 |
| L-Valine | 1.000 | 6.51 | 6.000 |
| L-Arginine HCl[a] | 3.628 | 23.61 | 21.768 |
| L-Glutamine | 4.000 | 26.03 | 24.000 |
| N-Acetyl L-cysteine | 0.300 | 1.95 | 1.800 |
| Citric Acid, anhydrous | 0.667 | 4.34 | 4.002 |
| Lecithin | 1.667 | 10.85 | 10.002 |
| Xanthan Gum | 0.200 | 1.30 | 1.200 |
| Sucralose, powder | 0.067 | 0.44 | 0.402 |
| Orange flavor, natural and WONF | 0.350 | 2.28 | 2.100 |
| N-C custard flavor, natural and artificial | 0.060 | 0.39 | 0.360 |
| FD&C Yellow No. 6 | 0.009 | 0.06 | 0.054 |
| Low substituted hydroxypropyl cellulose | 0.100 | 0.65 | 0.600 |
| Silicon dioxide | 0.300 | 1.95 | 1.800 |
| Magnesium stearate | 0.020 | 0.13 | 0.120 |
| AAs (less HCl) | 11.30 | 73.53 | 67.800 |
| Total | 15.368 | 100.00 | 92.208 |

AA = amino acid
Note:
Total may be >100% due to rounding off
[a]Arginine is sourced as arginine monohydrochloride The Test Article is supplied in a dry powder form that is dissolved in approximately 6 oz (approximately 180 mL) of water to form a uniform suspension and is administered orally, twice daily, as an orange-flavored drink.

Study Endpoints

Rationale for Choosing PCr Recovery as the Primary Endpoint:

The primary objective of this study was to assess the impact of LIVRQNac on muscle function (metabolism) following exercise. A change in the time constant of phosphocreatine (PCr) recovery from baseline after 4 weeks treatment as measured by $^{31}$P-MRS was chosen as the primary endpoint as it is objective and sensitive to changes in mitochondrial function. In brief, $^{31}$P-MRS is used to estimate the concentration of high-energy phosphate compounds; thus, the bioenergetic state of a tissue can be characterized in vivo as it may reflect changes in mitochondrial function (Prompers 2006; Kemp 2015; Valković 2016). $^{31}$P-MRS has been used to assess mitochondrial function in a variety of conditions, including heart failure patients (Menon 2021), diabetes (Ripley 2018), and mitochondrial abnormalities following drug administration (Fleischman 2007). If, as expected, a composition comprising LIVRQNac improves mitochondrial oxidative capacity, then a decrease, relative to subject baseline, in the phosphocreatine recovery time is predicted. The assumption at the beginning of the trial was that individuals with prolonged fatigue after COVID-19 would have a baseline PCr of 50 seconds, which would be comparable to aged individuals or those with heart failure.

Rationale for Choosing CFO-11 and 6 MWT to Assess Fatigue:

The Chalder Fatigue Scale (CFQ-11) and the 6 MWT have been utilized in multiple therapeutic areas and several indications and have been paramount in characterizing the patient's condition and overall quality of life. Both these tests are suitable in evaluating scientifically supported and logical combination of symptoms that are common in patients with long COVID-19 with fatigue and inform the design of a subsequent study with appropriate power to detect differences in these key endpoints.

While many instruments are available to assess fatigue, the CFQ-11 has been validated in a number of different patient population including those with myalgic encephalomyelitis/chronic fatigue syndrome (Whitehead 2009; Morriss 1998; Crawley 2013) which has parallels to the clinical presentation of patients with long COVID-19 experiencing fatigue (U.S). There has also been use of the CFQ-11 in patients with long COVID-19 (Staven 2021, Tuzon 2021, Townsend 2021). Given the reliability of this instrument in a wide range of conditions, ongoing public health emergency and the serious unmet medical need for patients with long COVID with fatigue, the use of such existing, reliable functional assessment and PROs to assess clinical benefit outweighed the risks of not performing additional validation in the target patient population.

The fatigue scale developed by Chalder et al. is an 11-item scale intended to measure the severity of fatigue-related symptoms, both mental and physical, experienced by individuals with myalgic encephalomyelitis/chronic fatigue syndrome (ME/CFS). The scale has two scoring systems: bimodal and Likert. In the bimodal system, respondents answer each question with a 1 or a 0 to indicate the questions apply to them or not. In the Likert system, respondents can give a score of 0 to 3 to indicate how each statement applies to them, from "less than usual" to "much more than usual". The scores are then summed, and a higher score indicates more severe fatigue-related symptomatology. The "Physical Fatigue" items include questions such as "Do you have problems with tiredness?" or "Do you lack energy?" The remaining items constitute a "Mental Fatigue" factor with questions such as "Do you have difficulty concentrating?" or "Do you make slips of the tongue when speaking?" The total scale demonstrated sufficient internal consistency with alpha coefficients of 0.89 (Chalder 1993). At the 90% sensitivity level for the CFQ-11 Scale (with a score ≥14.50) a specificity of 0.61 was detected, and these scales were able to identify 90% of those individuals with CFS (Jason 2011). As an example of a measure of fatigue intensity alone, Chalder et al.'s Fatigue Scale is a verbal rating measure that has strong internal consistency. Using an ROC curve analysis, (Jason 1997), this scale was able to discriminate a CFS sample from a healthy control sample. Near-maximal scoring on six physical fatigue scale items from the total of 14 items constituting the Chalder fatigue scale supports the validity of scoring the physical fatigue scale on a two-point scale (presence or absence) rather than the four-point scoring. As noted in the paragraph above, the CFQ-11 has been applied to the study of outcomes in COVID-19 (Steven 2021, Tuzon 2021, Townsend 2021).

Additionally, the 6-minute walk test (6 MWT) is a validated clinical test to assess the cardiopulmonary reserve and fundamentally designed for use in adults with chronic respiratory disease (Holland 2014) and therefore may be an appropriate test to evaluate functional status of COVID-19 patients.

Results from this Analysis of this Study

An analysis was conducted after 20 subjects (10 subjects taking Test Article and 10 taking Placebo) in the study completed 4 weeks of treatment. The analysis was focused on the study endpoints including; CFQ-11, 6-MWT, MRS, and safety and tolerability.

Figure 9:
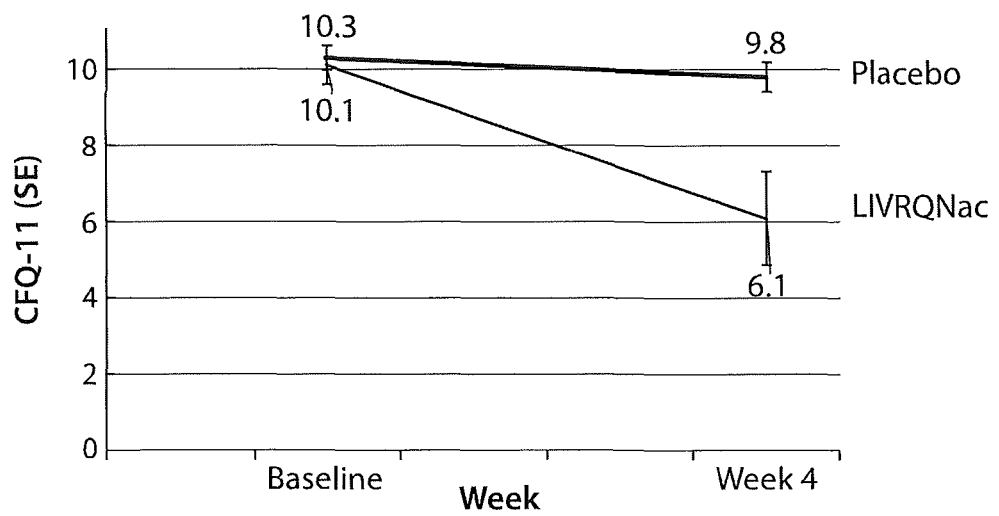
FIG. 9 is a graph showing the change from baseline in CFQ-11 score. The graph shows CFQ-11 change from baseline at week 4 of −4.00 and −0.50 of LIVRQNac and placebo, respectively.

Subjects who received LIVRQNac Test Article, relative to placebo, achieved statistically significant improvements in the CFQ-11. A major entry criterion for the study was the presence of moderate to severe fatigue (score of ≥8, with a score of 4 or more indicative of fatigue using bimodal score, with scores ranging from 0-11). Relative to placebo, subjects who received LIVRQNac Test Article had a 4 point improvement in the CFQ-11 score (Table 56, FIG. 9).

In addition to the bimodal scoring, CFQ-11 can also be scored on a Likert scale, with subscales for both physical and mental domains. On the Likert scoring, there was also a statistically significant improvement in both physical and mental subscales, with a notable shift in the severity of symptoms toward milder disease in subjects who received LIVRQNac Test Article, and little evidence of such improvement in those who received placebo (Table 58). Additionally, further analysis of the CFQ-11 results for the individual subjects confirmed the clinically and statistically significant change in the LIVRQNac Test Article Group utilizing both the Bimodal scoring (Baseline=10.10, SD=1.595, and Week 4=6.10, SD=3.872) versus the Placebo Group (Baseline=10.30, SD=1.059, and Week 4=9.8, SD=1.229), and the Likert scoring (Baseline=25.5, SD=4.743, and Week 4=18.40, SD=5.948) versus the Placebo Group (Baseline=27.5, SD=2.461, and Week 4=25.9, SD=4.458) at Week 4 (P=0.0194).

Moreover, analyses of the CFQ-11 results for both the Physical and the Mental Domains, utilizing the Likert scoring (Table 57 below) confirmed the clinically and statistically significant change in the LIVRQNac Test Article Group (Total Score: mean=−7.10, SD=5.131), Physical (mean=−5.00, SD=3.300), and Mental (mean=−2.10, SD=2.025) versus the Placebo Group (Total Score: mean=−1.60, SD=4.427), Physical (mean=−1.50, SD=3.629), and Mental (mean=−0.10, SD=1.197), with P values of 0.0194, 0.0367, and 0.0150 for the Total score, Physical, and Mental Domains respectively (Table 57 below).

TABLE 56

Change from baseline in CFQ-11 score (Bimodal)

| | PBO (n = 10) | LIVRQNac Test Article (n = 10) |
|---|---|---|
| Baseline | | |
| Mean | 10.30 | 10.10 |
| SD, SE | 1.059, 0.335 | 1.595, 0.504 |
| Min, Max | 8.00, 11.00 | 6.00, 11.00 |
| Week 4 | | |
| Mean | 9.80 | 6.10 |
| SD, SE | 1.229, 0.389 | 3.872, 1.224 |
| Min, Max | 8.00, 11.00 | 0.00, 11.00 |
| Change from Baseline at week 4 | | |
| Mean | −0.50 | −4.00* |
| SD, SE | 0.850, 0.269 | 4.000, 1.265 |
| Min, Max | −2.00, 0.00 | −11.00, 0.00 |

Difference (95% CI) in LS Mean −3.61 (−6.33,−0.88), p = 0.0126 (two-sided)

TABLE 57

Change from baseline in CFQ-11 score (Likert)

| | Change from baseline | Placebo (N = 10) | LIVRQNac Test Article (N = 10) | P |
|---|---|---|---|---|
| Total | Mean | −1.60 | −7.10 | 0.0194 |
| | SD | 4.427 | 5.131 | |
| Physical | Mean | −1.50 | −5.00 | 0.0367 |
| | SD | 3.629 | 3.300 | |
| Mental | Mean | −0.10 | −2.10 | 0.0150 |
| | SD | 1.197 | 2.025 | |

TABLE 58

Change in Fatigue Status of Patients from baseline to Week 4 (Physical Domain):

| Visit | Baseline Category | Post-Baseline Category | Placebo BID (N = 10) | LIVRQNac Test Article 33.9 g BID (N = 10) |
|---|---|---|---|---|
| Baseline | Normal | | 0 | 0 |
| | Mild | | 0 | 2 (20.0) |
| | Moderate/Severe | | 10 (100.0) | 8 (80.0) |
| Week 4 | Normal | Normal | 0 | 0 |
| | | Mild | 0 | 0 |
| | | Moderate/Severe | 0 | 0 |
| | Mild | Normal | 0 | 2 (20.0) |
| | | Mild | 0 | 0 |
| | | Moderate/Severe | 0 | 0 |
| | Moderate/Severe | Normal | 0 | 1 (10.0) |
| | | Mild | 3 (30.0) | 6 (60.0) |
| | | Moderate/Severe | 7 (70.0) | 1 (10.0) |

TABLE 59

Change in Fatigue Status of Patients from baseline to Week 4 (Mental Domain):

| Visit | Baseline Category | Post-Baseline Category | Placebo BID (N = 10) | LIVRQNac Test Article 33.9g BID (N = 10) |
|---|---|---|---|---|
| Baseline | Normal | | 0 | 0 |
| | Mild | | 3 (30.0) | 2 (20.0) |
| | Moderate/Severe | | 7 (70.0) | 8 (80.0) |
| Week 4 | Normal | Normal | 0 | 0 |
| | | Mild | 0 | 0 |
| | | Moderate/Severe | 0 | 0 |
| | Mild | Normal | 0 | 0 |
| | | Mild | 3 (30.0) | 2 (20.0) |
| | | Moderate/Severe | 0 | 0 |
| | Moderate/Severe | Normal | 0 | 0 |
| | | Mild | 0 | 4 (40.0) |
| | | Moderate/Severe | 7 (70.0) | 4 (40.0) |

In the LIVRQNac Test Article Group, 8 out of 10 subjects showed clinically significant improvement (Baseline: mean=10.10, SD=1.595, and the change at Week 4: mean=−4.00, SD=4.000, with 9500 CI) compared to 3 of 10 subjects in the Placebo Group (Baseline: mean=10.30 SD=1.059, and the change at Week 4: mean=−0.50, SD=0.850, with 95% CI), at Week 4 (P=0.0698) (Fisher's exact test).

A point of interest is that in the LIVRQNac Test Article Group, 2 out of 10 subjects had normal scores, compared to 0 out of 10 subjects in the Placebo Group, on the CFQ-11 Scale at Week 4. The difference was not statistically significant.

Furthermore, these results were analyzed for any improvement (Responders Analysis), which indicated that 10 out of 10 subjects in the LIVRQNac Test Article Group showed improvement in the Total score versus 6 out 10 subjects in the Placebo Group (P=0.0867), 7 out of 10 subjects in LIVRQNac Test Article Group showed improvement in the Mental Domain versus 2 out of 10 subjects in the Placebo Group (P=0.0698) (Fisher's exact test). Although the differences in the Physical Domain did not show statistical significance between the two Groups on the Likert scoring, a trend was observed by the Bimodal scoring (P=0.0698).

It is noteworthy that the results of the subjects in the LIVRQNac Test Article Group showed greater shifts from Moderate/Severe to Mild, from Baseline to Week 4 in both the Physical and the Mental Domains.

Conclusion

The overall results from this analysis from this study in patients with moderate to severe fatigue related to long COVID suggest that LIVRQNac is effective in providing clinically meaningful benefit by improving the patient's symptom of fatigue using a well-defined and a reliable patient reported outcome instrument, and may be useful for the treatment of patients with persistent fatigue after COVID-19 infection (variously called post-acute sequalae of COVID [PASC], or long COVID).

Example 13: Six Minute Walk Test

The results for the 6 MWT, measured as described Example 12, showed that there was no significant change from Baseline in the LIVRQNac Test Article Group versus the Placebo Group in the distance walked at Week 4 whether calculated as absolute change in distance or percent predicted. The mean 6 MWT was 533 M±106 M, or approximately 85% predicted with approximately one quarter of subjects below the 75% of the predicted distance based on age or gender; these results are consistent with the literature. These results may be due to the relatively short duration of the study (4 weeks) and the unexpected severity and magnitude of fatigue encountered by this patient population.

Example 14: Magnetic Resonance Spectroscopy

PCr results, measured as described Example 12, indicated an unexpectedly large variation in both Baseline and deviation from the mean (mean 84.56 sec±30.816). There was no difference in the change from Baseline in PCr between the LIVRQNac Test Article Group and the Placebo Group at Week 4 as examined by both absolute and percent change, whether unadjusted or adjusted statistical models were used. There was no correlation with either Fatigue score or 6-MWT.

Additional MRS assessments showed positive trending changes in the LIVRQNac Test Article Group from Baseline as compared to the Placebo Group at Week 4 including; Intramyocellular Lipid Content: LIVRQNac Test Article Group (Baseline mean=0.42, Week 4 change=−0.17) versus Placebo Group (Baseline mean=0.36, Week 4 change=0.16), Peak Lactate: LIVRQNac Test Article Group (Baseline mean=1.74, Week 4 change=−0.53) versus Placebo Group (baseline mean=2.11, Week 4 change=−0.20), and Carnosine: LIVRQNac Test Article Group (Baseline mean=4.43, Week 4 change=0.78) versus Placebo Group (Baseline mean=4.38, Week 4 change=−0.56).

The safety results in this analysis of the first 20 subjects showed no safety issues in the LIVRQNac Test Article Group: two subjects had the adverse events of abdominal pain, and headache which were mild and resolved. There were two adverse events of diarrhea (one in subject with upper respiratory infection), and the other one in subject with nasal congestion, nausea post MRI. One subject had COVID. In the Placebo Group, there was an increase in liver function tests which was most likely related to concomitant medications. These results proved a benign safety and tolerability profile for LIVRQNac which is consistent with the published literature on LIVRQNac constituent AAs and safety data gathered from other clinical studies conducted with LIVRQNac in NASH.

Example 15: Method of Producing the Amino Acid Compositions

The amino acid compositions of the instant disclosure and formulations thereof may be made according to methods known in the art. They may also be made by the methods described below.

The starting materials (individual amino acids and excipients) are blended, milled and dry granulated to generate a powder blend, which is filled into stick packs or sachets. The contents of the stick packs or sachets are dispersed in water at time of use for oral administration. An example of the formulations made thereby, is provided below in Table 60.

TABLE 60

Exemplary composition comprising amino acids

| Ingredient | Formulation dry weight (g) | Dry Weight % wt/wt |
|---|---|---|
| L-Leucine | 2.0000 | 14.85 |
| L-Isoleucine | 1.0000 | 7.42 |
| L-Valine | 1.0000 | 7.42 |
| L-Arginine HCl [1] | 3.6280 | 26.94 |
| L-Glutamine | 4.0000 | 29.70 |
| N-Acetyl-L-cysteine | 0.3000 | 2.23 |
| Amino Acids (-HCl) | 11.3000 | 83.90 |
| Citric Acid | 0.4000 | 2.97 |
| Soybean Lecithin | 0.3000 | 2.23 |
| Xanthan Gum 180 | 0.2000 | 1.48 |
| Sucralose | 0.0300 | 0.22 |
| Orange Flavor | 0.2000 | 1.48 |
| N-C Custard Type Flavor | 0.0500 | 0.37 |
| FD&C Yellow No 6 | 0.0090 | 0.07 |
| Low-Substituted Hydroxypropyl Cellulose | 0.1000 | 0.74 |
| Silicon Dioxide | 0.1320 | 0.98 |
| Magnesium Stearate | 0.0200 | 0.15 |
| Disodium EDTA | 0.1000 | 0.74 |
| Total | 13.4690 | 100.00 |

Example 16: Plasma Biomarkers in Clinical Trial Samples from Long COVID Subjects Treated with LIVRQNac This example demonstrates an improvement in PASC biomarkers in human subjects upon treatment with LIVRQNac.

In order to develop a mechanistic understanding of LIVRQNac bioactivities in subjects from the study in Example 12 above, serum and plasma samples were collected at Visit 2 (baseline; BL) and Visit 4 (end of trial: EOT). Samples were processed using various methodologies to assess the serum/plasma levels of numerous exploratory biomarkers selected based on published literature and internal research. The biomolecules evaluated represent markers of relevant disease pathophysiologies, including inflammation, mitochondrial function, metabolism, skeletal muscle and endothelial dysfunction.

The data presented below reflect analyses conducted on samples available at the time of the analysis of the first 20 subjects in the study shown in Example 12, or at End of Trial (EOT), with samples from all 41 subjects from that study. For all markers, data are expressed as change from BL at EOT to correct for potential intrinsic (treatment unrelated) differences between treatment and placebo groups. The statistical test applied is Wilcoxon (Mann-Whitney), a non-parametric test based on ranks. This approach has less statistical power than a parametric test but is more conservative, as it avoids spurious conclusions based on inadequacy of a distribution model.

LIVRONac Increases Plasma Levels of MOTS-c Peptide

Background:

MOTS-c (Human Mitochondrial Open Reading Frame Of The 12S rRNA-c) is a recently discovered mitochondrially-encoded signaling peptide that primarily targets skeletal muscle and contributes to metabolic homeostasis (Lee et al., 2015, supra). MOTS-c exerts its activities by modulating the folate-methionine cycle leading to an accumulation of AICAR, increased NAD+ levels and AMPK activation (Lee et al., 2016, supra). Metabolic and oxidative stress stimulate translocation of MOTSc to the nucleus where it modulates gene expression to restore homeostasis by improving glucose and lipid metabolism and reducing oxidative stress and inflammation (Benayoun and Lee, 2019, supra; Rochette et al., 2021, supra; Yoon et al., 2022, supra). Decreased circulating MOTS-c concentrations are associated with metabolic diseases and aging, whereas exercise induces upregulation of MOTS-c in skeletal muscle and the systemic circulation (Merry et al., 2020, supra; Miller et al., 2021, supra; Reynolds et al., 2021, supra; Yoon et al., 2022, supra). Administration of exogenous MOTS-c in preclinical models promotes improvement in metabolic disorders including obesity, diabetes and cardiovascular disease, as well as age-related physical decline (Merry et al., 2020, supra; Dabravolski et al., 2021, supra; Reynolds et al., 2021, supra). Within skeletal muscle, MOTS-c has been shown to improve metabolism, promote resistance of myoblasts to metabolic stress (Reynolds et al., 2020), reduce myostatin expression and inhibit atrophic signaling pathways resulting from a high-fat diet (Reynolds et al., 2021, supra).

Although MOTS-c remains insufficiently studied in the context of SARS-Cov-2 induced pathophysiology, significantly reduced levels of MOTS-c and another mitochondrial peptide, humanin, were recently described in neuronal and astrocyte-derived extracellular vesicles (EV) of Long COVID patients with neuropsychiatric manifestations (Peluso et al., 2022, supra). In contrast, the SARS-Cov-2 S1 subunit and nucleocapsid (N) proteins were elevated in EVs, indicating that S1, N, humanin and MOTS-c might serve as diagnostic biomarkers for Long COVID and efficacy markers for novel Long-COVID therapeutics. Given its prominent role in metabolic homeostasis and fatigue-relevant physiological processes, MOTS-c concentrations were measured in plasma samples from the first 20 subjects in the study described in Example 12 above.

Methods:

Plasma concentrations of MOTS-c were analyzed by ELISA (Abclonal, Woburn, Mass.). Despite ELISA optimization to establish appropriate sample dilutions, many samples fell above the linear range of the assay. Therefore, only seven samples were available for the MOTS-c statistical analysis (five treatment and two placebo).

Figure 10A:
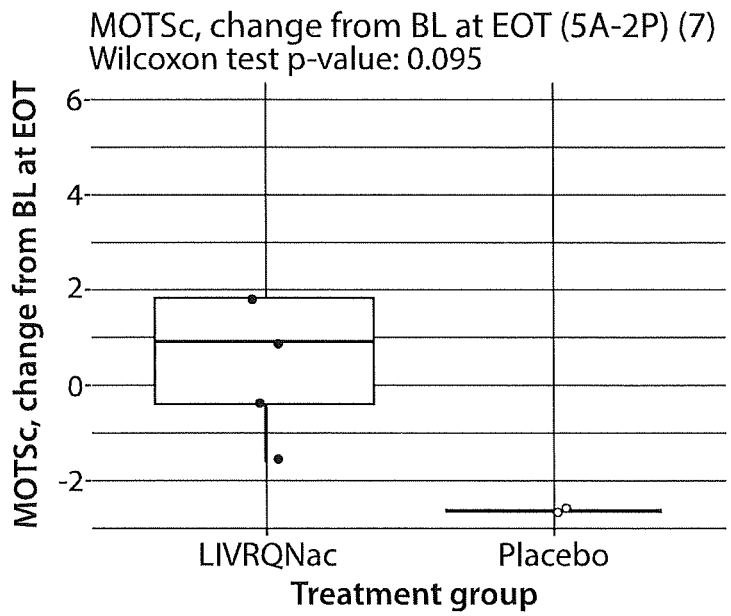
FIG. 10A is a box plot showing the change in plasma concentrations of MOTS-c from baseline (BL) to end of trial (EOT). The data reflect a strong trend toward increased MOTS-c plasma concentrations with 28 day LIVRQNac treatment but not with placebo.
Figure 10B:
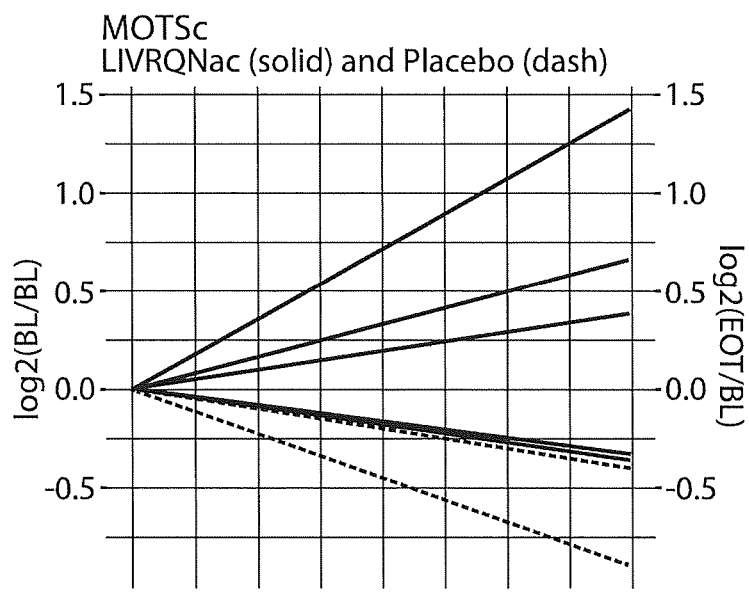
FIG. 10B is a graph showing the change in plasma MOTS-c over time for individual subjects.

Results:

Despite the limited sample number, statistical analysis of the data yielded a Wilcoxon test p-value of 0.095, which is the smallest p-value possible in a comparison with five treated versus two placebo subjects (FIG. 10A). These data thus reflect a strong trend toward increased MOTS-c plasma concentrations with 28 day LIVRQNac treatment but not with placebo. In both placebo subjects, MOTS-c plasma concentrations decreased over time, while three of the five treated subjects exhibited a pronounced increase in plasma MOTS-c concentrations (FIG. 10B). In two treated subjects, plasma MOTS-c concentrations decreased. However, since the amplitude of the decrease was small relative to placebo, there is perfect separation between LIVRQNac and placebo in terms of ranks. Bootstrap simulations ($10^5$), based on values observed with 10 treated and 10 placebo samples (including out-of-range values), yielded a 92% likelihood of $p<0.05$ with 20 treated and 20 placebo samples (full study data).

These data suggest that LIVRQNac treatment might be triggering increased production of MOTS-c and contributing to the improvement in study subject PROs by resolving mitochondrial and metabolic dysfunction and/or reducing oxidative stress.

LIVRQNac Decreases Serum Levels of $CO_2$

Background:

$CO_2$ is a byproduct of metabolic processes involved in ATP production. Blood delivers oxygen to tissues to support ATP production and removes $CO_2$; $CO_2$ is then exhaled through the lungs during respiration. $CO_2$ is often measured clinically as part of a basic metabolic or electrolyte panel. Abnormal $CO_2$ values might represent lung or kidney dysfunction or indicate a wide range of conditions including metabolic disease.

Methods:

Serum concentrations of $CO_2$ (measured as bicarbonate) were analyzed by photometry. Samples from all 41 subjects from the study described in Example 12, above, fell within the quantifiable range of the assay, enabling estimation of Wilcoxon test p-values for changes in $CO_2$ levels at EOT versus baseline in Treatment and Placebo groups.

Figure 11A:
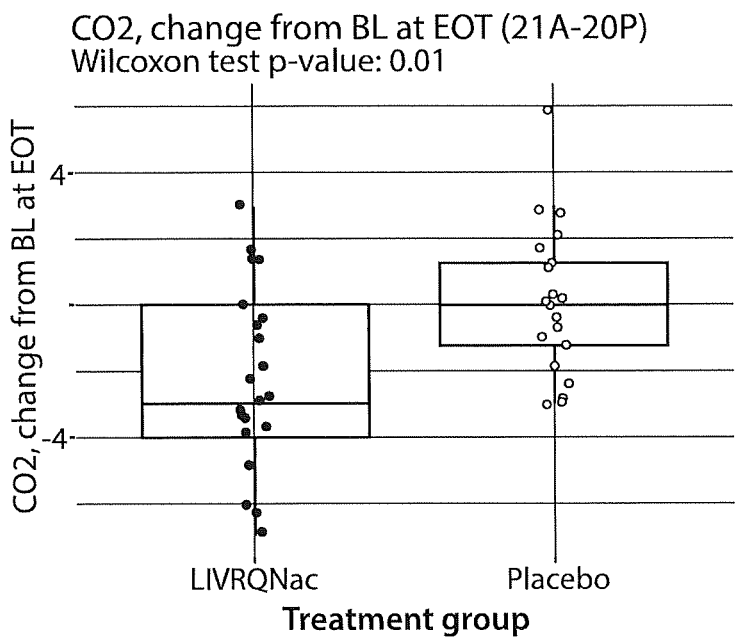
FIG. 11A is a box plot showing the change in serum concentrations of CO2 from baseline (BL) to end of trial (EOT). The data show a decreased serum CO2 level relative to baseline in LIVRQNac treated subjects, while in the placebo group CO2 appeared to increase (p=0.054).
Figure 11B:
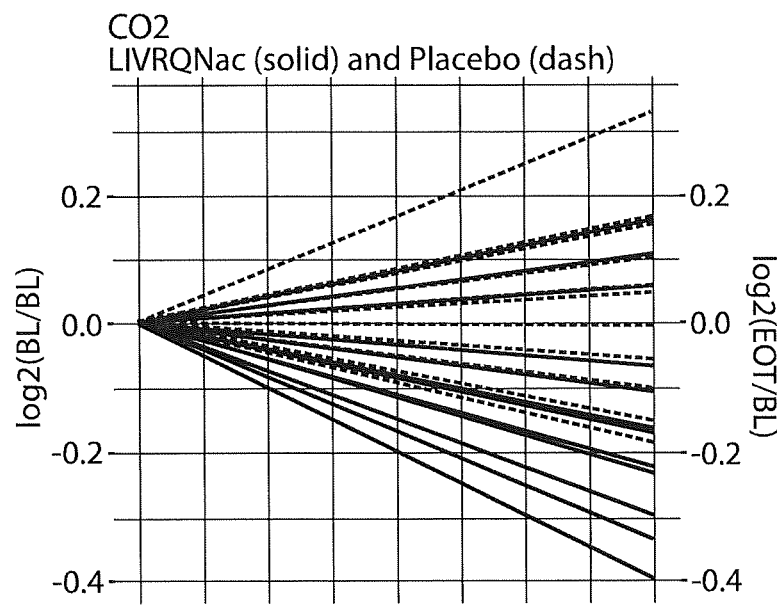
FIG. 11B is a graph showing the change in serum CO2 over time for individual subjects.

Results:

Changes in serum $CO_2$ levels at EOT versus BL in Treatment and Placebo groups was determined (FIG. 11A). In LIVRQNac treated subjects, serum $CO_2$ levels decreased relative to baseline, while in the placebo group, $CO_2$ appeared to increase (p=0.054). Change from BL to EOT in individual study subjects in FIG. 11B. A clear trend is observed toward a higher number of LIVRQNac treated subjects that exhibit decreasing serum $CO_2$ levels versus placebo. Bootstrap simulations ($10^5$), based on values observed with 10 treated and 10 placebo samples, yield an 85% likelihood of p<0.05 with 20 treated and 20 placebo samples.

These data suggest that LIVRQNac treatment promotes a decrease in plasma $CO_2$ in Long COVID subjects. The mechanism behind this reduction requires additional study. The data might reflect a shift in metabolic fuel source from glucose to lipids, as less $CO_2$ is generated through ATP production from fatty acids versus carbohydrates. Alternatively, it is possible that LIVRQNac-driven improvements in endothelial health (as described below) might promote improved gas exchange in the pulmonary microvasculature.

LIVRONac Decreases Serum Levels of sVCAM-1

Background:

Vascular cell adhesion molecule 1 (VCAM-1) is expressed on the surface of endothelial cells and facilitates adhesion of inflammatory cells through interaction with leukocyte integrins (Smadja et al., 2021, supra). Constitutive expression of VCAM-1 is low in healthy individuals but upregulated on the cell surface in response to inflammatory conditions, including COVID-19 (Ambrosino et al., 2022, supra). Increases in circulating VCAM-1 (soluble VCAM-1; sVCAM-1) is a marker of vascular inflammation and endothelial activation. In COVID-19 patients, elevated sVCAM-1 levels are associated with higher viral load, greater disease severity and increased mortality (Bermejo-Martin et al., 2020, supra; Tong et al., 2020, supra; Birnhuber et al., 2021, supra; Spadaro et al., 2021, supra; Vieceli Dalla Sega et al., 2021, supra). Recently, platelet-derived and endothelial-cell-derived microparticles from intubated COVID-19 patients have been shown to induce VCAM-1 expression and apoptosis in in vitro cultured endothelial cells (Garnier et al., 2021, supra). Given its potential role as a biomarker of COVID-19 induced vascular dysfunction, sVCAM-1 concentrations were measured in plasma samples from subjects in the study described in Example 12 above.

Methods:

Serum concentrations of VCAM-1 were analyzed by electrochemiluminescence immunoassay (ECLIA) at the MedPace Central Laboratory (MRL, United States). Samples from all 41 subjects from the study described in Example 12 fell within the quantifiable range of the assay, enabling estimation of a Wilcoxon test p-value.

Figure 12A:
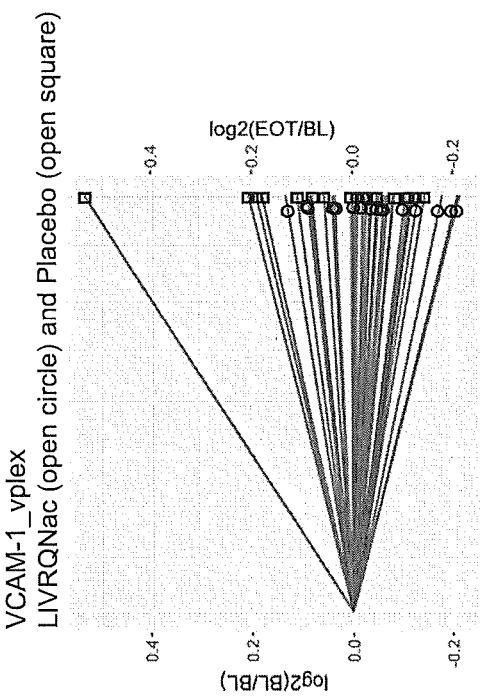
FIG. 12A is a box plot showing the change in serum concentrations of VCAM-1 from baseline (BL) to end of trial (EOT). The data show a decreased serum VCAM-1 level relative to baseline in LIVRQNac treated subjects, while in the placebo group a trend toward increased VCAM-1 was observed (p=0.017).
Figure 12B:
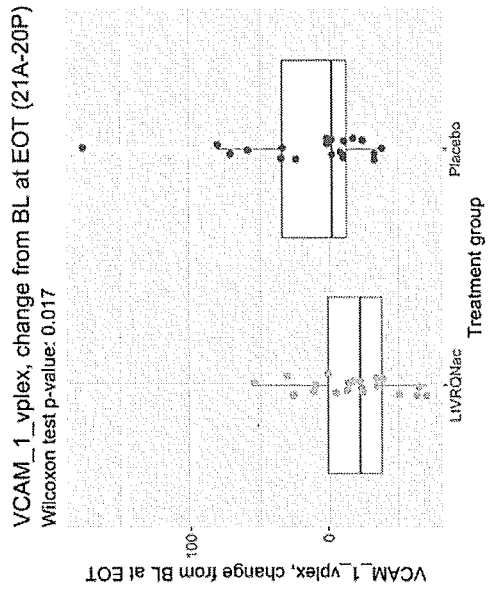
FIG. 12B is a graph showing the change in serum VCAM-1 over time for individual subjects.

Results:

Changes in serum VCAM-1 levels at EOT versus BL in Treatment and Placebo groups was determined (FIG. 12A). In LIVRQNac treated subjects, serum VCAM-1 levels decreased relative to baseline, while in the placebo group a trend toward increased VCAM-1 was observed (p=0.017). A clear trend was observed in the change from BL to EOT within individual subject with regard to decreasing VCAM-1 in treated subjects versus placebo (FIG. 12B).

These data suggest that LIVRQNac treatment could reduce expression of VCAM-1 in the endothelium of Long COVID study subjects. It is possible that LIVRQNac could act directly on the activated endothelium to reduce the inflammatory state and downregulate VCAM-1. Alternatively, LIVRQNac could act indirectly by diminishing the systemic inflammation that triggers VCAM-1 expression. Additional studies will be planned to better address LIVRQNac mechanism-of-action.

Example 17: LIVRONac Reduces Oxidative Stress in Skeletal Muscle Cells

Skeletal muscle is a major storage organ for carbohydrates and amino acids and one of the primary sources of energy production in the human body. Numerous studies have shown that the musculoskeletal system is detrimentally affected by COVID-19 leading to fatigue, myalgia and muscle weakness (De Giorgio et al., ("The impact of SARS-CoV-2 on skeletal muscles." Acta Myol 39(4): 307-312, 2020); Seixas et al., ("Unraveling Muscle Impairment Associated With COVID-19 and the Role of 3D Culture in Its Investigation." Front Nutr 9:825629, 2022)). Moreover, these symptoms frequently persist well beyond the acute stage of COVID-19 (dos Santos et al., ("The Musculoskeletal Involvement After Mild to Moderate COVID-19 Infection." Front Physiol 13:813924, 2022); Soares et al., 2022). One potential mechanism by which skeletal muscle might be impacted in COVID-19 is by direct binding of SARS-CoV-2 to the ACE2 or TMPRSS2 receptors. However, the ability of SARS-CoV-2 to directly infect skeletal muscle has not yet been clearly demonstrated. Alternatively, skeletal muscle dysfunction might be triggered indirectly by the aberrant inflammatory environment present during COVID-19 and Long COVID (Mehandru and Merad, ("Pathological sequelae of long-haul COVID." Nat Immunol 23(2): 194-202, 2022)). Cytokines elevated in COVID-19 and Long COVID, such as IL-6, IL-8, IFN-γ and TNF-α, promote muscle fiber proteolysis, and inhibit protein synthesis and myogenesis (dos Santos et al., 2022, supra). Excessive release of cytokines are also correlated with an increase in ROS production leading to oxidative stress, which in turn amplifies the inflammatory response (Cecchini and Cecchini, 2020).

An in vitro model of Long COVID was established using primary human iPSC-derived skeletal muscle cells at three distinct stages of differentiation. Multiple disease-relevant stimuli were applied including IL-8, TNF-α and a recombinant SARS-Cov-2 spike S1 subunit.

Methods

Coating Plates for IPSC and Skeletal Muscle Lines:

500 µl of Geltrex™ Matrix solution was diluted in 50 mL of pre-chilled (4° C.) DMEM/F-12 medium (1% final concentration). 1.5 mL of diluted geltrex was used to coat each well of a 6 well plate.

Coated plates were incubated at 37° C. for 30 to 60 minutes.

Geltrex matrix solution was aspirated before platting the cells in pre-equilibrated cell culture medium.

Thawing and maintaining IPSC lines: IPSC lines were plated in pre-warmed mTser plus media containing 10 uM ROCK Inhibitor on the geltrex coated plate.

24 hrs later, media was switched to mTser Plus media without ROCK Inhibitor.

Cells were passaged after 5 days or when they reached approximately 80% confluence, with 90% undifferentiated cells.

Skeletal Muscle Differentiation from Human iPSC

To generate stage 1 myogenic precursor cells:

IPSCs were pretreated with 10 µM ROCK Inhibitor for 1 hrs at 37° C.

Cells were detached using ACCUTASE™ for 5-10 minutes at 37° C.

IPSCs cell were seeded at 5000 to 10000/cm^2 density in Muscle Induction medium (Amsbio SKM01) on geltrex coated plates. Media was changed every other day.

To generate stage 2 myoblast cells:

Stage 1 cells were detached using 0.25% trypsin-EDTA for 5 min at 37° C.

IPSCs cell were seeded at 5000 to 10000/cm^2 density in Myoblast Medium (Amsbio SKM02) on geltrex coated plates. Media was changed every other day.

To generate stage 3 myotubes:

SKM02 media was completely removed when stage 2 cells reached 80-90% confluence, which is around 6-8 days post-seeding stage 2 myoblast.

Cells were grown in Myotube Medium (Amsbio SKM03) for 6 to 8 days. Media was changed every other day.

Disease Stimulus and LIVRQNac Treatment

TNF-α, IL-8 and a recombinant SARS-Cov-2 spike S1 subunit were used as disease stimuli in 15 ng/ml, 50 ng/ml, and 10 µg/ml concentrations, respectively. Stimuli were prepared in 1×DMEM medium with defined custom AA concentrations (HLMVEC 1×HMDB) to reflect healthy human plasma (as per values published in the Human Metabolome Database). Treatment medium was prepared with either PBS (Vehicle) or LIVRQNac added at specified fold concentrations (7.5× or 15×) above plasma level (1× is L-Leucine: 152.7 µM; L-Isoleucine: 66.4 µM; L-Valine: 234.2 µM; L-Arginine: 108.8 µM; L-Glutamine: 46.8 µM [below plasma level]; N-acetylcysteine: 250 µM [not endogenous]). Cells were treated with disease stimuli and LIVRQNac for 24 hrs prior to running assays.

Oxidative Stress Measurement (CELLROX Green)

Cells were treated with 5 µM CELLROX (Invitrogen) in 1×DMEM medium for 30 min 37° C. and fixed with 4% PFA for 5 min. Cells were then washed once with 1×PBS and stained with DAPI for 10 min. Cells were imaged using FITC and DAPI filter on ImageXpress Micro Confocal high-content imaging system from Molecular Devices. Integrated intensity was measured using a multiwavelength scoring program using MetaXpress software.

Figure 13:
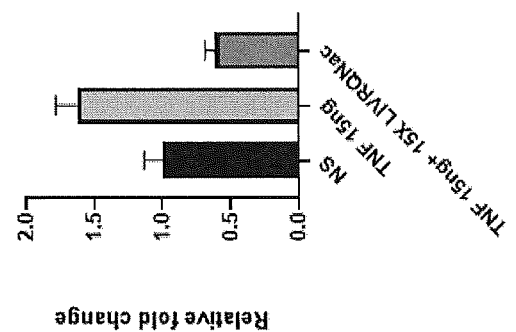
FIG. 13 is a bar graph showing the relative fold change in the level of oxidative stress in stage 2 skeletal muscle. The data show a reduced ROS content in stage 2 cells following 24 hour treatment with TNF-α and subsequent LIVRQNac.
Figure 14:
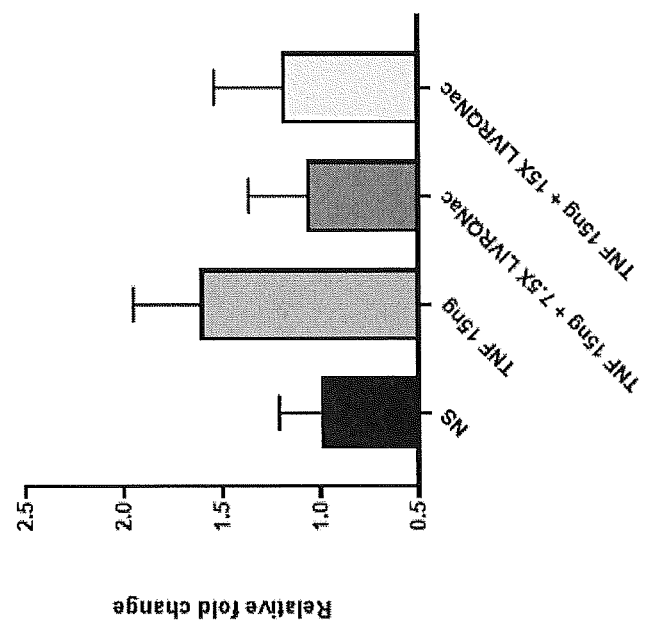
FIG. 14 is a bar graph showing the relative fold change in the level of oxidative stress in stage 2 skeletal muscle. The data show a reduced ROS content in stage 2 cells following 24 hour treatment with TNF-α and subsequent LIVRQNac.

Results:

LIVRONac Decreases Oxidative Stress in Stage 2 (Myoblasts) Skeletal Muscle Cells Two independent experiments using Stage 2 myoblasts were performed (FIGS. 13 and 14). Data are graphed as the relative fold change in the integrated intensity of CELLROX inside the Stage 2 cells following 24 hour treatment with TNF-α, with and without LIVRQNac at 7.5× and 15×. LIVRQNac reduced ROS content in the presence of TNF-α stimulation.

Example 18: Endothelial HLMVEC Cell Experiments

Rationale:

Vascular dysfunction is now well-established as a significant pathophysiology underlying COVID-19 and Long COVID (Jin et al., ("Endothelial activation and dysfunction in COVID-19: from basic mechanisms to potential therapeutic approaches." Signal Transduct Target Ther 5(1): 293, 2020); Pretorius et al., 2021; Wang et al., ("Long COVID: The Nature of Thrombotic Sequelae Determines the Necessity of Early Anticoagulation." Front Cell Infect Microbiol 12: 861703, 2022); Korompoki et al., ("Late-onset hematological complications post COVID-19: An emerging medical problem for the hematologist." Am J Hematol 97(1): 119-128, 2022); Flaumenhaft et al., ("Vasculopathy in COVID-19." Blood, 2022)). It remains undetermined whether the vascular endothelium is subject to direct viral infection or whether the rise in inflammatory cytokines or other circulating mediators in response to SARS-CoV-2 infection are the main triggers of endothelial activation and injury (Bernard et al., 2021; Flaumenhaft et al., 2021). Regardless, endothelial cells (EC), which contribute to vascular health during homeostasis, appear to undergo functional changes during COVID-19, leading to pathological angiogenesis (Ackermann et al., ("Pulmonary Vascular Endothelialitis, Thrombosis, and Angiogenesis in Covid-19." N Engl J Med 383(2): 120-128, 2020); Smadja et al., 2021, supra), increased adhesion and infiltration of leukocytes, a pro-coagulatory state, and tissue hypoxia (Madureira and Soares, ("The misunderstood link between SARS-CoV-2 and angiogenesis. A narrative review." Pulmonology, 2021). The endothelial damage incurred during acute COVID-19 can persist, leading to prolonged activation of these disease manifestations and contributing to the development of Long COVID (Fogarty et al., ("Persistent endotheliopathy in the pathogenesis of long COVID syndrome." J Thromb Haemost 19(10): 2546-2553, 2021)).

Dysregulation of numerous proteins associated with endothelial activation have been documented in COVID-19 and Long COVID (Hadid et al., 2022). For instance, elevated blood levels of fibronectin, which plays an important role in coagulation (Hansen, "Fibronectin and coagulation factor XIII increases blood platelet adhesion to fibrin." Thromb Res 34(6): 551-556, 1984) and can lead to excessive extracellular matrix deposition and impaired pulmonary gas exchange (Proal and VanElzakker, ("Long COVID or Post-acute Sequelae of COVID-19 (PASC): An Overview of Biological Factors That May Contribute to Persistent Symptoms." Front Microbiol 12:698169, 2021)) are associated with COVID-19 disease severity (Lemanska-Perek et al., ("Fibronectin as a Marker of Disease Severity in Critically Ill COVID-19 Patients." Cells 11(9), 2022)). Likewise, Von Willebrand Factor, which is critical to platelet adhesion and activation and for stabilization of circulating Factor VIII (Cortes et al., (Physiology, Von Willebrand Factor. Stat- Pearls. Treasure Island (FL), 2022)), is elevated in COVID-19 and Long COVID and associated with increased disease severity and reduced exercise endurance (Ladikou et al., ("Von Willebrand factor (vWF): marker of endothelial damage and thrombotic risk in COVID-19?" Clin Med (Lond) 20(5): e178-e182, 2020); Prasannan et al., "Impaired exercise capacity in post-COVID-19 syndrome: the role of VWF-ADAMTS13 axis." Blood Adv 6(13): 4041-4048, 2022)). Activated EC recruit leukocytes by upregulating the expression of adhesion proteins and secrete numerous cytokines (Sprague and Khalil, ("Inflammatory cytokines in vascular dysfunction and vascular disease." Biochem Pharmacol 78(6): 539-552, 2009)), thus contributing to local and systemic immune regulation.

Persistent exposure to an inflammatory, thrombotic or hypoxic environment can trigger rapid formation of new blood vessels by a process termed intussusceptive angiogenesis (IA) (Nagy et al., ("VEGF-A and the induction of pathological angiogenesis." Annu Rev Pathol 2: 251-275, 2007); Jeong et al., ("Pathological angiogenesis and inflammation in tissues." Arch Pharm Res 44(1): 1-15, 2021)). Although this compensatory vascular response has been observed in the context of various pathologies (De Spiegelaere et al., ("Intussusceptive angiogenesis: a biologically relevant form of angiogenesis." J Vasc Res 49(5): 390-404, 2012)), it appears to be more prevalent in COVID-19 relative to other respiratory viruses, such as influenza, and could lead to aberrant blood flow (Ackermann et al., 2020, supra). Significant literature supports the role of growth factors such as platelet-derived growth factors (PDGF), vascular endothelial growth factors (VEGF), fibroblast growth factors (FGF) and angiopoietins (Meini et al., ("Intussusceptive angiogenesis in Covid-19: hypothesis on the significance and focus on the possible role of FGF2." Mol Biol Rep 47(10): 8301-8304, 2020)). Members of all these growth factor families have been found at elevated levels in COVID-19 and are associated with disease severity (Smadja et al., ("Angiopoietin-2 as a marker of endothelial activation is a good predictor factor for intensive care unit admission of COVID-19 patients." Angiogenesis 23(4): 611-620, 2020); Henry et al., ("Circulating level of Angiopoietin-2 is associated with acute kidney injury in coronavirus disease 2019 (COVID-19)." Angiogenesis 24(3): 403-406, 2021); Villa et al., ("Dynamic angiopoietin-2 assessment predicts survival and chronic course in hospitalized patients with COVID-19." Blood Adv 5(3): 662-673, 2021); Nossent et al., ("Pulmonary Procoagulant and Innate Immune Responses in Critically Ill COVID-19 Patients." Front Immunol 12:664209, 2021); Petrey et al., ("Cytokine release syndrome in COVID-19: Innate immune, vascular, and platelet pathogenic factors differ in severity of disease and sex." J Leukoc Biol 109(1): 55-66, 2021; Vassiliou et al., ("ICU Admission Levels of Endothelial Biomarkers as Predictors of Mortality in Critically Ill COVID-19 Patients." Cells 10(1), 2021)).

Given their critical role in regulating physiological processes impacted by COVID-19, EC are a highly logical cell type for evaluation of disease mechanism-of-action and for evaluations of therapeutic efficacy. Of particular interest are primary human lung microvascular endothelial cells (HLMVECs), as this EC subtype is most proximal to the site of initial infection and SARS-CoV-2 mediated damage to the lung microvascular endothelium has been previously reported (Ackermann et al., 2020, supra; Tarnawski and Ahluwalia, ("Endothelial cells and blood vessels are major targets for COVID-19-induced tissue injury and spreading to various organs." World J Gastroenterol 28(3): 275-289, 2022)). While the question of direct viral infection and replication in the endothelium remains unresolved in COVID-19 patients, studies have demonstrated that primary endothelial cells undergo a pathological response in vitro when exposed to SARS-CoV-2 components and COVID-19 relevant inflammatory stimuli (Flaumenhaft et al., 2022; Ma et al., ("A human pluripotent stem cell-based model of SARS-CoV-2 infection reveals an ACE2-independent inflammatory activation of vascular endothelial cells through TLR4." Stem Cell Reports 17(3): 538-555, 2022)).

A series of in vitro experiments was conducted to evaluate the effect of LIVRQNac on this phenotypically relevant cell type. HLMVECs were exposed to disease stimuli relevant to COVID-19 and Long COVID, including the inflammatory cytokines IL-8 and TNFα, and a recombinant SARS-Cov-2 spike S1 subunit. The response of the cells to disease stimuli was evaluated along with the efficacy of LIVRQNac in reversing disease phenotypes.

Methods:

Cell Culture and Treatment

One donor of HLMVEC (LONZA, Lot #18TL065690) was grown in Lonza EGM-2MV media prepared with Endothelial Basal Medium (LONZA) and EGM-2MV SingleQuot (LONZA). Cells were grown to 80-90% confluence before passaging or plating. Cells were plated at Passage 7 at 6000 cells/well on 96-well plates and kept in EGM-2MV media overnight. Throughout the study cells were incubated at 37° C./5% $CO_2$.

Cells were treated for 24 hr in a Custom Media prepared with an AA-Free Endothelial Basal Medium MCDB 121 (US Biologicals), containing defined custom AA concentrations that matched those found in healthy human plasma (values published in the Human Metabolome Database; HLMVEC 1×HMDB). This custom media was supplemented as needed with stimuli associated with COVID-19 and Long COVID (1.5-15 ng/mL TNFα (Invitrogen), 5-50 ng/mL IL-8 (R&D Systems), and 1-10 µg/mL recombinant SARS-Cov-2 spike S1 subunit (R&D Systems)) and either PBS (Vehicle) or LIVRQNac were added at specified fold concentrations above plasma level (1× is L-Leucine: 152.7 µM; L-Isoleucine: 66.4 µM; L-Valine: 234.2 µM; L-Arginine: 108.8 µM; L-Glutamine: 46.8 µM [below plasma level]; N-acetylcysteine: 250 µM [not endogenous]). After treatment, supernatants were collected and stored at −80° C. Cells were fixed in 4% Paraformaldehyde for 5-10 min. Cells were stained and imaged no more than 10 days after fixation.

Cell Staining

Cells were first blocked with 1% BSA in 0.5% Triton X/PBS, then incubated in VWF primary antibody (Abcam) diluted 1:100 in 0.1% BSA/0.5% Triton X/PBS solution overnight at 4° C. Cells were washed after incubation with 0.1% BSA/Triton X/PBS then blocked with goat serum diluted 1:1000 in 1% BSA/0.5% Triton X/PBS for 45 minutes. Serum block was discarded and cells were incubated in goat-anti-rabbit 568 secondary antibody (Invitrogen) diluted 1:500 in 1% BSA/0.5% Triton X/PBS for one hour at room temperature. Secondary antibody solution was then removed, and cells were washed twice with 0.5% Triton X/PBS solution. Cells were incubated in Hoechst diluted 1:2500 in PBS for 30 minutes before imaging or storing at 4° C. Imaging was performed using a Molecular Devices ImageXpress Micro Confocal imaging system and analyzed with the Granularity program in MetaXpress software.

Luminex Panel

Cell Supernatants collected after treatment of HLMVECs were shipped to the Analytical Core Laboratory at Boston University (Boston, Mass.) for analysis. Samples were analyzed using a Luminex Magpix system with the following Luminex kits obtained from Bio-Techne (Minneapolis, Minn.): Human XL Cytokine Luminex Performance Panel 43-Plex (Catalog #FCSTM18-43) and two custom Human Luminex Discovery Assay panels (LXSAHM-18 and LXSAHM-07) designed to evaluate endothelial dysfunction. All assays were performed according to manufacturer protocols.

Results:

LIVRONac Reduces VWF Expression in the Presence or Absence of Disease Stimuli

Cells were stained with Primary—VWF (Abcam), Secondary—Alexa Fluor 568 (Invitrogen) and Hoechst (Invitrogen) for Nuclei. Cell images were captured using high content confocal imaging on a Molecular Devices ImageXpress Micro Confocal imaging system and analyzed using the Granularity program of the MetaXpress software.

Figure 15:
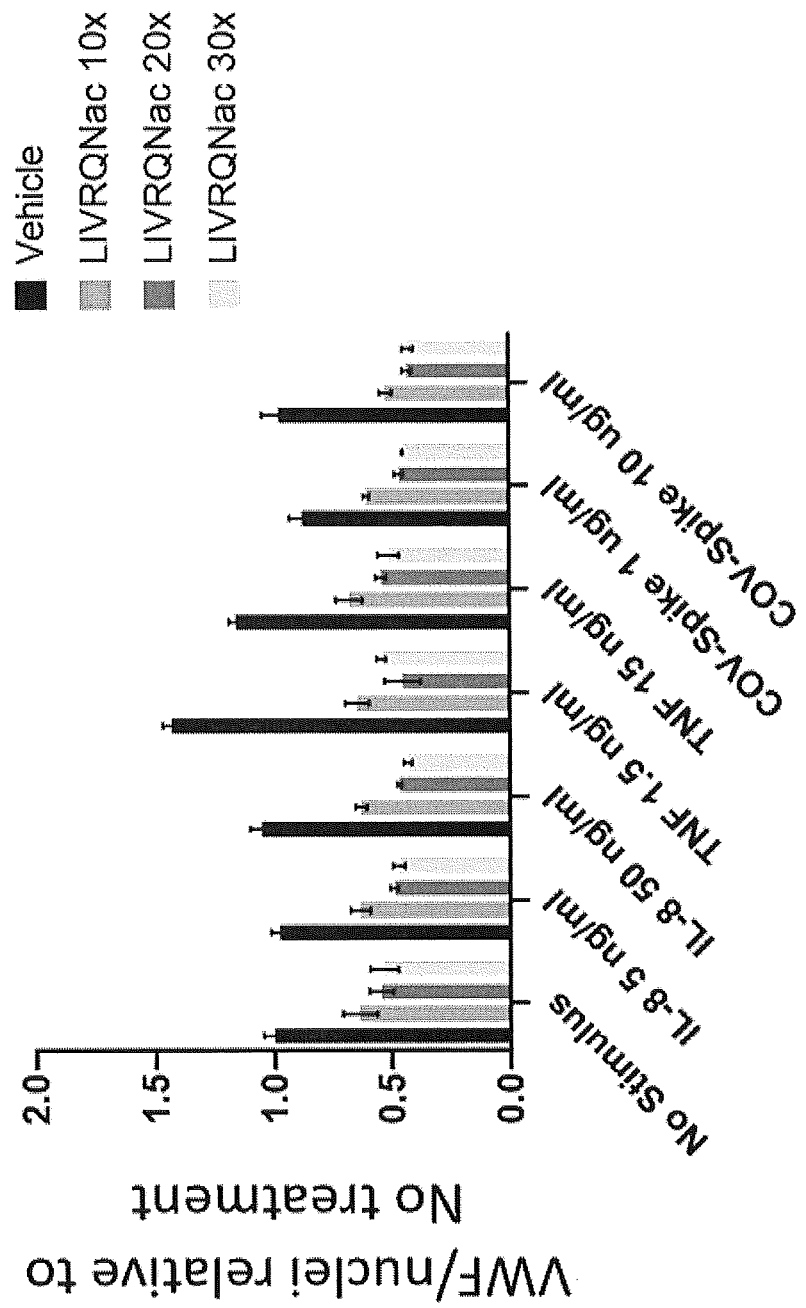
FIG. 15 is a bar graph showing reduced cellular VWF protein expression in a dose-dependent manner in both stimulated and unstimulated cells.
Figure 16:
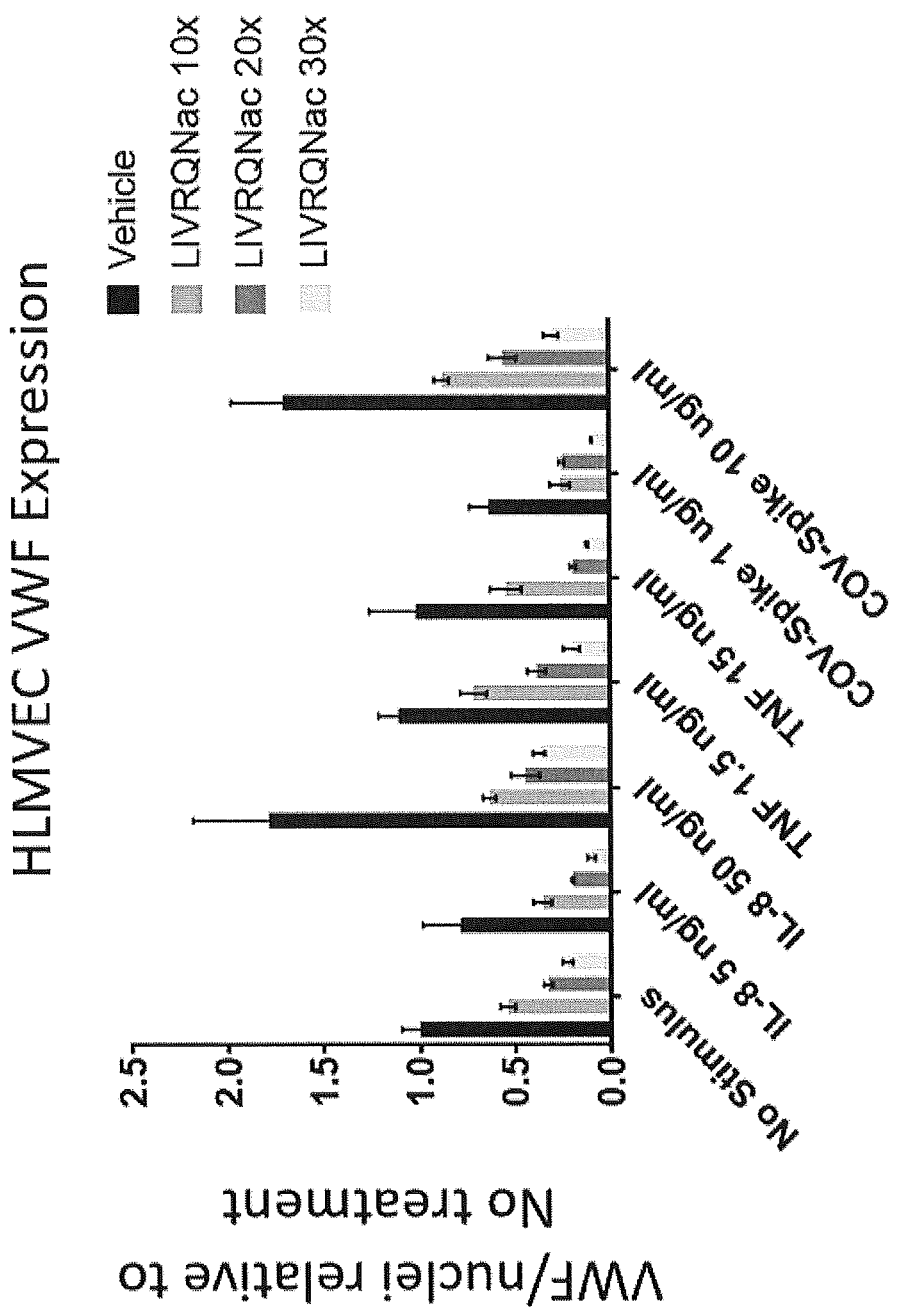
FIG. 16 is a bar graph showing reduced cellular VWF protein expression in a dose-dependent manner in both stimulated and unstimulated cells.

HLMVEC were treated with three different disease stimuli and LIVRQNac as described in Methods. LIVRQNac reduced cellular VWF protein expression in a dose-dependent manner across both experiments, in both stimulated and unstimulated cells. Variability was observed in the response to stimuli, with VWF expression appearing to increase in response to TNF-α in Experiment 1 (FIG. 15) and in response to IL-8 and the recombinant SARS-Cov-2 spike S1 subunit in Experiment 2 (FIG. 16). Data represents the fold change in granules/nuclei relative to the no treatment, no stimulus control condition, with error bars representing standard deviation between replicate wells.

LIVRONac Reduces Expression of Proteins Associated with Endothelial Activation

Figure 17:
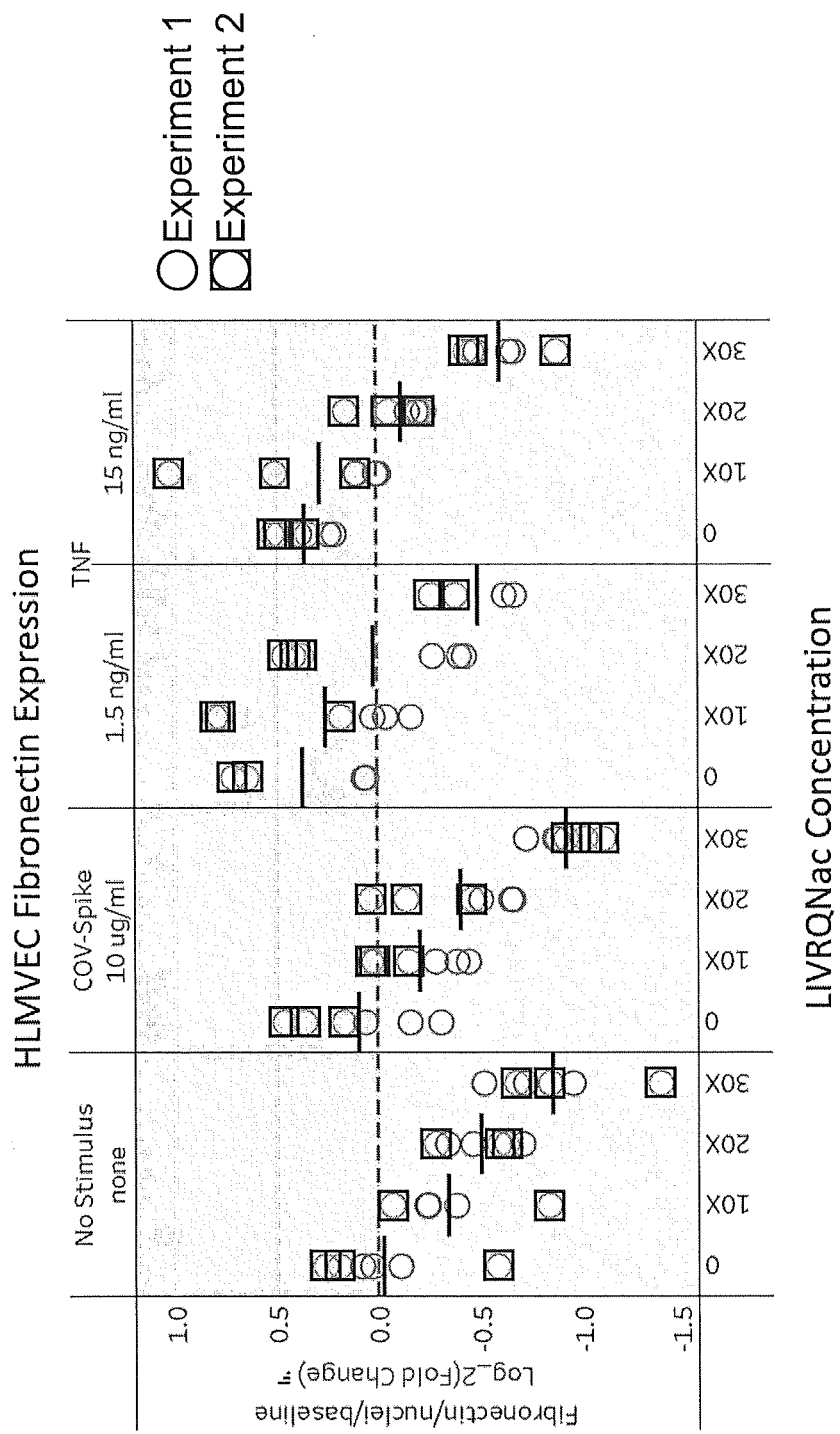
FIG. 17 is a plot showing reduced cellular Fibronectin expression in a dose-dependent manner in both stimulated and unstimulated cells.
Figure 18:
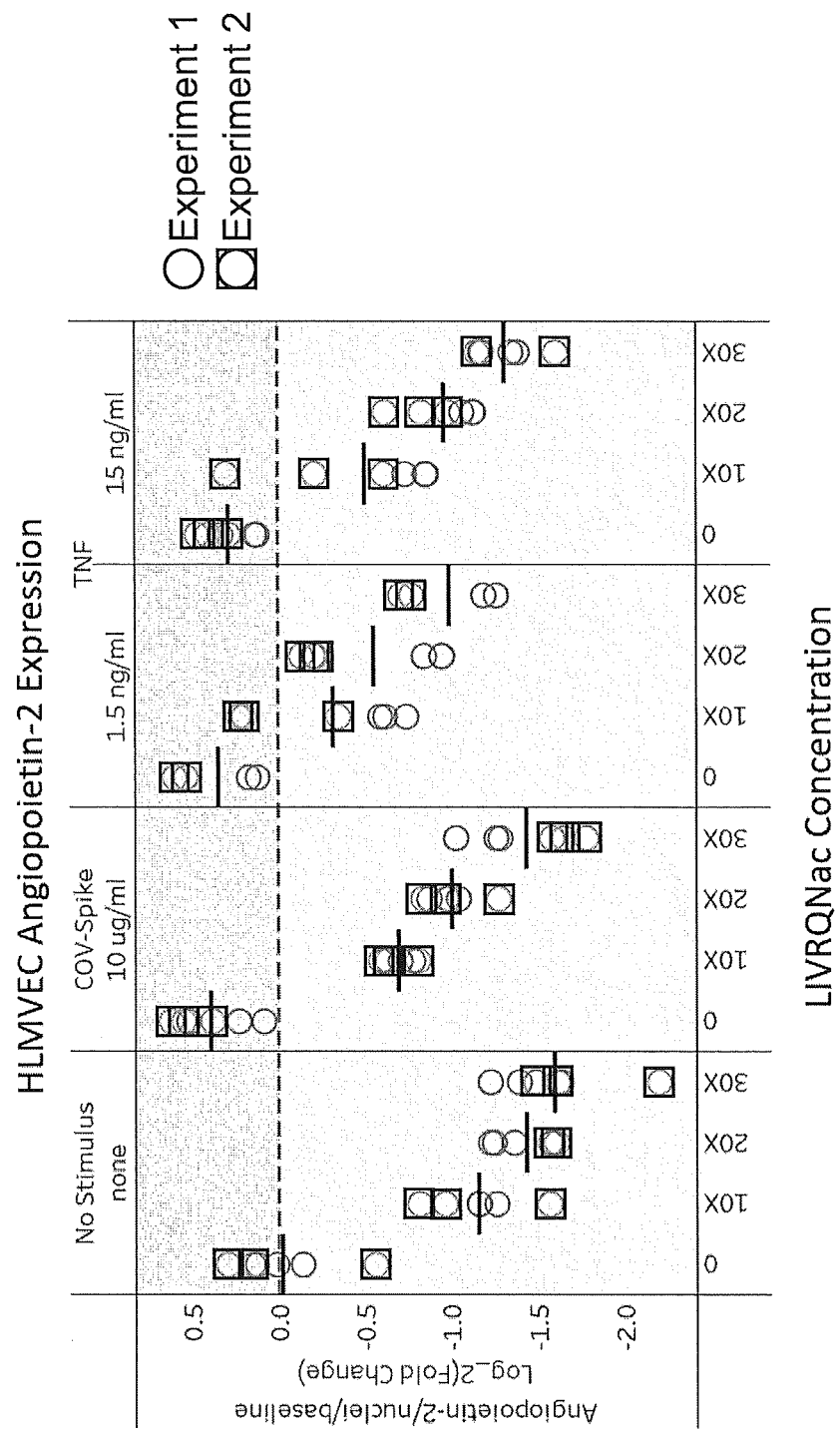
FIG. 18 is a plot showing reduced cellular angiopoietin 2 expression in a dose-dependent manner in both stimulated and unstimulated cells.
Figure 19:
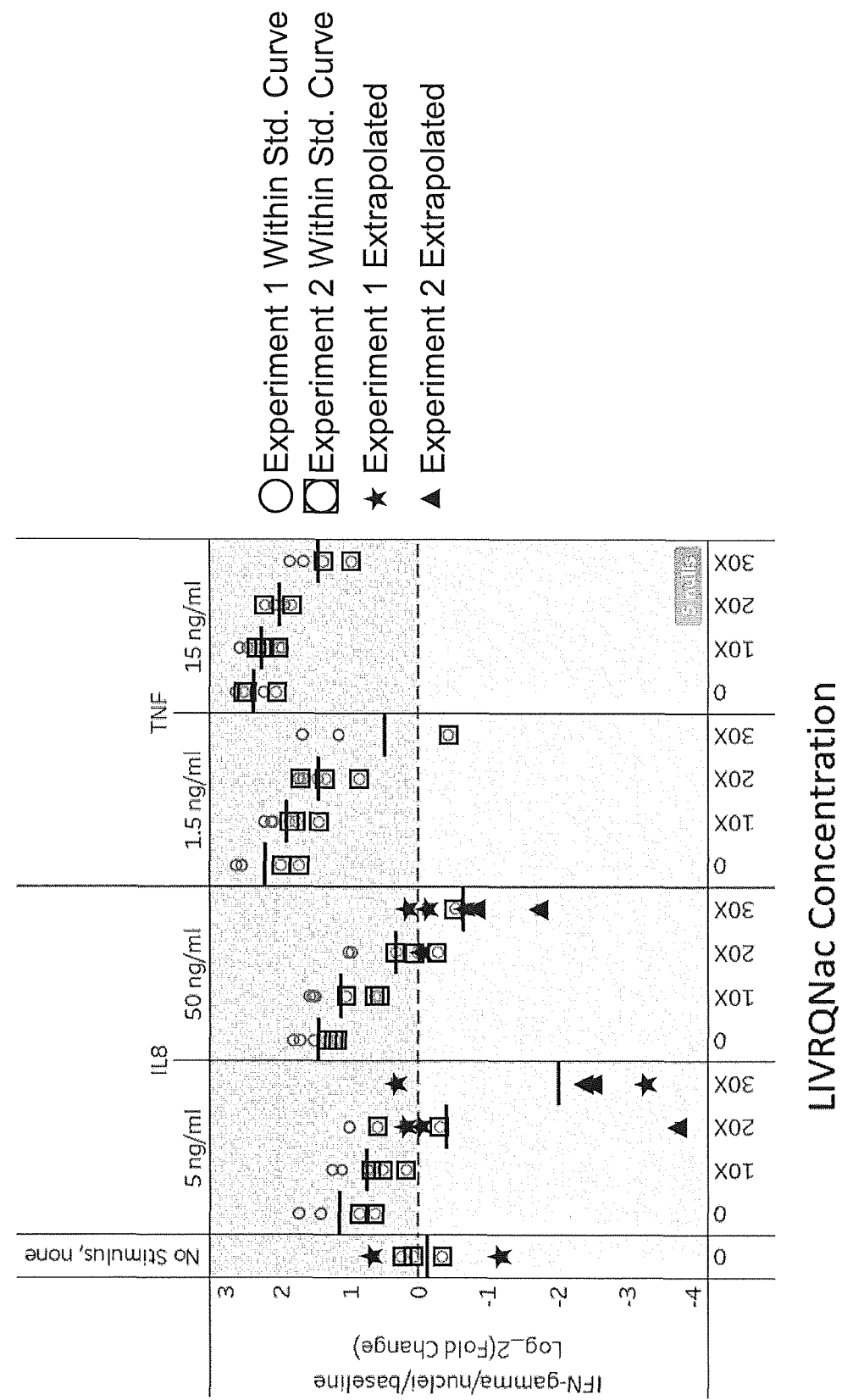
FIG. 19 is a plot showing reduced cellular IFN-γ expression in a dose-dependent manner in both stimulated and unstimulated cells.
Figure 20:
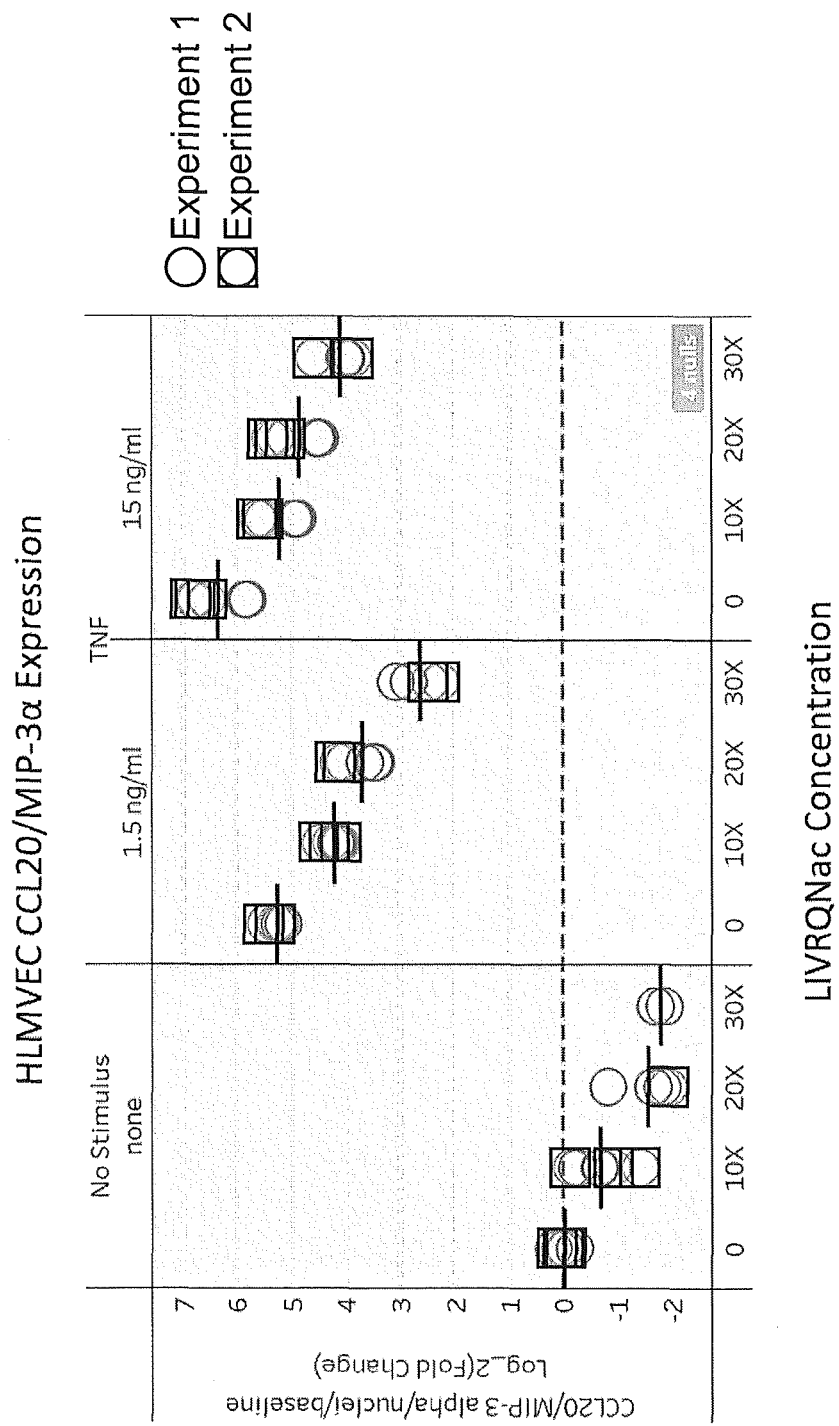
FIG. 20 is a plot showing reduced cellular CCL20/MIP3a expression in a dose-dependent manner in both stimulated and unstimulated cells.
Figure 21:
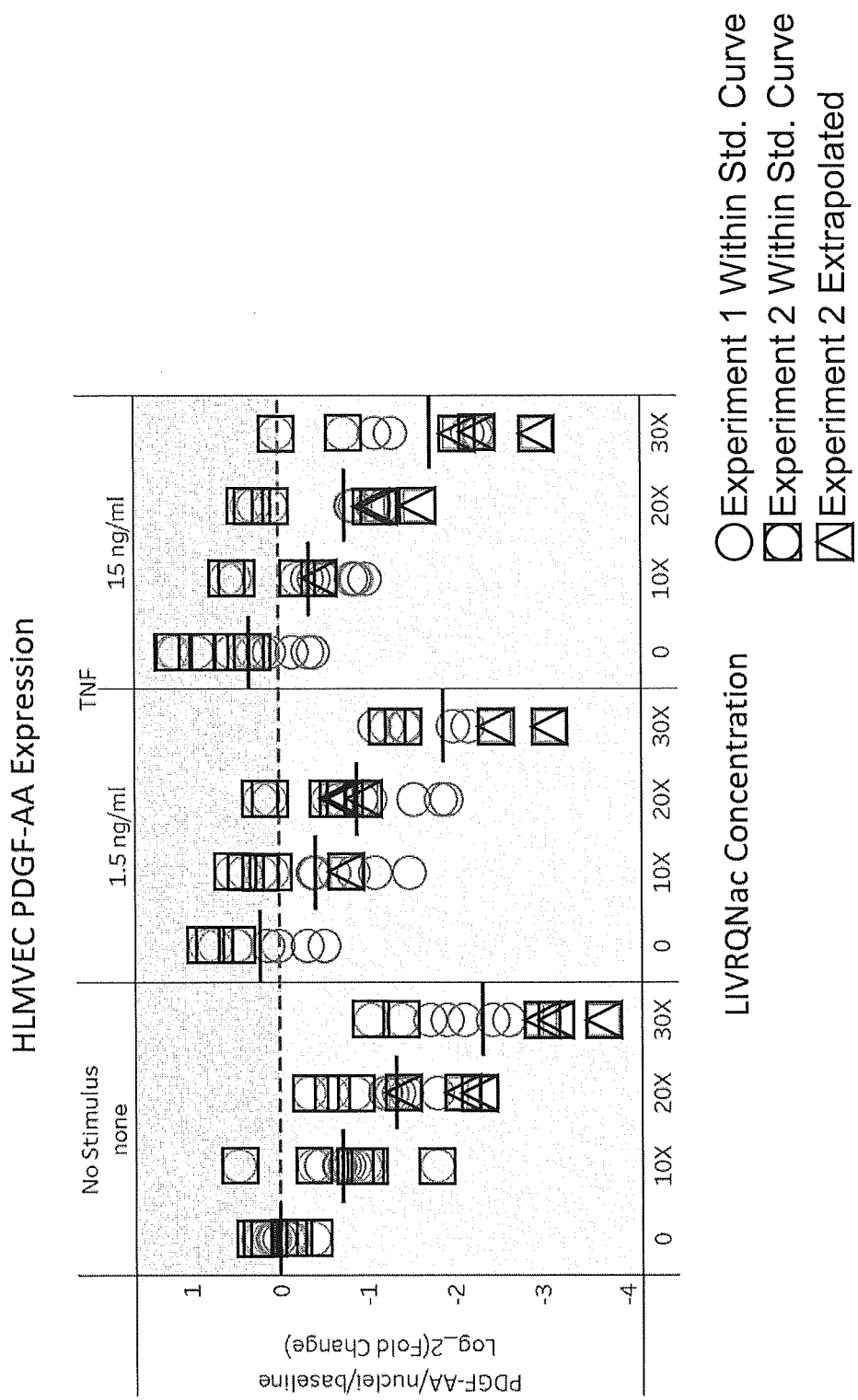
FIG. 21 is a plot showing reduced cellular PDGF-AA expression in a dose-dependent manner in both stimulated and unstimulated cells.
Figure 22:
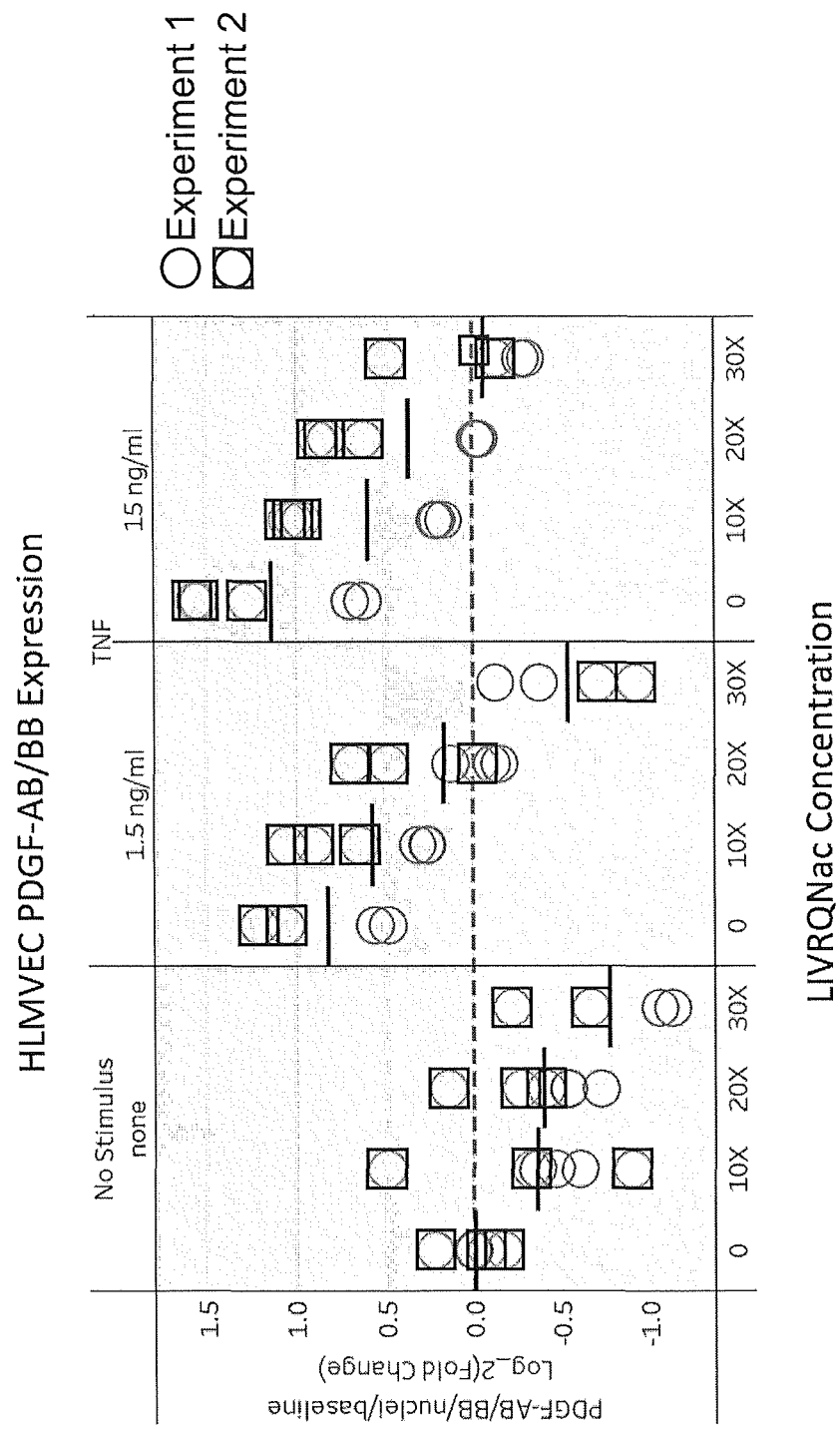
FIG. 22 is a plot showing reduced cellular PDGF-AA/BB expression in a dose-dependent manner in both stimulated and unstimulated cells.
Figure 23:
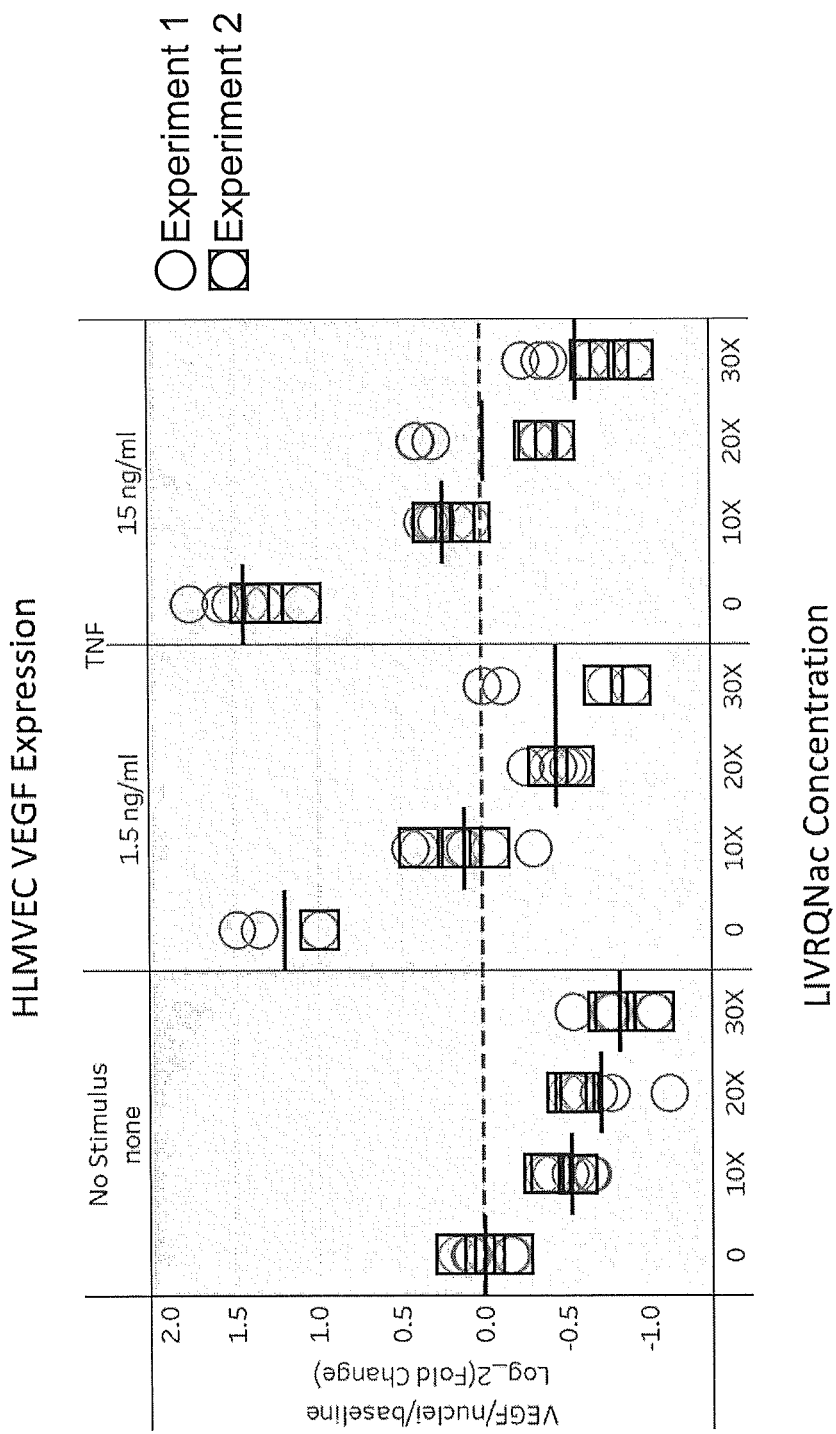
FIG. 23 is a plot showing reduced cellular VEGF expression in a dose-dependent manner in both stimulated and unstimulated cells.

HLMVECs were incubated for 24 hours with or without disease stimuli and supernatants were analyzed by Magpix as described in methods. Increased secretion of fibronectin (FIG. 17), angiopoietin 2 (FIG. 18), IFN-γ (FIG. 19), CCL20/MIP3a (FIG. 20), PDGF-AA (FIG. 21), PDGF-AB/BB (FIG. 20), VEGF (FIG. 23), and was observed in response to no stimulus, SARS-CoV-2 or TNFα stimuli. Irrespective of the stimulus, LIVRQNac dose-dependently decreased expression of all targets. Data are presented as log 2(fold change) from the no stimulus, no treatment control condition, and represents the average across two independent experiments using cells from one donor.

Conclusions:

In response to biological stimuli relevant to COVID-19 and Long COVID, primary HLMVEC increase expression and/or secretion of proteins relevant to inflammation (IFNγ and CCL20/MIP3a), coagulation (VWF and fibronectin) and intussusceptive angiogenesis (angiopoietin-2, VEGF, PDGF-AA and PDGF-AB/BB). Treatment of activated HLMVEC with LIVRQNac reduces expression of all proteins in a dose-dependent manner. These data suggest that LIVRQNac could effectively reduce the pathological activation of endothelial cells in COVID-19 or Long COVID patients, reducing the risk of microclotting, persistent inflammation, tissue hypoxia and oxidative stress.

Example 19: Summary of Examples 12-18

Covid-19 viral infection has been demonstrated to impact multiple body systems, including immune, metabolic, skeletal muscle, lung and cardiac, amongst others, primarily via entry into ACE2 cell receptor. Viral impact on cell metabolism is achieved as a result of tissue/organ level dysfunctions to endothelial system, cardiac, lung and other functions. While some systems recover post-acute infection, others persist and lead to what is known as post-acute sequelae of COVID-19, otherwise known as long COVID. Long COVID encompasses a wide variety of dysregulated systems and symptoms, with fatigue being the most predominant of these symptoms.

Risk factors that have been implicated in long COVID include diabetes/obesity/CV, EBV reactivation, circulating viral RNA fragments (potentially reflective of documented viral depots in adipose and other tissue compartments), and auto-immune disorders. These risk factors can manifest clinically or can be dysregulated and sub-clinical (not previously known to the individual).

Systems and mechanisms implicated in acute infection that persist into long COVID include endothelial dysfunction and micro-vascular hypoxia/compromised perfusion, complement activation, pro-inflammatory environment, increased oxidative stress environment or dysregulated balance between available antioxidant pools and ROS levels. Complement activation and endothelial dysfunction lead to a pro-coagulatory environment and increased risk of microclots and thrombotic microangiopathies. In addition to being implicated during acute infection and persistent in segments of long COVID fatigue patients, several of these dys-regulated systems have also been reported historically with previous coronaviruses (SARS and/or MERS).

As evidenced from published data and current investigation and analysis of clinical registries and EHR databases, these systemic alterations lead to dys-regulated lipid metabolism and down-regulation of fatty acid metabolism and oxidative phosphorylation, increased glycolysis, in a suppressed metabolic state, driven by reduced substrate availability from under-perfused tissue, pro-inflammatory and coagulatory states, and increased oxidative cellular environment.

The results described above, including from primary liver, skeletal muscle, and endothelial cell pre-clinical models, as well as human clinical study and biomarker investigation, highlight the following pertinent improvements in biology or biological markers relevant to improvement of fatigue in long COVID driven by LIVRQNac:

1. Significant reduction in patient reported fatigue scores in results from clinical study in patients with moderate to severe fatigue related to long COVID-19, suggests that LIVRQNac may be useful for the treatment of patients with long COVID and/or persistent fatigue after COVID-19 infection (e.g., Example 12)

2. Upregulated fatty acid oxidation and increased BHB, also pointing to increased cellular metabolism and increased ketone bodies (e.g., Example 2; Example 10; Example 11)

3. Increased availability of antioxidants, and potential for reduced ROS (e.g., Example 17; skeletal muscle: ROS)

4. Reduced inflammation/inflammatory markers (e.g., Example 2; Example 18: endothelial model: IFN-γ and CCL20/MIP3a; PHH)

5. Improved endothelial function and decreased vascular inflammation (e.g., Example 16: VCAM-1; Example 16: endothelial model 6. Improved markers of mitochondrial metabolism and insulin sensitivity (e.g., Example 10; Example 16: MOTS-C)

7. Potential for improvement in intra-myocellular lipid content in skeletal muscle (e.g., Example 12: MRS)

8. Potential reduction in glycolysis, as evidenced by trend towards reduced lactate in clinical study (e.g., Example 6, Example 10, Example 12)

9. Improvement in markers associated with pro-coagulatory environment and/or regulation clotting factors (e.g., Example 18: endothelial preclinical model: vWF and fibronectin)

10. Restore dysregulated angiogenesis (e.g., Example 18: endothelial model: PDGF-AA, PDGF-AB/BB, VEGF and angiopoietin-2)

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

What is claimed is:

1. A method of treating a subject having post-acute sequelae of COVID-19 (PASC), wherein the subject has one or more symptoms or signs selected from the group consisting of fatigue, myalgia, fibromyalgia, myalgic encephalomyelitis/chronic fatigue syndrome (ME/CFS), idiopathic pulmonary fibrosis, confusion, muscle dysfunction, mitochondrial dysfunction, dyspnea after exertion, postural orthostatic tachycardia syndrome, tachycardia, mood disorders, and depression, comprising administering to the subject:
   a) a leucine (L)-amino acid or salt thereof;
   b) an arginine (R)-amino acid or salt thereof;
   c) a glutamine (Q)-amino acid or salt thereof; and
   d) N-acetylcysteine (NAC) or a salt thereof.

2. The method of claim 1, wherein the subject experiences fatigue.

3. The method of claim 2, wherein the fatigue comprises one or both of persistent fatigue and exertional fatigue.

4. The method of claim 2, wherein the fatigue comprises one or both of mental fatigue and physical fatigue.

5. The method of claim 2, wherein the subject experiences fatigue at at least 4 weeks after infection with SARS-Cov-2.

6. The method of claim 1, wherein prior to administration of (a)-(d) the subject has a score of greater than or equal to 8 on a CFQ-11 test using bimodal scoring.

7. The method of claim 1, wherein after administration of (a)-(d) the subject has a decrease of at least 1 point on a CFQ-11 test using bimodal scoring, relative to the subject's score before administration.

8. The method of claim 1, wherein administration of (a)-(d) results in an increase in MOTS-c levels in the subject.

9. The method of claim 1, wherein administration of (a)-(d) results in a decrease in bicarbonate levels or sVCAM-1 levels in the subject.

10. The method of claim 1, wherein (a)-(d) are administered separately to the subject.

11. The method of claim 1, which comprises administering a composition comprising (a)-(d) to the subject.

12. The method of claim 1, wherein (a)-(d) are administered to the subject twice per day (BID) for at least 4 weeks.

13. The method of claim 1, wherein at least 50 wt. % of the total wt. of components administered to the subject is one or more amino acid entities in free form.

14. The method of claim 11, wherein the total wt. % of (a)-(d) is greater than the total wt. % of other amino acid entities in the composition.

15. The method of claim 1, wherein at least one of (a)-(d) is in a salt form.

16. The method of claim 1, wherein one, two, three, or more of methionine (M), tryptophan (W), or cysteine (C) is absent, or if present, is present at less than 10 weight (wt.) %.

17. The method of claim 1, wherein a wt. ratio of the L-amino acid or salt thereof, the R-amino acid or salt thereof, the Q-amino acid or salt thereof, and the NAC or salt thereof administered to the subject is 0.5 to 3:0.5 to 4:1 to 4:0.1 to 2.5.

18. The method of claim 1, further comprising administering one or both of:
   (e) an isoleucine (I)-amino acid or salt thereof; and
   (f) a valine (V)-amino acid or salt thereof.

19. The method of claim 18, wherein the wt. ratio of the L-amino acid or salt thereof, the I-amino acid or salt thereof, the V-amino acid or salt thereof, the R-amino acid or salt thereof, the Q-amino acid or salt thereof, and the NAC or salt thereof administered is 0.5 to 2:0.1 to 1:0.1 to 1:0.5 to 3:0.5 to 4:0.1 to 0.5.

20. The method of claim 11, wherein 25-40 g of the composition is administered to the subject BID, wherein weight includes amino acids or salts thereof and NAC but does not include excipients.

21. The method of claim 1, wherein the subject has been hospitalized for acute COVID-19.

22. The method of claim 1, wherein the subject had not been vaccinated for COVID-19 prior to contracting COVID-19.

23. The method of claim 1, wherein the subject had been vaccinated for COVID-19 prior to contracting COVID-19.

24. The method of claim 1, wherein the subject tested positive for SARS-COV-2 and developed symptoms consistent with infection.

25. The method of claim 1, wherein the subject tested positive for SARS-COV-2 and was asymptomatic, but later developed symptoms consistent with PASC.

* * * * *